United States Patent
Jimbo et al.

(10) Patent No.: US 8,883,050 B2
(45) Date of Patent: Nov. 11, 2014

(54) CURABLE COLORED COMPOSITIONS, COLOR FILTERS AND PROCESSES FOR PREPARING THEM, LIQUID CRYSTAL DISPLAY DEVICES, SOLID-STATE IMAGE SENSORS, AND DYE COMPOUNDS

(71) Applicant: FUJIFILM Corporation, Tokyo (JP)

(72) Inventors: Yoshihiro Jimbo, Haibara-gun (JP);
Yutaro Norizuki, Haibara-gun (JP);
Yohei Ishiji, Haibara-gun (JP);
Kazunari Yagi, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/970,750

(22) Filed: Aug. 20, 2013

(65) Prior Publication Data

US 2013/0334474 A1    Dec. 19, 2013

Related U.S. Application Data

(63) Continuation-in-part of application No. PCT/JP2012/052668, filed on Feb. 7, 2012.

(30) Foreign Application Priority Data

Feb. 24, 2011  (JP) ................. 2011-038731
Sep. 9, 2011  (JP) ................. 2011-197416

(51) Int. Cl.
| | |
|---|---|
| *G02B 5/23* | (2006.01) |
| *G02B 1/04* | (2006.01) |
| *G03F 7/105* | (2006.01) |
| *C07D 207/44* | (2006.01) |
| *G03F 7/027* | (2006.01) |
| *C09B 55/00* | (2006.01) |
| *C09B 69/10* | (2006.01) |
| *C07D 401/04* | (2006.01) |
| *G03F 7/00* | (2006.01) |
| *C07D 417/04* | (2006.01) |
| *C09B 57/10* | (2006.01) |
| *G03F 1/00* | (2012.01) |
| *G03F 7/033* | (2006.01) |
| *G02B 5/22* | (2006.01) |
| *G03F 7/032* | (2006.01) |

(52) U.S. Cl.
CPC . *G02B 1/04* (2013.01); *G03F 7/033* (2013.01); *G03F 7/105* (2013.01); *C07D 207/44* (2013.01); *G02B 5/223* (2013.01); *G03F 7/027* (2013.01); *G03F 7/032* (2013.01); *C09B 55/009* (2013.01); *C09B 69/109* (2013.01); *C07D 401/04* (2013.01); *G03F 7/0007* (2013.01); *C07D 417/04* (2013.01); *C09B 57/10* (2013.01)
USPC ............ 252/586; 252/582; 430/7; 430/270.1; 430/282.1; 548/403

(58) Field of Classification Search
USPC ............... 252/582, 586; 430/7, 282.1, 270.1; 544/4, 58.2, 226, 350; 546/6, 12, 113, 546/256; 548/365.1, 402, 403, 468, 518, 548/521
See application file for complete search history.

(56) References Cited

U.S. PATENT DOCUMENTS

| | | |
|---|---|---|
| 7,740,995 B2 | 6/2010 | Aizawa et al. |
| 8,197,994 B2 | 6/2012 | Mizukawa et al. |
| 8,367,282 B2 | 2/2013 | Mizukawa et al. |
| 2007/0037076 A1 | 2/2007 | Aizawa et al. |
| 2007/0287086 A1* | 12/2007 | Shinada et al. .................. 430/75 |
| 2008/0076044 A1* | 3/2008 | Mizukawa et al. ............... 430/7 |
| 2010/0230647 A1 | 9/2010 | Mizukawa et al. |
| 2012/0138877 A1 | 6/2012 | Mizukawa et al. |
| 2012/0238752 A1 | 9/2012 | Mizukawa et al. |

FOREIGN PATENT DOCUMENTS

| | | | |
|---|---|---|---|
| JP | 6-75375 A | 3/1994 | |
| JP | 3387541 B2 | 3/2003 | |
| JP | 2006-251076 | * 9/2006 | ............... G02B 5/22 |
| JP | 2006-251076 A | 9/2006 | |
| JP | 2007-039478 A | 2/2007 | |
| JP | 2008-292970 A | 12/2008 | |
| JP | 2009-31713 A | 2/2009 | |
| JP | 2010-13639 A | 1/2010 | |
| JP | 2010-18788 A | 1/2010 | |

OTHER PUBLICATIONS

International Search Report for PCT/JP2012/052668 dated May 1, 2012.
International Preliminary Report on Patentability mailed Sep. 6, 2013 in PCT/JP2012/052668.
English translation of International Preliminary Report on Patentability dated Sep. 6, 2013 in PCT/JP2012/052668.

* cited by examiner

*Primary Examiner* — Bijan Ahvazi
(74) *Attorney, Agent, or Firm* — Sughrue Mion, PLLC

(57) ABSTRACT

Provided is a curable colored composition, transmitting the light in the magenta region and absorbing the light in the cyan region. A curable colored composition comprising a metal complex in which a compound represented by formula (I) below is coordinated to a metal atom or a metal compound.

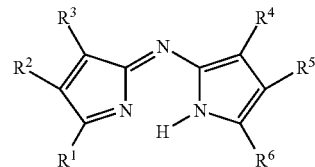

Formula (I)

14 Claims, No Drawings

CURABLE COLORED COMPOSITIONS, COLOR FILTERS AND PROCESSES FOR PREPARING THEM, LIQUID CRYSTAL DISPLAY DEVICES, SOLID-STATE IMAGE SENSORS, AND DYE COMPOUNDS

The present application is a continuation in part of PCT/JP2012/052668 filed on Feb. 7, 2012 and claims priority under 35 U.S.C. §119 of Japanese Patent Application No. 197416/2011, filed on Sep. 9, 2011, and Japanese Patent Application No. 038731/2011, filed on Feb. 24, 2011.

FIELD OF THE INVENTION

The present invention relates to curable colored compositions, color filters using the curable colored compositions and processes for preparing them, liquid crystal display devices and solid-state image sensors using the curable colored compositions, and dye compounds for use in the curable colored compositions.

DESCRIPTION OF THE RELATED ART

Conventionally, color filters have been prepared by using a colored composition comprising a pigment dispersion composition containing an organic pigment or an inorganic pigment dispersed therein, a polyfunctional monomer, a polymerization initiator, an alkali-soluble resin, and optionally other components to form a colored pattern by photolithography, inkjet printing or the like.

Recently, color filters tend to expand their applications in the field of liquid crystal displays (LCDs) from computer monitors to television (TV) sets. This trend to expanding applications requires color filters to have high level color properties in chromaticity, contrast and the like. Color filters for use in image sensors (solid-state image sensors) are also required to have further improved color properties such as more even color, improved color resolution and the like.

However, it is often difficult to further improve contrast and luminance using conventional pigment dispersions because they often involve problems such as scattering by coarse particles of pigments, an increase of viscosity due to insufficient dispersion stability and the like.

For this reason, proposals have been made to use not only pigments but also dyes as colorants (see e.g., JP-A-H6-75375). It is said that dyes are advantageously used as colorants because their own color purity and bright hue enhance hue or luminance in displayed images and the absence of coarse particles contributes to improvements in contrast.

Examples of known dyes include a wide variety of dye-based compounds such as arylmethane dyes, dipyrromethene dyes, pyrimidine azo dyes, pyrazole azo dyes, xanthene dyes and the like (see e.g., JP-A2008-292970, JP-A2007-039478, and Japanese Patent No. 3387541). Dipyrromethene dyes are known to improve heat resistance/light resistance when they are complexed with metals, and examples of applications of this technique to blue color filters have been known (see e.g., JP-A2008-292970, JP-A2009-31713, JP-A2010-13639, and JP-A2010-18788).

SUMMARY OF THE INVENTION

However, conventionally available dipyrromethene metal complex dyes had the disadvantage that they have absorption in the violet region at shorter wavelengths unsuitable for use as cyan dyes so that their applicability is greatly limited when they are to be used as green color filters. The present invention was made to solve such a disadvantage of the prior art, and aims to provide curable colored compositions having heat resistance and capable of transmitting the light in the magenta region and absorbing the light in the cyan region and color filters using such compositions and processes for preparing them, as well as liquid crystal display devices and solid-state image sensors capable of displaying images with bright colors and high contrast.

Means for Solving the Problems

As a result of careful studies, we achieved the present invention on the basis of the finding that curable colored compositions having favorable absorption wavelength characteristics consisting in transmitting the light in the magenta region and absorbing the light in the cyan region can be provided by using azapyrromethene metal complexes. Thus, the present invention provides the following as specific means for solving the problems described above.

[1] A curable colored composition comprising a metal complex in which a compound represented by formula (1) below is coordinated to a metal atom or a metal compound.

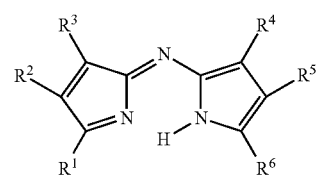

Formula (1)

In formula (1), $R^1$, $R^2$, $R^3$, $R^4$, $R^5$ and $R^6$ each represent a hydrogen atom or a substituent.

[2] A curable colored composition comprising a metal complex represented by formula (2) below:

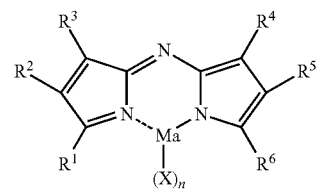

Formula (2)

In formula (2), $R^1$, $R^2$, $R^3$, $R^4$, $R^5$ and $R^6$ each represent a hydrogen atom or a substituent. Ma represents a metal atom or a metal compound, X each represents a substituent. Ma and X form a covalent bond, coordinate bond or ionic bond. n is an integer of 2 to 4.

[3] A curable colored composition comprising a metal complex represented by formula (2-2) below:

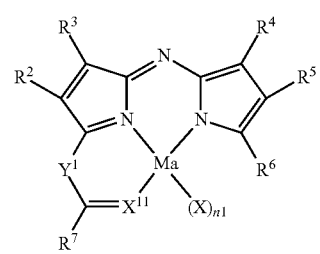

Formula (2-2)

In formula (2-2), $R^2$, $R^3$, $R^4$, $R^5$ and $R^6$ each represent a hydrogen atom or a substituent. $R^7$ represents alkyl, alkenyl, aryl, heterocyclyl, alkoxy, aryloxy, alkylamino, arylamino, or heterocyclylamino. Ma represents a metal atom or a metal compound, X each represents a substituent. $X^{11}$ represents NR (wherein R represents a hydrogen atom, alkyl, alkenyl, aryl, heterocyclyl, acyl, alkylsulfonyl, or arylsulfonyl), nitrogen atom, oxygen atom or sulfur atom. $Y^1$ represents NRc (wherein Rc represents a hydrogen atom, alkyl, alkenyl, aryl, heterocyclyl, acyl, alkylsulfonyl, or arylsulfonyl), nitrogen atom or carbon atom. Ma and X form a covalent bond, coordinate bond or ionic bond. n1 is an integer of 2 to 4.

[4] A curable colored composition comprising a metal complex represented by formula (3) below:

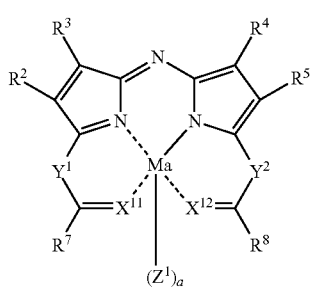

Formula (3)

In formula (3), $R^2$, $R^3$, $R^4$ and $R^5$ each represent a hydrogen atom or a substituent. $R^7$ and $R^8$ each represent alkyl, alkenyl, aryl, heterocyclyl, alkoxy, aryloxy, alkylamino, arylamino or heterocyclylamino. Ma represents a metal atom or a metal compound. $X^{11}$ and $X^{12}$ each represent NR (wherein R represents a hydrogen atom, alkyl, alkenyl, aryl, heterocyclyl, acyl, alkylsulfonyl, or arylsulfonyl), nitrogen atom, oxygen atom or sulfur atom. $Y^1$ and $Y^2$ each represent NRc (wherein Rc represents a hydrogen atom, alkyl, alkenyl, aryl, heterocyclyl, acyl, alkylsulfonyl, or arylsulfonyl), nitrogen atom, or carbon atom. $Z^1$ represents a group capable of forming a bond with Ma, and a represents 0, 1 or 2.

[5] A curable colored composition comprising a metal complex in which a compound represented by formula (4) below is coordinated to a metal atom or a metal compound.

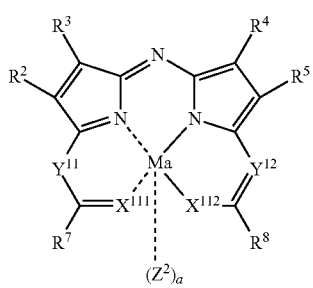

Formula (4)

In formula (4), $R^2$, $R^3$, $R^4$ and $R^5$ each represent a hydrogen atom or a substituent. $R^7$ and $R^8$ each represent alkyl, alkenyl, aryl, heterocyclyl, alkoxy, aryloxy, alkylamino, arylamino or heterocyclylamino. Ma represents a metal atom or a metal compound. $X^{111}$ represents NR (wherein R represents a hydrogen atom, alkyl, alkenyl, aryl, heterocyclyl, acyl, alkylsulfonyl, or arylsulfonyl), nitrogen atom, oxygen atom, or sulfur atom, $X^{112}$ represents NRa (wherein Ra represents a hydrogen atom, alkyl, alkenyl, aryl, heterocyclyl, acyl, alkylsulfonyl, or arylsulfonyl), oxygen atom or sulfur atom. $Y^{11}$ represents NRc (wherein Rc represents a hydrogen atom, alkyl, alkenyl, aryl, heterocyclyl, acyl, alkylsulfonyl, or arylsulfonyl), nitrogen atom, or carbon atom, $Y^{12}$ represents a nitrogen atom or a carbon atom. $Z^2$ represents a group capable of forming a bond with Ma, and a represents 0, 1 or 2.

[6] The curable colored composition according to any one of [1] to [5], wherein $R^5$ represents 2,6-di-tert-butyl-4-methyl-cyclohexyloxycarbonyl.

[7] The curable colored composition according to any one of [1] to [5], wherein $R^2$ and $R^5$ represent 2,6-di-tert-butyl-4-methylcyclohexyloxycarbonyl.

[8] The curable colored composition according to any one of [1] to [5], wherein $R^2$ and $R^5$ each represent an optionally substituted heteroaryl.

[9] The curable colored composition according to any one of [1] to [5], wherein $R^2$ and $R^5$ are each represented by formula (18-1) below:

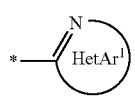

Formula (18-1)

In formula (18-1), HetAr1 represents an optionally substituted heteroaryl ring. Further, the substituents may be joined together to form a single ring or a fused ring system. $R^2$ and $R^5$ are each attached to the central moiety at *.

[10] The curable colored composition according to any one of [1] to [5] wherein $R^2$ and $R^5$ are each represented by any one of formulae (19-1) to (19-3):

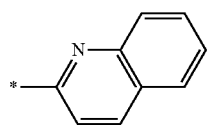

Formula (19-1)

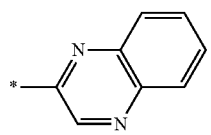

Formula (19-2)

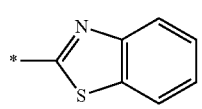

Formula (19-3)

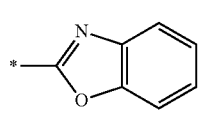

Formula (19-4)

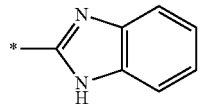

Formula (19-5)

In formulae (19-1) to (19-5) above, $R^2$ and $R^5$ are each attached to the central moiety at *. These groups may be substituted.

[11] The curable colored composition according to any one of [1] to [5], wherein $R^2$ and $R^5$ each represent an optionally substituted alkoxycarbonyl, aryloxycarbonyl, amide, imide, or cyano.

[12] The curable colored composition according to any one of [1] to [11], further comprising a yellow dye.

[13] The curable colored composition according to any one of [1] to [12], further comprising a green dye.
[14] The curable colored composition according to any one of [1] to [13], further comprising a monomer and a polymerization initiator.
[15] A color filter comprising a colored layer using the curable colored composition according to any one of [1] to [14].
[16] A process for preparing a color filter, comprising: applying the curable colored composition according to any one of [1] to [14] to form a colored layer; and exposing the resulting colored layer in a pattern.
[17] A liquid crystal display device comprising the color filter according to [15] or a color filter prepared by the process according to [16].
[18] A solid-state image sensor comprising the color filter according to [15] or a color filter prepared by the process according to [16].
[19] A compound represented by formula (5-1) or (5-2) below:

Formula (5-1)

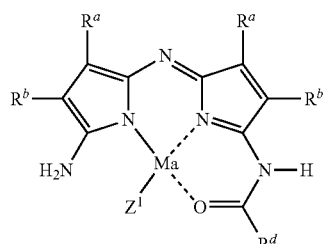

Formula (5-1)

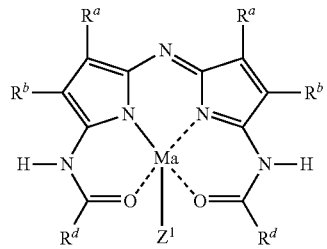

In formula (5-1) and formula (5-2), $R^a$ each represents an optionally substituted aryl or alkyl, $R^b$ each represents 2,6-di-tert-butyl-4-methylcyclohexyloxycarbonyl or cyano, $R^d$ represents an optionally substituted alkyl, aryl, heteroaryl or alkenyl, Ma represents a metal atom or a metal compound, and $Z^1$ represents a group capable of forming a bond with Ma.

[20] A compound represented by formula (5-3) below:

Formula (5-3)

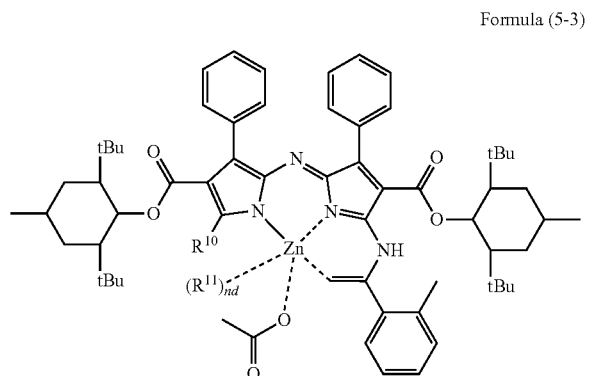

In formula (5-3), $R^{10}$ represents a substituent containing a nitrogen atom, $R^{11}$ represents a substituent, or $R^{10}$ and $R^{11}$ may be joined together to form a ring. nd represents 0 or 1.

[21] A compound represented by either of the formulae below:

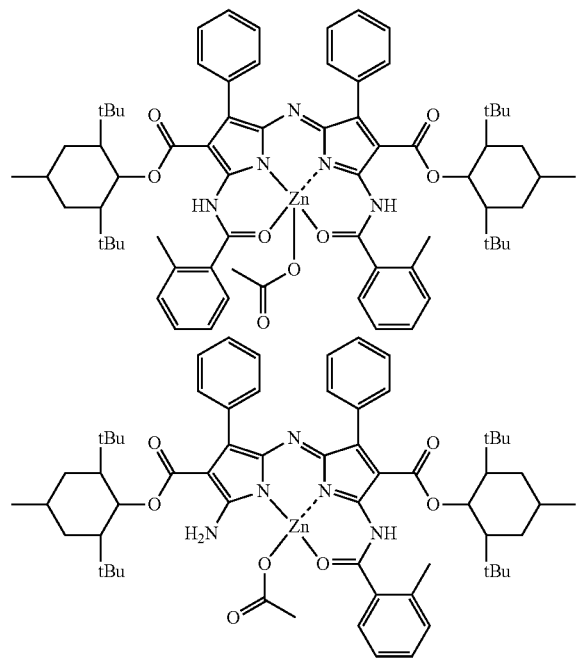

[22] A compound represented by formula (1-1) or formula (1-2) below:

Formula (1-1)

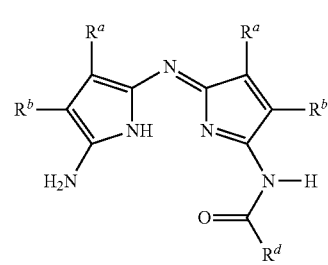

Formula (1-2)

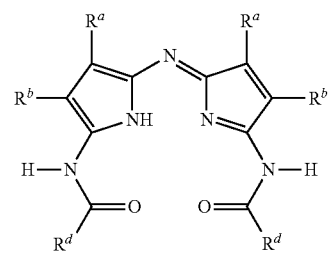

In formulae (1-1) and (1-2), $R^a$ each represents an optionally substituted aryl or alkyl, $R^b$ each represents 2,6-di-tert-butyl-4-methylcyclohexyloxycarbonyl or cyano, and $R^d$ represents an optionally substituted alkyl, aryl, heteroaryl or alkenyl.

[23] A compound represented by any one of the formulae below:

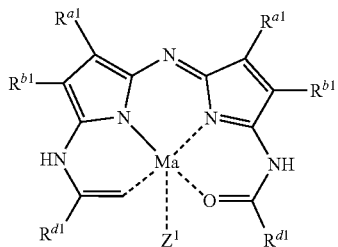

Formula (21-1)

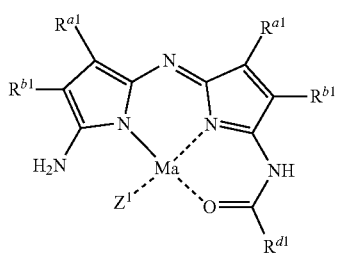

Formula (21-2)

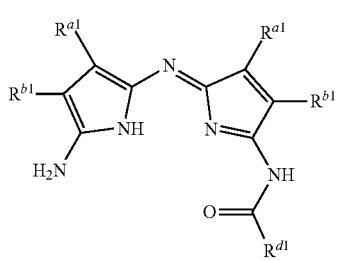

Formula (21-3)

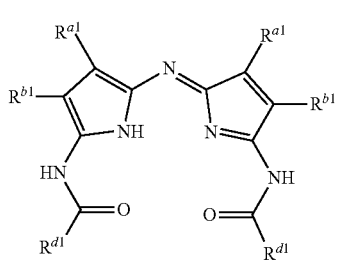

Formula (21-4)

In formulae (21-1) to (21-4) above, $R^{a1}$ each represents an optionally substituted aryl or alkyl or heteroaryl, $R^{b1}$ represents an optionally substituted heteroaryl, $R^{d1}$ represents an optionally substituted alkyl, aryl, heteroaryl or alkenyl, Ma represents a metal atom or a metal compound, and $Z^1$ represents a group capable of forming a bond with Ma.

[24] The compound according to [23], wherein $R^{b1}$ is represented by formula (22-1) below:

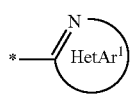

Formula (22-1)

In formula (22-1), HetAr1 represents an optionally substituted heteroaryl ring. Further, the substituents may be joined together to form a single ring or a fused ring system. $R^{b1}$ is attached to the central moiety at *.

[25] The compound according to [23], wherein $R^{b1}$ is each represented by any one of formulae (23-1) to (23-5) below:

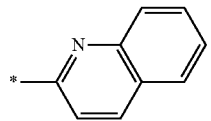

Formula (23-1)

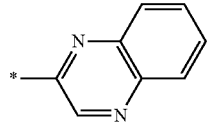

Formula (23-2)

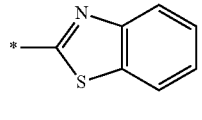

Formula (23-3)

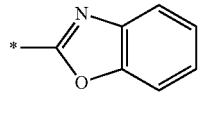

Formula (23-4)

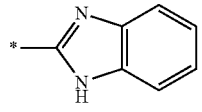

Formula (23-5)

In formulae (23-1) to (23-5) above, $R^b$ is each attached to the central moiety at *. These groups may be substituted.

[26] A compound represented by any one of the formulae below:

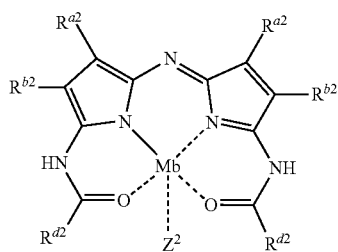

Formula (25-1)

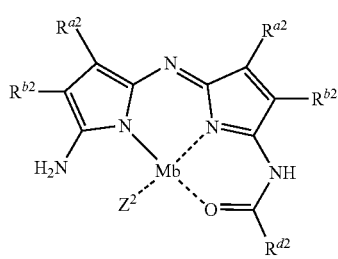

Formula (25-2)

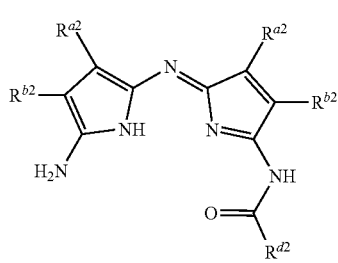

Formula (25-3)

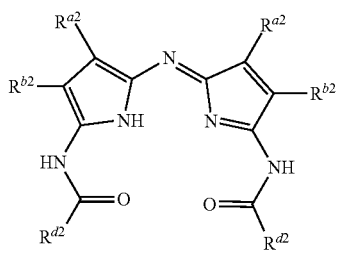
Formula (25-4)

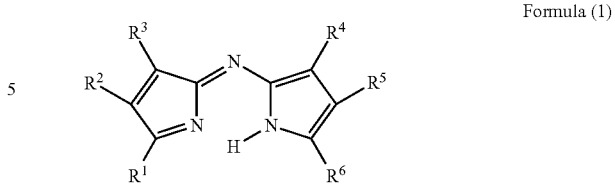
Formula (1)

In formulae (25-1) to (25-4) above, $R^{a2}$ each represents an optionally substituted aryl or alkyl or heteroaryl, $R^{b2}$ each represents an optionally substituted alkoxycarbonyl, aryloxycarbonyl, amide, imide or cyano, $R^{d2}$ each represents an optionally substituted alkyl, aryl, heteroaryl or alkenyl, Mb represents a metal atom or a metal compound, and $Z^2$ represents a group capable of forming a bond with Ma.

Advantages of the Invention

The curable colored compositions of the present invention have heat resistance and favorable absorption characteristics consisting in transmitting the light in the magenta region and absorbing the light in the cyan region. Further, curable colored compositions that are especially effective for use in green-colored elements can be provided by adding a yellow dye compound or the like. According to the present invention, curable colored compositions having high color purity, high absorption coefficient in thin layers, and excellent durability (especially heat resistance and light resistance) and voltage retention can be provided as well as color filters using such compositions and processes for preparing them. According to the present invention, liquid crystal display devices and solid-state image sensors capable of displaying images with bright colors and high contrast can also be provided. By using the present invention, liquid crystal display devices and solid-state image sensors capable of displaying images with bright colors and high contrast can be provided.

THE BEST MODES FOR CARRYING OUT THE INVENTION

The curable colored compositions of the present invention, the color filters using the curable colored compositions of the present invention and processes for preparing them, the liquid crystal display devices and solid-state image sensors using the curable colored compositions of the present invention, as well as the dye compounds of the present invention are described in detail below. The dye compounds of the present invention can be used as coloring components of the curable colored compositions.

Curable Colored Compositions of the Present Invention

The curable colored compositions of the present invention comprise a metal complex in which a compound represented by formula (1) below is coordinated to a metal atom or a metal compound.

In formula (1), $R^1$, $R^2$, $R^3$, $R^4$, $R^5$ and $R^6$ each represent a hydrogen atom or a substituent.

The substituent refers to include, for example, a halogen atom (e.g., fluorine, chlorine, bromine), alkyl (preferably straight-chain, branched or cyclic alkyl containing 1 to 48, more preferably 1 to 24 carbon atoms, e.g., methyl, ethyl, propyl, isopropyl, butyl, t-butyl, pentyl, hexyl, heptyl, octyl, 2-ethylhexyl, dodecyl, hexadecyl, cyclopropyl, cyclopentyl, cyclohexyl, 1-norbornyl, 1-adamantyl), alkenyl (preferably alkenyl containing 2 to 48, more preferably 2 to 18 carbon atoms, e.g., vinyl, allyl, 3-buten-1-yl), aryl (preferably aryl containing 6 to 48, more preferably 6 to 24 carbon atoms, e.g., phenyl, naphthyl), heterocyclyl (preferably heterocyclyl containing 1 to 32, more preferably 1 to 18 carbon atoms, preferably heteroaryl, e.g., 2-thienyl, 4-pyridyl, 2-furyl, 2-pyrimidinyl, 1-pyridyl, 2-benzothiazolyl, 1-imidazolyl, 1-pyrazolyl, benzotriazole-1-yl), silyl (preferably silyl containing 3 to 38, more preferably 3 to 18 carbon atoms, e.g., trimethylsilyl, triethylsilyl, tributylsilyl, t-butyldimethylsilyl, t-hexyldimethylsilyl), hydroxyl, cyano, nitro, alkoxy (preferably alkoxy containing 1 to 48, more preferably 1 to 24 carbon atoms, e.g., methoxy, ethoxy, 1-butoxy, 2-butoxy, isopropoxy, t-butoxy, dodecyloxy, cycloalkyloxy, e.g., cyclopentyloxy, cyclohexyloxy), aryloxy (preferably aryloxy containing 6 to 48, more preferably 6 to 24 carbon atoms, e.g., phenoxy, 1-naphthoxy), heterocyclyloxy (preferably heterocyclyloxy containing 1 to 32, more preferably 1 to 18 carbon atoms, e.g., 1-phenyltetrazole-5-oxy, 2-tetrahydropyranyloxy), silyloxy (preferably silyloxy containing 1 to 32, more preferably 1 to 18 carbon atoms, e.g., trimethylsilyloxy, t-butyldimethylsilyloxy, diphenylmethylsilyloxy), acyloxy (preferably acyloxy containing 2 to 48, more preferably 2 to 24 carbon atoms, e.g., acetoxy, pivaloyloxy, benzoyloxy, dodecanoyloxy), alkoxycarbonyloxy (preferably alkoxycarbonyloxy containing 2 to 48, more preferably 2 to 24 carbon atoms, e.g., ethoxycarbonyloxy, t-butoxycarbonyloxy, cycloalkyloxycarbonyloxy, e.g., cyclohexyloxycarbonyloxy), aryloxycarbonyloxy (preferably aryloxycarbonyloxy containing 7 to 32, more preferably 7 to 24 carbon atoms, e.g., phenoxycarbonyloxy), carbamoyloxy (preferably carbamoyloxy containing 1 to 48, more preferably 1 to 24 carbon atoms, e.g., N,N-dimethylcarbamoyloxy, N-butylcarbamoyloxy, N-phenylcarbamoyloxy, N-ethyl-N-phenylcarbamoyloxy), sulfamoyloxy (preferably sulfamoyloxy containing 1 to 32, more preferably 1 to 24 carbon atoms, e.g., N,N-diethylsulfamoyloxy, N-propylsulfamoyloxy), alkylsulfonyloxy (preferably alkylsulfonyloxy containing 1 to 38, more preferably 1 to 24 carbon atoms, e.g., methylsulfonyloxy, hexadecylsulfonyloxy, cyclohexylsulfonyloxy), arylsulfonyloxy (preferably arylsulfonyloxy containing 6 to 32, more preferably 6 to 24 carbon atoms, e.g., phenylsulfonyloxy), acyl (preferably acyl containing 1 to 48, more preferably 1 to 24 carbon atoms, e.g., formyl, acetyl, pivaloyl, benzoyl, tetradecanoyl, cyclohexanoyl), alkoxycarbonyl (preferably alkoxycarbonyl containing 2 to 48, more preferably 2 to 24 carbon atoms, e.g., methoxycarbonyl, ethoxycarbonyl, octadecyloxycarbonyl, cyclohexyloxycarbonyl, 2,6- di-tert-butyl-4-methylcyclohexyloxycarbonyl), aryloxycarbonyl (preferably aryloxycarbonyl containing 7 to 32, more preferably 7 to 24 carbon atoms, e.g., phenoxycarbonyl), carbamoyl (preferably carbamoyl containing 1 to 48, more preferably 1 to 24 carbon atoms, e.g., carbamoyl, N,N-diethylcarbamoyl, N-ethyl-N-octylcarbamoyl, N,N-dibutylcarbamoyl, N-propylcarbamoyl, N-phenylcarbamoyl, N-methyl-N-phenylcarbamoyl, N,N-dicyclohexylcarbamoyl), amino (preferably amino containing 32 or less, more preferably 24 or less carbon atoms, e.g., amino, methylamino, N,N-dibutylamino, tetradecylamino, 2-ethylhexylamino, cyclohexylamino), anilino (preferably anilino containing 6 to 32, more preferably 6 to 24 carbon atoms, e.g., anilino, N-methylanilino), heterocyclylamino (preferably heterocyclylamino containing 1 to 32, more preferably 1 to 18 carbon atoms, e.g., 4-pyridylamino), carboxamide (preferably carboxamide containing 2 to 48, more preferably 2 to 24 carbon atoms, e.g., acetamide, benzamide, tetradecanamide, pivaloylamide, cyclohexanamide), ureido (preferably ureido containing 1 to 32, more preferably 1 to 24 carbon atoms, e.g., ureido, N,N-dimethylureido, N-phenylureido), imide (preferably imide containing 36 or less, more preferably 24 or less carbon atoms, e.g., N-succinimide, N-phthalimide), alkoxycarbonylamino (preferably alkoxycarbonylamino containing 2 to 48, more preferably 2 to 24 carbon atoms, e.g., methoxycarbonylamino, ethoxycarbonylamino, t-butoxycarbonylamino, octadecyloxycarbonylamino, cyclohexyloxycarbonylamino), aryloxycarbonylamino (preferably aryloxycarbonylamino containing 7 to 32, more preferably 7 to 24 carbon atoms, e.g., phenoxycarbonylamino), sulfonamide (preferably sulfonamide containing 1 to 48, more preferably 1 to 24 carbon atoms, e.g., methanesulfonamide, butanesulfonamide, benzenesulfonamide, hexadecanesulfonamide, cyclohexane sulfonamide), sulfamoylamino (preferably sulfamoylamino containing 1 to 48, more preferably 1 to 24 carbon atoms, e.g., N,N-dipropylsulfamoylamino, N-ethyl-N-dodecylsulfamoylamino), azo (preferably azo containing 1 to 32, more preferably 1 to 24 carbon atoms, e.g., phenylazo, 3-pyrazolylazo), alkylthio (preferably alkylthio containing 1 to 48, more preferably 1 to 24 carbon atoms, e.g., methylthio, ethylthio, octylthio, cyclohexylthio), arylthio (preferably arylthio containing 6 to 48, more preferably 6 to 24 carbon atoms, e.g., phenylthio), heterocyclylthio (preferably heterocyclylthio containing 1 to 32, more preferably 1 to 18 carbon atoms, e.g., 2-benzothiazolylthio, 2-pyridylthio, 1-phenyltetrazolylthio), alkylsulfinyl (preferably alkylsulfinyl containing 1 to 32, more preferably 1 to 24 carbon atoms, e.g., dodecanesulfinyl), arylsulfinyl (preferably arylsulfinyl containing 6 to 32, more preferably 6 to 24 carbon atoms, e.g., phenylsulfinyl), alkylsulfonyl (preferably alkylsulfonyl containing 1 to 48, more preferably 1 to 24 carbon atoms, e.g., methylsulfonyl, ethylsulfonyl, propylsulfonyl, butylsulfonyl, isopropylsulfonyl, 2-ethylhexylsulfonyl, hexadecylsulfonyl, octylsulfonyl, cyclohexylsulfonyl), arylsulfonyl (preferably arylsulfonyl containing 6 to 48, more preferably 6 to 24 carbon atoms, e.g., phenylsulfonyl, 1-naphthylsulfonyl), sulfamoyl (preferably sulfamoyl containing 32 or less, more preferably 24 or less carbon atoms, e.g., sulfamoyl, N,N-dipropylsulfamoyl, N-ethyl-N-dodecylsulfamoyl, N-ethyl-N-phenylsulfamoyl, N-cyclohexylsulfamoyl), sulfo, phosphonyl (preferably phosphonyl containing 1 to 32, more preferably 1 to 24 carbon atoms, e.g., phenoxyphosphonyl, octyloxyphosphonyl, phenylphosphonyl), phosphinoylamino (preferably phosphinoylamino containing 1 to 32, more preferably 1 to 24 carbon atoms, e.g., diethoxyphosphinoylamino, dioctyloxyphosphinoylamino).

If the substituents $R^1$ to $R^6$ in formula (1) are groups that can be further substituted, they may have the substituents described for $R^1$ to $R^6$ above, and if they are substituted by two or more substituents, these substituents may be identical or different.

Preferably, $R^1$ and $R^6$ each represent a hydrogen atom, alkyl, alkenyl, aryl, heterocyclyl, silyl, hydroxyl, cyano, alkoxy, aryloxy, heterocyclyloxy, acyl, alkoxycarbonyl, carbamoyl, amino, anilino, heterocyclylamino, carboxamide, ureido, imide, alkoxycarbonylamino, aryloxycarbonylamino, sulfonamide, azo, alkylthio, arylthio, heterocyclylthio, alkylsulfonyl, arylsulfonyl, or phosphinoylamino.

Preferably, $R^2$ and $R^5$ each represent a hydrogen atom, halogen atom, alkyl, alkenyl, aryl, heterocyclyl (more preferably heteroaryl), hydroxyl, cyano, nitro, alkoxy, aryloxy, heterocyclyloxy, acyl, alkoxycarbonyl, aryloxycarbonyl, carbamoyl, imide, alkoxycarbonylamino, sulfonamide, azo, sulfonyl, alkylthio, arylthio, heterocyclylthio, alkylsulfonyl, arylsulfonyl, or sulfamoyl, more preferably a hydrogen atom, halogen atom, aryl, heterocyclyl (more preferably heteroaryl), cyano, alkoxycarbonyl, or sulfonyl. $R^2$ and $R^5$ may be different, but they are preferably identical.

Especially preferably, $R^2$ and $R^5$ include the three embodiments described below. It should be understood that the present invention does not exclude other than these embodiments.

A preferred first embodiment of the present invention is an embodiment wherein $R^2$ and $R^5$ each represent alkoxycarbonyl, more preferably 2,6-di-tert-butyl-4-methylcyclohexyloxycarbonyl.

A preferred second embodiment of the present invention is an embodiment wherein $R^2$ and $R^5$ are each an optionally substituted heteroaryl. The heteroaryl ring is preferably a 5- or 6-membered ring. The heteroatom contained in the heteroaryl ring is preferably any one or more of nitrogen, oxygen and sulfur atoms, more preferably a nitrogen and/or sulfur atom.

The substituents present on the heteroaryl ring are as defined for $R^1$, $R^2$, $R^3$, $R^4$, $R^5$ and $R^6$ above, preferably halogen atom, alkyl, alkenyl, aryl, heterocyclyl, silyl, hydroxyl, cyano, alkoxy, aryloxy, heterocyclyloxy, acyl, alkoxycarbonyl, carbamoyl, anilino, carboxamide, ureido, imide, alkoxycarbonylamino, sulfonamide, azo, alkylthio, arylthio, heterocyclylthio, alkylsulfonyl, arylsulfonyl, sulfamoyl, or phosphinoylamino, more preferably alkyl, aryl or heterocyclyl, even more preferably halogen atom and/or alkyl.

Preferably, the heteroaryl ring is a structure represented by formula (18-1):

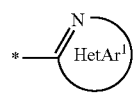

Formula (18-1)

In formula (18-1), HetAr1 represents an optionally substituted heteroaryl ring. Further, the substituents may be joined together to form a single ring or a fused ring system. $R^2$ and $R^5$ are each attached to the central moiety at *.

The heteroaryl ring is preferably a fused ring system. The heteroatom contained in the heteroaryl ring is preferably a nitrogen atom alone or a nitrogen atom and an oxygen atom and/or sulfur atom.

The substituents on HetAr1 are as defined for $R^1$, $R^2$, $R^3$, $R^4$, $R^5$ and $R^6$, preferably halogen atom, alkyl, alkenyl, aryl, heterocyclyl, silyl, hydroxyl, cyano, alkoxy, aryloxy, heterocyclyloxy, acyl, alkoxycarbonyl, carbamoyl, anilino, carboxamide, ureido, imide, alkoxycarbonylamino, sulfonamide, azo, alkylthio, arylthio, heterocyclylthio, alkylsulfonyl, arylsulfonyl, sulfamoyl, or phosphinoylamino, more preferably alkyl, aryl or heterocyclyl, even more preferably halogen atom and/or alkyl.

Preferably, $R^2$ and $R^5$ are each represented by any one of formulae (19-1) to (19-5):

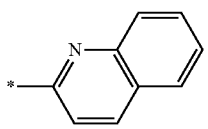

Formula (19-1)

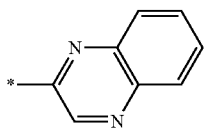

Formula (19-2)

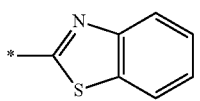

Formula (19-3)

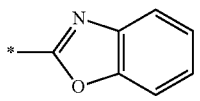

Formula (19-4)

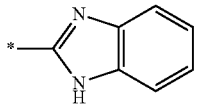

Formula (19-5)

In formulae (19-1) to (19-5) above, $R^2$ and $R^5$ are each attached to the central moiety at *. These groups may be substituted.

Formula (19-1) to formula (19-5) are preferably any one of formula (19-1), formula (19-3), and formula (19-4), more preferably formula (19-1) or formula (19-3), even more preferably formula (19-3).

The substituents optionally present on formula (19-1) to formula (19-5) are as defined for $R^1$, $R^2$, $R^3$, $R^4$, $R^5$ and $R^6$, preferably halogen atom, alkyl, alkenyl, aryl, heterocyclyl, silyl, hydroxyl, cyano, alkoxy, aryloxy, heterocyclyloxy, acyl, alkoxycarbonyl, carbamoyl, anilino, carboxamide, ureido, imide, alkoxycarbonylamino, sulfonamide, azo, alkylthio, arylthio, heterocyclylthio, alkylsulfonyl, arylsulfonyl, sulfamoyl, or phosphinoylamino, more preferably alkyl, aryl or heterocyclyl, even more preferably halogen atom and/or alkyl.

A preferred third embodiment of the present invention is an embodiment wherein $R^2$ and $R^5$ each represent an optionally substituted alkoxycarbonyl, aryloxycarbonyl, amide, imide, or cyano.

The optionally substituted alkoxycarbonyl or aryloxycarbonyl is preferably linked to an aryl or alkyl or heteroaryl via alkoxycarbonyl or aryloxycarbonyl.

The amide group is preferably linked to one or more aryl or alkyl or heteroaryl via amide, and the imide group preferably linked to one or more aryl or alkyl or heteroaryl via thioamide.

$R^2$ and $R^5$ are preferably alkoxycarbonyl, aryloxycarbonyl, cyano, or amide, more preferably alkoxycarbonyl, aryloxycarbonyl, or cyano, especially preferably alkoxycarbonyl, or aryloxycarbonyl.

Preferably, $R^3$ and $R^4$ each represent a hydrogen atom, halogen atom, alkyl, alkenyl, aryl, heterocyclyl, silyl, hydroxyl, cyano, alkoxy, aryloxy, heterocyclyloxy, acyl, alkoxycarbonyl, carbamoyl, anilino, carboxamide, ureido, imide, alkoxycarbonylamino, sulfonamide, azo, alkylthio, arylthio, heterocyclylthio, alkylsulfonyl, arylsulfonyl, sulfamoyl, or phosphinoylamino, more preferably alkyl, aryl or heterocyclyl, even more preferably aryl, still more preferably phenyl.

In formula (1), $R^1$ and $R^2$, $R^2$ and $R^3$, $R^4$ and $R^5$ and/or $R^5$ and $R^6$ may be joined together to form a 5-, 6- or 7-membered saturated or unsaturated ring. If the 5-, 6- and 7-membered rings formed are groups that can be further substituted, they may be substituted by the substituents described for $R^1$ to $R^6$ above, and if they are substituted by two or more substituents, these substituents may be identical or different.

A first embodiment of the present invention is preferably exemplified by cases in which the compound represented by formula (1) is represented by formula (1-1) or formula (1-2) below:

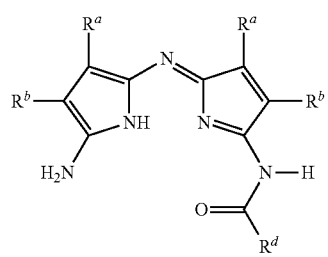

Formula (1-1)

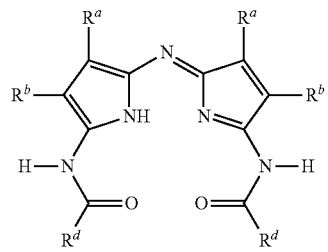

Formula (1-2)

In formulae (1-1) and (1-2), $R^a$ each represents an optionally substituted aryl or alkyl, $R^b$ each represents 2,6-di-tert-butyl-4-methylcyclohexyloxycarbonyl or cyano, and $R^d$ represents an optionally substituted alkyl, aryl, heteroaryl or alkenyl.

A second embodiment of the present invention is preferably exemplified by cases in which the compound represented by formula (1) is represented by formula (21-3) or formula (21-4) below:

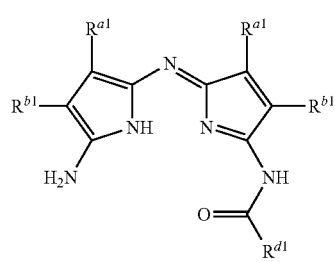

Formula (1-3)

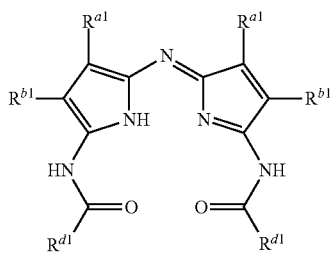

Formula (1-4)

In formulae (21-3) and (21-4) above, $R^{a1}$ each represents an optionally substituted aryl or alkyl or heteroaryl, $R^{b1}$ represents an optionally substituted heteroaryl, and $R^{d1}$ represents an optionally substituted alkyl, aryl, heteroaryl or alkenyl.

$R^{a1}$ each represents an optionally substituted aryl (preferably containing 6 to 14, more preferably 6 to 10, especially preferably 6 ring carbon atoms, e.g., phenyl, naphthalene, anthracenyl and the like), alkyl (preferably containing 1 to 10, more preferably 2 to 8, more preferably 3 to 6 carbon atoms, e.g., methyl, ethyl, butyl, isopropyl, t-butyl, cyclohexyl and the like), heteroaryl (preferably containing 10 or less, more preferably 5 to 10, especially preferably 5 to 9 ring carbon atoms, e.g., pyridyl, pyrimidyl, pyrazyl, quinolinyl, furanyl, thiophenyl, thiazolyl, oxazolyl, benzothiazolyl, benzoxazolyl and the like), preferably aryl and/or alkyl.

The substituents optionally present on $R^{a1}$ are as defined for $R^1$, $R^2$, $R^3$, $R^4$, $R^5$ and $R^6$, preferably halogen atom, alkyl, alkenyl, aryl, heterocyclyl, silyl, hydroxyl, cyano, alkoxy, aryloxy, heterocyclyloxy, acyl, alkoxycarbonyl, carbamoyl, anilino, carboxamide, ureido, imide, alkoxycarbonylamino, sulfonamide, azo, alkylthio, arylthio, heterocyclylthio, alkylsulfonyl, arylsulfonyl, sulfamoyl, or phosphinoylamino, more preferably alkyl, aryl or heterocyclyl, even more preferably halogen atom and/or alkyl.

$R^{b1}$ each represents pyridyl, pyrimidyl, pyrazyl, quinolinyl, furanyl, thiophenyl, thiazolyl, oxazolyl, benzothiazolyl, benzoxazolyl and the like, and preferably contains 10 or less, more preferably 5 to 10, especially preferably 5 to 9 ring carbon atoms. The two $R^{b1}$ groups are preferably identical. $R^{b1}$ is preferably represented by formula (22-1) below:

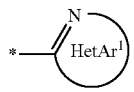

Formula (22-1)

In formula (22-1), HetAr1 represents an optionally substituted heteroaryl ring. Further, the substituents may be joined together to form a single ring or a fused ring system. $R^{b1}$ is attached to the central moiety at *. Formula (22-1) is as defined for formula (18-1), and also covers the same preferred range of substituents.

More preferably, $R^{b1}$ is each represented by any one of formulae (23-1) to (23-5) below:

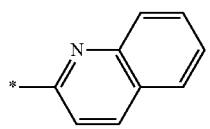

Formula (23-1)

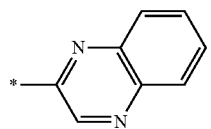

Formula (23-2)

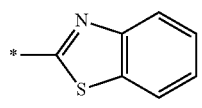

Formula (23-3)

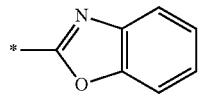

Formula (23-4)

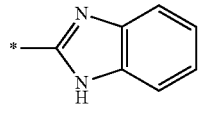

Formula (23-5)

In formulae (23-1) to (23-5) above, $R^b$ is each attached to the central moiety at *. These groups may be substituted. Formula (23-1) to formula (23-5) are as defined for formula (19-1) to formula (19-6), respectively, and also cover the same preferred range of substituents.

The metal complex in which the compound represented by formula (1) is coordinated to a metal atom or a metal compound is preferably a metal complex represented by formula (2).

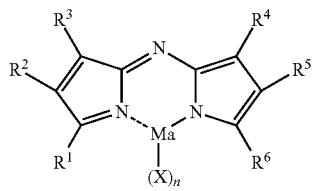

Formula (2)

In formula (2), $R^1$, $R^2$, $R^3$, $R^4$, $R^5$ and $R^6$ each represent a hydrogen atom or a substituent. Ma represents a metal atom or a metal compound, and X each represents a substituent. Ma and X form a covalent bond, coordinate bond or ionic bond. n is an integer of 2 to 4.

In formula (2) above, the dashed line indicates a coordinate bond (hereinafter the same shall apply for formula (3) and so forth).

$R^1$, $R^2$, $R^3$, $R^4$, $R^5$ and $R^6$ each have the same meaning as defined for $R^1$, $R^2$, $R^3$, $R^4$, $R^5$ and $R^6$ in formula (1), and also cover the same preferred ranges. $R^2$ and $R^5$ preferably include both of the first embodiment and second embodiment.

Here, $R^1$ and X, and $R^6$ and X may be joined together to form a 5-, 6- or 7-membered ring.

Preferably, at least one of the bonds between Ma and X is a coordinate bond. n is an integer of 2 to 4, preferably 3.

Ma is preferably Zn, Mg, Sc, Fe, Al, Cr, Si, Pt, Pd, Mo, Mn, Cu, Ni, Co, TiO or VO, more preferably Zn, Mg, Sc, Fe, Al, Mn, Cu, Ni, Co, TiO or VO, especially preferably Zn, Cu or Co.

The metal complex represented by formula (2) is preferably a metal complex represented by formula (2-2):

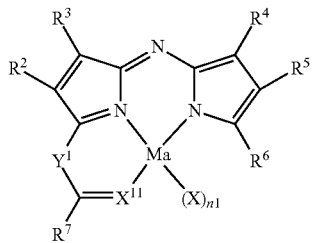

In formula (2-2), $R^2$, $R^3$, $R^4$, $R^5$ and $R^6$ each represent a hydrogen atom or a substituent. $R^7$ represents alkyl, alkenyl, aryl, heterocyclyl, alkoxy, aryloxy, alkylamino, arylamino, or heterocyclylamino. Ma represents a metal atom or a metal compound, and X each represents a substituent. $X^{11}$ represents NR (wherein R represents a hydrogen atom, alkyl, alkenyl, aryl, heterocyclyl, acyl, alkylsulfonyl, or arylsulfonyl), nitrogen atom, oxygen atom or sulfur atom. $Y^1$ represents NRc (wherein Rc represents a hydrogen atom, alkyl, alkenyl, aryl, heterocyclyl, acyl, alkylsulfonyl, or arylsulfonyl), nitrogen atom, or carbon atom. Ma and X form a covalent bond, coordinate bond or ionic bond. n1 is an integer of 2 to 4.
$R^7$ and $Y^1$, $R^7$ and $X^{11}$, and $X^{11}$ and X may be joined together to form a 5-, 6- or 7-membered ring.
In formula (2-2), $R^2$, $R^3$, $R^4$, $R^5$ and $R^6$ have the same meanings as defined for $R^2$, $R^3$, $R^4$, $R^5$ and $R^6$ respectively in formula (2), and also cover the same preferred ranges.
In formula (2-2), $R^7$ preferably represents alkyl or aryl, more preferably aryl, even more preferably phenyl. These may be substituted. The substituent is preferably alkyl, more preferably C1-3 alkyl.
In formula (2-2), Ma has the same meaning as defined for Ma in formula (2), and also covers the same preferred ranges.
In formula (2-2), $X^{11}$ is preferably an oxygen atom.
In formula (2-2), $Y^1$ is preferably NRc. Rc is preferably a hydrogen atom.
The metal complex represented by formula (1) is more preferably a metal complex represented by formula (3):

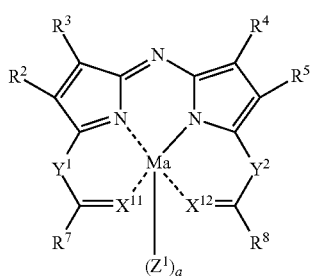

Formula (3)

In formula (3), $R^2$, $R^3$, $R^4$ and $R^5$ each represent a hydrogen atom or a substituent. $R^7$ and $R^8$ each represent alkyl, alkenyl, aryl, heterocyclyl, alkoxy, aryloxy, alkylamino, arylamino or heterocyclylamino. Ma represents a metal atom or a metal compound. $X^{11}$ and $X^{12}$ each represent NR (wherein R represents a hydrogen atom, alkyl, alkenyl, aryl, heterocyclyl, acyl, alkylsulfonyl, or arylsulfonyl), nitrogen atom, oxygen atom or sulfur atom. $Y^1$ and $Y^2$ each represent NRc (wherein Rc represents a hydrogen atom, alkyl, alkenyl, aryl, heterocyclyl, acyl, alkylsulfonyl, or arylsulfonyl), nitrogen atom, or carbon atom. $Z^1$ represents a group capable of forming a bond with Ma, and a represents 0, 1 or 2.

$R^7$ and $Y^1$ may be joined together to form a 5-, 6- or 7-membered ring, and $R^8$ and $Y^2$ may be joined together to form a 5-, 6- or 7-membered ring. Further, $R^7$ and $X^{11}$, $R^8$ and $X^{12}$, $R^7$ and $Z^1$, and $R^8$ and $Z^1$ may be joined together to form a 5-, 6- or 7-membered ring.
In formula (3), $R^2$, $R^3$, $R^4$ and $R^5$ have the same meanings as defined for $R^2$, $R^3$, $R^4$ and $R^5$ respectively in formula (2), and also cover the same preferred ranges.
In formula (3), $R^7$ and $R^8$ preferably each represent alkyl or aryl, more preferably aryl, even more preferably phenyl. These may be substituted. The substituent is preferably alkyl, more preferably C1-3 alkyl.
In formula (3), Ma has the same meaning as defined for Ma in formula (2), and also covers the same preferred ranges. In formula (3), $X^{11}$ and $X^{12}$ preferably each represent an oxygen atom.
In formula (3), $Y^1$ and $Y^2$ preferably each represent NRc. Rc is preferably a hydrogen atom.
$Z^1$ represents a group capable of forming an ionic or covalent bond with Ma. $Z^1$ includes tetrafluoroborate ion, hexafluorophosphate ion, hexafluoroantimonate ion, tris(trifluoromethanesulfonate)methide ion, perchlorate ion, cyano, halogen (preferably chlorine), alkylcarboxylate (preferably containing 2 to 20, more preferably 2 to 12, especially preferably 2 to 8 carbon atoms, e.g., acetate, lactate, decanecarboxylate and the like), arylcarboxylate (preferably containing 2 to 20, more preferably 2 to 11, especially preferably 2 to 7 carbon atoms, e.g., benzoate, anthraquinonecarboxylate, naphthalenecarboxylate and the like), alkylsulfonate (preferably containing 2 to 20, more preferably 2 to 12, especially preferably 2 to 8 carbon atoms, e.g., methanesulfonate, trifluoromethanesulfonate), arylsulfonate (preferably containing 2 to 20, more preferably 2 to 11, especially preferably 2 to 7 carbon atoms, e.g., benzenesulfonate, p-toluenesulfonate, naphthalenesulfonate), hydroxyl, imide (preferably containing 2 to 20, more preferably 2 to 12, especially preferably 2 to 8 carbon atoms, e.g., phthalimide, diacetimide, bistrifluoromethanesulfonimide and the like), aryloxy (preferably containing 2 to 20, more preferably 2 to 12, especially preferably 2 to 8 carbon atoms, e.g., phenoxy and the like), alkylthio (preferably containing 2 to 20, more preferably 2 to 12, especially preferably 2 to 8 carbon atoms, e.g., dodecylthio and the like), arylthio (preferably containing 2 to 20, more preferably 2 to 12, especially preferably 2 to 8 carbon atoms, e.g., benzenethio) and the like. Among others, alkylcarboxylate, arylcarboxylate, arylsulfonate, and imide are preferred, alkylcarboxylate, more preferably imide, especially preferably alkylcarboxylate.
Preferably, a is 1.
The metal complex represented by formula (1) is also preferably a metal complex represented by formula (4):

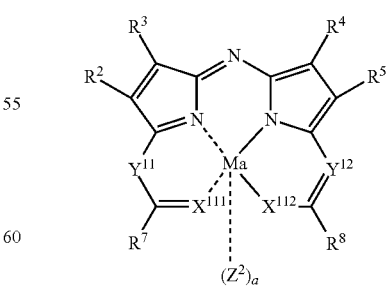

Formula (4)

In formula (4), $R^2$, $R^3$, $R^4$ and $R^5$ each represent a hydrogen atom or a substituent. $R^7$ and $R^8$ each represent alkyl, alkenyl, aryl, heterocyclyl, alkoxy, aryloxy, alkylamino, arylamino or heterocyclylamino. Ma represents a metal atom or a metal compound. $X^{111}$ represents NR (wherein R represents a hydrogen atom, alkyl, alkenyl, aryl, heterocyclyl, acyl, alkylsulfonyl, or arylsulfonyl), nitrogen atom, oxygen atom, or sulfur atom, $X^{112}$ represents NRa (wherein Ra represents a hydrogen atom, alkyl, alkenyl, aryl, heterocyclyl, acyl, alkylsulfonyl, or arylsulfonyl), oxygen atom, or sulfur atom. $Y^{11}$ represents NRc (wherein Rc represents a hydrogen atom, alkyl, alkenyl, aryl, heterocyclyl, acyl, alkylsulfonyl, or arylsulfonyl), nitrogen atom, or carbon atom, $Y^{12}$ represents a nitrogen atom or carbon atom. $Z^2$ represents a group capable of forming a bond with Ma, and a represents 0, 1 or 2.

$R^7$ and $Y^{11}$ may be joined together to form a 5-, 6- or 7-membered ring, and $R^8$ and $Y^{12}$ may be joined together to form a 5-, 6- or 7-membered ring. Further, $R^7$ and $X^{111}$, $R^8$ and $X^{122}$, $R^7$ and $Z^2$, and $R^8$ and $Z^2$ may be joined together to form a 5-, 6- or 7-membered ring.

In formula (4), $R^2$, $R^3$, $R^4$ and $R^5$ have the same meanings as defined for $R^2$, $R^3$, $R^4$ and $R^5$ respectively in formula (1), and also cover the same preferred ranges.

In formula (4), $R^7$ and $R^8$ have the same meanings as defined for $R^7$ and $R^8$ in formula (3), and also cover the same preferred ranges.

In formula (4), $Y^{11}$ is preferably NRc or a nitrogen atom. Rc is preferably a hydrogen atom.

In formula (4) $Y^{12}$ is preferably a nitrogen atom.

In formula (4), $X^{111}$ and $X^{112}$ are preferably an oxygen atom.

In formula (4), $Z^2$ represents a group capable of forming a coordinate bond with Ma. $Z^2$ includes ether (tetrahydrofuran, diethyl ether), alkylcarboxylate (preferably containing 2 to 20, more preferably 2 to 12, especially preferably 2 to 8 carbon atoms, e.g., acetate, lactate, decanecarboxylate and the like), arylcarboxylate (preferably containing 2 to 20, more preferably 2 to 11, especially preferably 2 to 7 carbon atoms, e.g., benzoate, anthraquinonecarboxylate, naphthalenecarboxylate and the like), alkylsulfonate (preferably containing 2 to 20, more preferably 2 to 12, especially preferably 2 to 8 carbon atoms, e.g., methanesulfonate, trifluoromethanesulfonate), arylsulfonate (preferably containing 2 to 20, more preferably 2 to 11, especially preferably 2 to 7 carbon atoms, e.g., benzenesulfonate, p-toluenesulfonate, naphthalenesulfonate), water, imide (preferably containing 2 to 20, more preferably 2 to 12, especially preferably 2 to 8 carbon atoms, e.g., phthalimide, diacetimide, bistrifluoromethanesulfonimide and the like), alkyl alcohol (preferably containing 2 to 20, more preferably 2 to 12, especially preferably 1 to 8 carbon atoms, e.g., methanol, butanol, isopropyl alcohol and the like), aryl alcohol (preferably containing 2 to 20, more preferably 2 to 12, especially preferably 2 to 8 carbon atoms, e.g., phenol and the like), aryl mercaptan (preferably containing 2 to 20, more preferably 2 to 12, especially preferably 2 to 8 carbon atoms, e.g., benzenethiol and the like), alkylthio (preferably containing 2 to 20, more preferably 2 to 12, especially preferably 2 to 8 carbon atoms, e.g., dodecanethiol) and the like. Among others, water, alkylcarboxylate, arylcarboxylate, arylsulfonate and imide are preferred, more preferably alkylcarboxylate and hydroxyl, especially preferably alkylcarboxylate. Preferably, a is 1.

Especially, the compound represented by formula (1) is preferably a compound represented by formula (5-1), formula (5-2), formula (21-1), formula (22-2), formula (21-3) above, formula (21-4) above, or formula (25-1) to formula (25-4). Among compounds of formulae (5-1) and (5-2), those of formula (5-3) described hereinbelow are especially preferred. Among compounds of formula (21-1) to formula (21-4), those of formula (21-1) are especially preferred.

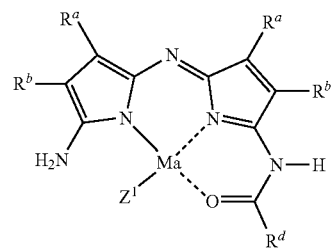

Formula (5-1)

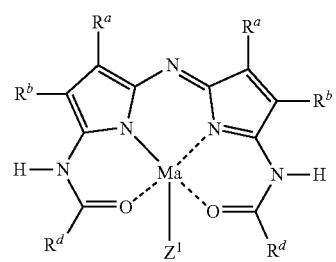

Formula (5-2)

In formula (5-1) and formula (5-2), $R^a$ each represents an optionally substituted aryl or alkyl, $R^b$ each represents 2,6-di-tert-butyl-4-methylcyclohexyloxycarbonyl or cyano, $R^d$ represents an optionally substituted alkyl, aryl, heteroaryl or alkenyl, Ma represents a metal atom or a metal compound, and $Z^1$ represents a group capable of forming a bond with Ma.

In formula (5-1) or (5-2), $R^a$ preferably each represents aryl.

The optionally substituted aryl is preferably a substituted or unsubstituted phenyl, a substituted or unsubstituted tolyl, a substituted or unsubstituted chlorophenyl, a substituted or unsubstituted bromophenyl, or a substituted or unsubstituted cyanophenyl, more preferably a substituted or unsubstituted phenyl, or a substituted or unsubstituted tolyl, even more preferably a substituted or unsubstituted phenyl.

The alkyl is preferably methyl, ethyl, butyl, isopropyl, or t-butyl, more preferably ethyl, or isopropyl.

In formula (5-1) or (5-2), $R^b$ is preferably 2,6-di-tert-butyl-4-methylcyclohexyloxycarbonyl. The two $R^b$ groups are preferably identical.

In formula (5-1) or (5-2), $R^d$ preferably each represents alkyl or aryl, more preferably aryl.

The optionally substituted alkyl is preferably a secondary alkyl, or tertiary alkyl, more preferably a tertiary alkyl, especially preferably t-butyl. The aryl is preferably phenyl, tolyl, xylyl or naphthyl, more preferably tolyl, or phenyl, especially preferably tolyl.

The alkenyl is preferably β-styryl.

In formula (5-1) or (5-2), Ma has the same meaning as defined for Ma in formula (2), and also covers the same preferred ranges.

In formula (5-1) or (5-2), $Z^1$ has the same meaning as defined for $Z^1$ in formula (3), and also covers the same preferred ranges.

The compound represented by formula (5-1) or (5-2) is especially preferably a compound represented by formula (5-3):

Formula (5-3)

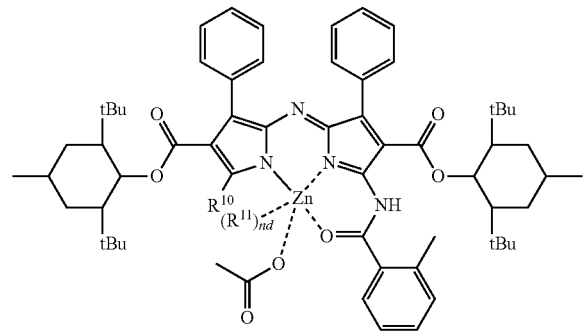

In formula (5-3), $R^{10}$ represents a substituent containing a nitrogen atom, $R^{11}$ represents a substituent, and $R^{10}$ and $R^{11}$ may be joined together to form a ring. nd represents 0 or 1.

Formula (21-1)

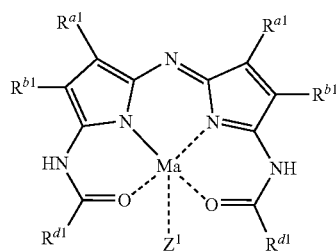

Formula (21-2)

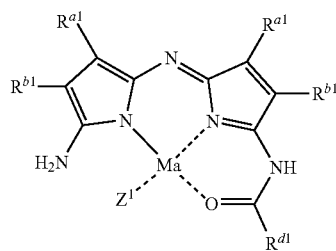

In formulae (21-1) and (21-2) above, $R^{a1}$ each represents an optionally substituted aryl or alkyl or heteroaryl, $R^{b1}$ represents an optionally substituted heteroaryl, $R^{d1}$ represents an optionally substituted alkyl, aryl, heteroaryl or alkenyl, Ma represents a metal atom or a metal compound, and $Z^1$ represents a group capable of forming a bond with Ma.

$R^{a1}$ and $R^{b1}$ have the same meanings as defined for $R^{a1}$ and $R^{b1}$ respectively in formulae (21-3) and (21-4) above, and also cover the same preferred ranges.

$R^{d1}$ has the same meaning as defined for Rd in formula (5-1), and also covers the same preferred ranges.

Ma represents a metal atom or a metal compound, and Ma represents preferably Zn, Mg, Sc, Fe, FeCl, Al, Cr, Si, Pt, Pd, Mo, Mn, Cu, Ni, Co, TiO, TiCl, VO, or VCl, more preferably Zn, Mg, Sc, Fe, Al, Mn, Cu, Ni, Co, TiO, TiCl, VO or VCl, especially preferably Zn, Cu or Co.

$Z^1$ represents a group capable of forming a bond with Ma. $Z^1$ includes tetrafluoroborate ion, hexafluorophosphate ion, hexafluoroantimonate ion, tris(trifluoromethanesulfonate) methide ion, perchlorate ion, cyano, halogen (preferably chlorine), alkylcarboxylate (preferably containing 2 to 20, more preferably 2 to 12, especially preferably 2 to 8 carbon atoms, e.g., acetate, lactate, decanecarboxylate and the like), arylcarboxylate (preferably containing 2 to 20, more preferably 2 to 11, especially preferably 2 to 7 carbon atoms, e.g., benzoate, anthraquinonecarboxylate, naphthalenecarboxylate and the like), alkylsulfonate (preferably containing 2 to 20, more preferably 2 to 12, especially preferably 2 to 8 carbon atoms, e.g., methanesulfonate, trifluoromethanesulfonate), arylsulfonate (preferably containing 2 to 20, more preferably 2 to 11, especially preferably 2 to 7 carbon atoms, e.g., benzenesulfonate, p-toluenesulfonate, naphthalenesulfonate), hydroxyl, imide (preferably containing 2 to 20, more preferably 2 to 12, especially preferably 2 to 8 carbon atoms, e.g., phthalimide, diacetimide, bistrifluoromethanesulfonimide and the like), aryloxy (preferably containing 2 to 20, more preferably 2 to 12, especially preferably 2 to 8 carbon atoms, e.g., phenoxy and the like), alkylthio (preferably containing 2 to 20, more preferably 2 to 12, especially preferably 2 to 8 carbon atoms, e.g., dodecylthio and the like), arylthio (preferably containing 2 to 20, more preferably 2 to 12, especially preferably 2 to 8 carbon atoms, e.g., benzenethio) and the like. Among others, alkylcarboxylate, arylcarboxylate, arylsulfonate, and imide are preferred, more preferably alkylcarboxylate, and imide, especially preferably alkylcarboxylate.

Formula (25-1)

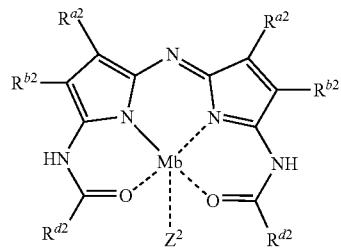

Formula (25-2)

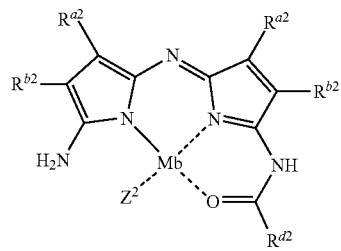

Formula (25-3)

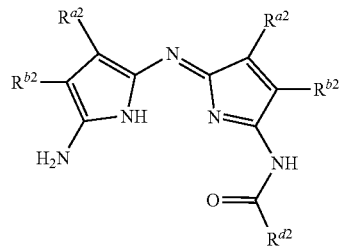

Formula (25-4)

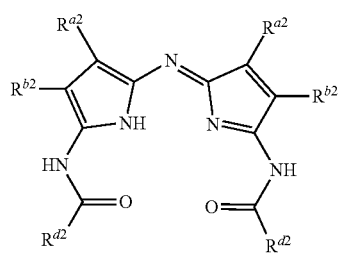

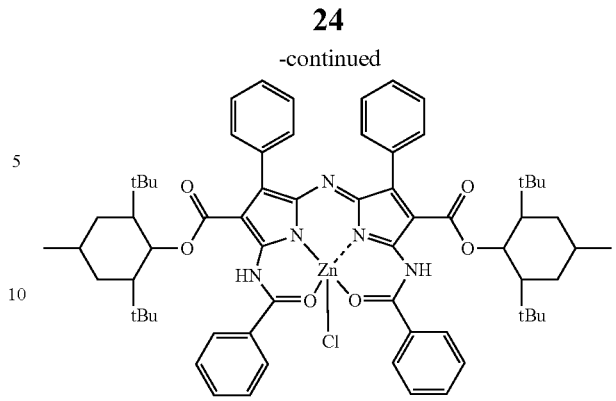

In formulae (25-1) to (25-4) above, $R^{a2}$ each represents an optionally substituted aryl or alkyl or heteroaryl, $R^{b2}$ each represents an optionally substituted alkoxycarbonyl, aryloxycarbonyl, amide, imide or cyano, $R^{d2}$ each represents an optionally substituted alkyl, aryl, heteroaryl or alkenyl, Mb represents a metal atom or a metal compound, and $Z^2$ represents a group capable of forming a bond with Ma. $R^{a2}$ has the same meaning as defined for $R^{a1}$ in formula (21-1) above, and also covers the same preferred ranges. Preferably, $R^{b1}$ is cyano.

Mb has the same meaning as defined for Ma in formula (21-1) above, and also covers the same preferred ranges.

$Z^2$ has the same meaning as defined for $Z^1$ in formula (21-1) above, and also covers the same preferred ranges.

Specific examples of metal complexes used in the present invention are shown below, but it should be understood that the present invention are not limited to these examples. It should be noted that in the compounds shown below, t-Bu represents t-butyl.

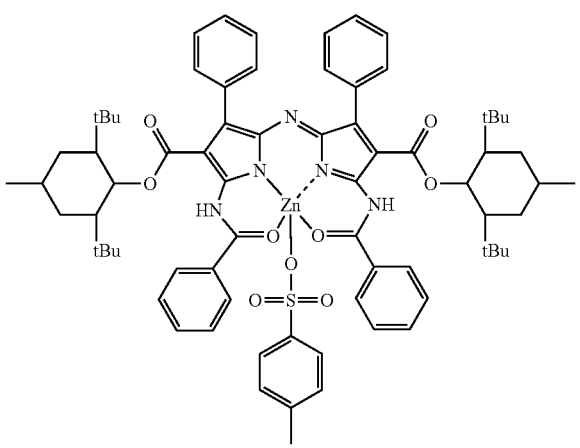

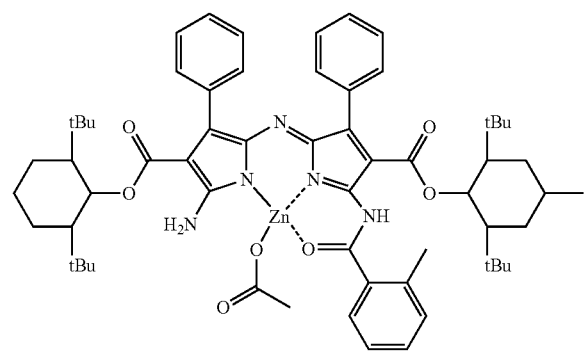

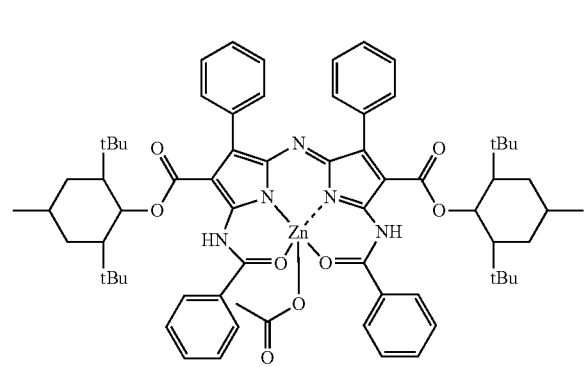

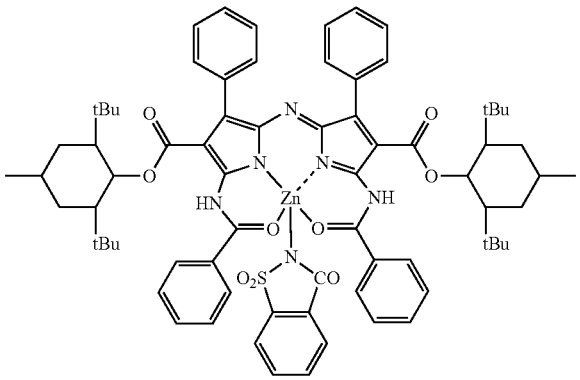

-continued
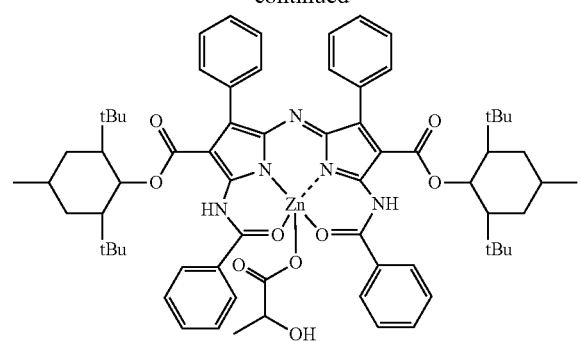
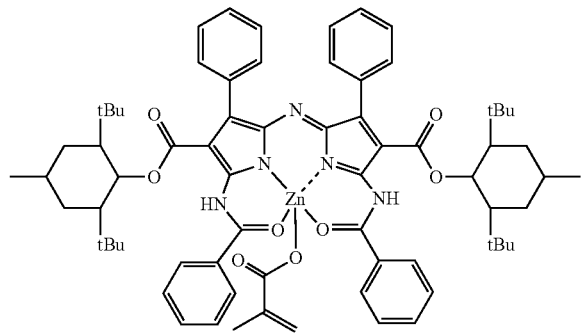
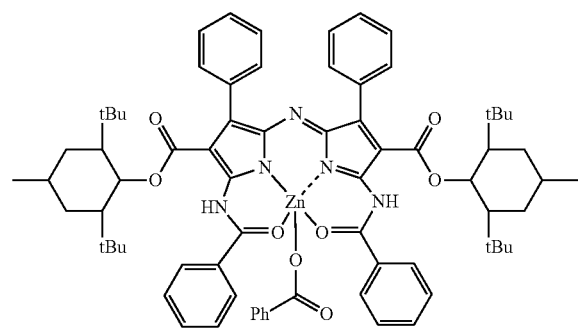
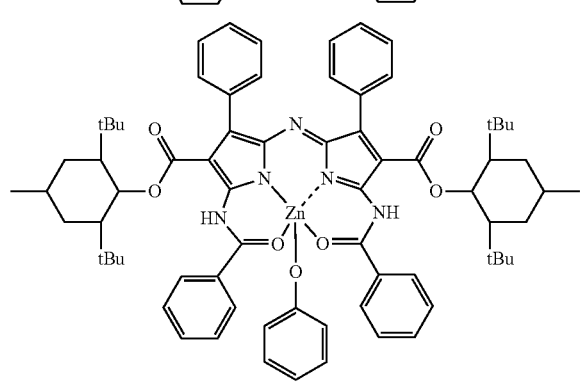
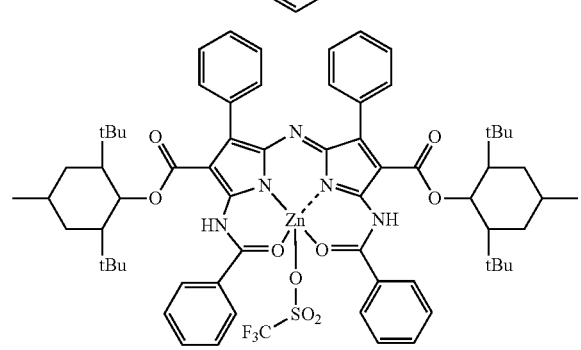
-continued
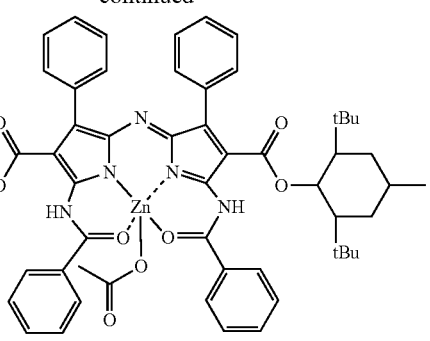
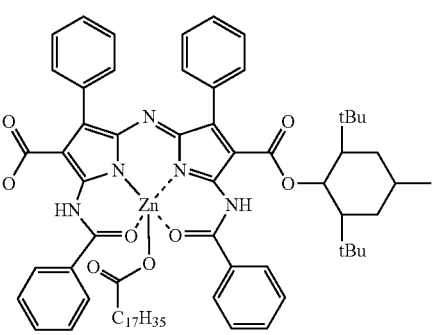
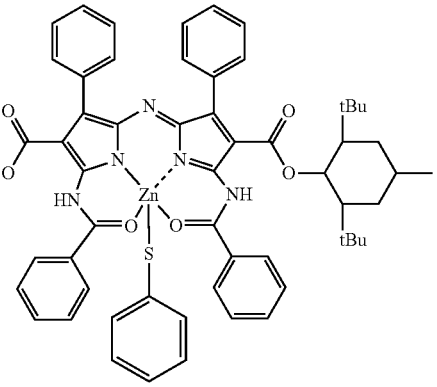
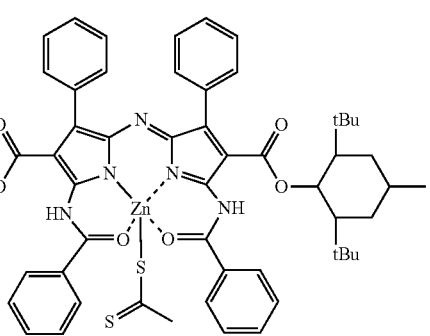

27
-continued
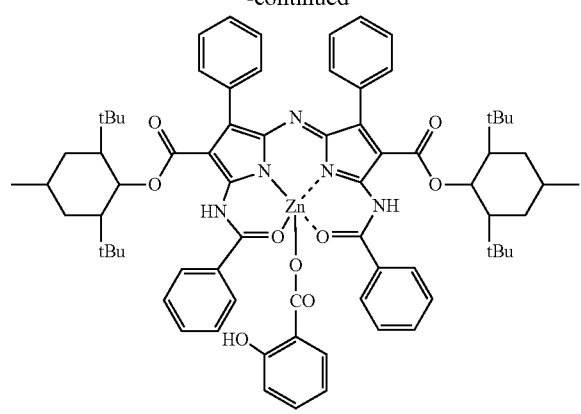
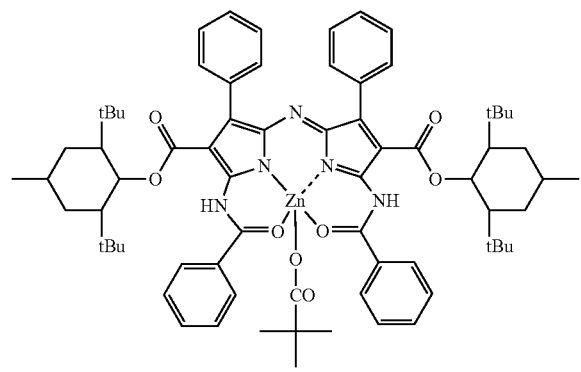
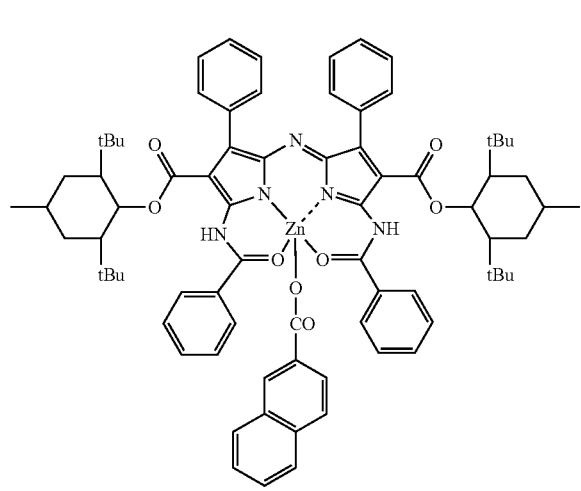
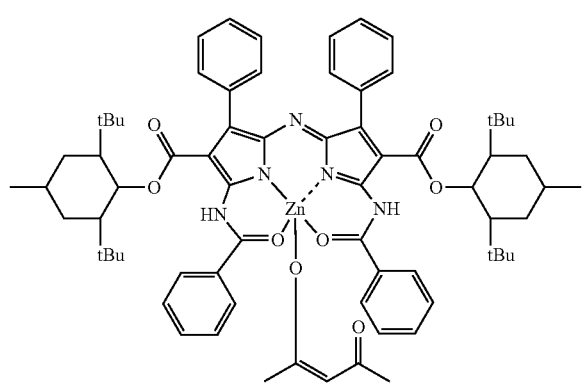
28
-continued
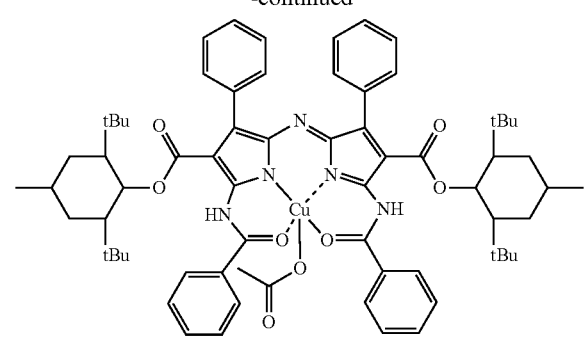
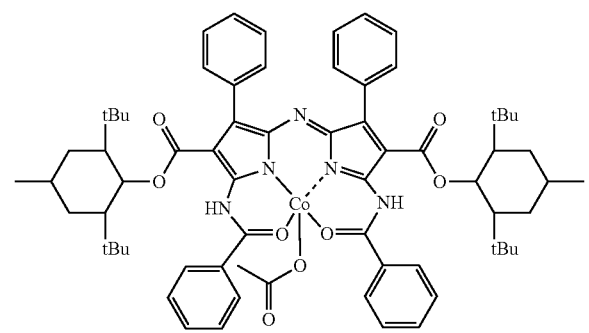
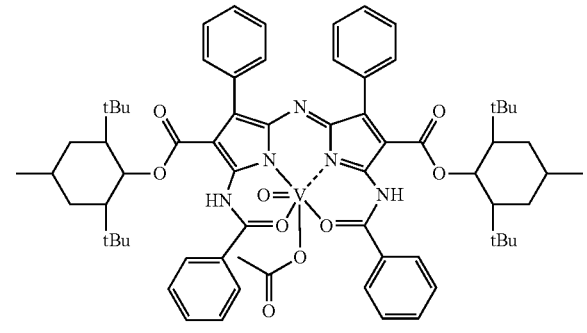
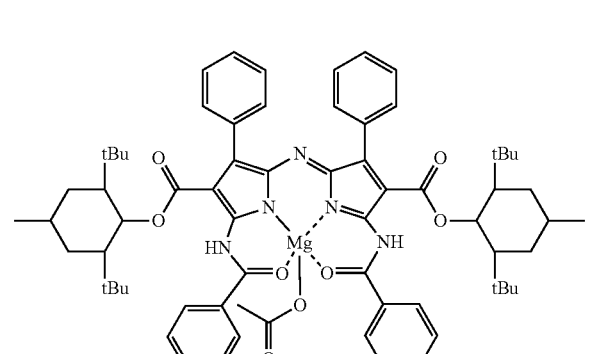
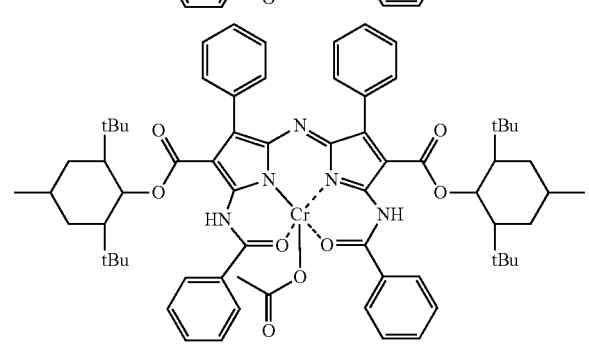

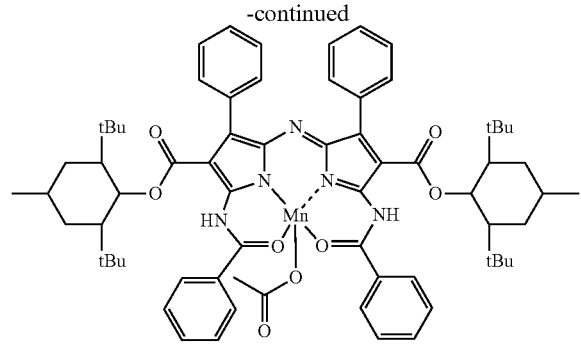
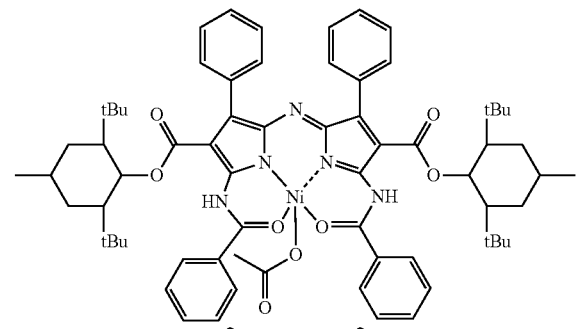
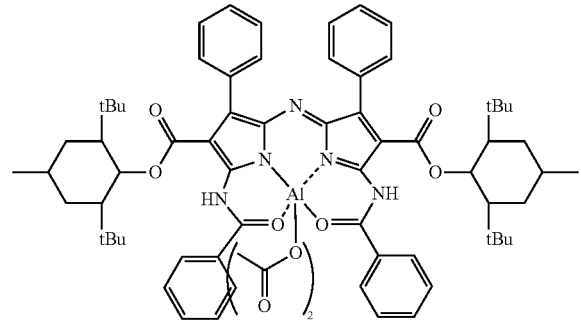
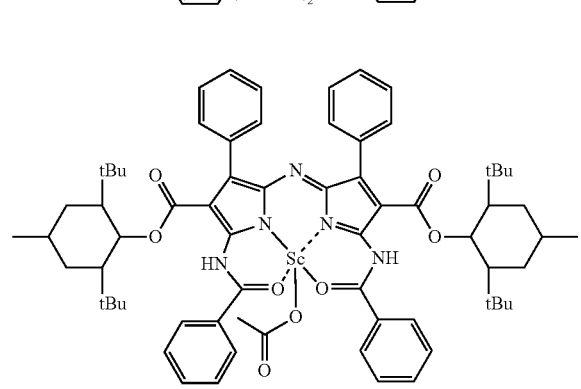
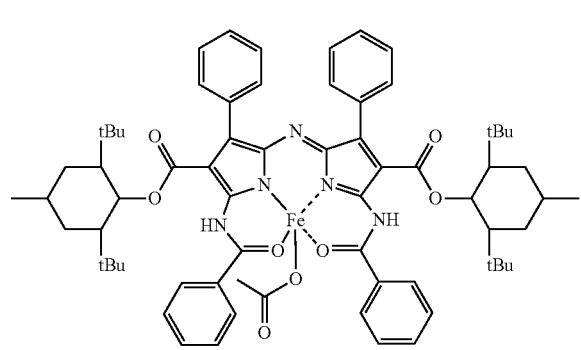
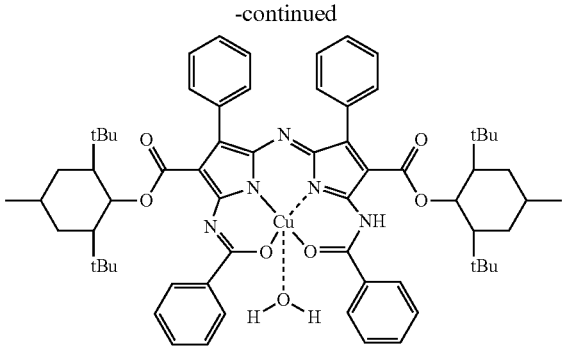
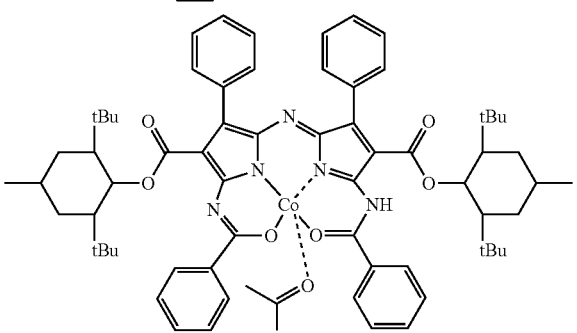
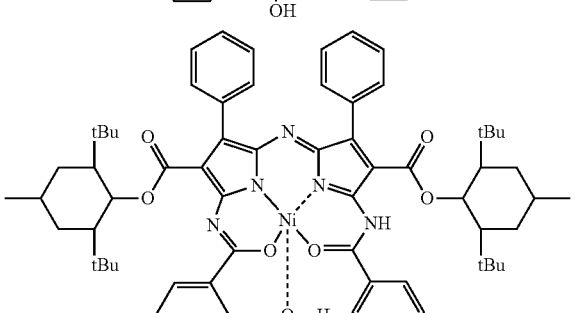
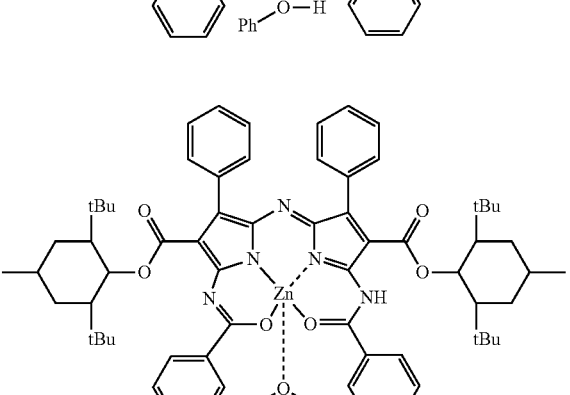
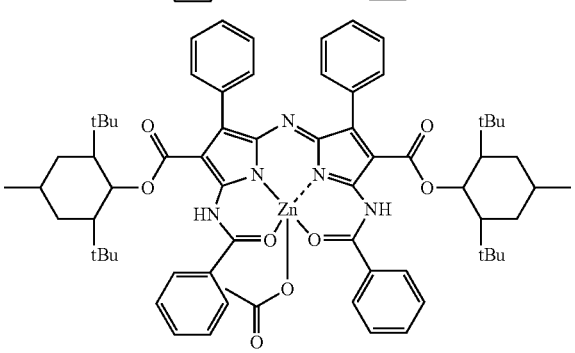

31
-continued
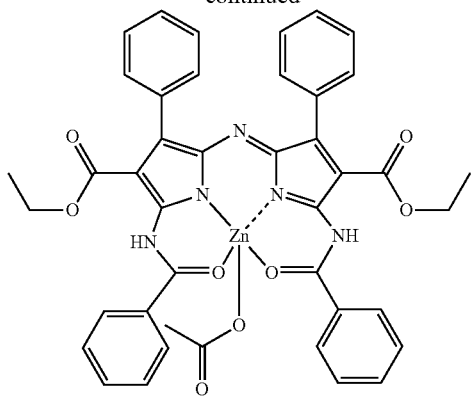
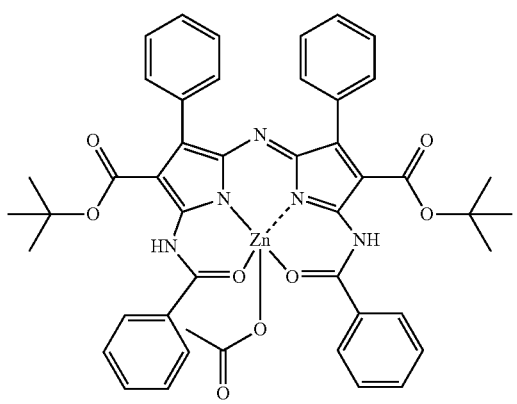
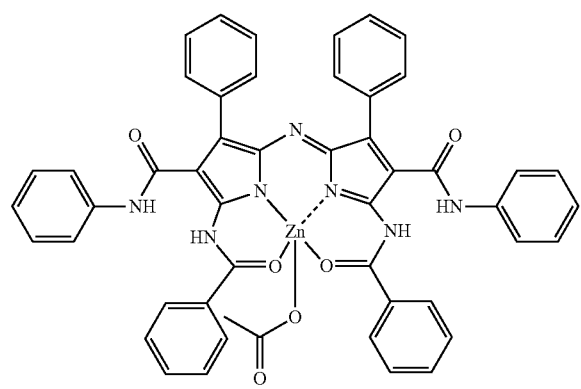
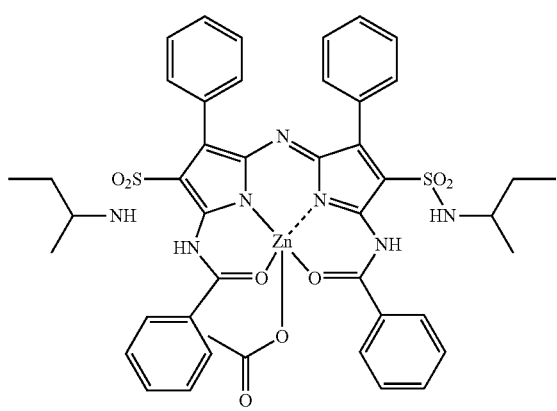
32
-continued
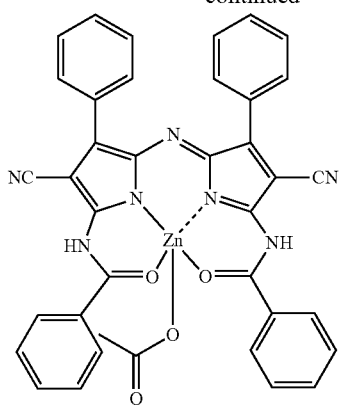
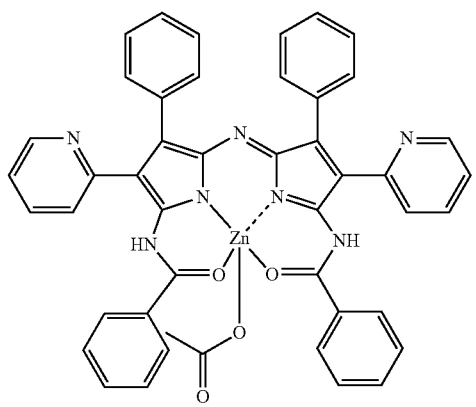
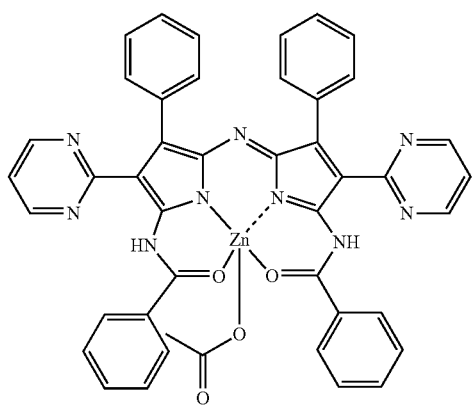
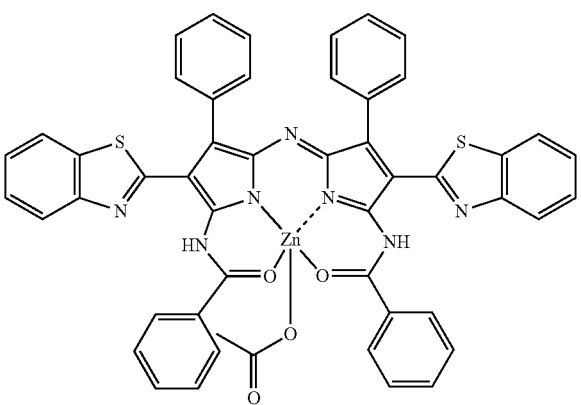

33
-continued
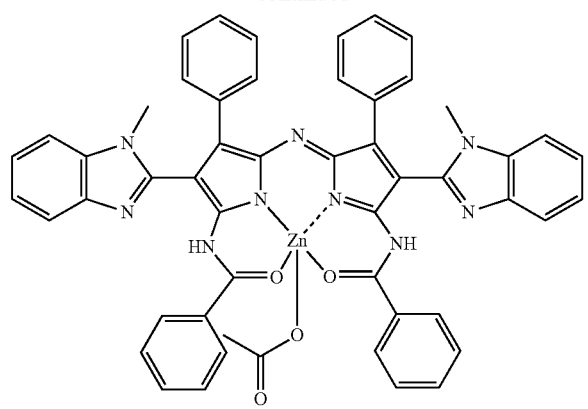
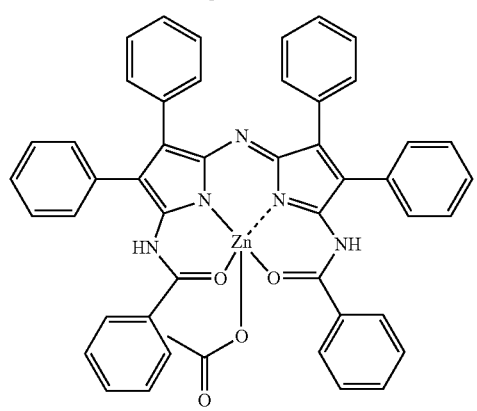
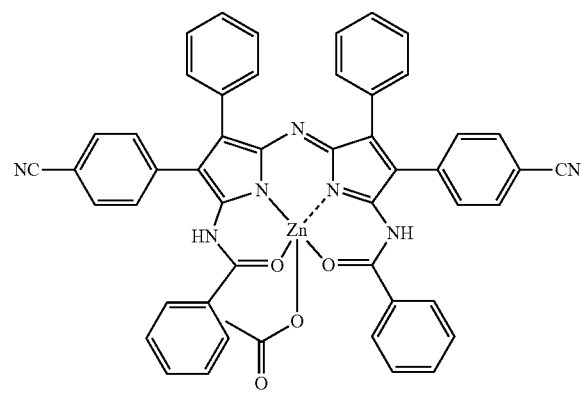
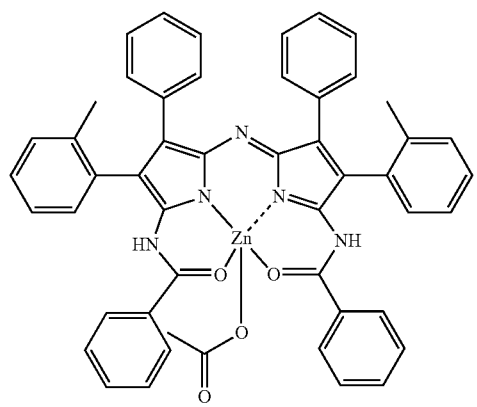
34
-continued
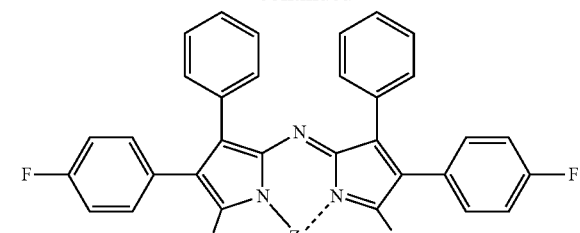
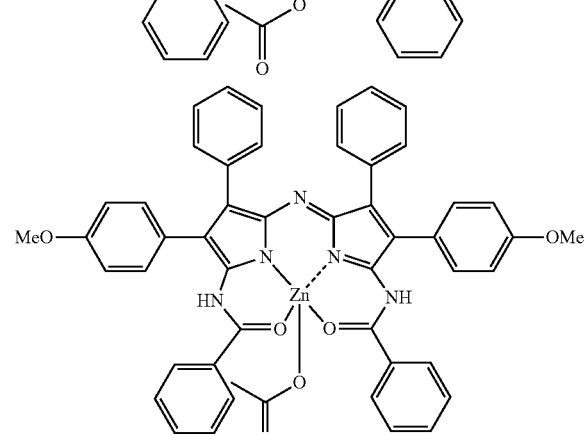
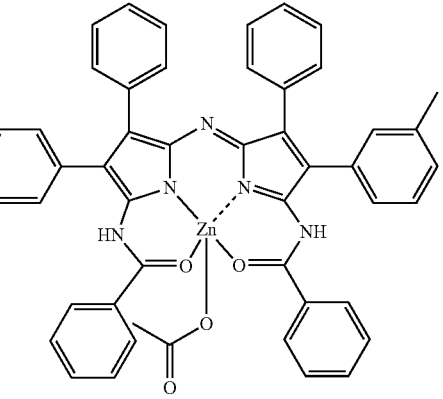
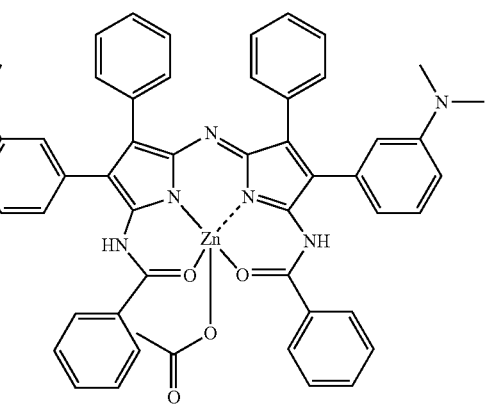

35
-continued
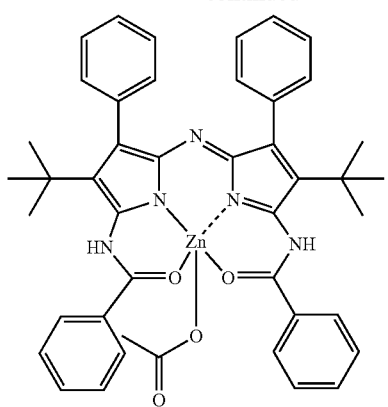
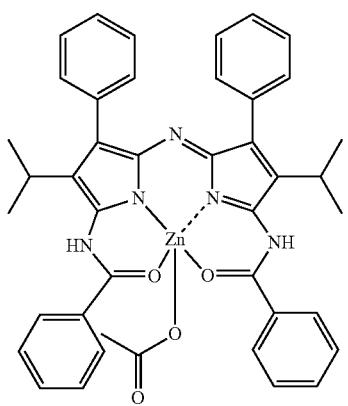
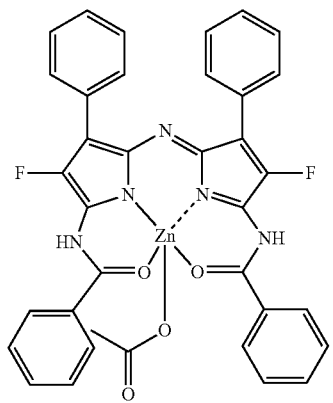
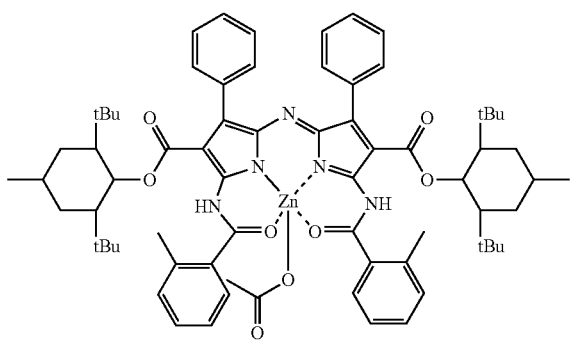
36
-continued
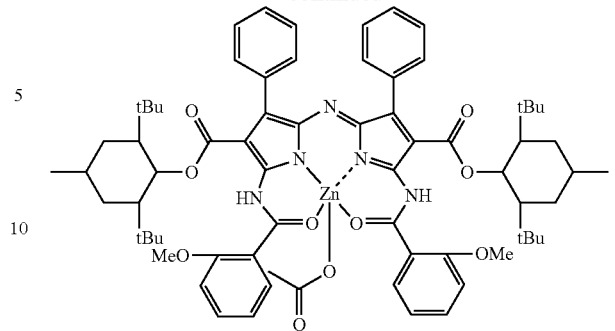
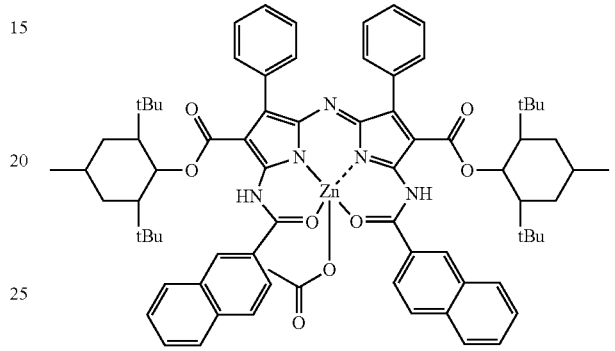
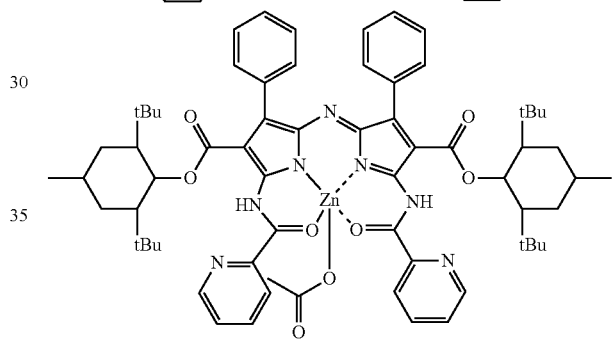
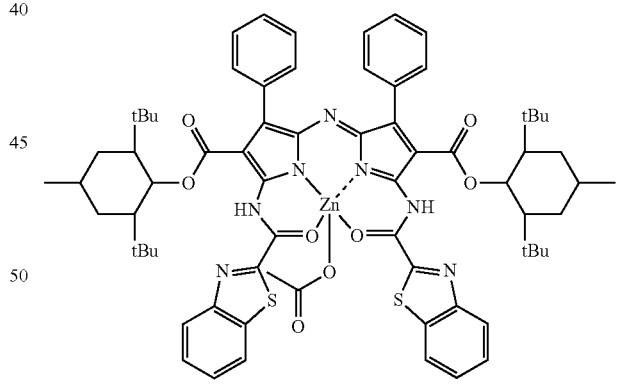
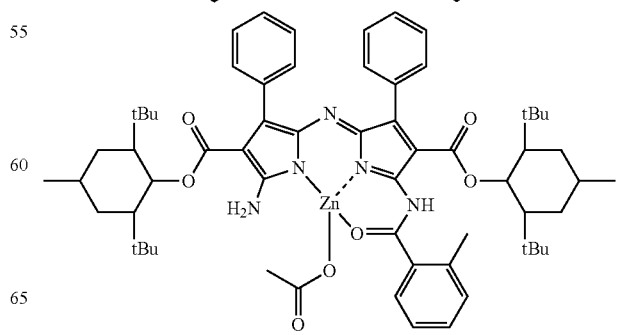

37
-continued
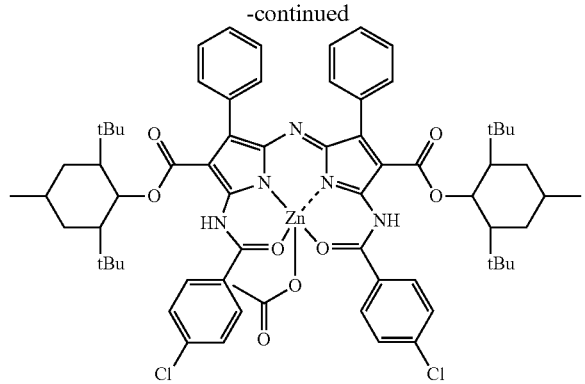
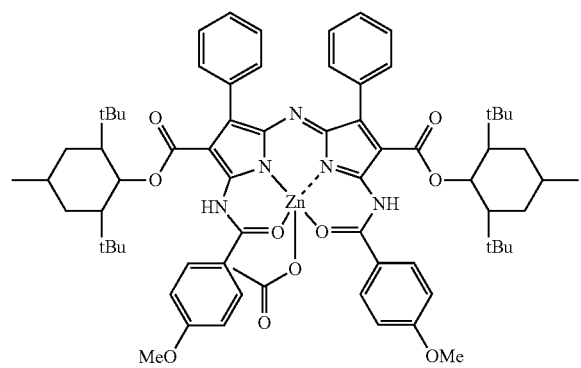
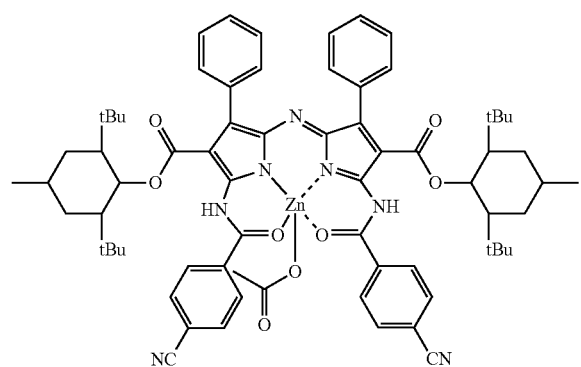
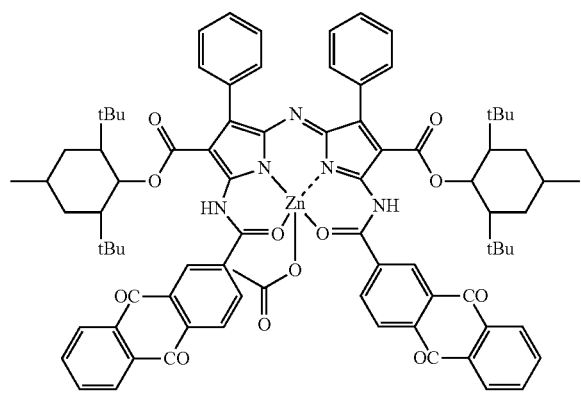
38
-continued
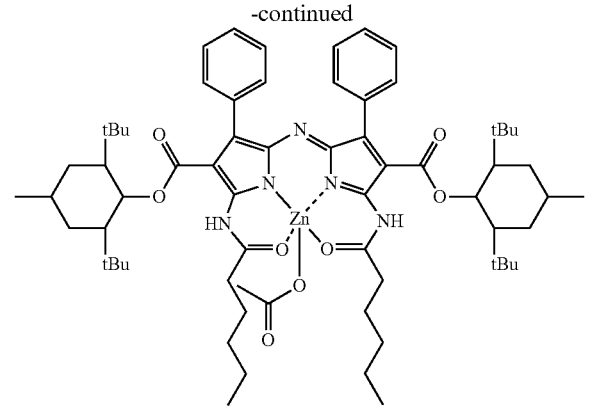
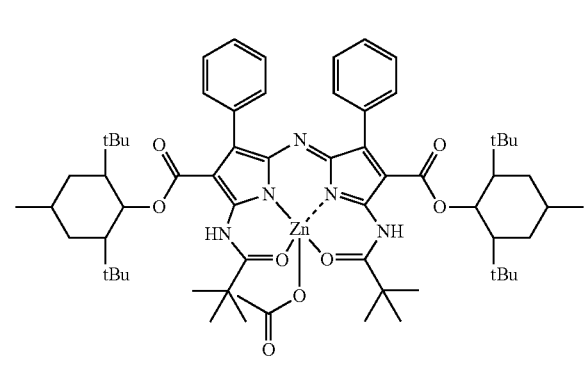
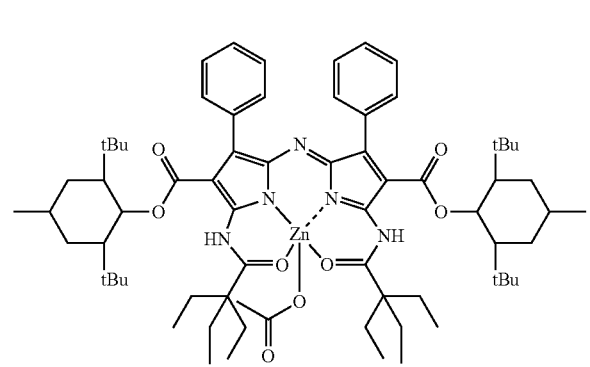
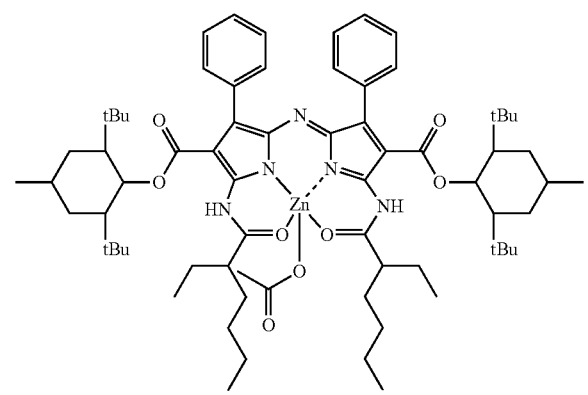

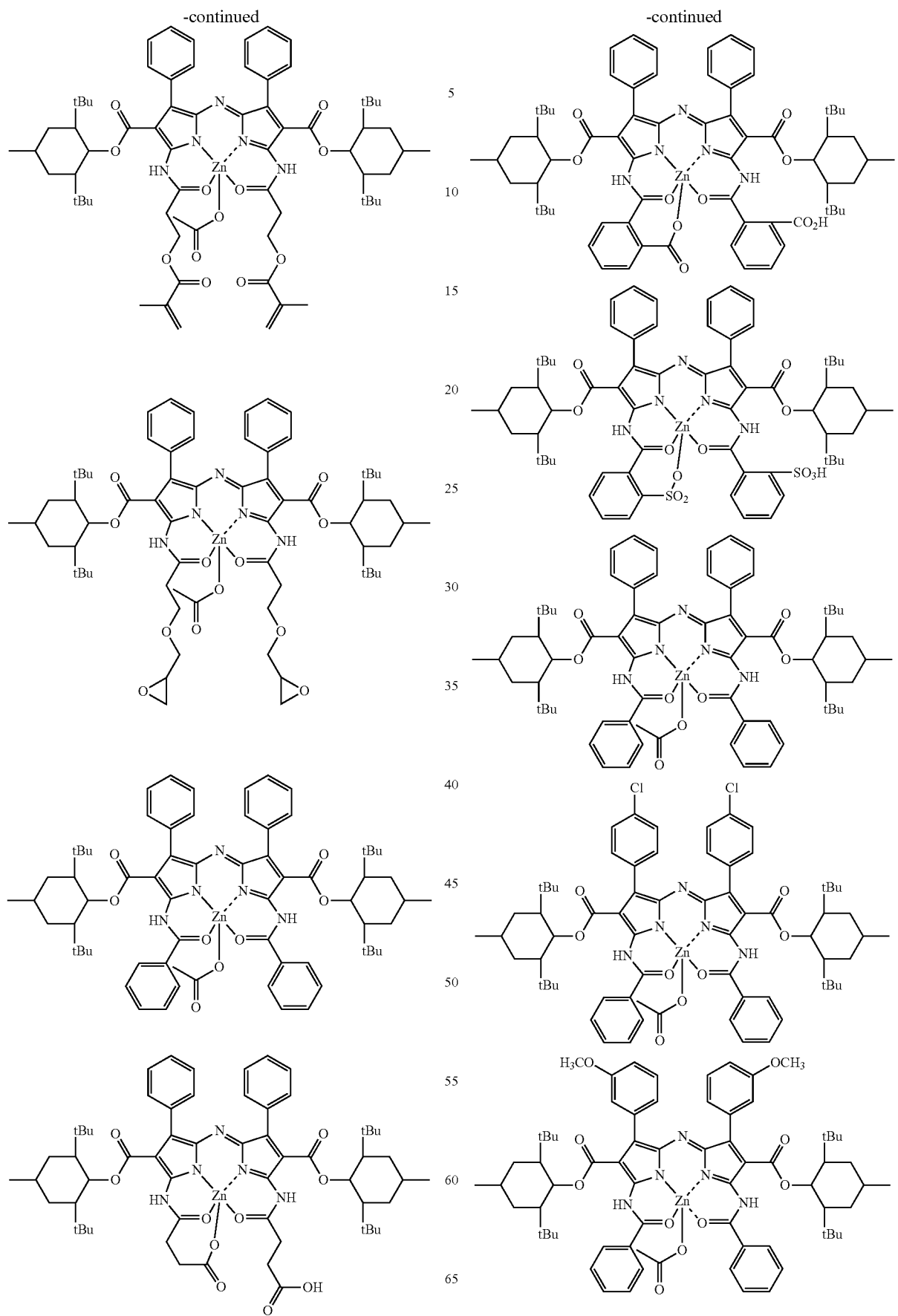

-continued
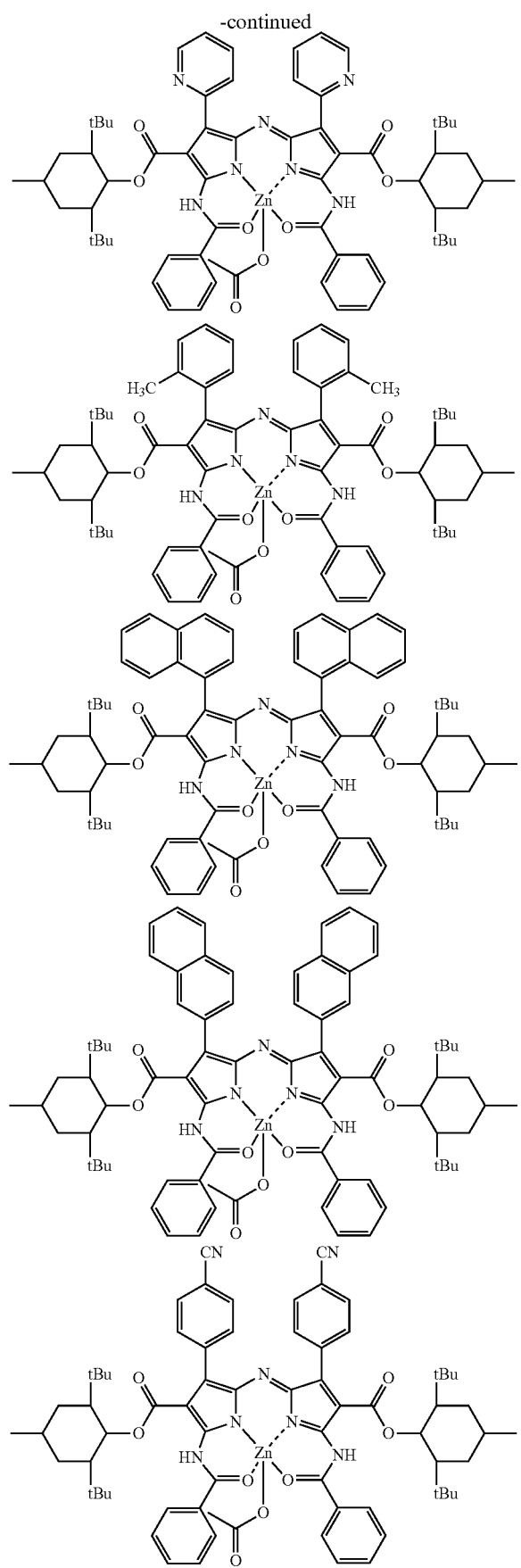
-continued
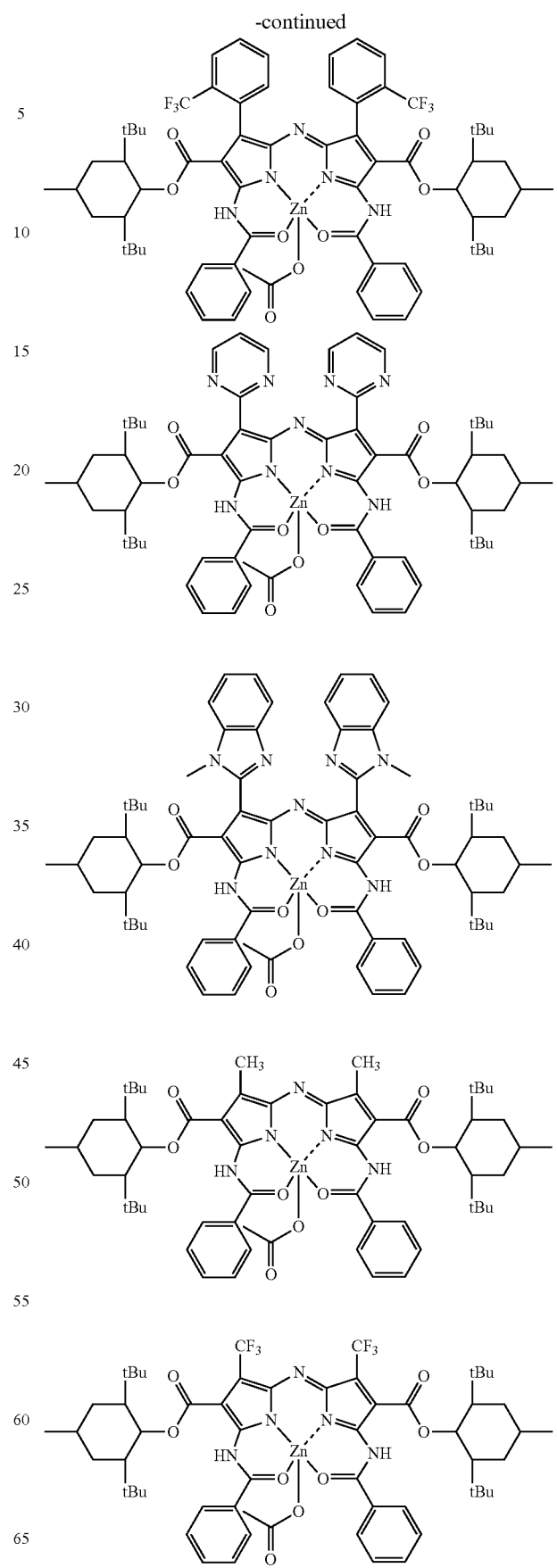

-continued
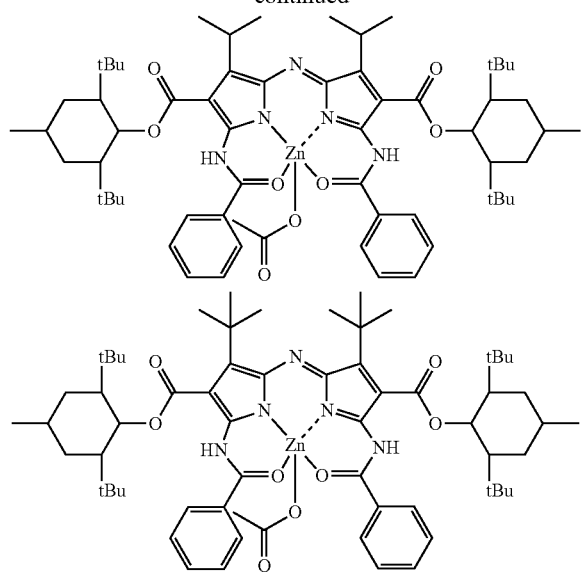
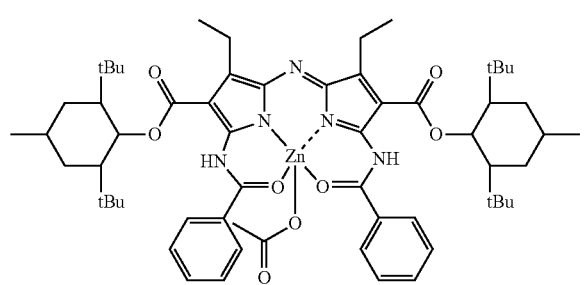
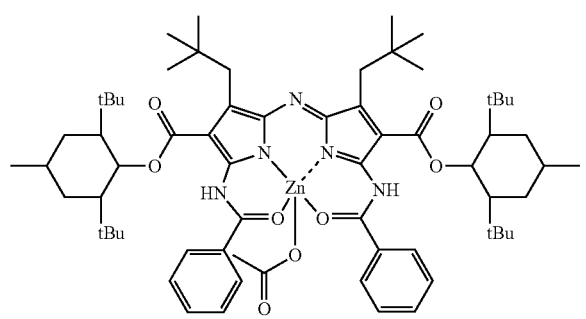
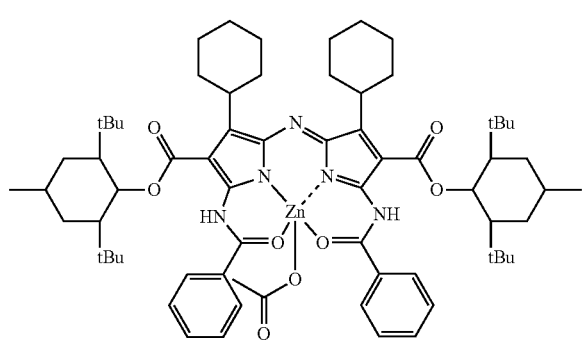
-continued
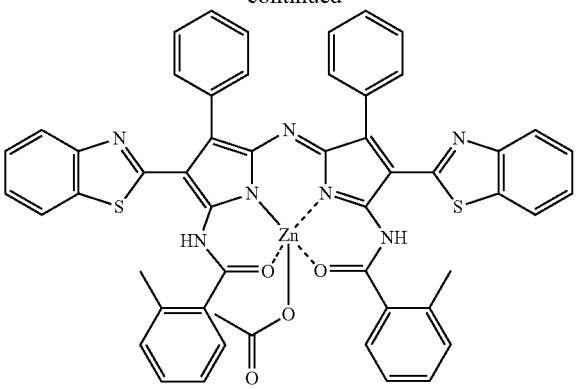
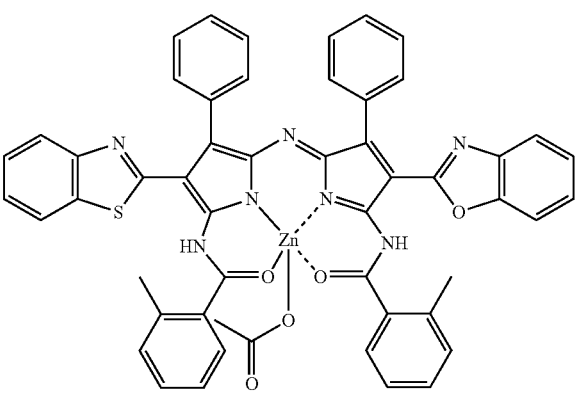
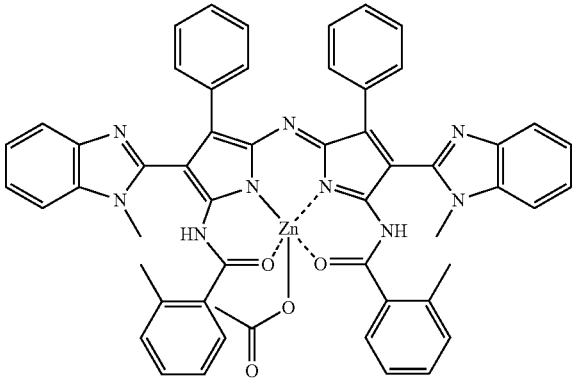
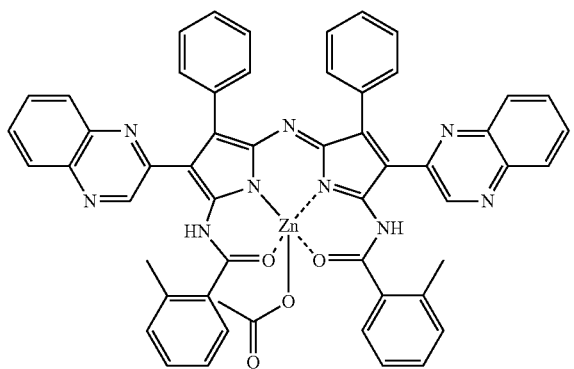

-continued
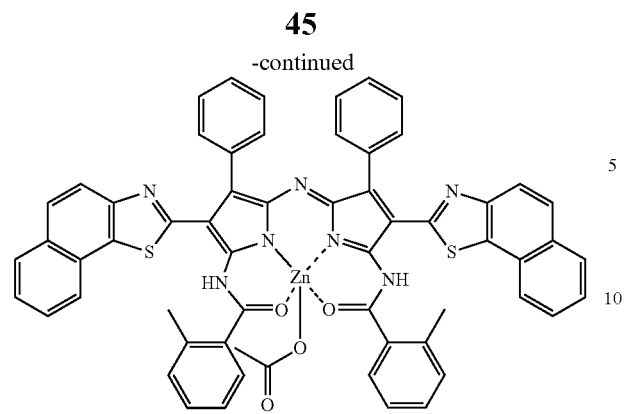
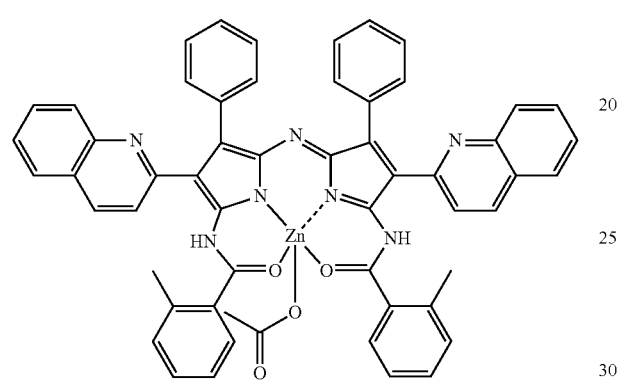
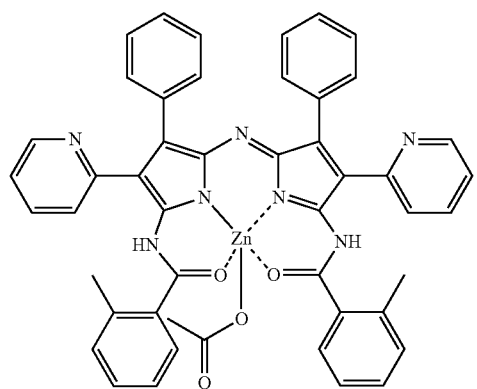
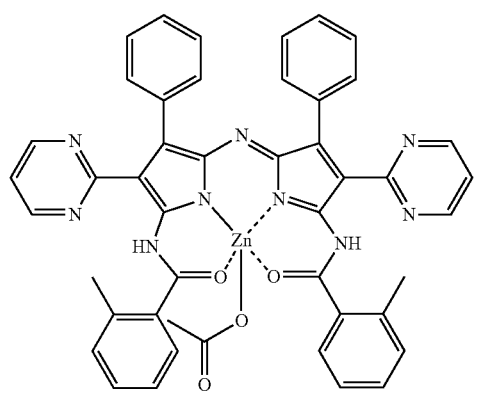
-continued
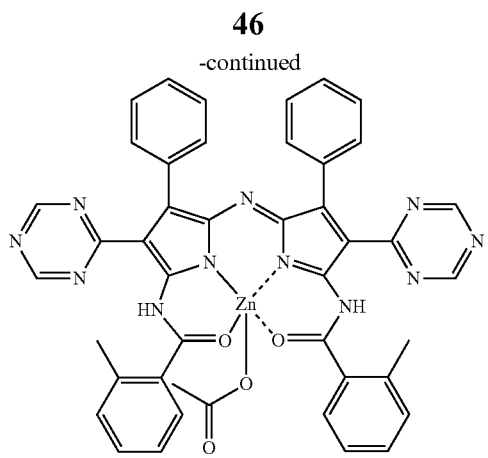
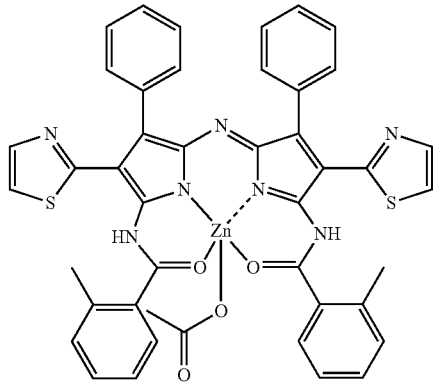
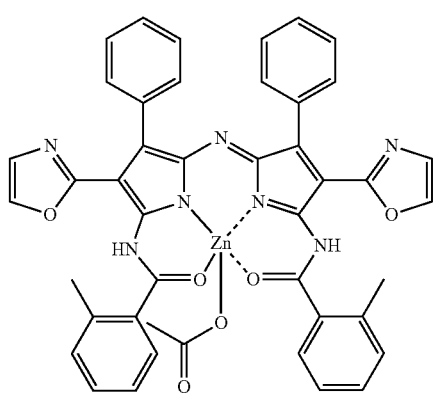
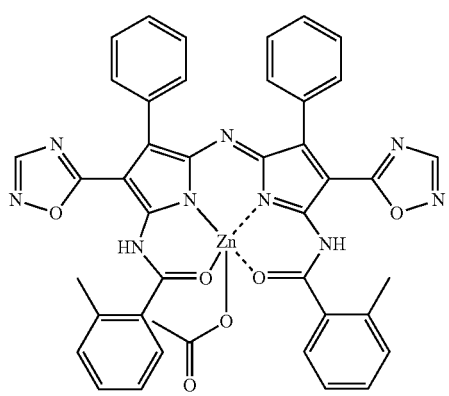

47
-continued
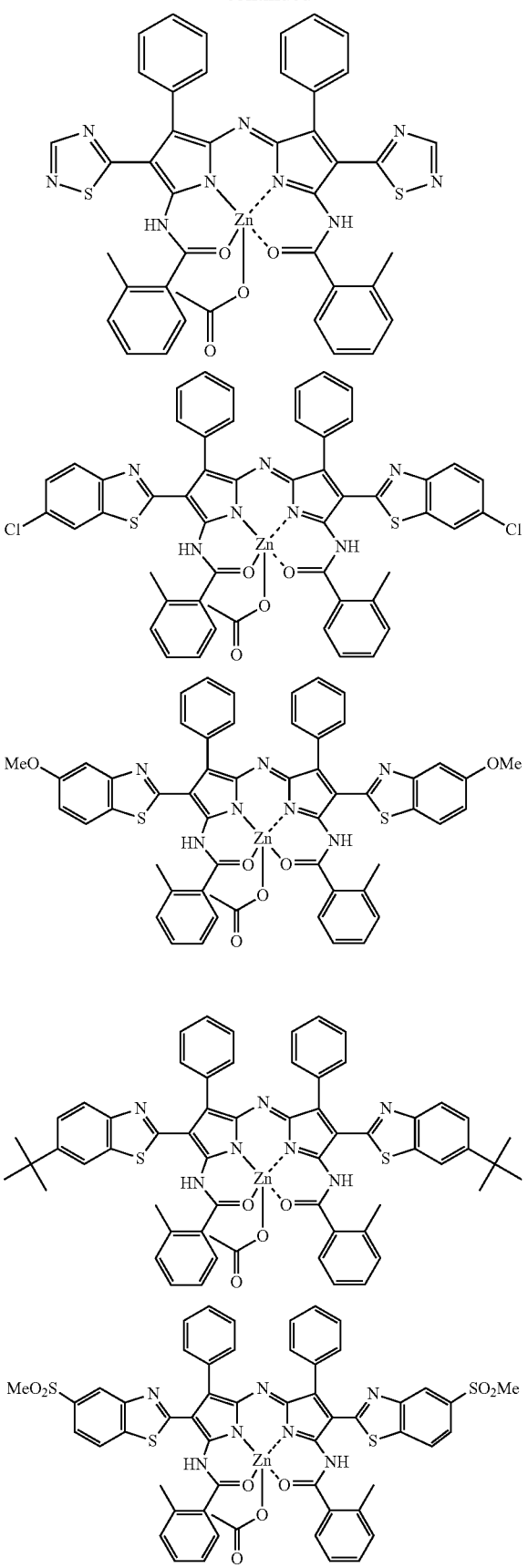
48
-continued
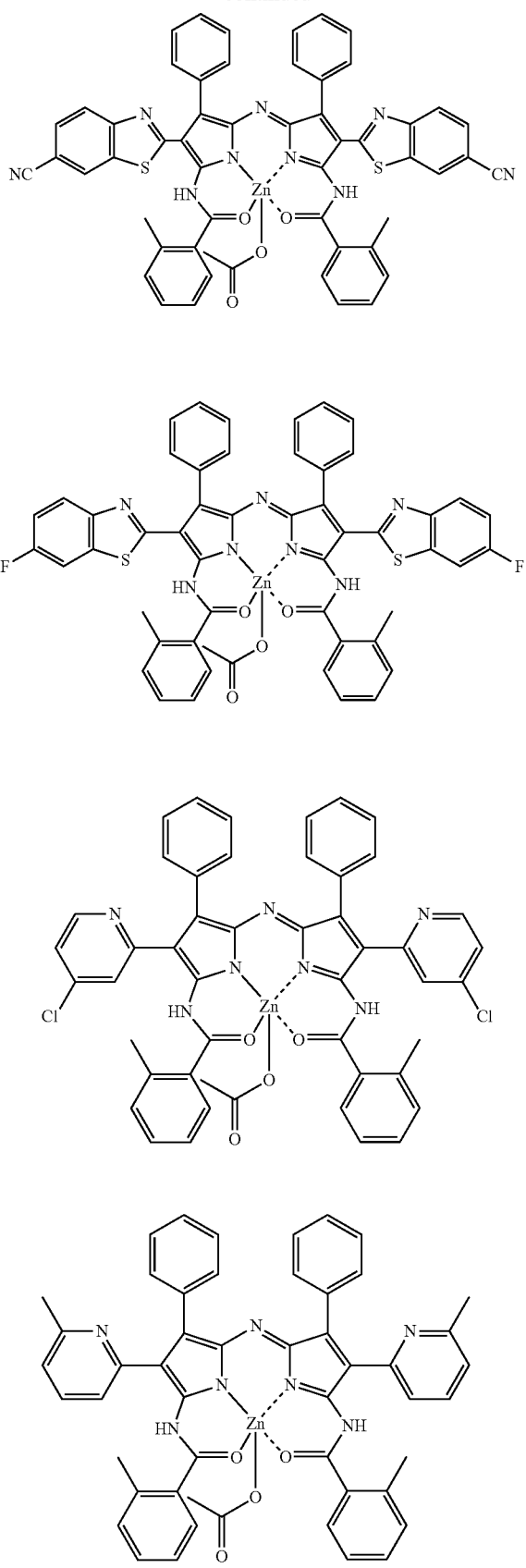

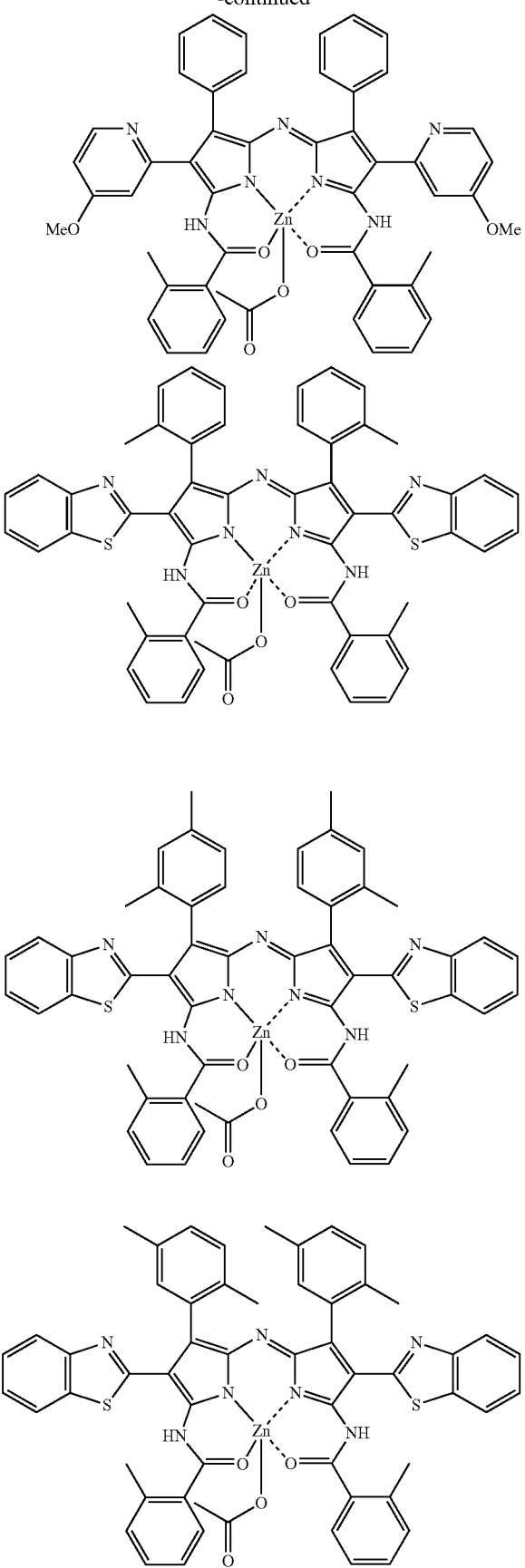
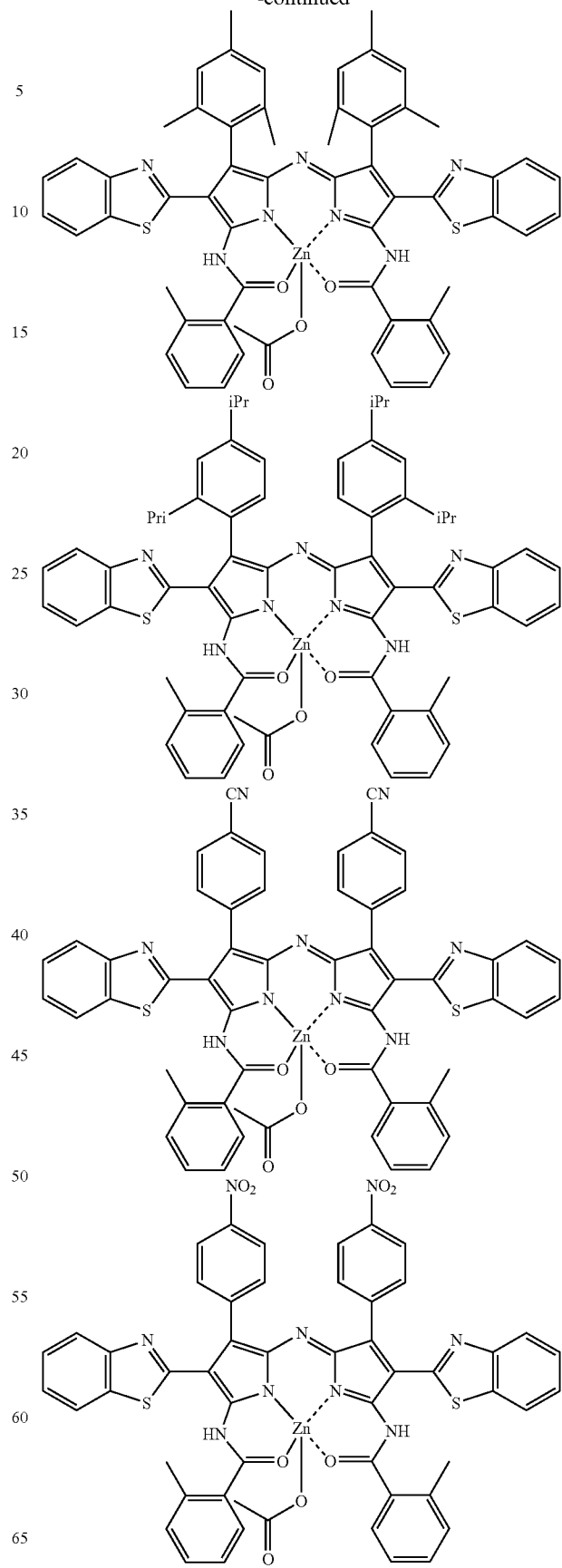

51
-continued
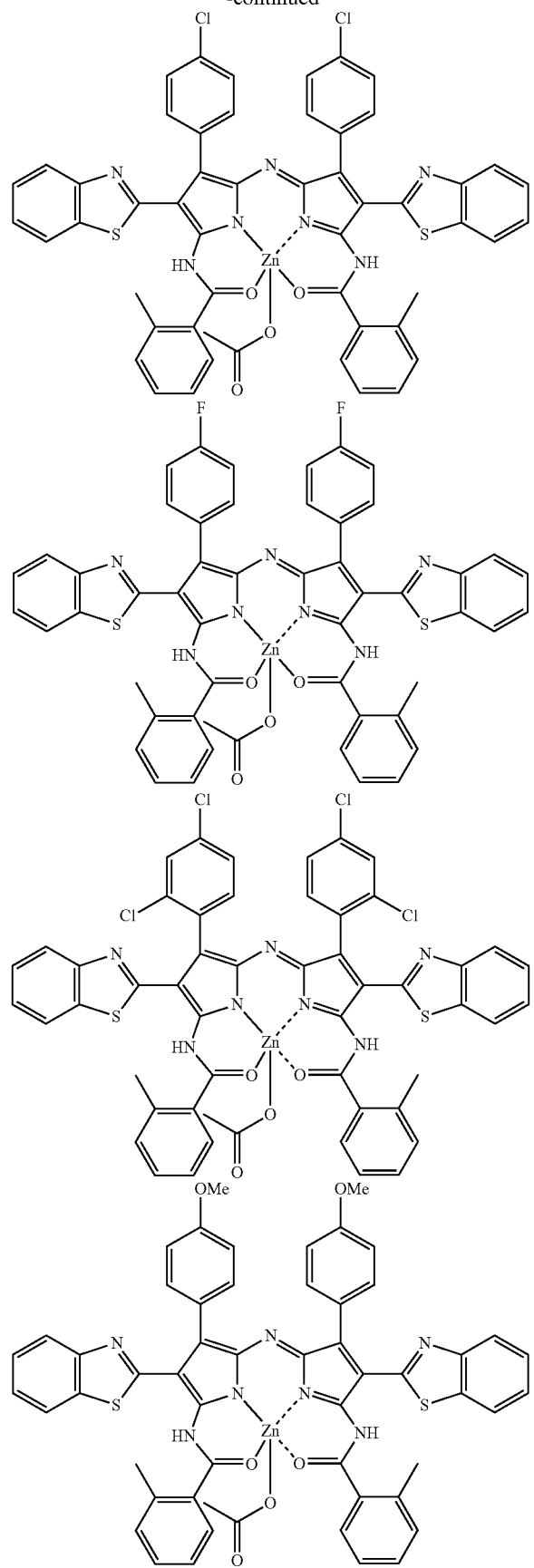
52
-continued
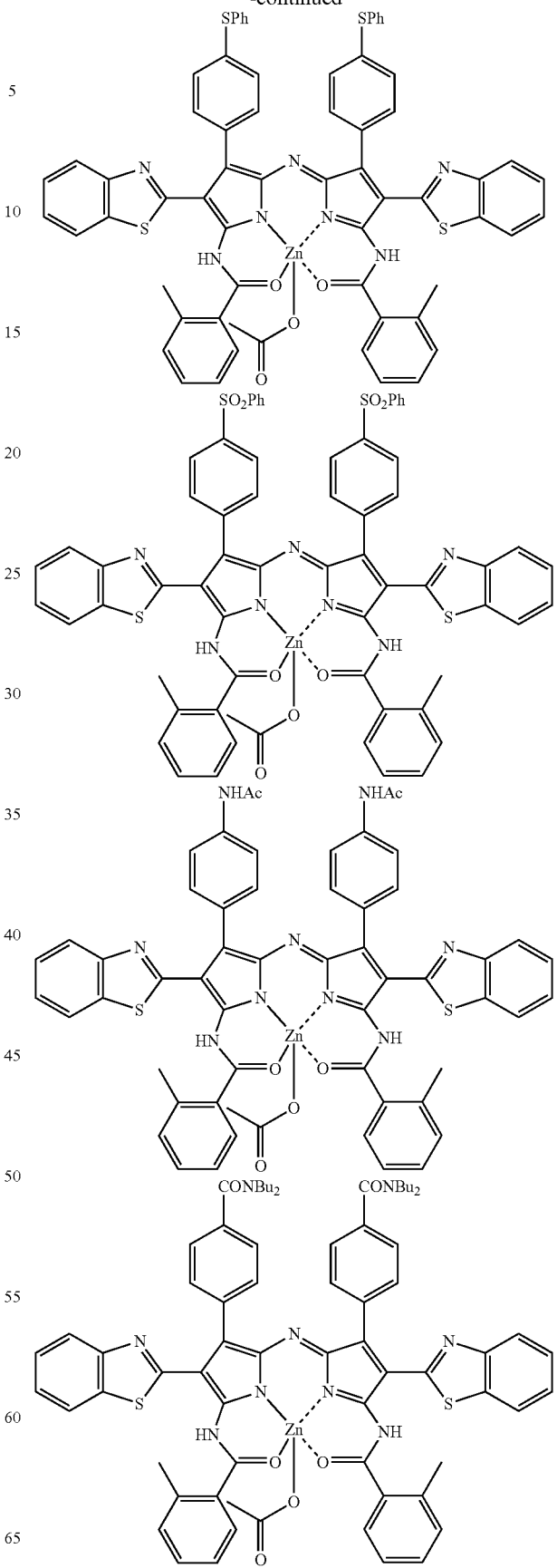

53
-continued
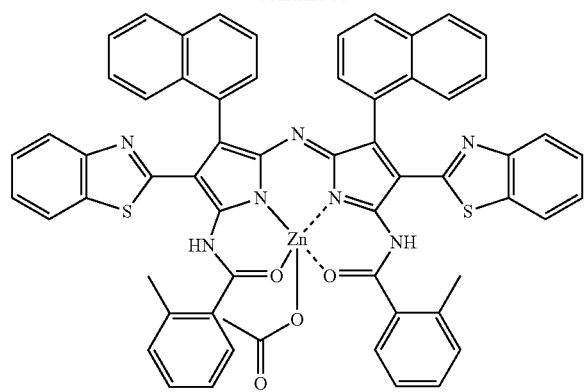
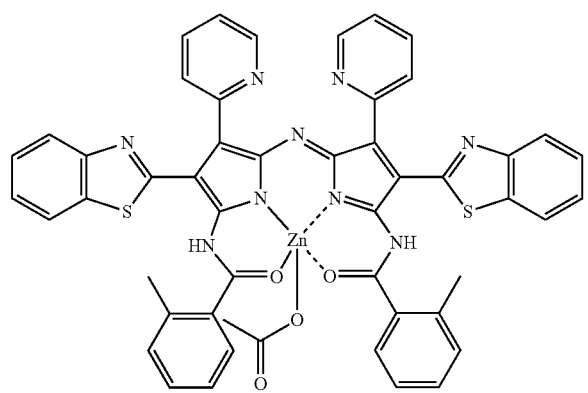
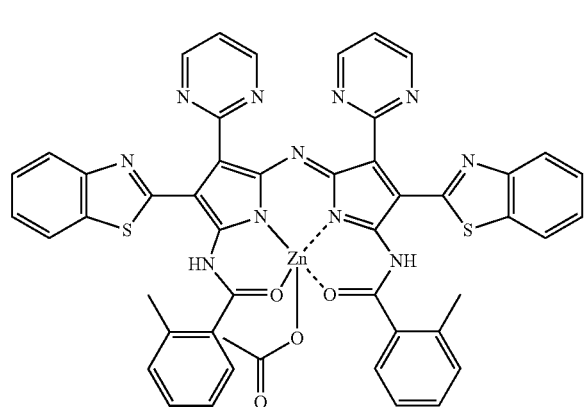
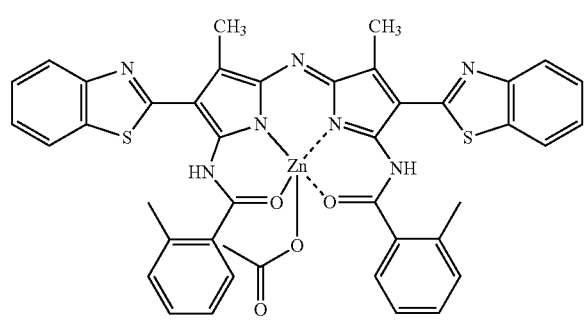
54
-continued
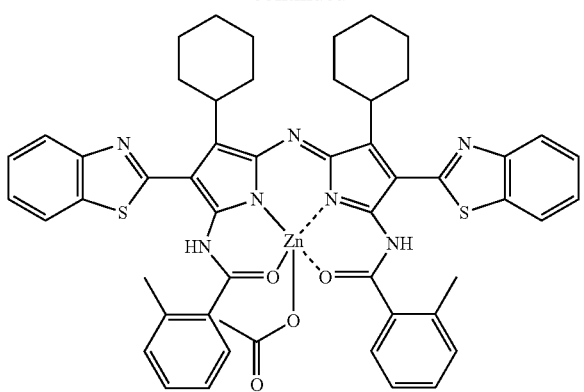
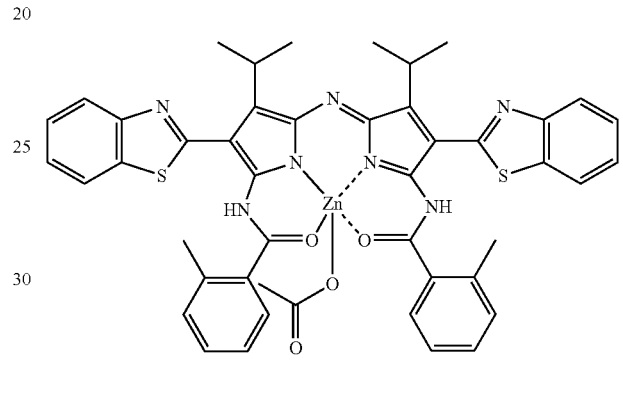
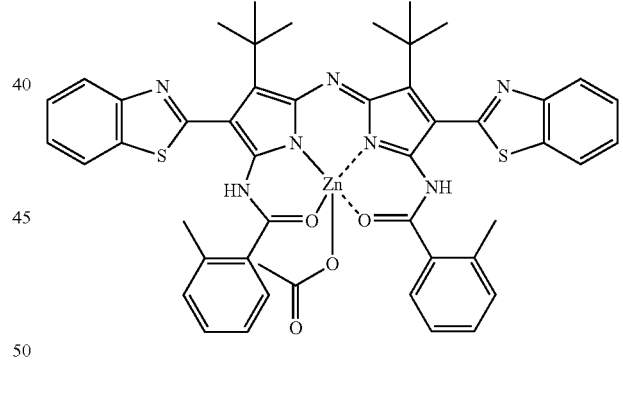
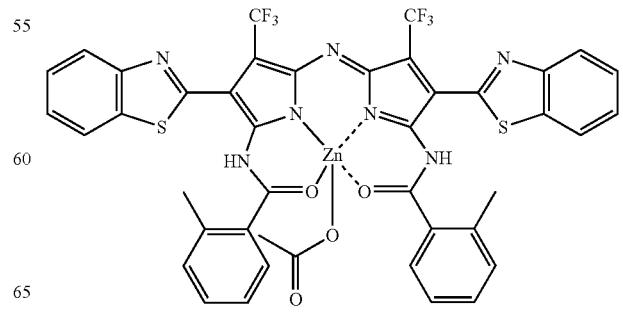

55
-continued
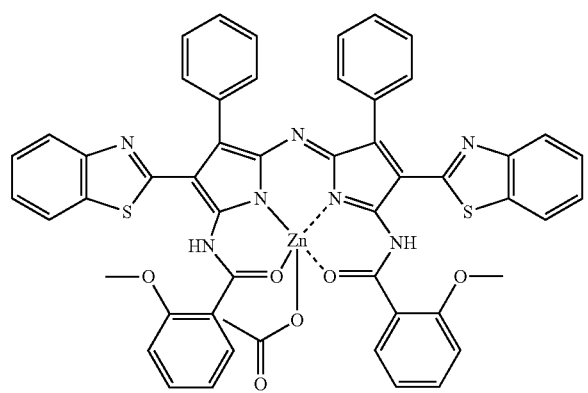
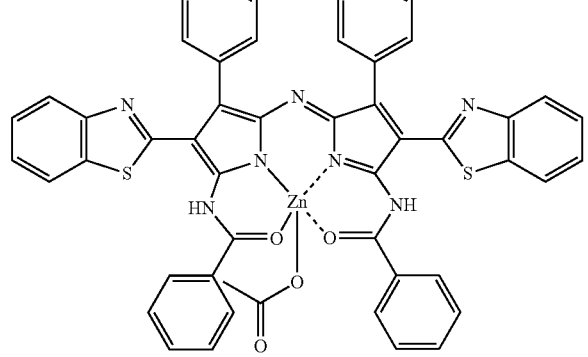
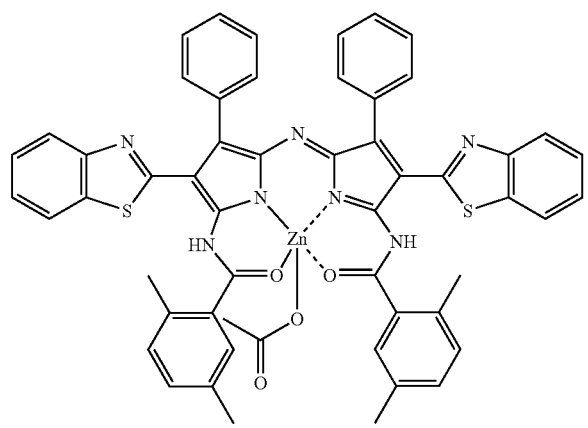
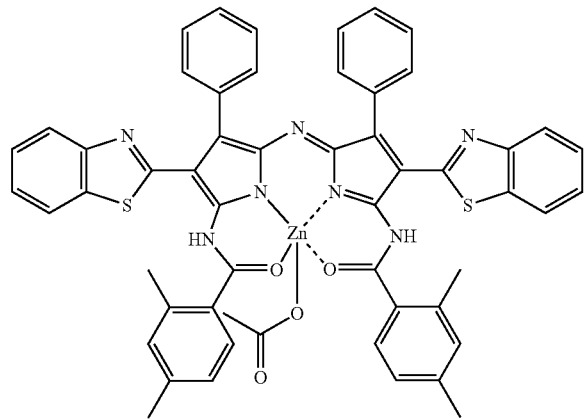
56
-continued
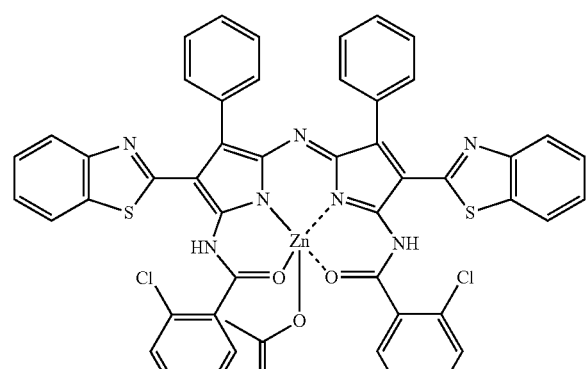
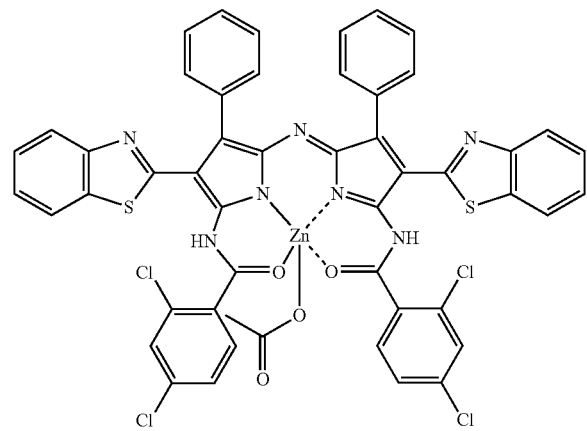
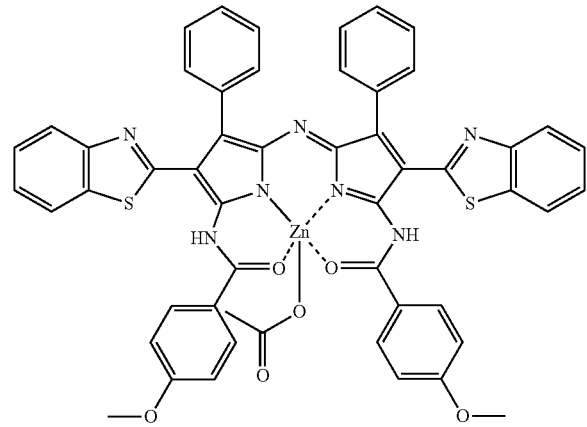
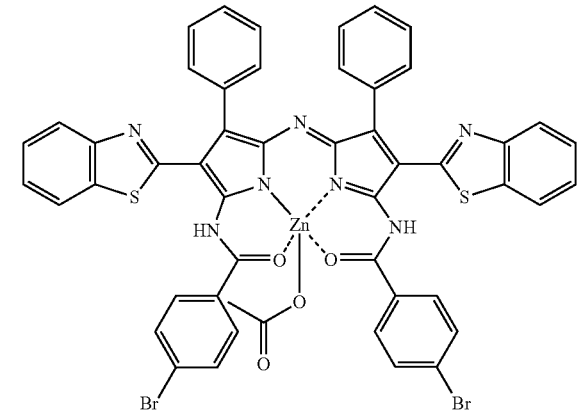

57
-continued
58
-continued
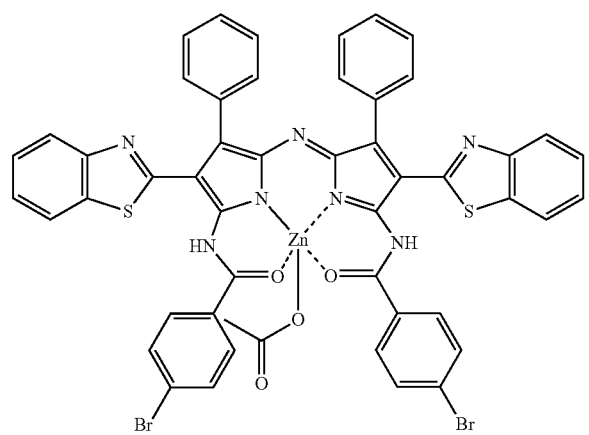
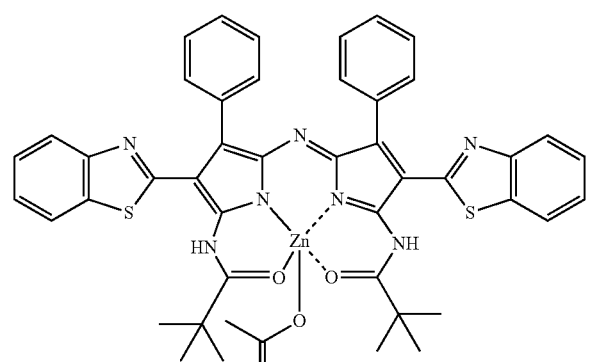
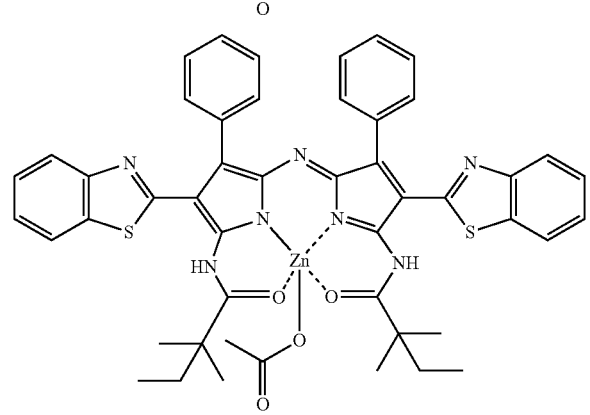
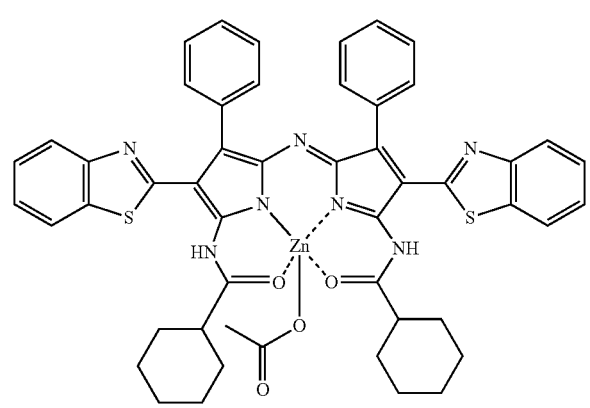
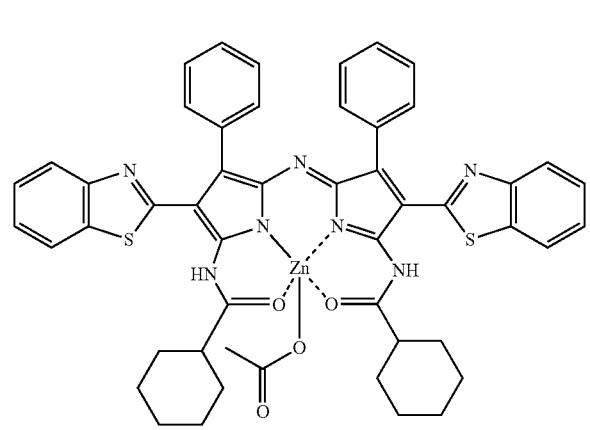

59
-continued
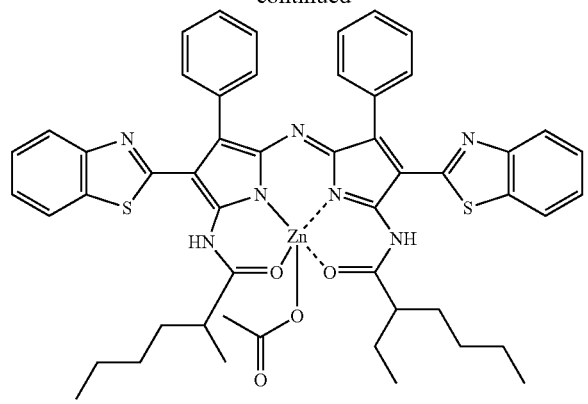
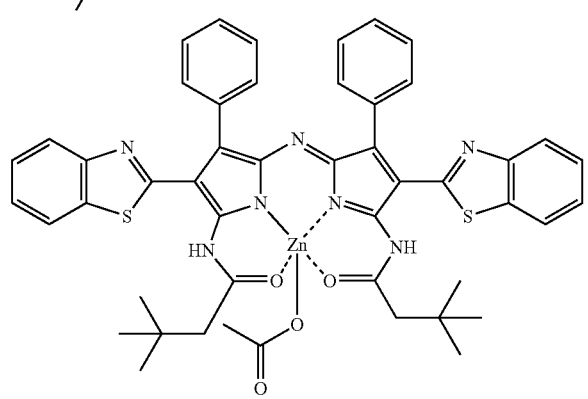
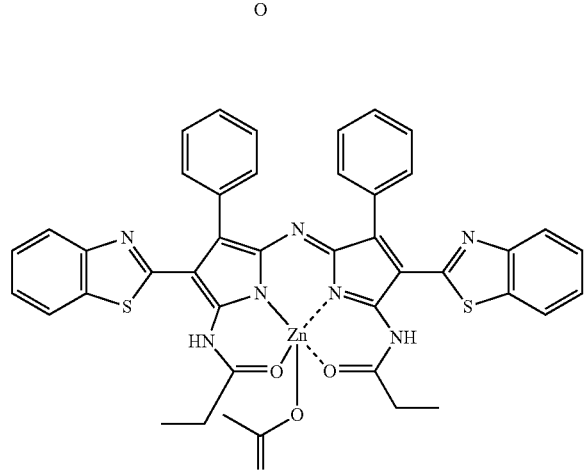
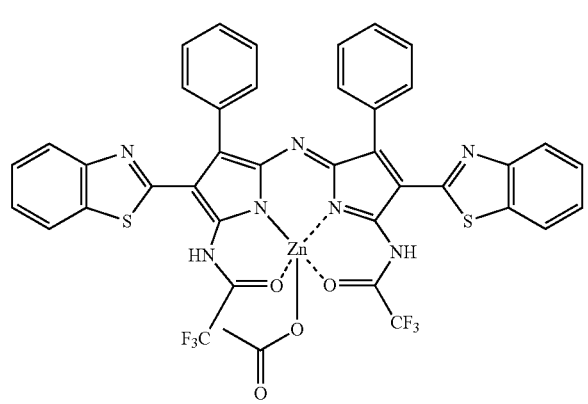
60
-continued
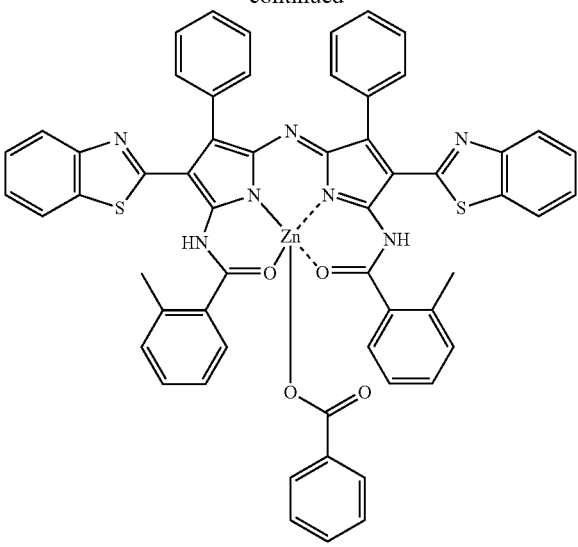
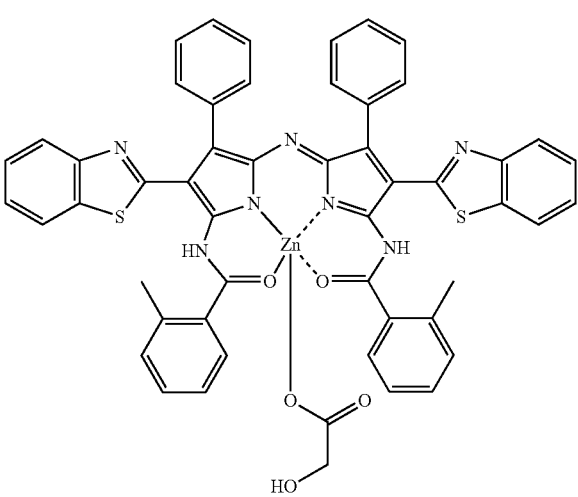
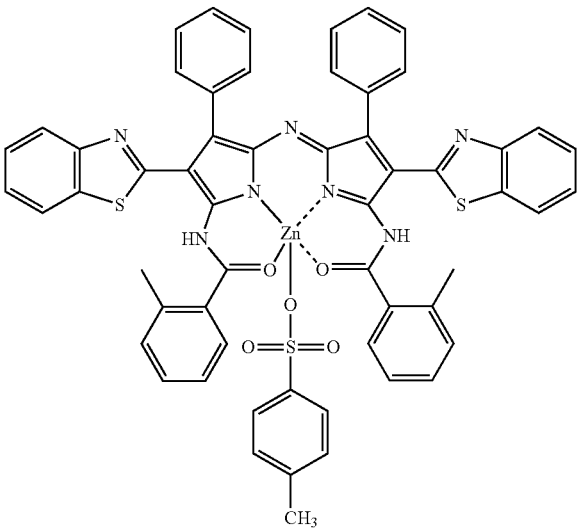

61
-continued
62
-continued
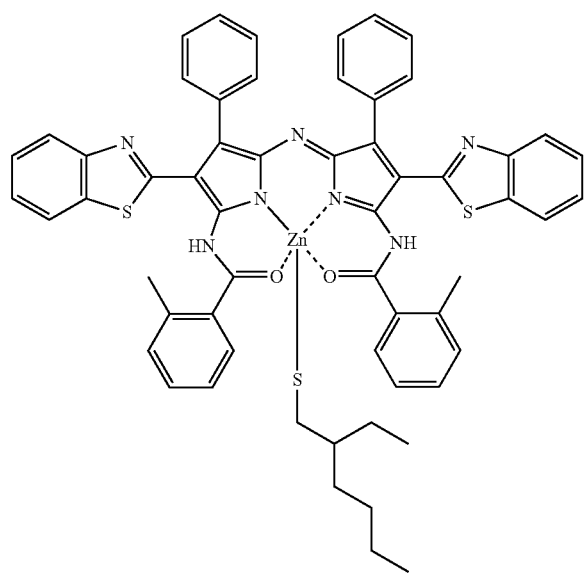
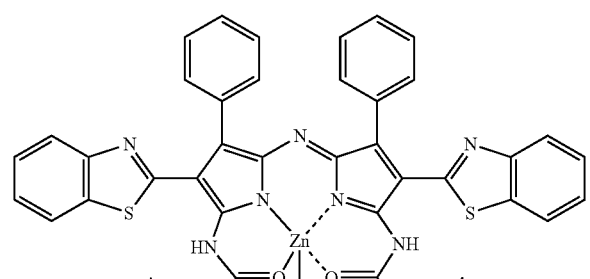
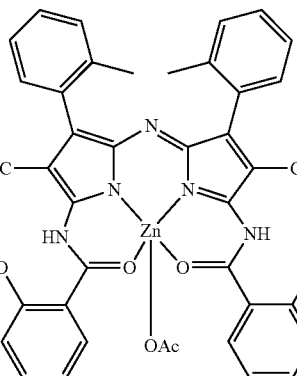
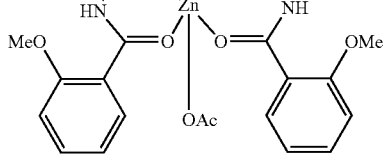
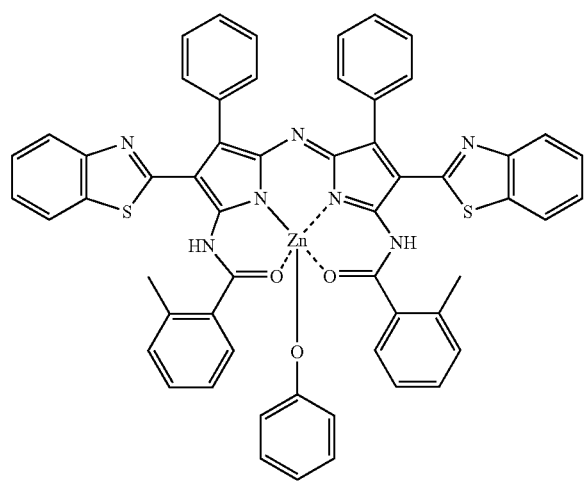
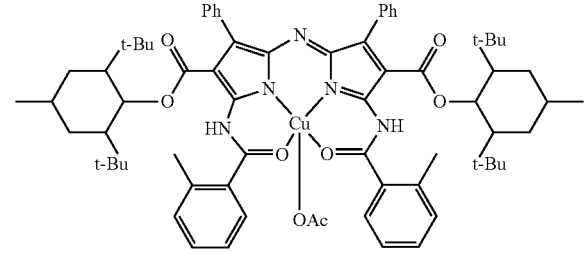
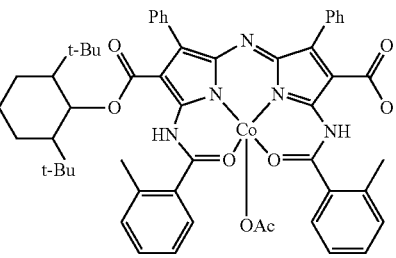
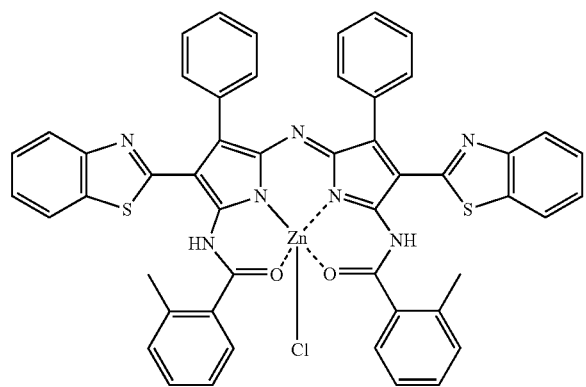
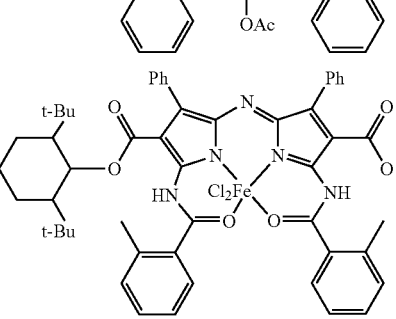

63
-continued
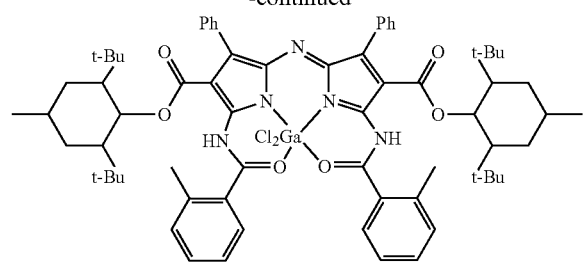
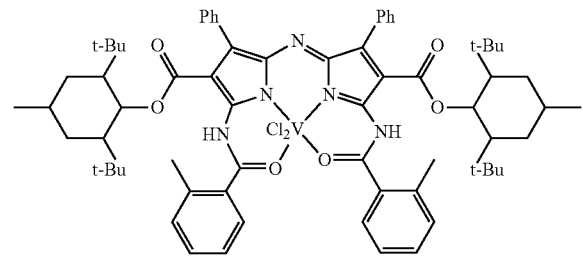
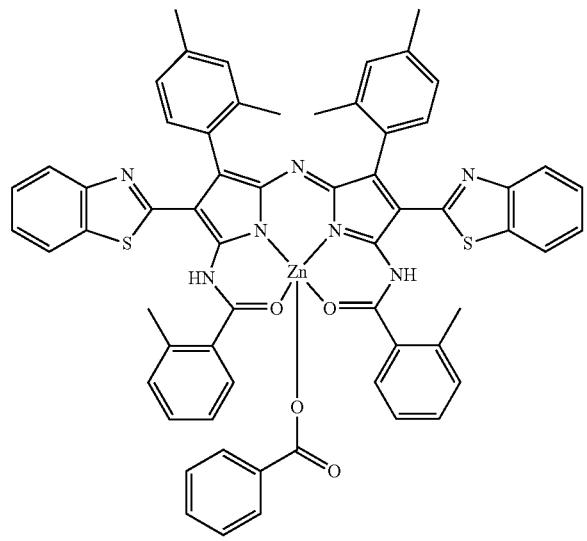
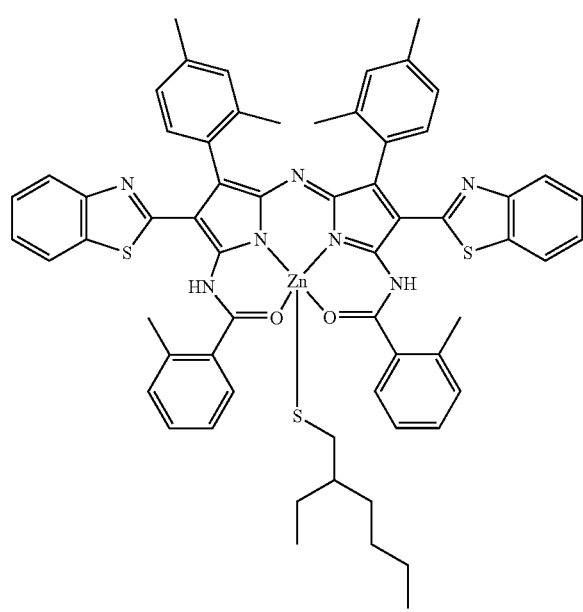
64
-continued
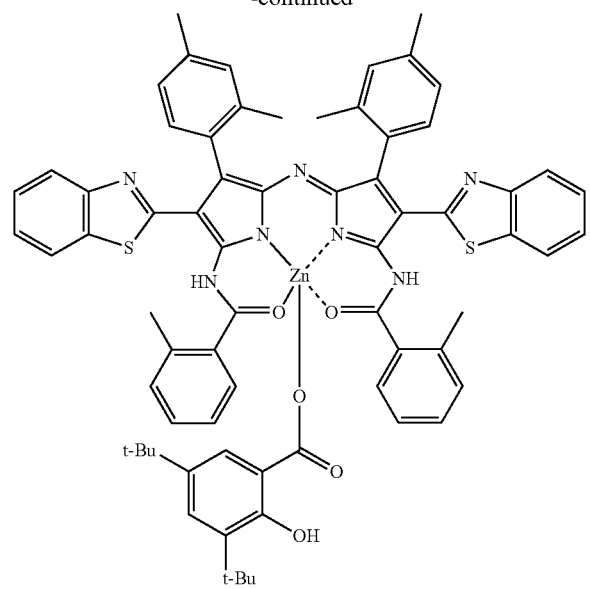
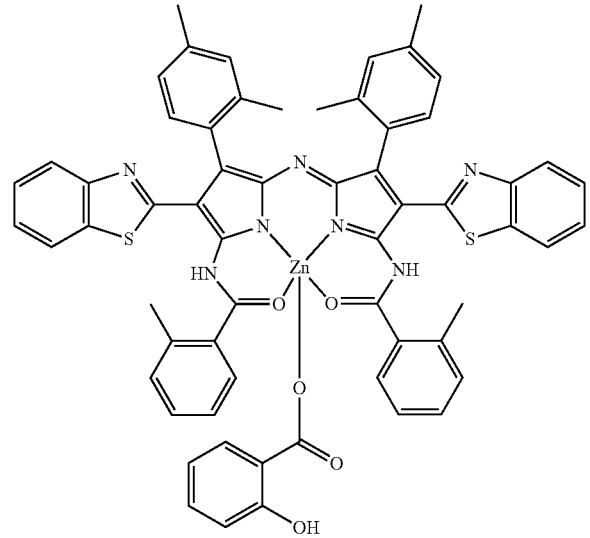
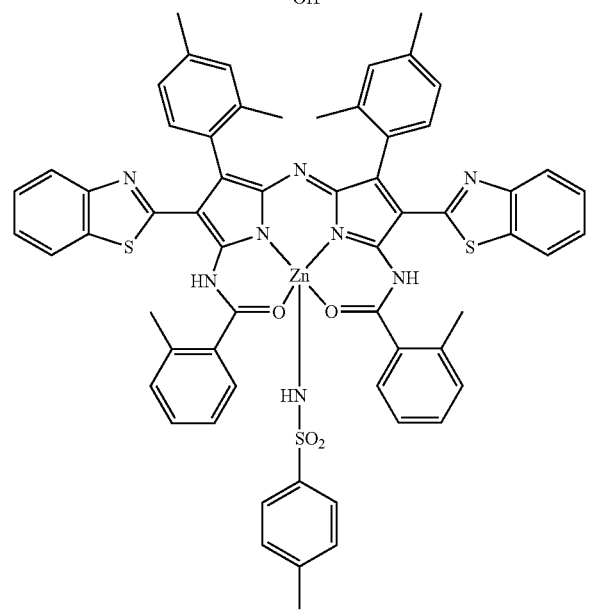

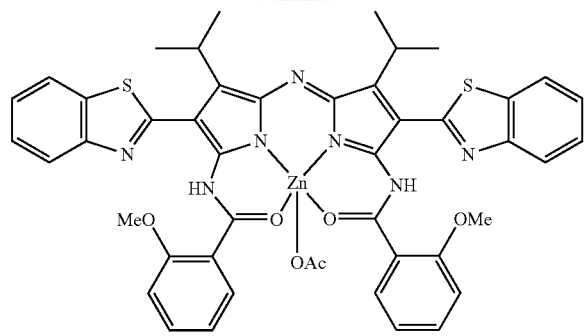
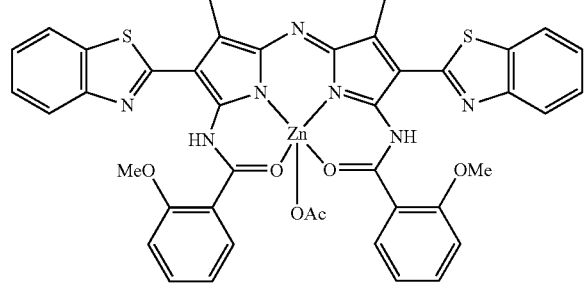
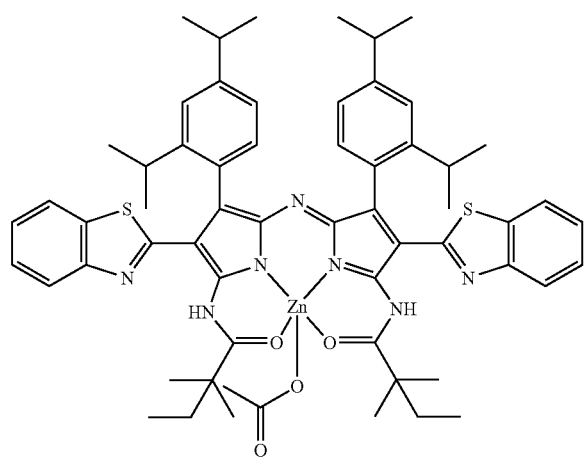
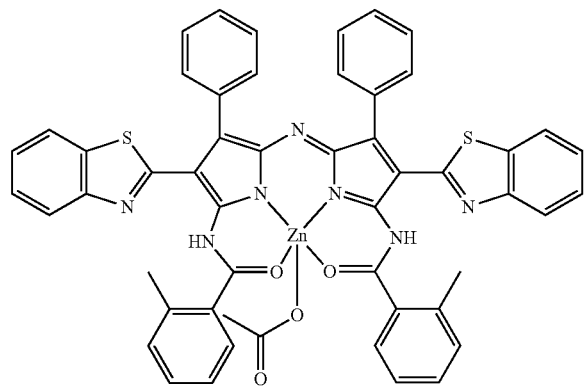
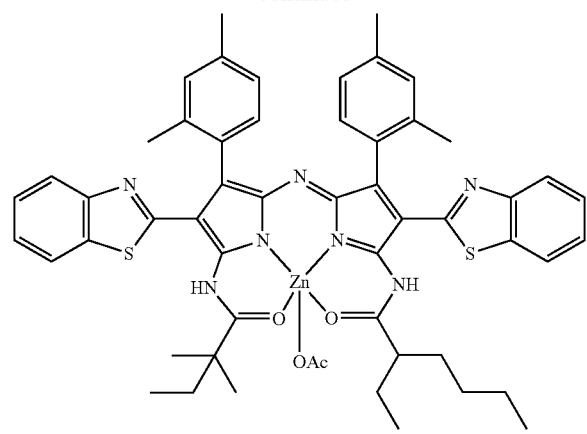
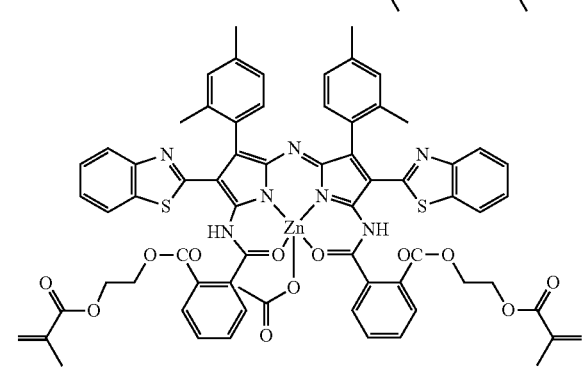
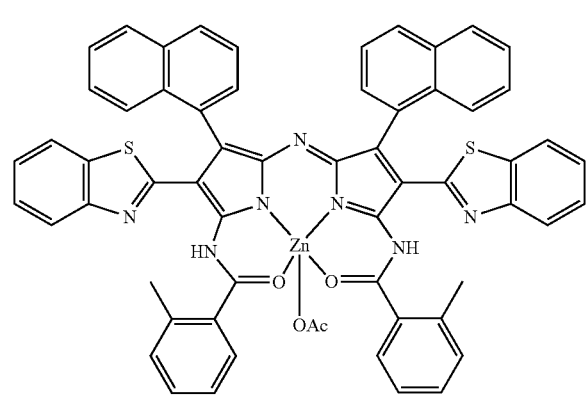
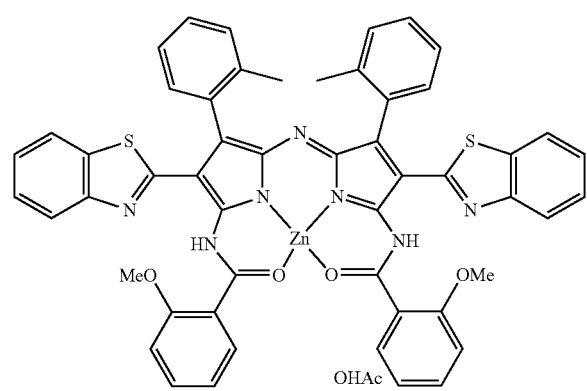

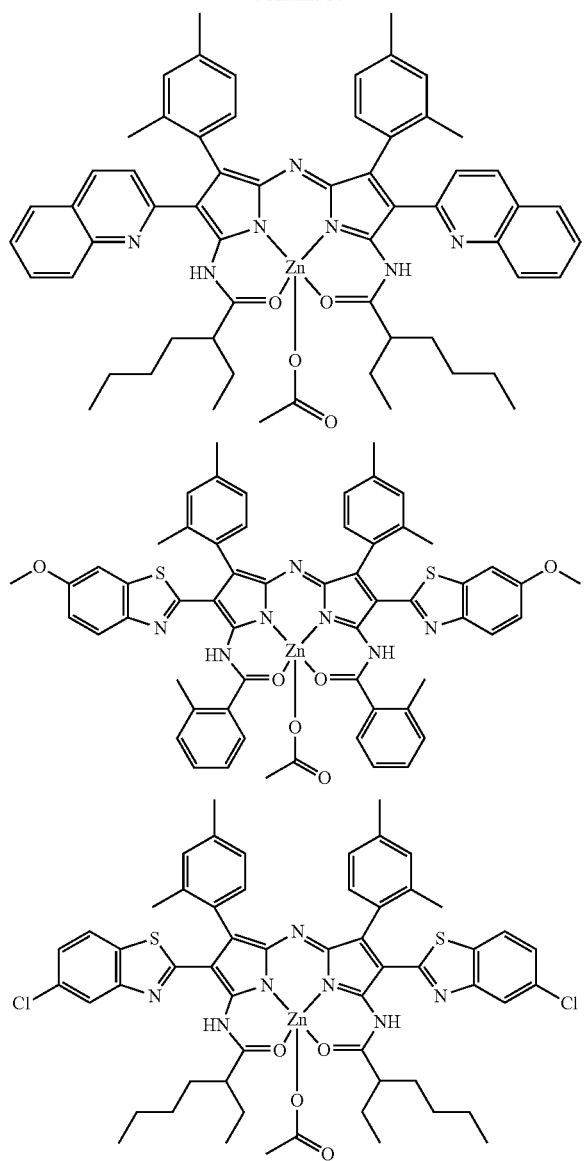

An example of a process for preparing an azapyrromethene compound contained in a curable colored composition of the present invention is shown below. However, the process is not limited to the example shown below.

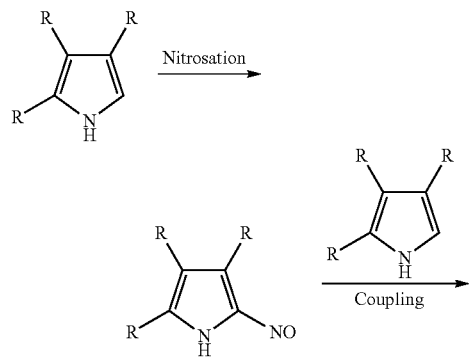

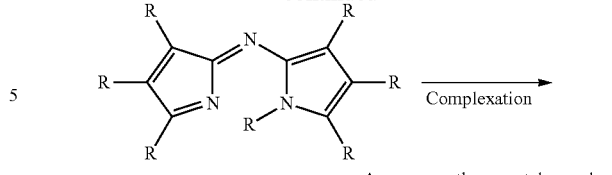

Each step is explained below.
The starting pyrrole compound can be prepared by reference to, for example, JP-A2008-292970 supra.
(1) Nitrosation
This step can be performed by reference to the method described in "Textbook of Experimental Chemistry" (published by Maruzen Company, Limited, 5th Edition, vol. 14, pp. 469-473). A specific example includes a reaction of nitrous acid (which may be generated by reacting a nitrite and an acid) with a pyrrole.
(2) Coupling
This step can be performed by reacting the nitrosated pyrrole with a pyrrole preferably in the presence of an appropriate acid as a catalyst and preferably in the presence of an appropriate acid anhydride as a dehydrating agent.
(3) Complexation
This step can be performed by reacting the dipyrromethene compound with a metal source in an appropriate solvent.

The curable colored compositions of the present invention may contain only one or two or more of the dye compound represented by formula (1).

The content of the dye compound represented by formula (1) in the curable colored compositions of the present invention depends on the molecular weight and the absorption coefficient, but it is preferably 1 to 70% by mass, more preferably 10 to 50% by mass based on the total solids of the curable colored compositions. If the content of the dye is 10% by mass or more, a good color density (e.g., a color density suitable for display by liquid crystals) can be achieved, and if it is 50% by mass or less, patterning of pixels are advantageously improved.

Further, the curable colored compositions of the present invention may contain dye compounds of other structures or pigment compounds and dispersions thereof. The dye compounds may have any structure that does not affect the hue of the colored image, and include, for example, anthraquinone dyes (e.g., the anthraquinone compounds described in JP-A2001-108815), phthalocyanine dyes (e.g., the phthalocyanine compounds described in U.S. Patent Application Publication No. 2008/0076044), xanthene dyes (e.g., C.I. Acid Red 289), triarylmethane dyes (e.g., C.I. Acid Blue 7, C.I. Acid Blue 83, C.I. Acid Blue 90, C.I. Solvent Blue 38, C.I. Acid Violet 17, C.I. Acid Violet 49, C.I. Acid Green 3), squarylium dyes, pyrazole azo dyes, methine dyes, pyrazolone azo dyes, barbituric acid-azo dyes and the like. Dyes soluble in organic solvents include, for example, C.I. Solvent Yellow 4, C.I. Solvent Yellow 88, C.I. Solvent Yellow 14, C.I. Solvent Yellow 15, C.I. Solvent Yellow 24, C.I. Solvent Yellow 94, C.I. Solvent Yellow 98, C.I. Solvent Yellow 162, C.I. Solvent Yellow 82 and the like.

Pigment compounds include perylene, perinone, quinacridone, quinacridone quinone, anthraquinone, anthanthrone, benzimidazolone, disazo condensation, disazo, azo, indanthrone, phthalocyanine, triaryl carbonium, dioxazine, aminoanthraquinone, diketopyrrolopyrrole, indigo, thioindigo, isoindoline, isoindolinone, pyranthrone or isoviolanthrone and the like. More specifically, examples are perylene compound pigments such as Pigment Red 190, Pigment Red 224, Pigment Violet 29 and the like; perinone compound pigments such as Pigment Orange 43, or Pigment Red 194; quinacridone compound pigments such as Pigment Violet 19, Pigment Violet 42, Pigment Red 122, Pigment Red 192, Pigment Red 202, Pigment Red 207, or Pigment Red 209; quinacridone quinone compound pigments such as Pigment Red 206, Pigment Orange 48, or Pigment Orange 49; anthraquinone compound pigments such as Pigment Yellow 147; anthanthrone compound pigments such as Pigment Red 168; benzimidazolone compound pigments such as Pigment Brown 25, Pigment Violet 32, Pigment Orange 36, Pigment Yellow 120, Pigment Yellow 180, Pigment Yellow 181, Pigment Orange 62, or Pigment Red 185; disazo condensation compound pigments such as Pigment Yellow 93, Pigment Yellow 94, Pigment Yellow 95, Pigment Yellow 128, Pigment Yellow 166, Pigment Orange 34, Pigment Orange 13, Pigment Orange 31, Pigment Red 144, Pigment Red 166, Pigment Red 220, Pigment Red 221, Pigment Red 242, Pigment Red 248, Pigment Red 262, or Pigment Brown 23; disazo compound pigments such as Pigment Yellow 13, Pigment Yellow 83, or Pigment Yellow 188; azo compound pigments such as Pigment Red 187, Pigment Red 170, Pigment Yellow 74, Pigment Yellow 150, Pigment Red 48, Pigment Red 53, Pigment Orange 64, or Pigment Red 247; indanthrone compound pigments such as Pigment Blue 60; phthalocyanine compound pigments such as Pigment Green 7, Pigment Green 36, Pigment Green 37, Pigment Green 58, Pigment Blue 16, Pigment Blue 75, or Pigment Blue 15; triaryl carbonium compound pigments such as Pigment Blue 56, or Pigment Blue 61; dioxazine compound pigments such as Pigment Violet 23, or Pigment Violet 37; aminoanthraquinone compound pigments such as Pigment Red 177; diketopyrrolopyrrole compound pigments such as Pigment Red 254, Pigment Red 255, Pigment Red 264, Pigment Red 272, Pigment Orange 71, or Pigment Orange 73; thioindigo compound pigments such as Pigment Red 88; isoindoline compound pigments such as Pigment Yellow 139, or Pigment Orange 66; isoindolinone compound pigments such as Pigment Yellow 109, or Pigment Orange 61; pyranthrone compound pigments such as Pigment Orange 40, or Pigment Red 216; or isoviolanthrone compound pigments such as Pigment Violet 31.

The dyes and pigments can be used at any content that does not affect the benefits of the present invention, but preferably 0.5% by mass to 70% by mass based on the total solids of the curable colored compositions of the present invention.

When the curable colored compositions of the present invention are to be prepared by incorporating the dyes or pigments as dispersions, they can be prepared as described in JP-A-H9-197118 and JP-A2000-239544.

(Resins Having a Dye Structure)

When a high concentration of a dye is dispersed in a resin, the dye may be deposited to cause a problem. To solve this problem, the metal complex (dye) in the present invention may be bound to a resin precursor, whereby it may be used as a resin having a dye structure (A).

The resin having a dye structure (A) is preferably a resin having a dye structure comprising at least one of the structural units represented by formula (A), formula (B), and formula (C) below. These units are explained below in order.

<Structural Unit Represented by Formula (A)>

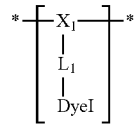

Formula (A)

In formula (A), $X^1$ represents a linking group formed by polymerization, and $L^1$ represents a single bond or a divalent linking group. DyeI represents a dye structure derived from a metal complex in the present invention. Formula (A) is described in detail below.

In formula (A), $X_1$ represents a linking group formed by polymerization, namely a moiety forming a repeat unit corresponding to a main chain formed by polymerization reaction. The moiety defined by two asterisks (*) forms the repeat unit. $X_1$ is not specifically limited so far as it is a linking group formed from a known polymerizable monomer, but preferably a linking group represented by (XX-1) to (X-24) below, most preferably a (meth)acrylic linking chain represented by (XX-1) and (XX-2), a styrene linking chain represented by (XX-10) to (XX-17), and a vinyl linking chain represented by (XX-24). In (XX-1) to (XX-24), the asterisk (*) represents the point of attachment to $L_1$. Me represents methyl. In (XX-18) and (XX-19), R represents a hydrogen atom, C1-5 alkyl or phenyl.

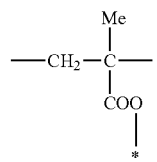

(XX-1)

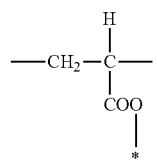

(XX-2)

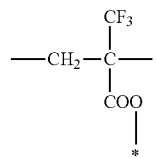

(XX-3)

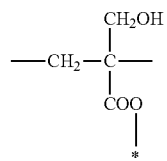

(XX-4)

(XX-5) 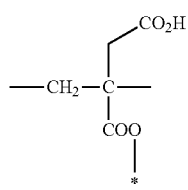
(XX-6) 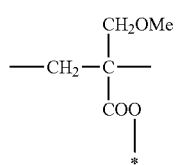
(XX-7) 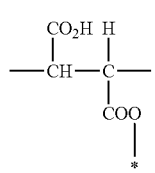
(XX-8) 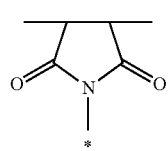
(XX-9) 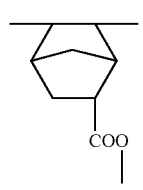
(XX-10) 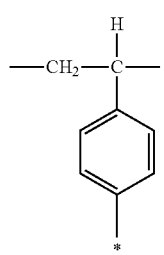
(XX-11) 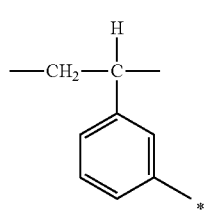
(XX-12) 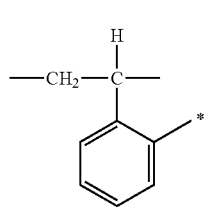
(XX-13) 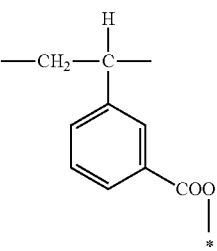
(XX-14) 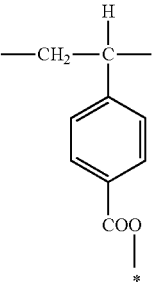
(XX-15) 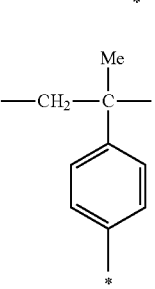
(XX-16) 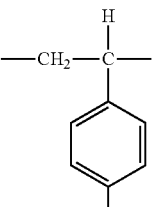
(XX-17) 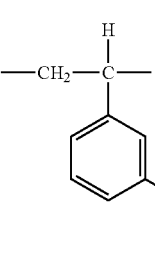
(XX-18) 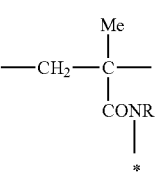

-continued

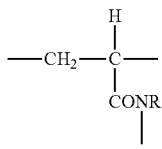
(XX-19)

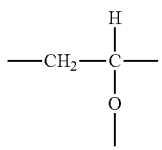
(XX-20)

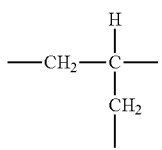
(XX-21)

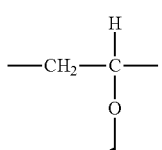
(XX-22)

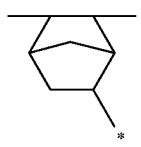
(XX-23)

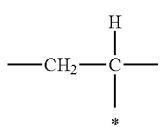
(XX-24)

In formula (A), $L^1$ represents a single bond or a divalent linking group. When $L^1$ represents a divalent linking group, the divalent linking group is a substituted or unsubstituted alkylene containing 1 to 30 carbon atoms (e.g., methylene, ethylene, trimethylene, propylene, butylene or the like), a substituted or unsubstituted arylene containing 6 to 30 carbon atoms (e.g., phenylene, naphthalene or the like), a substituted or unsubstituted heterocyclic linking group, —CH═CH—, —O—, —S—, —C(═O)—, —CO$_2$—, —NR—, —CONR—, —O$_2$C—, —SO—, —SO$_2$— or a linking group formed by linking two or more of them, wherein R each independently represents a hydrogen atom, alkyl, aryl, or heterocyclyl.

In formula (A), Dye1 represents a dye structure derived from a metal complex in the present invention. A dye compound is bound to the resin of formula (A) as follows. A compound represented by formula (3) used in the present invention is preferably bound to the resin of formula (A) via $R^7$ or $R^8$ or $Z^1$, more preferably $R^7$ or $R^8$, especially preferably $R^7$ for convenience of preparation. A compound represented by formula (4) used in the present invention is preferably bound to the resin of formula (A) via $R^7$ or $R^8$ or $Z^2$, more preferably $R^7$ or $R^8$, especially preferably $R^7$ for convenience of preparation.

The resin having a dye structure comprising a structural unit represented by formula (A) can be synthesized by (1) addition polymerization using a monomer having a dye structure, or (2) reacting a polymer having a highly reactive functional group such as isocyanate, acid anhydride or epoxy with a dye having a functional group capable of reacting with the highly reactive group (hydroxyl, primary or secondary amino, carboxyl or the like). During the addition polymerization (1), the peak area occupied by components having a molecular weight of 20,000 or more can be conveniently reduced to 10% or less of the total peak area in the molecular weight distribution of resin (A) by applying (i) the preparation process involving a polymerization reaction in the presence of a polymerization inhibitor as described above. Further, the addition polymerization may be followed by (ii) the preparation process involving adding a poor solvent (such as water) for high molecular weight components of 20,000 or more to the polymerization solution obtained and removing the precipitated high molecular weight components of 20,000 or more by filtration as described above.

Similarly, the polymer having a highly reactive functional group used for the reaction (2) may be a resin synthesized by (i) the preparation process involving a polymerization reaction in the presence of an polymerization inhibitor as described above, or the polymer or a polymer reacted with the dye may be subjected to (ii) the preparation process involving adding a poor solvent for high molecular weight components of 20,000 or more to the polymerization solution and removing the precipitated high molecular weight components of 20,000 or more by filtration as described above.

The addition polymerization can be performed by applying known addition polymerization techniques (radical polymerization, anionic polymerization, cationic polymerization), among which radical polymerization is especially preferred because of milder reaction conditions enough to protect the dye structure against degradation. For radical polymerization, known reaction conditions can be applied.

Especially, the resin having a dye structure comprising a structural unit represented by formula (A) in the present invention is preferably a radical polymer obtained by radically polymerizing a dye monomer containing an ethylenically unsaturated bond (a monomer having a dye structure) to prevent migration of residues onto other colored patterns and to control coating defects.

Specific examples of structural units represented by formula (A) are shown below, but the present invention is not limited to these examples.

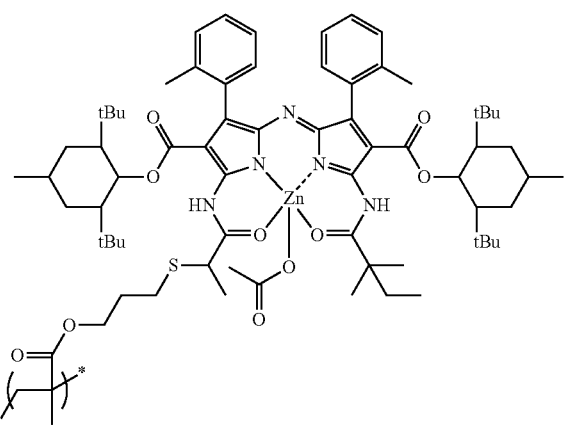

75
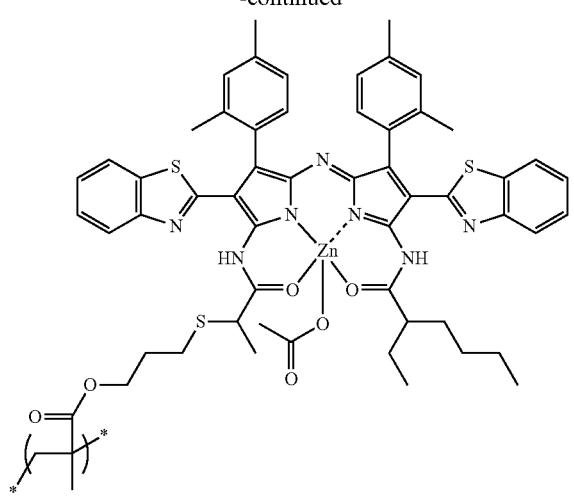
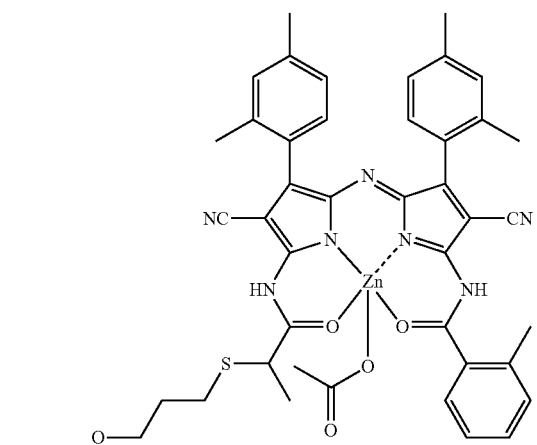
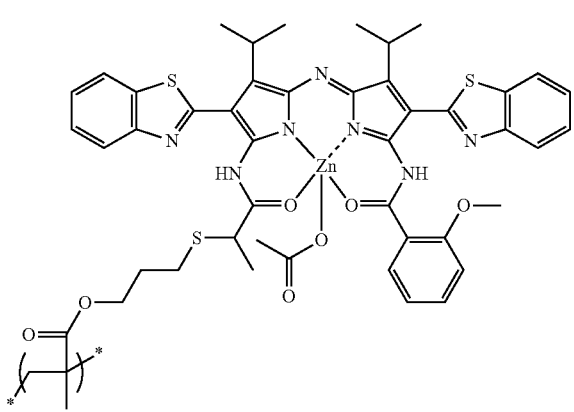
76
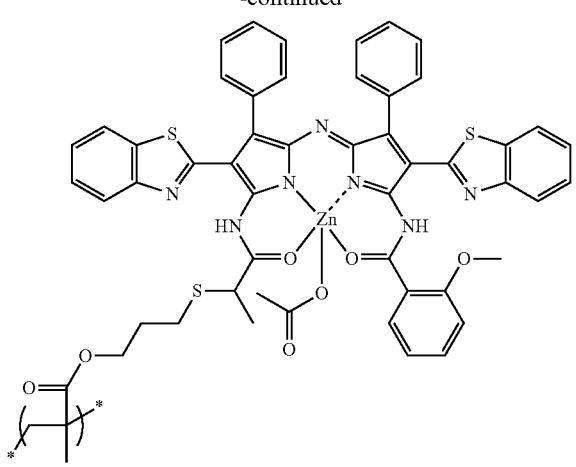
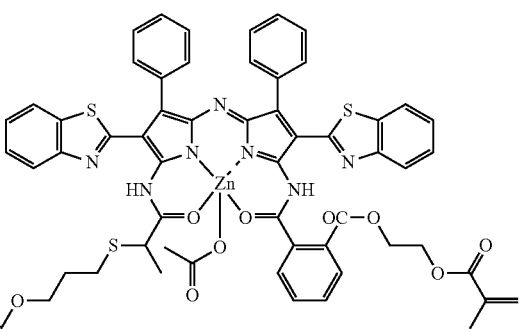
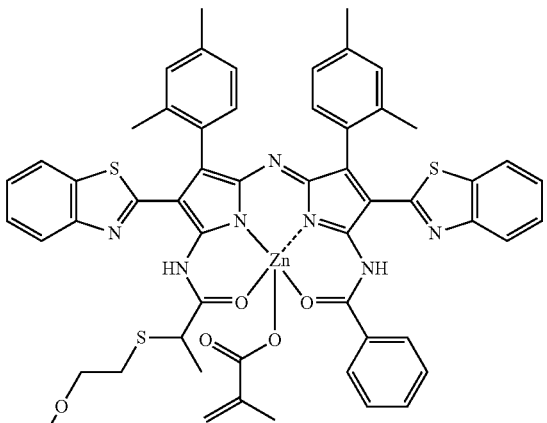

-continued

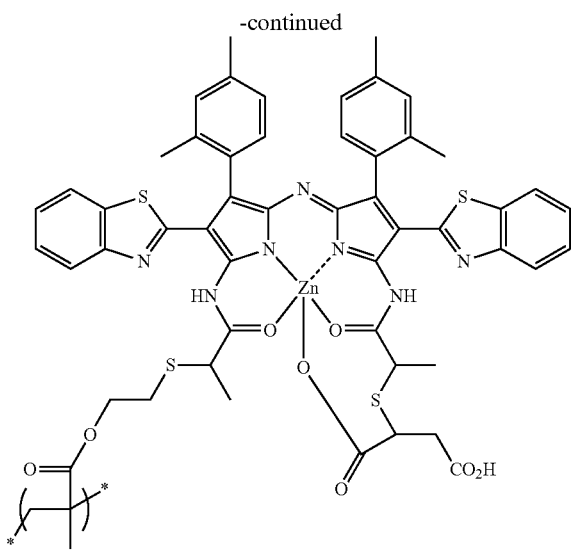

<Structural Unit Represented by Formula (B)>
Next, the structural unit represented by formula (B) is explained in detail.

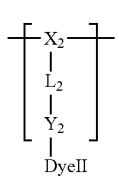

Formula (B)

In formula (B), $X_2$ has the same meaning as defined for $X_1$ in formula (A) above. $L_2$ has the same meaning as defined for $L_1$ in formula (A) above. $Y_2$ represents a group capable of forming an ionic bond or a coordinate bond with DyeII. DyeII represents a dye structure derived from a metal complex in the present invention. A detailed description is as follows.

In formula (B), $X_2$ has the same meaning as defined for $X_1$ in formula (A) above, and also covers the same preferred ranges. $L_2$ has the same meaning as defined for $L_1$ in formula (A) above, and also covers the same preferred ranges. $Y_2$ may be a group capable of forming an ionic bond or a coordinate bond with DyeII, and may be either an anionic group or a cationic group. Anionic groups include $COO^-$, $PO_3H^-$, $SO_3^-$, $-SO_3NH^-$, $-SO_3N^-CO-$ and the like, preferably $COO^-$, $PO_3H^-$, and $SO_3^-$.

Cationic groups include substituted or unsubstituted onium cations (e.g., ammonium, pyridinium, imidazolium and phosphonium, etc), especially preferably ammonium cation.

$Y_2$ can be bonded to the anionic moiety ($COO^-$, $SO_3^-$, $O^-$ and the like) or cationic moiety (the onium cations or metal cations or the like) on DyeII.

A dye compound is bound to the resin of formula (B) as follows. A compound represented by formula (3) used in the present invention is preferably bound to the resin of formula (B) via $R^7$ or $R^8$ or $Z^1$, more preferably $R^7$ or $R^8$, especially preferably $R^7$ for convenience of preparation. A compound represented by formula (4) used in the present invention is preferably bound to the resin of formula (B) via $R^7$ or $R^8$ or $Z^2$, more preferably $R^7$ or $R^8$, especially preferably $R^7$ for convenience of preparation.

The resin having a dye structure comprising a structural unit represented by formula (B) in the present invention can be synthesized in the same manner as described for the resin having a dye structure comprising a structural unit represented by formula (A).

To conveniently reduce the peak area occupied by components having a molecular weight of 20,000 or more to 10% or less of the total peak area in the molecular weight distribution of resin (A), (i) the preparation process involving a polymerization reaction in the presence of an polymerization inhibitor or (ii) the preparation process involving adding a poor solvent (such as water) for high molecular weight components of 20,000 or more to the polymerization solution and removing the precipitated high molecular weight components of 20,000 or more by filtration as described above may also be applied.

Especially, the resin having a dye structure comprising a structural unit represented by formula (B) is preferably a radical polymer obtained by radically polymerizing a dye monomer containing an ethylenically unsaturated bond (a monomer having a dye structure) to prevent migration of residues onto other colored patterns and to control coating defects.

Specific examples of structural units represented by formula (B) are shown below, but the present invention is not limited to these examples.

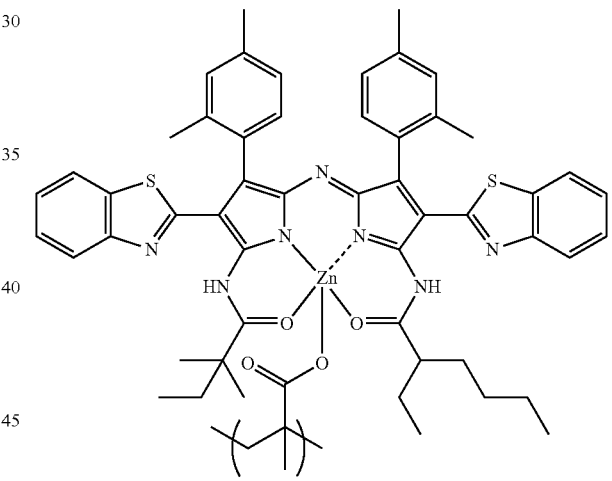

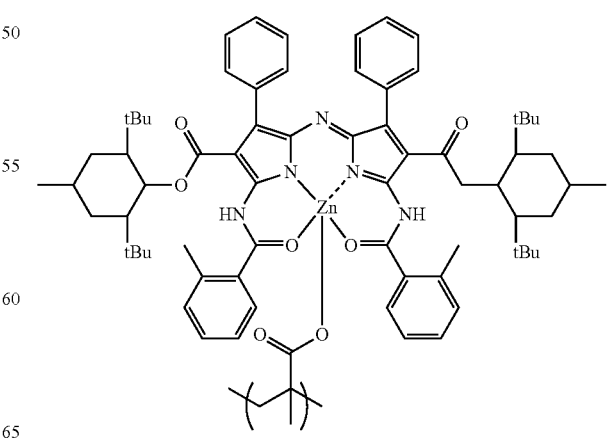

<Structural Units Represented by Formula (C)>

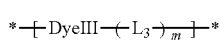

Formula (C)

In formula (C) above, $L_3$ represents a single bond or a divalent linking group. DyeIII represents a dye structure derived from a metal complex in the present invention. m represents 0 or 1. A detailed description is as follows.

In formula (C) above, the divalent linking group represented by $L_3$ is preferably a substituted or unsubstituted straight-chain, branched or cyclic alkylene containing 1 to 30 carbon atoms (e.g., methylene, ethylene, trimethylene, propylene, butylene or the like), a substituted or unsubstituted arylene containing 6 to 30 carbon atoms (e.g., phenylene, naphthalene or the like), a substituted or unsubstituted heterocyclic linking group, —CH=CH—, —O—, —S—, —NR— (wherein R each independently represents a hydrogen atom, alkyl, aryl, or heterocyclyl), —C(=O)—, —SO—, —SO$_2$—, or a linking group formed by linking two or more of them. m represents 0 or 1, preferably 1. In formula (C), DyeI represents a dye structure derived from a metal complex in the present invention.

A dye compound is bound to the resin of formula (C) as follows. A compound represented by formula (3) used in the present invention is preferably bound to the resin of formula (C) via $R^7$ or $R^8$ or $Z^1$, more preferably $R^7$ or $R^8$, especially preferably $R^7$ for convenience of preparation. A compound represented by formula (4) used in the present invention is preferably bound to the resin of formula (C) via $R^7$ or $R^8$ or $Z^2$, more preferably $R^7$ or $R^8$, especially preferably $R^7$ for convenience of preparation.

Specific examples of divalent linking groups represented by $L_3$ in formula (C) that can be preferably used are shown below, but $L_3$ of the present invention is not limited to these examples.

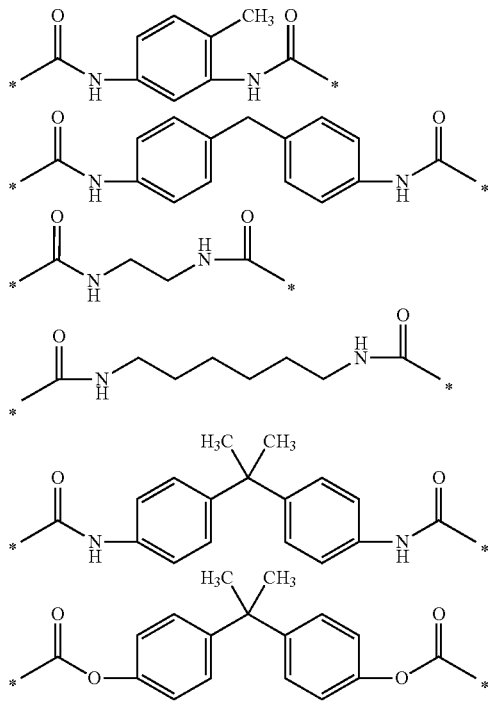

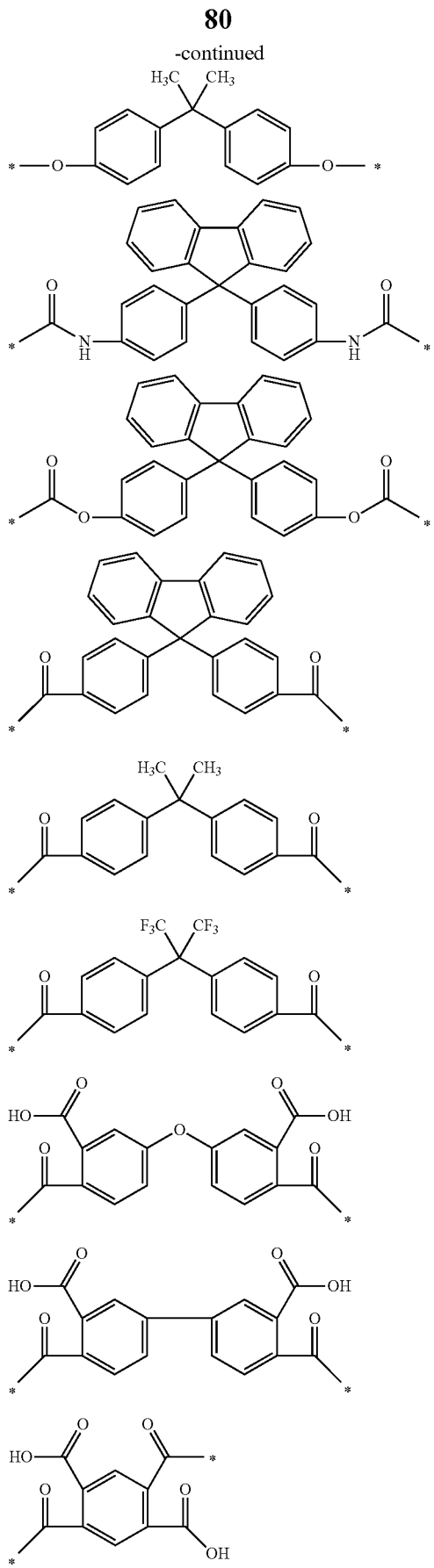

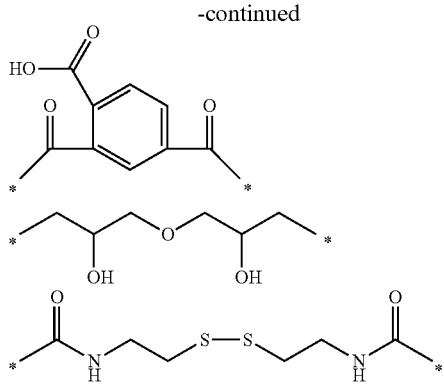

The resin having a dye structure comprising a structural unit represented by formula (C) is synthesized by sequential polymerization. The sequential polymerization includes polyaddition (e.g., the reaction between a diisocyanate compound and a diol, the reaction between a diepoxy compound and a dicarboxylic acid, the reaction between a tetracarboxylic dianhydride and a diol, etc.) and polycondensation (e.g., the reaction between a dicarboxylic acid and a diol, the reaction between a dicarboxylic acid and a diamine, etc.). Among others, the synthesis by polyaddition reaction is especially preferred because of milder reaction conditions enough to protect the dye structure against degradation. For sequential polymerization, known reaction conditions can be applied. During sequential polymerization, the peak area occupied by components having a molecular weight of 20,000 or more can be conveniently reduced to 10% or less of the total peak area in the molecular weight distribution of resin (A) by applying (i) the preparation process involving a polymerization reaction in the presence of a polymerization inhibitor as described above. Further, the sequential polymerization may be followed by (ii) the preparation process involving adding a poor solvent (such as water) for high molecular weight components of 20,000 or more to the polymerization solution obtained and removing the precipitated high molecular weight components of 20,000 or more by filtration as described above.

Specific examples of structural units represented by formula (C) are shown below, but the present invention is not limited to these examples.

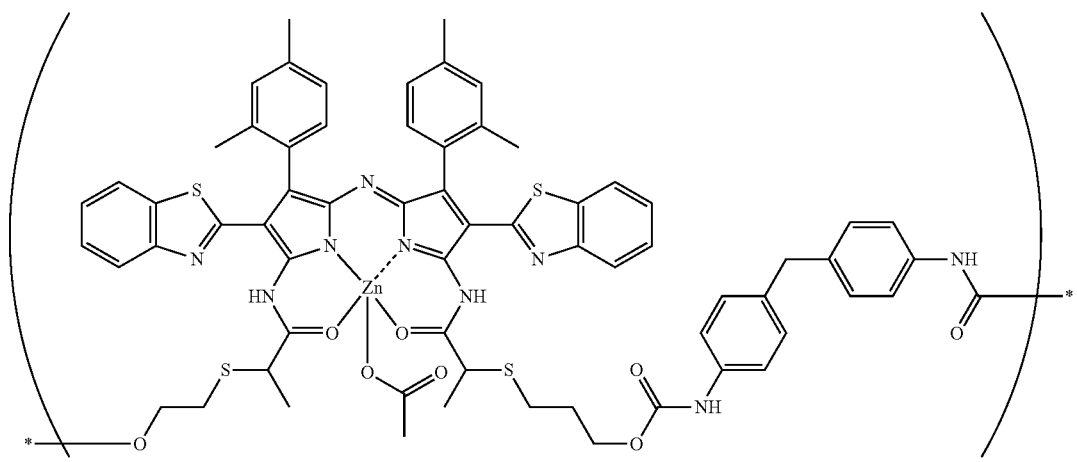

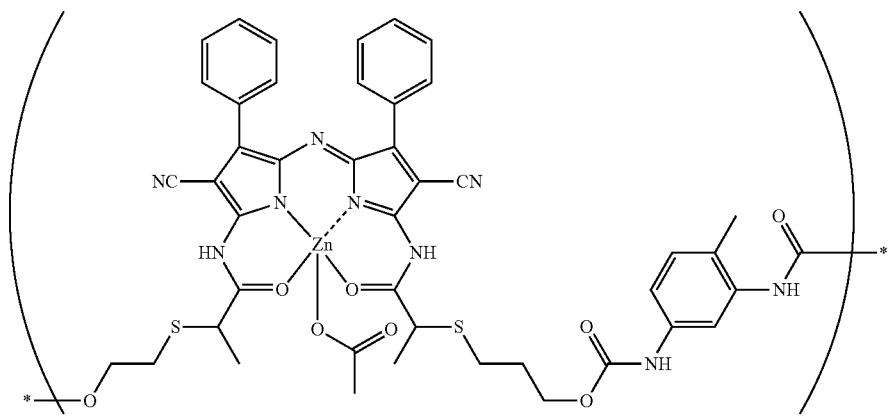

-continued

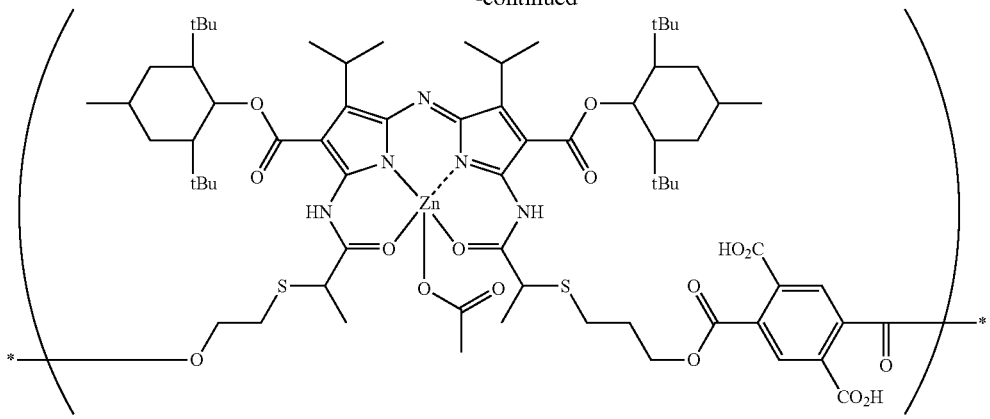

Among the resins having a dye structure comprising a structural unit represented by formula (A), formula (B) and/or formula (C), the resins having a dye structure comprising a structural unit represented by formula (A) and formula (C) comprise substructures derived from a dye linked via covalent bonds in the molecular structure so that colored compositions containing the resins having a dye structure are excellent in heat resistance. Thus, the colored compositions are preferably applied to patterning involving high temperature processes because they are effective for preventing color migration to adjacent other colored patterns. Especially, the compound represented by formula (A) is preferred because the molecular weight of the resin having a dye structure can be readily controlled.

(Polymerizable Group Contained in the Resin Having a Dye Structure (A))

The resin having a dye structure (A) in the present invention preferably contains a polymerizable group. This allows cured colored films to be formed with highlight resistance, heat resistance, solvent resistance and the like even in thin layers as well as good patternability. Polymerizable groups that can be used include known polymerizable groups that can be crosslinked by free radical mechanism or exposure to acids or heat, e.g., ethylenically unsaturated bond-containing groups, cyclic ethers (epoxy, oxetane), methylol and the like, especially preferably ethylenically unsaturated bond-containing groups, more preferably (meth)acryloyl, most preferably (meth)acryloyl derived from glycidyl(meth)acrylate and 3,4-epoxy-cyclohexylmethyl(meth)acrylate.

The method for introducing a polymerizable group include: (1) modifying a resin having a dye structure with a compound containing a polymerizable group to introduce it, or (2) copolymerizing a dye monomer with a compound containing a polymerizable group to introduce it, or the like. A detailed description is as follows.

(1) Modifying a Resin Having a Dye Structure with a Compound Containing a Polymerizable Group to Introduce It Any known method for modifying a resin having a dye structure with a compound containing a polymerizable group to introduce it can be used without specific limitation. For example, it preferably includes the following methods for convenience of preparation: (a) reacting a carboxylic acid contained in the resin having a dye structure with an unsaturated bond epoxy-containing compound; (b) reacting a hydroxyl or amino group contained in the resin having a dye structure with an unsaturated bond-containing isocyanate compound; and (c) reacting an epoxy compound contained in the resin having a dye structure with an unsaturated bond-containing carboxylic acid compound.

In the method (a) reacting a carboxylic acid contained in the resin having a dye structure with an unsaturated bond-containing epoxy compound, the unsaturated bond-containing epoxy compound includes glycidyl methacrylate, glycidyl acrylate, allylglycidyl ether, 3,4-epoxycyclohexylmethyl acrylate, 3,4-epoxycyclohexylmethyl methacrylate and the like, among which glycidyl methacrylate and 3,4-epoxycyclohexylmethyl methacrylate are especially preferred because of excellent crosslinking properties and shelf stability. Known reaction conditions can be used.

In the method (b) reacting a hydroxyl or amino group contained in the resin having a dye structure with an unsaturated bond-containing isocyanate compound, the unsaturated bond-containing isocyanate compound includes 2-isocyanatoethyl methacrylate, 2-isocyanatoethyl acrylate, 1,1-bis(acryloyloxymethyl)ethyl isocyanate and the like, among which 2-isocyanatoethyl methacrylate is preferred because of excellent crosslinking properties and shelf stability. Known reaction conditions can be used.

In the method (c) reacting an epoxy compound contained in the resin having a dye structure with an unsaturated bond-containing carboxylic acid compound, the unsaturated bond-containing carboxylic acid compound is not specifically limited, and any known carboxylic acid compound containing a (meth)acryloyloxy group can be used, but methacrylic acid and acrylic acid are preferred, and methacrylic acid is especially preferred because of excellent crosslinking properties and shelf stability. Known reaction conditions can be used.

(2) Copolymerizing a Dye Monomer with a Compound Containing a Polymerizable Group to Introduce it Any known method for (2) copolymerizing a dye monomer with a compound containing a polymerizable group to introduce it can be used without specific limitation, but it preferably includes the following methods: (d) copolymerizing a radically polymerizable dye monomer with a radically polymerizable group-containing compound, and (e) copolymerizing an addition-polymerizable dye monomer with an addition-polymerizable group-containing compound.

In the method (d) copolymerizing a radically polymerizable dye monomer with a radically polymerizable group-containing compound, the radically polymerizable group-containing compound specifically includes allyl-containing compounds (e.g., allyl(meth)acrylate and the like), epoxy-containing compounds (e.g., glycidyl(meth)acrylate, 3,4-epoxycyclohexylmethyl(meth)acrylate and the like), oxetane-containing compounds (e.g., 3-methyl-3-oxetanylmethyl (meth)acrylate and the like), methylol-containing compounds (e.g., N-(hydroxymethyl)acrylamide and the like), especially preferably epoxy compounds and oxetane compound. Known reaction conditions can be used.

In the method (e) copolymerizing an addition-polymerizable dye monomer with an addition-polymerizable group-containing compound, the addition-polymerizable group-containing compound includes unsaturated bond-containing diol compounds (e.g., 2,3-dihydroxypropyl(meth)acrylate and the like). Known reaction conditions can be used.

The method for introducing a polymerizable group most preferably includes reacting a carboxylic acid contained in the resin having a dye structure with an unsaturated bond-containing epoxy compound.

The amount of the polymerizable group contained in the resin having a dye structure (A) is preferably 0.1 to 2.0 mmol, more preferably 0.2 to 1.5 mmol, most preferably 0.3 to 1.0 mmol per gram of the resin having a dye structure (A)

The method for introducing the polymerizable group most preferably includes reacting a carboxylic acid contained in the resin having a dye structure with an unsaturated bond-containing epoxy compound.

Specific examples of structural units having the polymerizable groups are shown below. However, the present invention is not limited to these examples.

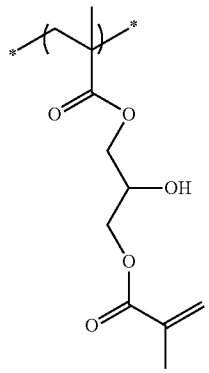
(G-1)

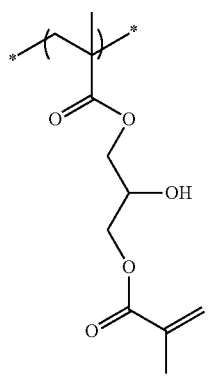
(G-2)

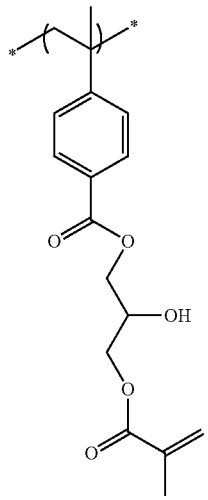
(G-3)

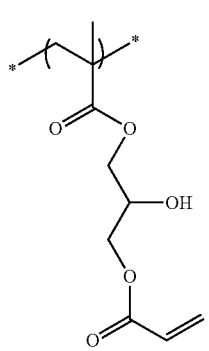
(G-4)

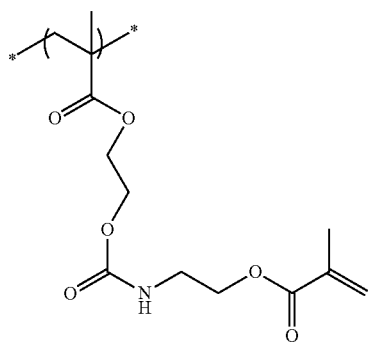
(G-5)

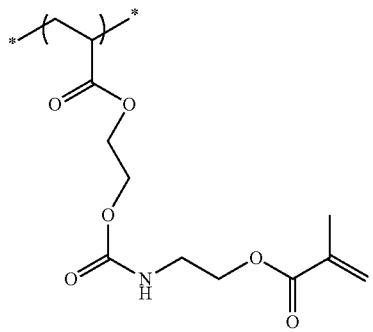
(G-6)

(G-7)
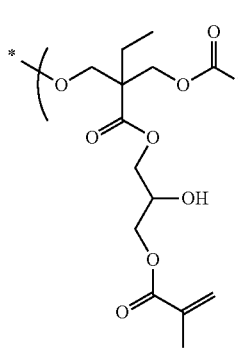
(G-8)
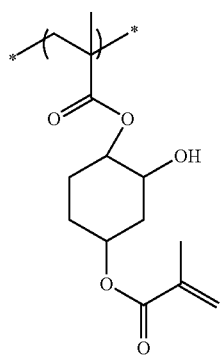
(G-9)
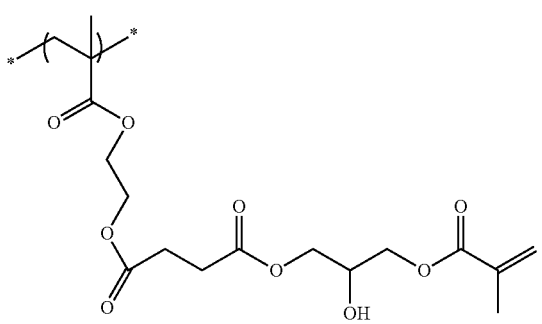
(G-10)
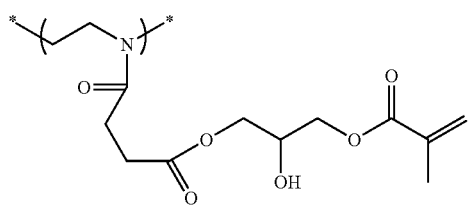
(G-11)
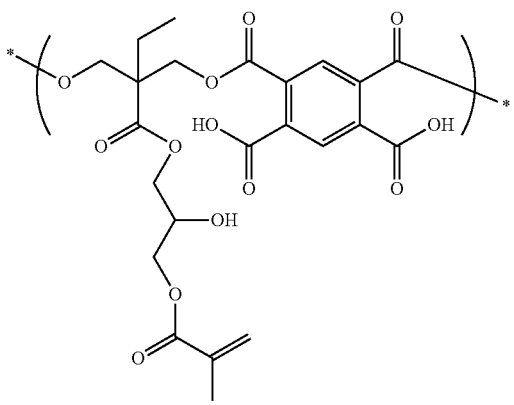
(G-12)
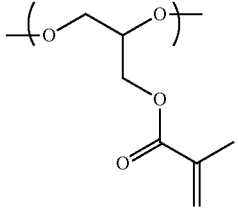
(G-13)
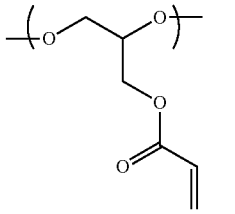
(G-14)
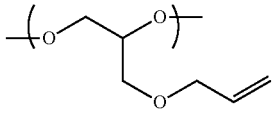
(G-15)
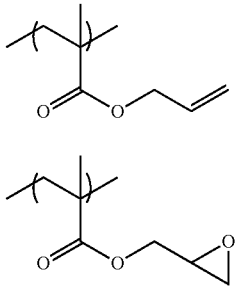
(G-16)
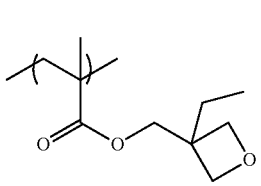
(G-17)
Among the specific examples shown above, ethylenically unsaturated bond-containing dye monomers are preferred, among which methacryloyl, acryloyl, styryl, or vinyloxy is preferred, most preferably methacryloyl because of adhesion to the substrate and surface roughness.

(Other Functional Groups Contained in the Resin Having a Dye Structure (A))

The resin having a dye structure (A) in the present invention may contain other functional groups. The other functional groups preferably include an alkali-soluble group such as carboxylic acid, sulfonic acid, phosphoric acid and phenolic hydroxyl. The alkali-soluble group is most preferably a carboxylic acid.

The method for introducing an alkali-soluble group into the resin having a dye structure includes preliminarily introducing the alkali-soluble group into a dye monomer, and copolymerizing a monomer having the alkali-soluble group other than dye monomers ((meth)acrylic acid, caprolactone-modified acrylic acid, succinic anhydride-modified 2-hydroxyethyl(meth)acrylate, phthalic anhydride-modified 2-hydroxyethyl(meth)acrylate, 1,2-cyclohexane dicarboxylic anhydride-modified 2-hydroxyethyl(meth)acrylate; carboxylic acid-containing monomers such as styrenecarboxylic acid, itaconic acid, maleic acid, norbornenecarboxylic acid; phosphoric acid-containing monomers such as acid phosphooxyethyl methacrylate, vinylphosphonic acid; sulfonic acid-containing monomers such as vinylsulfonic acid, 2-acrylamide-2-methylsulfonic acid), most preferably a combination of both methods.

The amount of the alkali-soluble group (acid value) contained in the resin having a dye structure (A) is preferably 0.3 mmol to 2.0 mmol, more preferably 0.4 mmol to 1.5 mmol, most preferably 0.5 mmol to 1.0 mmol per gram of the resin having a dye structure (A).

In the present invention, the acid value of the resin having a dye structure can be calculated from, for example, the average content of the alkali-soluble group (acid group) in the resin having a dye structure. Further, a resin having a desired acid value can be obtained by changing the content of the repeat unit (structural unit) containing an acid group constituting the resin having a dye structure.

Other functional groups contained in the resin having a dye structure (A) include development-promoting groups such as lactone, acid anhydrides, amides, —COCH₂CO—, cyano and the like; hydrophilic/hydrophobic balance controlling groups such as long-chain and cyclic alkyl, aralkyl, aryl, polyalkylene oxide, hydroxyl, maleimide, amino and the like, and they can be introduced as appropriate.

The method for introducing such a functional group includes preliminarily introducing it into a dye monomer, and copolymerizing a monomer having the functional group.

Specific examples of repeat units having the other functional groups contained in the resin having a dye structure (A) are shown below, but the present invention is not limited to these examples.

(H-1)

(H-2)

(H-3)

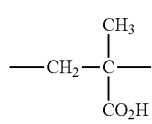
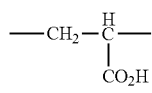
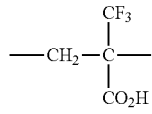

(H-4)
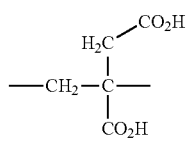

(H-5)
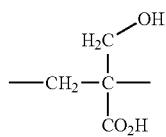

(H-6)
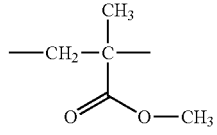

(H-7)
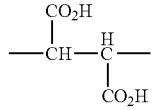

(H-8)
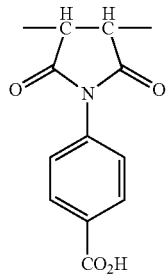

(H-9)
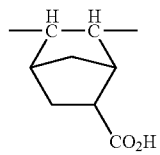

(H-10)
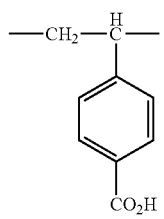

(H-11)
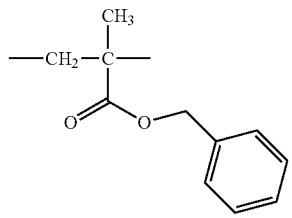

(H-12)
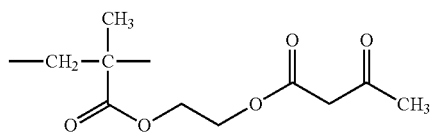

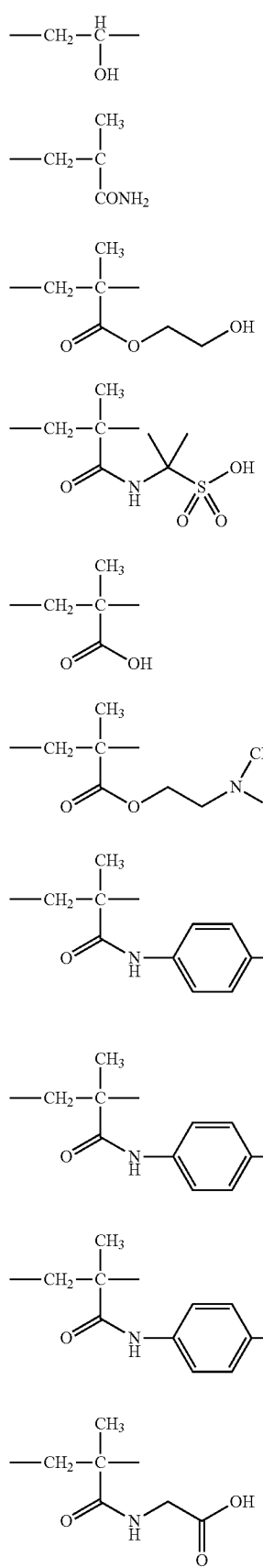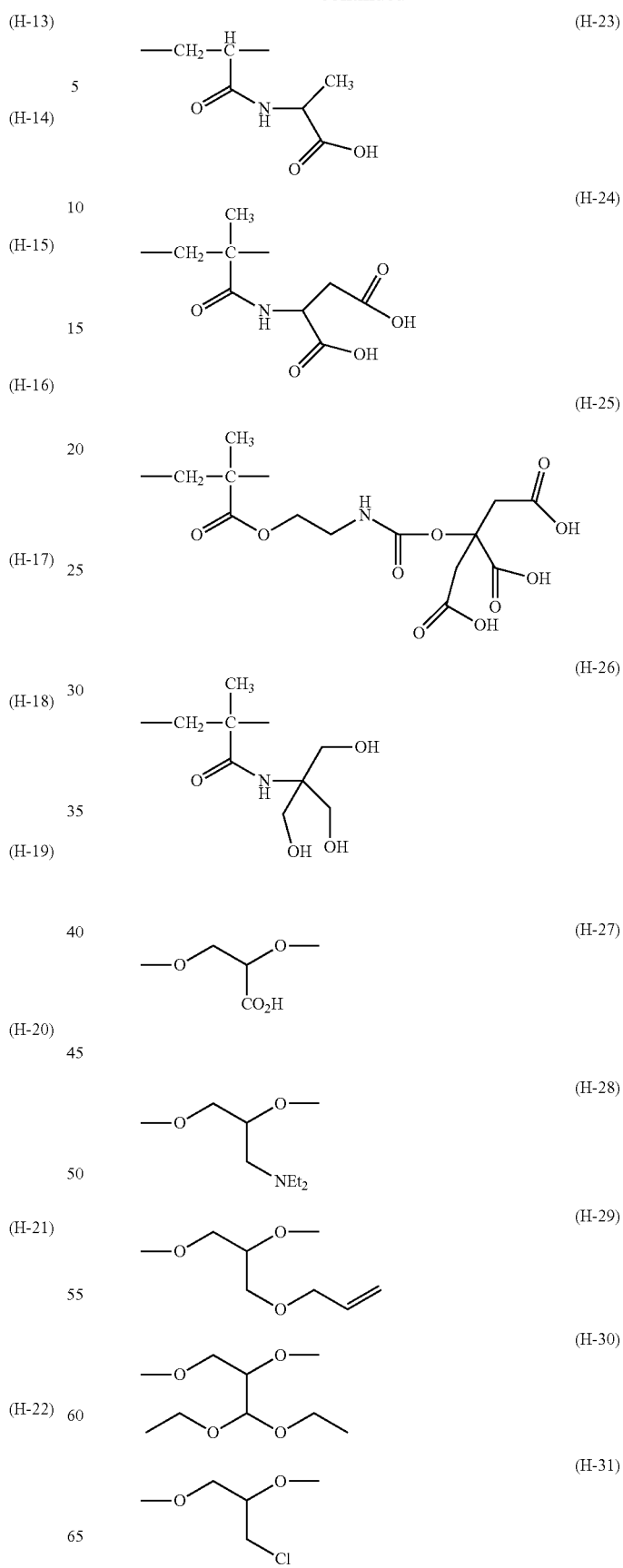

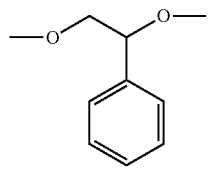
(H-32)

The resin having a dye structure (A) according to the present invention preferably has a Tg of 50° C. or more, more preferably 100° C. or more. Further, the temperature at which a weight loss of 5% occurs is preferably 120° C. or more, more preferably 150° C. or more, even more preferably 200° C. or more as measured by thermogravimetric analysis (TGA). If it is in these ranges, the variation in concentration caused by heat processes can be reduced when the colored compositions of the present invention are applied for the preparation of color filters and the like.

The resin having a dye structure according to the present invention also preferably has an absorption coefficient per unit weight (hereinafter referred to as $\epsilon'$, where $\epsilon'=\epsilon$/average molecular weight in L/g*cm) of 30 or more, more preferably 60 or more, even more preferably 100 or more. When it is in the above ranges, color filters with good color reproducibility can be prepared by applying the colored compositions of the present invention.

The molar absorption coefficient of the resin having a dye structure (A) used in the colored compositions of the present invention is preferably as high as possible to improve colorability.

The resin having a dye structure (A) according to the present invention is preferably a compound soluble in the organic solvents listed below.

It is preferably soluble at 1% by mass or more and 50% by mass or less, more preferably 5% by mass or more and 40% by mass or less, even more preferably 10% by mass or more and 30% by mass or less in organic solvents such as esters (e.g., methyl 3-ethoxypropionate, ethyl 3-ethoxypropionate, ethyl lactate, butyl acetate, methyl 3-methoxypropionate and the like), ethers (e.g. methyl cellosolve acetate, ethyl cellosolve acetate, propylene glycol monomethyl ether, propylene glycol monomethyl ether acetate and the like), ketones (e.g., methyl ethyl ketone, cyclohexanone, 2-heptanone, 3-heptanone and the like), aromatic hydrocarbons (e.g., toluene, xylene and the like). If the solubility is in these ranges, a favorable coating surface profile can be attained or the decrease in concentration due to dissolution after coating of other colors can be reduced when the colored compositions of the present invention are applied for the preparation of color filters and the like.

In the colored compositions of the present invention, the resin having a dye structure may be used alone or a combination of two or more such resins may be used.

In the present invention, curable green-colored compositions can be preferably provided especially by adding a yellow dye compound. The curable green-colored compositions thus provided have high color purity so that liquid crystal display devices and solid-state image sensors using them can display images with bright colors and high contrast.

The amount of the yellow dye compound added is preferably 1% by mass to 70% by mass, more preferably 10% by mass to 50% by mass based on the total solids of the curable colored compositions of the present invention.

Alternatively, the amount of the yellow dye compound added is preferably 10 parts by mass to 1000 parts by mass, more preferably 20 parts by mass to 500 parts by mass per 100 parts by mass of the dye compound of the present invention represented by formula (1).

[Polymerizable Compounds]

The colored compositions of the present invention preferably contain at least one polymerizable compound. The polymerizable compound may include, for example, an addition-polymerizable compound having at least one ethylenically unsaturated double bond.

Specifically, it is selected from compounds having at least one, preferably two or more ethylenically unsaturated terminal bonds. Such compounds are commonly known in the field of industry, and can be used in the present invention without specific limitation. These may be in any chemical forms such as, e.g., monomers, prepolymers, i.e., dimers, trimers and oligomers, or mixtures thereof and (co)polymers thereof.

Examples of monomers and (co)polymers thereof include unsaturated carboxylic acids (e.g., acrylic acid, methacrylic acid, itaconic acid, crotonic acid, isocrotonic acid, maleic acid and the like) and their esters, amides, and (co)polymers thereof, preferably esters of unsaturated carboxylic acids and aliphatic polyalcohol compounds, amides of unsaturated carboxylic acids and aliphatic polyamine compounds, and (co)polymers thereof. Further, the reaction products of unsaturated carboxylic acid esters or amides having a nucleophilic substituent such as a hydroxyl, amino or mercapto group by addition reaction with monofunctional or polyfunctional isocyanates or epoxies or by dehydrative condensation reaction with monofunctional or polyfunctional carboxylic acid and the like can also be conveniently used. Furthermore, the addition reaction products of unsaturated carboxylic acid esters or amides having an electrophilic substituent such as isocyanate or epoxy with monofunctional or polyfunctional alcohols, amines or thiols are also preferred, as well as the substitution reaction products of unsaturated carboxylic acid esters or amides having an eliminatable substituent such as halogen or tosyloxy with monofunctional or polyfunctional alcohols, amines or thiols. As alternative examples, compounds obtained by replacing the unsaturated carboxylic acids by unsaturated phosphonic acids, styrene, vinyl ethers or the like can also be used.

Specific examples of ester monomers of aliphatic polyalcohol compounds and unsaturated carboxylic acids include acrylic acid esters such as, e.g., ethylene glycol diacrylate, triethylene glycol diacrylate, 1,3-butanediol diacrylate, tetramethylene glycol diacrylate, propylene glycol diacrylate, neopentyl glycol diacrylate, trimethylolpropane triacrylate, trimethylolpropanetri(acryloyloxypropyl)ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol hexaacrylate, sorbitol triacrylate, sorbitol tetraacrylate, sorbitol pentaacrylate, sorbitol hexaacrylate, tri(acryloyloxyethyl)isocyanurate, polyester acrylate oligomer, isocyanuric acid EO-modified triacrylate and the like;

methacrylic acid esters such as, e.g., tetramethylene glycol dimethacrylate, triethylene glycol dimethacrylate, neopentyl glycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, sorbitol trimethacrylate, sorbitol tetramethacrylate, bis[p-(3-methacryloxy-2-hydroxypropoxy)phenyl]dimethylmethane, bis[p-(methacryloxyethoxy)phenyl]dimethylmethane and the like;

itaconic acid esters such as, e.g., ethylene glycol diitaconate, propylene glycol diitaconate, 1,3-butanediol diitaconate, 1,4-butanediol diitaconate, tetramethylene glycol diitaconate, pentaerythritol diitaconate, sorbitol tetraitaconate and the like;

crotonic acid ester such as, e.g., ethylene glycol dicrotonate, tetramethylene glycol dicrotonate, pentaerythritol dicrotonate, sorbitol tetradicrotonate and the like;

isocrotonic acid ester such as, e.g., ethylene glycol diisocrotonate, pentaerythritol diisocrotonate, sorbitol tetraisocrotonate and the like;

maleic acid esters such as, e.g., ethylene glycol dimaleate, triethylene glycol dimaleate, pentaerythritol dimaleate, sorbitol tetramaleate and the like.

Other esters can also be conveniently used, including e.g., the aliphatic alcohol esters described in JP-B-S51-47334, and JP-A-S57-196231; the esters having an aromatic skeleton described in JP-A-S59-5240, JP-A-S59-5241, and JP-A-H2-226149; the amino-containing esters described in JP-A-H1-165613 and the like. Further, the ester monomers listed above can also be used as mixtures.

Specific examples of amide monomers of aliphatic polyamine compounds and unsaturated carboxylic acids include methylenebisacrylamide, methylenebismethacrylamide, 1,6-hexamethylenebisacrylamide, 1,6-hexamethylenebismethacrylamide, diethylenetriamine trisacrylamide, xylylenebisacrylamide, xylylenebismethacrylamide and the like.

Examples of other preferred amide monomers include those having a cyclohexylene structure described in JP-B-S54-21726.

Urethane addition-polymerizable compounds prepared by using an addition reaction of isocyanate and hydroxyl are also preferred, specific examples of which include, for example, the vinyl urethane compounds containing two or more polymerizable vinyl groups in one molecule obtained by adding a hydroxyl-containing vinyl monomer represented by formula (B) below to a polyisocyanate compound containing two or more isocyanates in one molecule described in JP-B-S48-41708 and the like.

(B)

In formula (B), R and R' each independently represent H or $CH_3$.

Details of the method of using these polymerizable compounds including their structure, whether they are to be used alone or in combination, the amount to be added and the like can be selected at will to suit the final performance design of the curable colored compositions. For example, preferred structures contain much unsaturated groups per molecule and in many cases, preferably have a functionality of two or more to improve sensitivity. To increase the strength of cured colored films, those having a functionality of three or more are preferred, and both sensitivity and strength can be optimized by using compounds having different functionalities/different polymerizable groups (e.g., acrylic acid esters, methacrylic acid esters, styrene compounds, vinyl ether compounds) in combination. The method for selecting/using polymerizable compounds is also an important factor for compatibility and dispersibility with other components contained in the curable colored compositions (e.g., photoinitiators, colorants (pigments), binder polymers and the like), and for example, compatibility can be sometimes improved by using low-purity compounds or combining two or more compounds. It is also possible to select a specific structure to improve adhesion to hard surfaces such as base materials.

The content of the polymerizable compounds (the total content if two or more compounds are used) based on the total solids of the colored compositions is not specifically limited, but preferably 10% by mass to 80% by mass, more preferably 15% by mass to 75% by mass, especially preferably 20% by mass to 60% by mass to achieve the advantages of the present invention more effectively.

[Photoinitiators]

The colored compositions of the present invention preferably contain at least one photoinitiator. The photoinitiators is not specifically limited so far as it allows the polymerizable compound to be polymerized, and it is preferably selected based on the properties, initiation efficiency, absorption wavelength, availability, cost and other factors.

Photoinitiators include, for example, at least one active halogen compound selected from halomethyl oxadiazole compounds and halomethyl-s-triazine compounds, 3-aryl-substituted coumarin compounds, lophine dimers, benzophenone compounds, acetophenone compounds and derivatives thereof, cyclopentadiene-benzene-iron complexes and salts thereof, oxime compounds and the like. Specific examples of photoinitiators include those described in paragraphs [0070] to [0077] of JP-A2004-295116. Among others, oxime compounds are preferred because of rapid polymerization reaction or for other reasons.

The oxime compounds (hereinafter also referred to as "oxime photoinitiators") are not specifically limited, and include, for example, the oxime compounds described in JP-A2000-80068, WO02/100903A1, JP-A2001-233842, etc. Specific examples include 2-(O-benzoyloxime)-1-[4-(phenylthio)phenyl]-1,2-butanedione, 2-(O-benzoyloxime)-1-[4-(phenylthio)phenyl]-1,2-pentanedione, 2-(O-benzoyloxime)-1-[4-(phenylthio)phenyl]-1,2-hexanedione, 2-(O-benzoyloxime)-1-[4-(phenylthio)phenyl]-1,2-heptanedione, 2-(O-benzoyloxime)-1-[4-(phenylthio)phenyl]-1,2-octanedione, 2-(O-benzoyloxime)-1-[4-(methylphenylthio)phenyl]-1,2-butanedione, 2-(O-benzoyloxime)-1-[4-(ethylphenylthio)phenyl]-1,2-butanedione, 2-(O-benzoyloxime)-1-[4-(butylphenylthio)phenyl]-1,2-butanedione, 1-(O-acetyloxime)-1-[9-ethyl-6-(2-methylbenzoyl)-9H-carbazole-3-yl]ethanone, 1-(O-acetyloxime)-1-[9-methyl-6-(2-methylbenzoyl)-9H-carbazole-3-yl]ethanone, 1-(O-acetyloxime)-1-[9-propyl-6-(2-methylbenzoyl)-9H-carbazole-3-yl]ethanone, 1-(O-acetyloxime)-1-[9-ethyl-6-(2-ethylbenzoyl)-9H-carbazole-3-yl]ethanone, 1-(O-acetyloxime)-1-[9-ethyl-6-(2-butylbenzoyl)-9H-carbazole-3-yl]ethanone and the like. However, the present invention is not limited to these examples.

In the present invention, the oxime compounds are more preferably compounds represented by formula (11) below because of sensitivity, stability over time and discoloration during post-heating.

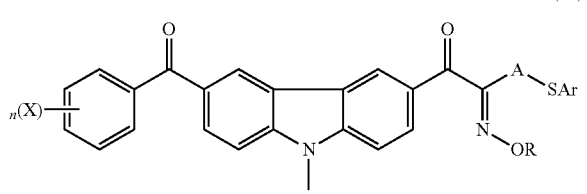

Formula (11)

In formula (11) above, R and X each independently represent a monovalent substituent, A represents a divalent organic group, and Ar represents an aryl. n is an integer of 1 to 5.

Preferably, R is acyl to increase sensitivity, specifically acetyl, propionyl, benzoyl, toluoyl.

Preferably, A is an unsubstituted alkylene, an alkylene substituted by an alkyl (e.g., methyl, ethyl, tert-butyl, dodecyl), an alkylene substituted by an alkenyl (e.g., vinyl, allyl), or an alkylene substituted by an aryl (e.g., phenyl, p-tolyl, xylyl, cumenyl, naphthyl, anthryl, phenanthryl, styryl) to increase sensitivity and prevent discoloration by heat over time.

Preferably, Ar is a substituted or unsubstituted phenyl to increase sensitivity and prevent discoloration by heat over time. In the case of a substituted phenyl, the substituent preferably includes, for example, a halogen such as fluorine atom, chlorine atom, bromine atom, iodine atom or the like.

Preferably, X is an optionally substituted alkyl, optionally substituted aryl, optionally substituted alkenyl, optionally substituted alkynyl, optionally substituted alkoxy, optionally substituted aryloxy, optionally substituted alkylthioxy, optionally substituted arylthioxy, or optionally substituted amino to improve solvent-solubility and absorption efficiency in long wavelength regions.

In formula (11), n is preferably 1 or 2.

In the curable colored compositions of the present invention, not only the photoinitiators described above but also other known photoinitiators described in paragraph [0079] of JP-A2004-295116 may be used.

The photoinitiators can be contained alone or as a combination of two or more of them.

The content of the photoinitiators (the total content if two or more initiators are used) based on the total solids of the curable colored compositions is preferably 3% by mass to 20% by mass, more preferably 4% by mass to 19% by mass, especially preferably 5% by mass to 18% by mass to achieve the advantages of the present invention more effectively.

[Organic Solvents]

The curable colored compositions of the present invention can contain at least one organic solvent.

Basically, the organic solvent is not specifically limited so far as it can satisfy the solubility of various coexisting components in it and the coatability of the resulting curable colored compositions, and it is preferably selected on the basis of the solubility of binders, coatability and safety.

Organic solvents preferably include esters such as, e.g., ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate, ethyl lactate, oxyacetic acid alkyl esters (e.g., methyl oxyacetate, ethyl oxyacetate, butyl oxyacetate (specifically, methyl methoxyacetate, ethyl methoxyacetate, butyl methoxyacetate, methyl ethoxyacetate, ethyl ethoxyacetate and the like)), 3-oxypropionic acid alkyl esters (e.g., methyl 3-oxypropionate, ethyl 3-oxypropionate and the like (specifically, methyl 3-methoxypropionate, ethyl 3-methoxypropionate, methyl 3-ethoxypropionate, ethyl 3-ethoxypropionate and the like)), 2-oxypropionic acid alkyl esters (e.g., methyl 2-oxypropionate, ethyl 2-oxypropionate, propyl 2-oxypropionate and the like (specifically, methyl 2-methoxypropionate, ethyl 2-methoxypropionate, propyl 2-methoxypropionate, methyl 2-ethoxypropionate, ethyl 2-ethoxypropionate and the like), methyl 2-oxy-2-methylpropionate and ethyl 2-oxy-2-methylpropionate (specifically, methyl 2-methoxy-2-methylpropionate, ethyl 2-ethoxy-2-methylpropionate and the like)), methyl pyruvate, ethyl pyruvate, propyl pyruvate, methyl acetoacetate, ethyl acetoacetate, methyl 2-oxobutanoate, ethyl 2-oxobutanoate and the like;

ethers such as, e.g., diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol monomethyl ether, propylene glycol monomethyl ether acetate, propylene glycol monoethyl ether acetate, propylene glycol monopropyl ether acetate and the like;

ketones such as, e.g., methyl ethyl ketone, cyclohexanone, 2-heptanone, 3-heptanone and the like; and aromatic hydrocarbons such as, e.g., toluene, xylene and the like.

These organic solvent are also preferably used as a mixture of two or more of them to improve the solubility of the various components described above, and the solubility of alkali-soluble binders, if present, the coating surface profile or the like. In this case, especially preferred are mixed solutions composed of two or more members selected from methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, propylene glycol methyl ether, and propylene glycol methyl ether acetate.

The organic solvents are preferably contained in the curable colored compositions in such an amount that the total solids content in the compositions is 10% by mass to 80% by mass, more preferably 15% by mass to 60% by mass.

[Other Components]

In addition to the components described above, the curable colored compositions of the present invention may further contain other components such as alkali-soluble binders, crosslinking agents and the like so far as the benefits of the present invention are not affected.

Alkali-Soluble Binders

Alkali-soluble binders are not specifically limited so far as they are soluble in alkalis, and can be preferably selected based on heat resistance, developability, availability and the like.

Preferred alkali-soluble binders are high-molecular weight organic linear polymers that are soluble in organic solvents and developable with aqueous weak bases. Such high-molecular weight organic linear polymers include polymers having a carboxylic acid in the side chain such as, e.g., the methacrylic acid copolymers, acrylic acid copolymers, itaconic acid copolymers, crotonic acid copolymers, maleic acid copolymers, partially esterified maleic acid copolymers and the like as described in JP-A-S59-44615, JP-B-S54-34327, JP-B-S58-12577, JP-B-S54-25957, JP-A-S59-53836, and JP-A-S59-71048, as well as acidic cellulose derivatives having a carboxylic acid in the side chain.

In addition to those described above, other useful alkali-soluble binders in the present invention include the addition reaction products of hydroxyl-containing polymers with acid anhydrides, polyhydroxystyrene resins, polysiloxane resins, poly(2-hydroxyethyl(meth)acrylate), polyvinylpyrrolidone, polyethylene oxide, polyvinyl alcohol and the like. Further, the high-molecular weight organic linear polymers may be copolymers of hydrophilic monomers. Examples of them include alkoxyalkyl(meth)acrylate, hydroxyalkyl(meth)acrylate, glycerol(meth)acrylate, (meth)acrylamide, N-methylol acrylamide, secondary or tertiary alkyl acrylamide, dialkylaminoalkyl(meth)acrylate, morpholine (meth)acrylate, N-vinylpyrrolidone, N-vinylcaprolactam, vinylimidazole, vinyltriazole, methyl(meth)acrylate, ethyl(meth)acrylate, branched or straight-chain propyl(meth)acrylate, branched or straight-chain butyl(meth)acrylate, or phenoxyhydroxypropyl(meth)acrylate and the like. Other useful hydrophilic monomers include monomers containing tetrahydrofurfuryl, phosphoric acid, phosphoric acid ester, quaternary ammonium salt, ethyleneoxy chain, propyleneoxy chain, sulfonic acid and groups derived from salts thereof, morpholinoethyl and the like.

To improve the crosslinking efficiency, the alkali-soluble binders may have a polymerizable group in the side chain, in which case polymers containing allyl, (meth)acryl, allyloxyalkyl or the like in the side chain and the like are also useful, for example. Examples of the polymers having a polymerizable group include commercial products such as KS RESIST-106 (from Osaka Organic Chemical Industry Ltd.), CYCLOMER P Series (from Daicel Chemical Industries, Ltd.) and the like. Further, alcohol-soluble nylons or polyethers of 2,2-bis-(4-hydroxyphenyl)propane with epichlorohydrin and the like are also useful to increase the strength of the cured films.

Among these various alkali-soluble binders, polyhydroxystyrene resins, polysiloxane resins, acrylic resins, acrylamide resins, and acrylic/acrylamide copolymer resins are preferred to improve heat resistance, while acrylic resins, acrylamide resins, and acrylic/acrylamide copolymer resins are preferred for optimizing developability.

The acrylic resins preferably include copolymers composed of monomers selected from benzyl(meth)acrylate, (meth)acrylic acid, hydroxyethyl(meth)acrylate, (meth)acrylamide and the like, and commercial products such as KS RESIST-106 (from Osaka Organic Chemical Industry Ltd.), CYCLOMER P Series (from Daicel Chemical Industries, Ltd.) and the like.

The alkali-soluble binders are preferably polymers having a weight average molecular weight (determined as a polystyrene equivalent molecular weight by GPC) of 1000 to $2\times10^5$, more preferably 2000 to $1\times10^5$, especially preferably 5000 to $5\times10^4$ to improve developability, liquid viscosity and the like.

Crosslinking Agents

In the curable colored compositions of the present invention, a crosslinking agent can additionally be used to further increase the hardness of cured colored films obtained by curing the curable colored compositions.

The crosslinking agent is not specifically limited so far as it allows films to be cured by crosslinking reaction, and includes, for example, (a) epoxy resins, (b) melamine compounds, guanamine compounds, glycoluril compounds or urea compounds substituted by at least one substituent selected from methylol, alkoxymethyl and acyloxymethyl, (c) phenol compounds, naphthol compounds or hydroxyanthracene compounds substituted by at least one substituent selected from methylol, alkoxymethyl and acyloxymethyl, among which polyfunctional epoxy resins are preferred.

Details of specific examples of crosslinking agents and the like can be found in paragraphs [0134] to [0147] of JP-A2004-295116.

Surfactants

The curable colored compositions of the present invention may contain a surfactant. Any of anionic, cationic, nonionic or zwitterionic surfactants can be used, but preferred surfactants are nonionic surfactants. Examples of nonionic surfactants include polyoxyethylene higher alkyl ethers, polyoxyethylene higher alkylphenyl ethers, higher fatty acid diesters of polyoxyethylene glycol, silicone surfactants, and fluorosurfactants. Commercial products include those available under the brand name series KP (from Shin-Etsu Chemical Co., Ltd.), POLYFLOW (from Kyoeisha Chemical Co., Ltd.), Eftop (from JEMCO), Megafac (from DIC Corporation), Fluorad (from Sumitomo 3M Limited), AsahiGuard and SURFLON (from ASAHI GLASS CO., LTD.), PolyFox (from OMNOVA) and the like.

Further, preferred examples of surfactants include copolymers comprising the structural unit A and structural unit B shown below as repeat units and having a weight average molecular weight (Mw) of 1,000 to 10,000, as determined as a polystyrene equivalent molecular weight by GPC.

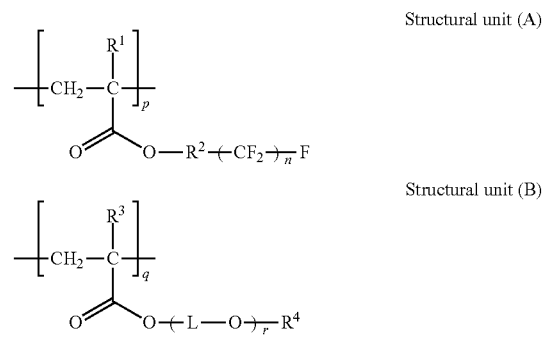

In structural units (A) and (B), R1 and R3 each independently represent a hydrogen atom or methyl, R2 represents a straight-chain alkylene containing 1 to 4 carbon atoms, R4 represents a hydrogen atom or an alkyl containing 1 to 4 carbons, L represents an alkylene containing 3 to 6 carbon atoms, preferably a branched alkylene represented by the formula below:

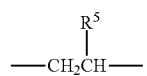

wherein R5 represents an alkyl containing 1 to 4 carbon atoms, preferably an alkyl containing 1 to 3 carbon atoms because of the compatibility and the wettability on the substrate surface, more preferably an alkyl containing 2 or 3 carbon atoms, p and q are the weight percentages representing the monomer ratios in the polymer, p represents a value of 10% by weight to 80% by weight, q represents a value of 20% by weight to 90% by weight, r represents an integer of 1 to 18, and n represents an integer of 1 to 10.

More preferably, surfactants consisting of copolymers comprising structural unit A and structural unit B as repeat units have a weight average molecular weight (Mw) of 1,500 to 5,000.

These surfactants may be used alone or as a mixture of two or more of them.

The amount of the surfactants incorporated into the curable colored compositions of the present invention is preferably 10 parts by weight or less, more preferably 0.01 to 10 parts by weight, even more preferably 0.01 to 1 part by weight per 100 parts by mass of the total of the other components.

Other Additives

The curable colored compositions of the present invention may optionally contain various additives such as e.g., fillers, polymer compounds other than those described above, accelerators, antioxidants, UV absorbers, deflocculating agents and the like. These additives include those described in paragraphs [0155] to [0156] of JP-A2004-295116.

The curable colored compositions of the present invention can contain the sensitizers and photostabilizers described in paragraph [0078] of JP-A2004-295116 and the thermal polymerization inhibitors described in ibid. paragraph [0081].

To promote the alkali solubility of unexposed regions to further improve the developability of the curable colored compositions, the compositions preferably contain an organic carboxylic acid, preferably a low-molecular weight organic carboxylic acid having a molecular weight of 1000 or less.

Specific examples include aliphatic monocarboxylic acids such as formic acid, acetic acid, propionic acid, butyric acid, valeric acid, pivalic acid, caproic acid, diethylacetic acid, enanthic acid, caprylic acid and the like; aliphatic dicarboxylic acids such as oxalic acid, malonic acid, succinic acid, glutaric acid, adipic acid, pimelic acid, suberic acid, azelaic acid, sebacic acid, brassylic acid, methylmalonic acid, ethylmalonic acid, dimethylmalonic acid, methylsuccinic acid, tetramethylsuccinic acid, citraconic acid and the like; aliphatic tricarboxylic acids such as tricarballylic acid, aconitic acid, camphoronic acid and the like; aromatic monocarboxylic acids such as benzoic acid, toluic acid, cuminic acid, hemellitic acid, mesitylenic acid and the like; aromatic polycarboxylic acids such as phthalic acid, isophthalic acid, terephthalic acid, trimellitic acid, trimesic acid, mellophanic acid, pyromellitic acid and the like; and other carboxylic acids such as phenylacetic acid, hydratropic acid, hydrocinnamic acid, mandelic acid, phenylsuccinic acid, atropic acid, cinnamic acid, methyl cinnamate, benzyl cinnamate, cinnamylidene acetic acid, coumaric acid, umbellic acid and the like.

Processes for Preparing the Curable Colored Compositions

The curable colored compositions of the present invention are prepared by mixing the components mentioned above and, if desired, optional components.

For preparing the curable colored compositions, various components of the curable colored compositions may be incorporated together, or various components may be dissolved/dispersed in solvents and then sequentially incorporated. The order of addition and operating conditions are not specifically limited. For example, all components may be dissolved/dispersed in a solvent simultaneously to prepare a composition, or if desired, two or more solutions/dispersions may be appropriately prepared from various components and mixed during use (during coating) to prepare a composition.

The curable colored compositions prepared as described above can be used after they are filtered off through a filter preferably having a pore size of about 0.01 µm to 3.0 µm, more preferably 0.05 µm to 0.5 µm or the like.

The curable colored compositions of the present invention can form cured colored films having excellent hue and contrast so that they can be conveniently used for forming colored pixels in color filters and the like used for liquid crystal display devices (LCDs) and solid-state image sensors (e.g., CCD, CMOS and the like) or for preparing inks for printing, inks for inkjet printing and paints and the like. Especially, they are suitable for forming colored pixels for liquid crystal display devices.

Color filters and processes for preparing them The color filters of the present invention comprise a colored region on a substrate. The colored region on the substrate consists of colored films of, e.g., red (R), green (G), blue (B) and the like forming pixels in the color filters. The color filters of the present invention are formed by incorporating a diarylmethane compound having a specific structure so that they display images with bright colors and high contrast and they are especially suitable for use in liquid crystal display devices.

The color filters of the present invention may be formed by any method that allows formation of a cured colored region (colored pattern) containing an arylmethane compound. Preferably, they are prepared by using a curable colored composition of the present invention.

Processes for preparing the color filters of the present invention comprise Step (A) applying a curable colored composition as described above on a base material to form a colored layer (also referred to as a colored composition layer), and Step (B) exposing the colored composition layer formed in Step (A) in a pattern (preferably through a mask) and developing uncured regions of the coating layer with a developer to form a colored region (colored pattern). Through these steps, a colored pattern consisting of primary colors (three or four colors) is formed, whereby a color filter can be obtained. In a preferred embodiment, the processes for preparing the color filters of the present invention further comprise Step (C) irradiating the colored pattern formed in Step (B) with UV light, and Step (D) heating the colored pattern irradiated with UV light in Step (C).

By using such a process, color filters for use in liquid crystal display devices or solid-state image sensors can be prepared with little difficulty in the process, high quality and low cost. The processes for preparing the color filters of the present invention are explained more specifically below.

Step (A)

In the processes for preparing the color filters of the present invention, a curable colored composition of the present invention as described above is first applied on a base material directly or via another layer by a desired coating method to form a coating layer of the curable colored composition (colored composition layer), and then precured (prebaked) as appropriate to dry the curable colored composition layer.

Base materials include, for example, non-alkali glass, sodium glass, Pyrex (registered trademark) glass, quartz glass, and these glasses having a transparent conducting layer deposited thereon for use in liquid crystal display devices and the like, or substrates for photoelectric transducers for use in solid-state image sensors and the like such as e.g., silicone substrates, plastic substrates or the like. On these base materials may be formed a black matrix separating pixels or a transparent resin layer to promote adhesion or for other purposes. Further, a primer layer may be provided on the base materials, if desired to improve adhesion to the overlying layers or to prevent diffusion of substances or to smoothen the surface.

Plastic substrates preferably have a gas barrier layer and/or solvent-resisstant layer on their surface.

Alternatively, a driving substrate on which is mounted a thin-film transistor (TFT) for thin-film transistor (TFT) color liquid crystal display devices (hereinafter referred to as a "driving substrate for TFT liquid crystals") can be used as a base material, and a colored pattern using a curable colored composition of the present invention can also be formed on the driving substrate to prepare a color filter.

Substrates in driving substrates for TFT liquid crystals include, for example, glass, silicone, polycarbonate, polyester, aromatic polyamide, polyamideimide, polyimide and the like. These substrates may have undergone an appropriate pretreatment such as chemical treatment with a silane coupling agent or the like, plasma treatment, ion plating, sputtering, gas phase reaction, vacuum vapor deposition or the like, if desired. For example, a driving substrate for TFT liquid crystals on which a passivation layer such as a silicon nitride layer has been formed can be used.

A curable colored composition of the present invention can be applied directly or via another layer on the substrate by a coating method such as spin coating, slit coating, flow coating, roll coating, bar coating, inkjet coating or the like to form a coating layer of the curable colored composition.

During the coating step, the curable colored composition of the present invention can be applied on the substrate by any method, but preferably a method using a slit nozzle such as slit and spin coating, spinless coating or the like (hereinafter referred to as slit nozzle coating). In slit nozzle coating, conditions for slit and spin coating and spinless coating depend on the size of the substrate, and when a fifth generation glass substrate (1100 mm×1250 mm) is to be coated by spinless coating, for example, the rate at which a curable colored composition is delivered from the slit nozzle is typically 500 μl/sec to 2000 μl/sec, preferably 800 μl/sec to 1500 μl/sec, and the coating speed is typically 50 mm/sec to 300 mm/sec, preferably 100 mm/sec to 200 mm/sec.

The solids content of the curable colored composition used in the coating step is typically 10% to 20%, preferably 13% to 18%.

When a coating layer of a curable colored composition of the present invention is to be formed on a substrate, the thickness of the coating layer (after prebaking) is typically 0.3 μm to 5.0 μm, desirably 0.5 μm to 4.0 μm, most desirably 0.5 μm to 3.0 μm.

In the case of color filters for solid-state image sensors, the thickness of the coating layer (after prebaking) is preferably in the range of 0.5 μm to 5.0 μm.

During the coating step, coating is typically followed by prebaking. If desired, prebaking may be preceded by vacuum treatment. Conditions for vacuum drying typically include a degree of vacuum of about 0.1 torr to 1.0 torr, preferably about 0.2 torr to 0.5 torr.

Prebaking can be performed using a hot plate, an oven or the like under conditions of a temperature range of 50° C. to 140° C., preferably about 70° C. to 110° C. for 10 seconds to 300 seconds. Prebaking may be combined with high frequency treatment or the like. High frequency treatment may also be used alone.

Prebaking conditions include heating with a hot plate or an oven at 70° C. to 130° C. for about 0.5 minutes to 15 minutes. Further, the thickness of the colored composition layer formed from the curable colored composition is appropriately selected for the intended purposes. In color filters for liquid crystal display devices, it is preferably in the range of 0.2 μm to 5.0 μm, more preferably in the range of 1.0 μm to 4.0 μm, most preferably in the range of 1.5 μm to 3.5 μm. In color filters for solid-state image sensors, it is preferably in the range of 0.2 μm to 5.0 μm, more preferably in the range of 0.3 μm to 2.5 μm, most preferably in the range of 0.3 μm to 1.5 μm.

It should be noted that the thickness of the colored composition layer is the film thickness after prebaking.

Step (B)

In the processes for preparing the color filters of the present invention, the coating layer of a colored composition (colored composition layer) formed on the base material as described above is then exposed through, for example, a photomask. The light or radiation that can be applied for exposure preferably includes g-line, h-line, i-line, j-line, KrF light and ArF light, especially preferably i-line. When i-line is used for irradiation, the exposure dose is preferably 100 mJ/cm$^2$ to 10000 mJ/cm$^2$.

Other exposure sources that can be used include mercury lamps at ultra-high pressure, high pressure, medium pressure, and low pressure, chemical lamps, carbon arc lamps, xenon lamps, metal halide lamps, various visible and UV laser sources, fluorescent lamps, tungsten lamps, solar light and the like.

Exposure Step Using a Laser Source

In the exposure method using a laser sources, a UV laser is used as a light source.

The radiation is preferably a UV laser having a wavelength in the range of 300 nm to 380 nm, more preferably a UV laser having a wavelength in the range of 300 nm to 360 nm because it conforms to the wavelength to which the resist is sensitive. Specifically, relatively inexpensive lasers with especially high output can be conveniently used, including solid-state lasers such as the third harmonic generation (355 nm) of Nd:YAG laser or excimer lasers XeCl (308 nm) and XeF (353 nm).

The exposure dose of the target (pattern) is in the range of 1 mJ/cm$^2$ to 100 mJ/cm$^2$, more preferably in the range of 1 mJ/cm$^2$ to 50 mJ/cm$^2$. Exposure doses in these ranges are preferred fir patterning productivity.

The exposure system is not specifically limited, and commercial products such as Callisto (from V-Technology Co., Ltd.), EGIS (from V-Technology Co., Ltd.), DF2200G (from DAINIPPON SCREEN MFG. CO., LTD.) and the like can be used. Other systems than those described above may also be conveniently used.

When color filters for liquid crystal display devices are to be prepared, exposure primarily using h-line, or i-line by a proximity exposure system or a mirror projection exposure system is preferably used. When color filters for solid-state image sensors are to be prepared, it is preferable to primarily use i-line in a stepper exposure system. The photomask used for preparing a color filter using a driving substrate for TFT liquid crystals has a pattern for forming a pixel (colored pattern) as well as a pattern for forming a through-hole or a U-shaped groove.

The colored composition layer exposed as described above can be heated.

Exposure can also be performed under a stream of nitrogen gas in the chamber to prevent oxidative discoloration of colorants in the colored composition layer.

Then, the exposed colored composition layer is developed with a developer. Thereby, a negative or positive colored pattern (resist pattern) can be formed. During the developing step, uncured regions of the exposed coating layer are dissolved in the developer while only cured regions remain on the substrate.

Any developer can be used so far as it dissolves the coating layer of the colored composition (colored composition layer) in uncured regions while it does not dissolve cured regions. For example, a combination of various organic solvents or an aqueous alkaline solution can be used. Organic solvents used for development include those already described as solvents that can be used to prepare the curable colored compositions of the present invention.

The aqueous alkaline solution includes, for example, an aqueous alkaline solution of an alkaline compound such as sodium hydroxide, potassium hydroxide, sodium carbonate, sodium hydrogen carbonate, sodium silicate, sodium metasilicate, aqueous ammonia, ethylamine, diethylamine, dimethylethanolamine, tetramethylammonium hydroxide, tetraethylammonium hydroxide, corrin, pyrrole, piperidine, or 1,8-diazabicyclo-[5,4,0]-7-undecene dissolved at a concentration of 0.001% by mass to 10% by mass, preferably 0.01% by mass to 1% by mass. When the developer is an aqueous alkaline solution, the alkaline concentration is preferably controlled to pH11 to 13, more preferably pH11.5 to 12.5.

The aqueous alkaline solution may contain appropriate amounts of water-soluble organic solvents such as methanol, ethanol and the like and surfactants and the like.

The developing temperature is typically in the range of 20° C. to 30° C., and the developing time is 20 seconds to 90 seconds.

Any development method can be used, such as dipping, shower, spray or the like, which may be combined with swing, spin, ultrasonic or the like. Uneven development can be prevented by wetting the surface to be developed with water or the like before it contacts the developer. Further, development can be performed while the substrate is inclined.

Puddle development is also used for preparing color filters for solid-state image sensors.

Development is followed by rinsing for washing away an excess of the developer, then drying, and then a heat treatment (postbaking) to complete curing.

Rinsing typically takes place using pure water, but alternatively may be performed by using pure water during final washing while using recycled pure water during initial washing to save water, or by washing the substrate inclined, or by washing under ultrasonic irradiation.

Rinsing is followed by water removal and drying, and then a heat treatment typically at about 200° C. to 250° C. This heat treatment (postbaking) can be performed on the developed coated layer by continuous or batch operation using a heating means such as a hot plate, a convection oven (hot air circulation dryer) or a high-frequency heater under the conditions described above.

Color filters comprising multiple colored cured films (colored patterns) can be prepared by successively repeating the above steps for each color to suit a desired number of hues. The color filters of the present invention have a high contrast, an even color density, and good color properties so that they can be conveniently used for solid-state image sensors or liquid crystal display devices.

Step (C)

Especially in the processes for preparing the color filters of the present invention, the colored pattern (pixel) formed by using a curable colored composition of the present invention can be postexposed by UV irradiation.

Step (D)

The colored pattern postexposed by UV irradiation as described above is preferably further subjected to a heat treatment. The heat treatment (so-called postbaking) of the formed colored pattern allows the colored pattern to be further cured. This heat treatment can be performed by using, for example, hot plates, various heaters, ovens or the like.

The temperature for the heat treatment is preferably 100° C. to 300° C., more preferably 150° C. to 250° C. The heating time is preferably about 10 minutes to 120 minutes.

The colored pattern obtained in this manner constitutes a pixel in a color filter. When a color filter having multiple hue pixels is to be prepared, the Step (A), Step (B), and optionally Step (C) or Step (D) may be repeated to suit a desired number of colors.

Alternatively, the Step (C) and/or Step (D) may be performed each time when the formation, exposure and development of a single colored composition layer is completed (for each color), or the Step (C) and/or Step (D) may be performed once after the formation, exposure and development of all colored composition layers of a desired number of colors have been completed.

The color filters obtained by the processes for preparing the color filters of the present invention (the color filters of the present invention) are excellent in hue and contrast because a curable colored composition of the present invention is used. The color filters of the present invention can be used for liquid crystal display devices or solid-state image sensors, and especially suitable for use in liquid crystal display devices. When they, are used for liquid crystal display devices, an image having excellent spectroscopic properties and contrast can be displayed while achieving good hue by using dyes as colorants.

The foregoing description relates to curable colored compositions of the present invention mainly for applications in which they are used for forming colored patterns in color filters, but they can also be applied for forming black matrices separating colored patterns (pixels) constituting color filters. Black matrices on a substrate can be formed by the steps of coating, exposure and development using a curable colored composition containing a processed pigment of black pigment such as carbon black, titanium black or the like, optionally followed by postbaking.

Liquid Crystal Display Devices and Solid-State Image Sensors

The liquid crystal display devices and solid-state image sensors of the present invention comprise a color filter of the present invention. More specifically, a panel or a liquid crystal display device of the present invention can be obtained by forming a polarizing film on the inner side of a color filter to face an electrode substrate and filling the gap with liquid crystals and sealing it, for example. Alternatively, a solid-state image sensor of the present invention can be obtained by forming a color filter on a light-capturing element, for example.

The definition of liquid crystal display devices and details of various display devices are described in, for example, "Electronic Display Devices (by Akio Sasaki, Kogyo Chosakai Publishing Co., Ltd., 1990)"; "Display Devices (by Sumiaki Ibuki, Sangyotosyo Inc., 1989)"; and the like. Further, liquid crystal display devices are described in, for example, "Next Generation Liquid Crystal Display Technology (edited by Tatsuo Uchida, Kogyo Chosakai Publishing Co., Ltd. 1994)". The liquid crystal display devices to which the present invention can be applied are not specifically limited, but the present invention can be applied to, for example, various types of liquid crystal display devices described in "Next Generation Liquid Crystal Display Technology", supra.

Among others, the color filters of the present invention are especially effective for color TFT liquid crystal display devices. Color TFT liquid crystal display devices are described in, for example, "Color TFT Liquid Crystal Displays (KYORITSU SHUPPAN CO., LTD., 1996)". The present invention can also be applied to wide viewing angle liquid crystal display devices such as In-Plane Switching (IPS) or Halftone-Grayscale Method such as MVA as well as STN, TN, VA, OCS, FFS, and R-OCB and the like.
Further, the color filters of the present invention can also be applied to a light high-definition mode called COA (Color-filter. On Array).

Liquid crystal display devices using the color filters of the present invention can achieve high contrast when they are combined with a three-wavelength tube of a conventionally known cold cathode tube, and they can further provide liquid crystal display devices with high luminance, high color purity and good color reproducibility when red, green and blue LED light sources (RGB-LEDs) are used as a backlight.

In order of color, blue light emitting diodes include those based on gallium nitride (GaN), specifically having a layer structure of sapphire substrate/n-GaN/n-A10.15Ga0.85N/MQW or SQW layer/p-A10.15Ga0.85N/p-GaN/electrode. The MQW or SQW layer here refers to a multiple quantum well structure (MQW) or single quantum well structure (SQW). An example of a material constituting these quantum well structures includes InxGaN1-xN, which generates blue at x=0.2 and green at around x=0.4. When the In (indium) fraction increases in this material, green emission is achieved, but the emission efficiency decreases because the crystallinity decreases as the In fraction increases.

As alternative materials for ensuring sufficient luminance of emission, GaInN green LED can be used or a combination of GaInN blue LED+green phosphor can also be used. These approaches allow a peak wavelength to be tuned to a suitable wavelength in the range of 520 to 570 nm.

Green phosphors that can be used include oxides, nitrides and acid nitrides activated by cerium and/or europium.

Satisfactory emission characteristics can be achieved by using AlInGaP-based LEDs as red LEDs. Alternative red LEDs include GaAlAs-based red LEDs having a layer structure of GaAs substrate/n-GaAs/n-InGaAlP/undoped InGaAlP/p-InGaAlP/p-GaAs/electrode. The emission wavelength can be changed by controlling the atomic ratios of the three elements of In, Ga, Al so that the atomic ratio of In is 0.5 to match the lattice constant to GaAs while the ratios of Ga and Al are changed. If the ratio of Al increases, emission shifts toward shorter wavelengths. When the atomic ratio of Ga is about 0.25 and the atomic ratio of Al is about 0.25, red emission occurs at a wavelength of about 600 nm.

The LEDs described above can be prepared by chemical vapor deposition using organic metals (MOCVD) so that the composition can be relatively easily controlled by controlling the proportions of organic metal materials introduced into the reaction chamber. Thus, it is relatively easy to tune the peak emission wavelength of blue LEDs to the range of 430 to 480 nm or the peak emission wavelength of red LEDs to the range of 600 to 660 nm.

Not only these LEDs but also fluorescent materials exhibiting the emission of each color can be used.

EXAMPLES

The following examples further illustrate the present invention, but the present invention should not be construed as being limited to these examples and various changes may be made without departing from the spirit of the invention. Unless otherwise specified, "parts" are based on mass.

Synthesis Example of Compound 201

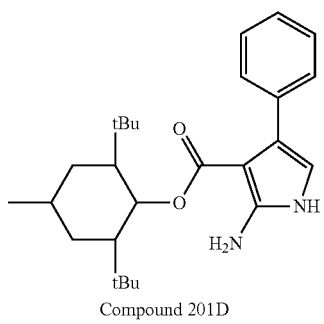

Compound 201D

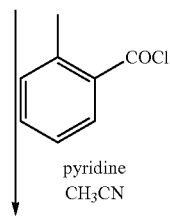

pyridine
CH₃CN

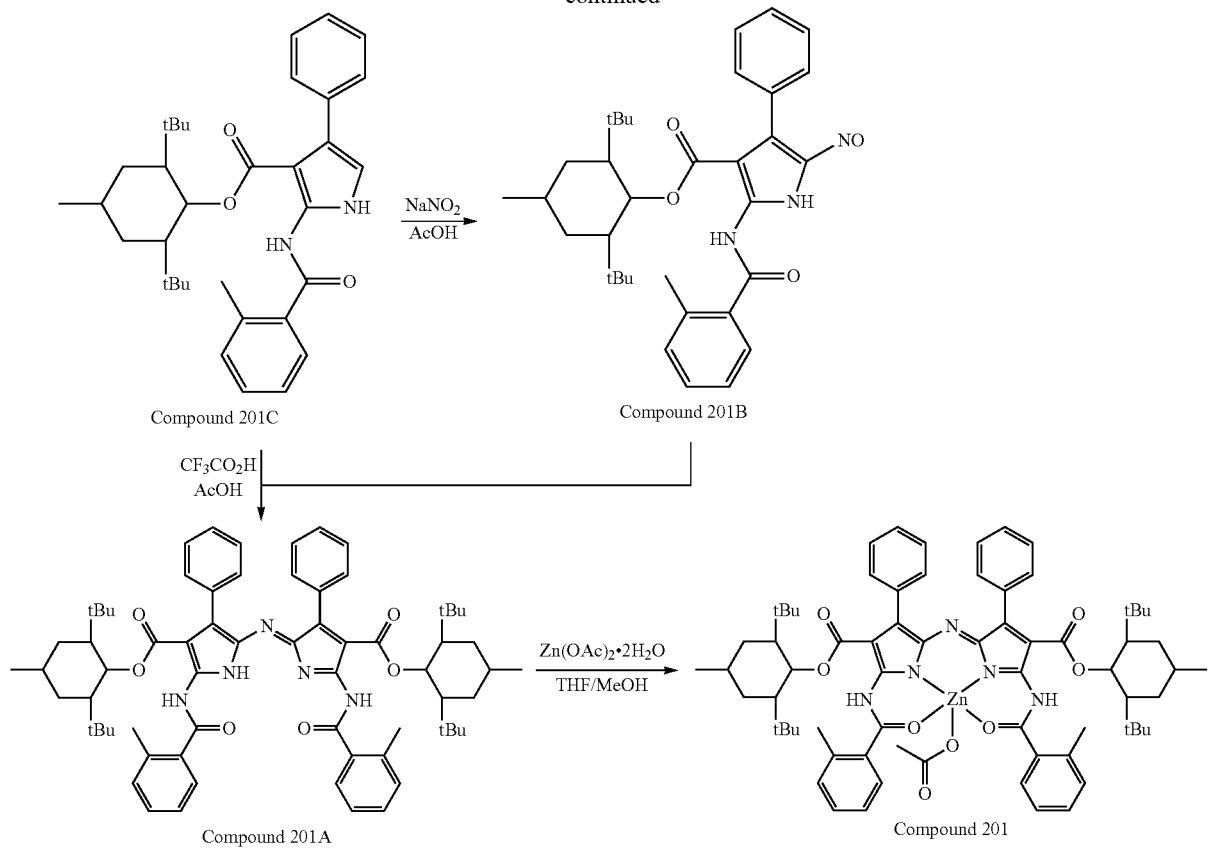

According to the scheme described above, compound 201 was synthesized.

Compound 201D used as a starting material was synthesized according to the procedure described in JP-A2008-292970.

Synthesis of Compound 201C

A 500-mL round-bottom flask was charged with compound 201D (103 g) and acetonitrile (300 mL). To this mixed solution were successively added 2-methylbenzoyl chloride (42.6 g) and pyridine (23.8 g) with ice-cooling while the dripping speed was controlled to keep the reaction temperature below 15° C. After the addition, the mixture was stirred with ice-cooling for 2 hours, and the resulting crystals were filtered off and washed with acetonitrile (750 mL). The crystals were dried at room temperature to give compound 201C (109 g).

Synthesis of Compound 201B

A 200-mL round-bottom flask was charged with compound 201C (5.3 g) and acetic acid (50 mL) to give a suspension. To this suspension was added dropwise an ice-cooled aqueous solution of sodium nitrite (0.8 g) dissolved in water (5 mL) with stirring. This reaction solution was stirred for 1 hour, and water (50 mL) was added. Crystals were filtered off from this reaction solution, washed with water, and then dried at room temperature to give compound 201B (6.0 g).

Synthesis of Compound 201A

A 100-mL round-bottom flask was successively charged with acetic acid (12 mL), trifluoroacetic acid (3 mL), compound 201B (2.2 g), and compound 201C (2.1 g), and the mixture was stirred for 2 days at room temperature. To this was added trifluoroacetic acid (3 mL), and the mixture was stirred for another 2 days at room temperature, and then the reaction solution was warmed to 60° C. and stirred for 3 hours. The resulting reaction solution was cooled to room temperature, and water (6 mL) and methanol (18 mL) successively were added. The resulting crystals were filtered off, and washed with methanol. The crystals were recrystallized from a mixed solvent of ethyl acetate (8 mL) and acetonitrile (16 mL) to give compound 201A (2.3 g).

$^1$H NMR (CDCl$_3$): 13.24 (bs, 1H), 11.32 (s, 2H), 7.76 (d, 2H), 7.20-7.48 (m, 18H), 5.86 (s, 2H), 2.89 (s, 6H), 0.40-1.32 (m, 56H).

Synthesis of Compound 201

A 100-mL round-bottom flask was charged with compound 201A (1.1 g) and tetrahydrofuran (3 mL), to which was added a solution of zinc acetate dihydrate (0.3 g) in methanol (3 mL). The mixture was stirred for 1 hour at room temperature, and then the resulting crystals were filtered off. The crystals were washed in 6 mL of methanol with stirring, collected by filtration and dried at room temperature to give compound 201 (0.9 g).

$^1$H NMR (CDCl$_3$): 11.78 (s, 2H), 7.77 (d, 2H), 7.18-8.00 (m, 18H), 5.88 (s, 2H), 2.70 (s, 6H), 1.97 (s, 3H), 0.56-1.30 (m, 56H).

Synthesis Example of Compound 202

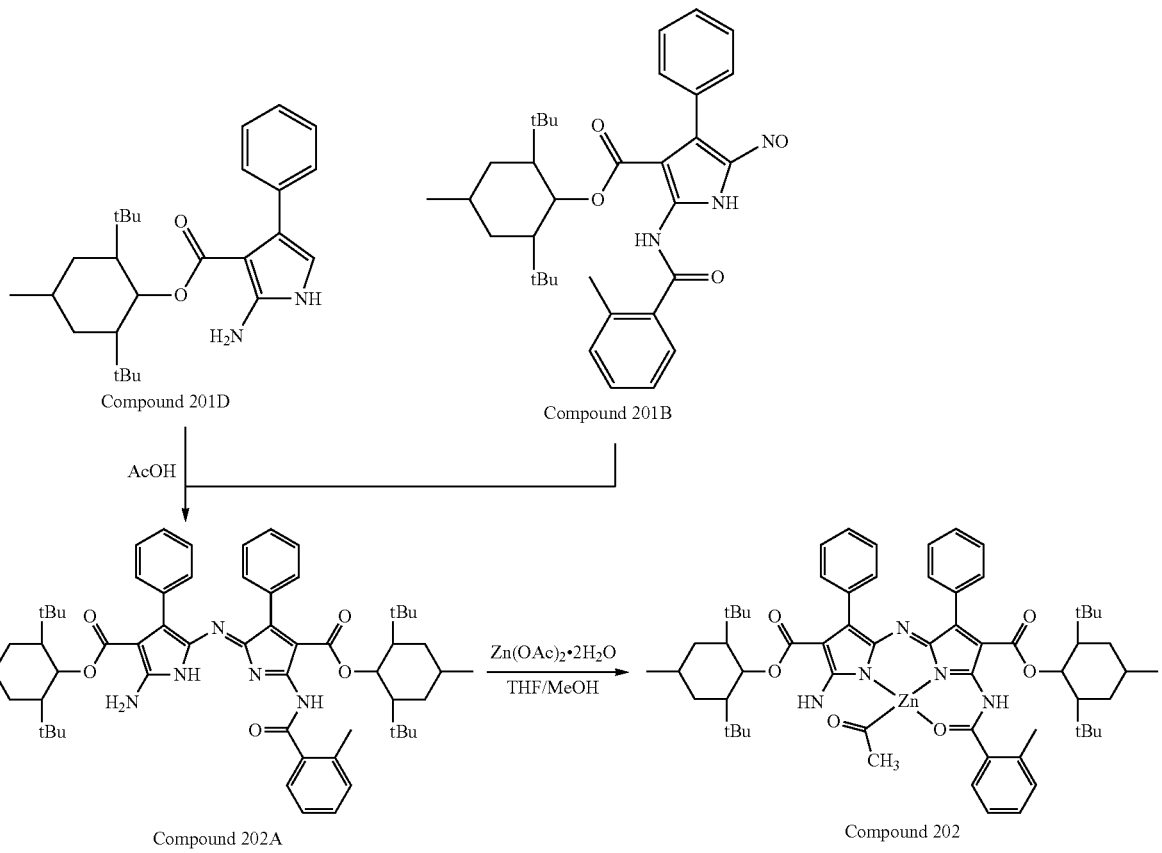

The title compound was synthesized according to the scheme described above.

Synthesis of Compound 202A

A 100-mL round-bottom flask was charged with compound 201B (1.7 g), compound 201D (1.3 g), and acetic acid (9 mL), and the mixture was stirred for 1 hour at room temperature. To the reaction solution were successively added water (3 mL) and methanol (9 mL), and the resulting crystals were collected by filtration and washed with methanol. The crystals were washed in acetonitrile (18 mL) with heating under reflux, and cooled to room temperature, and then the resulting crystals were filtered off and dried at room temperature to give compound 202A (2.0 g).

$^1$H NMR (CDCl$_3$): 13.36 (s, 1H), 11.15 (s, 1H), 7.64 (d, 2H), 7.20-7.48 (m, 13H), 5.95-6.18 (bs, 1H), 5.90 (s, 1H), 5.84 (s1H), 2.63 (s, 3H), 0.48-1.40 (m, 56H).

Synthesis of Compound 202

A 100-mL round-bottom flask was charged with compound 202A (1.4 g) and tetrahydrofuran (THF, 3 mL), to which was added a solution of zinc acetate dihydrate (0.4 g) in methanol (3 mL). The mixture was stirred for 1 hour at room temperature, and then the resulting crystals were filtered off. The crystals were washed in 12 mL of methanol with stirring, and collected by filtration. The crystals were dried at room temperature to give compound 201 (1.3 g).

$^1$H NMR (CDCl$_3$): 12.04 (s, 1H), 7.80-8.04 (bs, 1H), 7.73 (d, 2H), 7.00-7.42 (m, 13H), 5.81 (s, 1H), 5.72 (s, 1H), 2.64 (s, 3H), 2.03 (s, 3H), 0.36-1.32 (m, 56H).

Synthesis Example of Compound 301

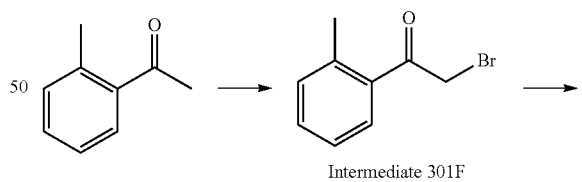

Intermediate 301F

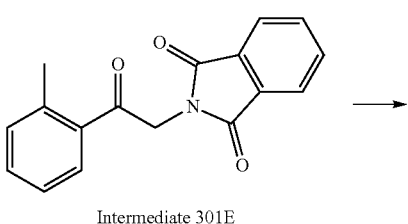

Intermediate 301E

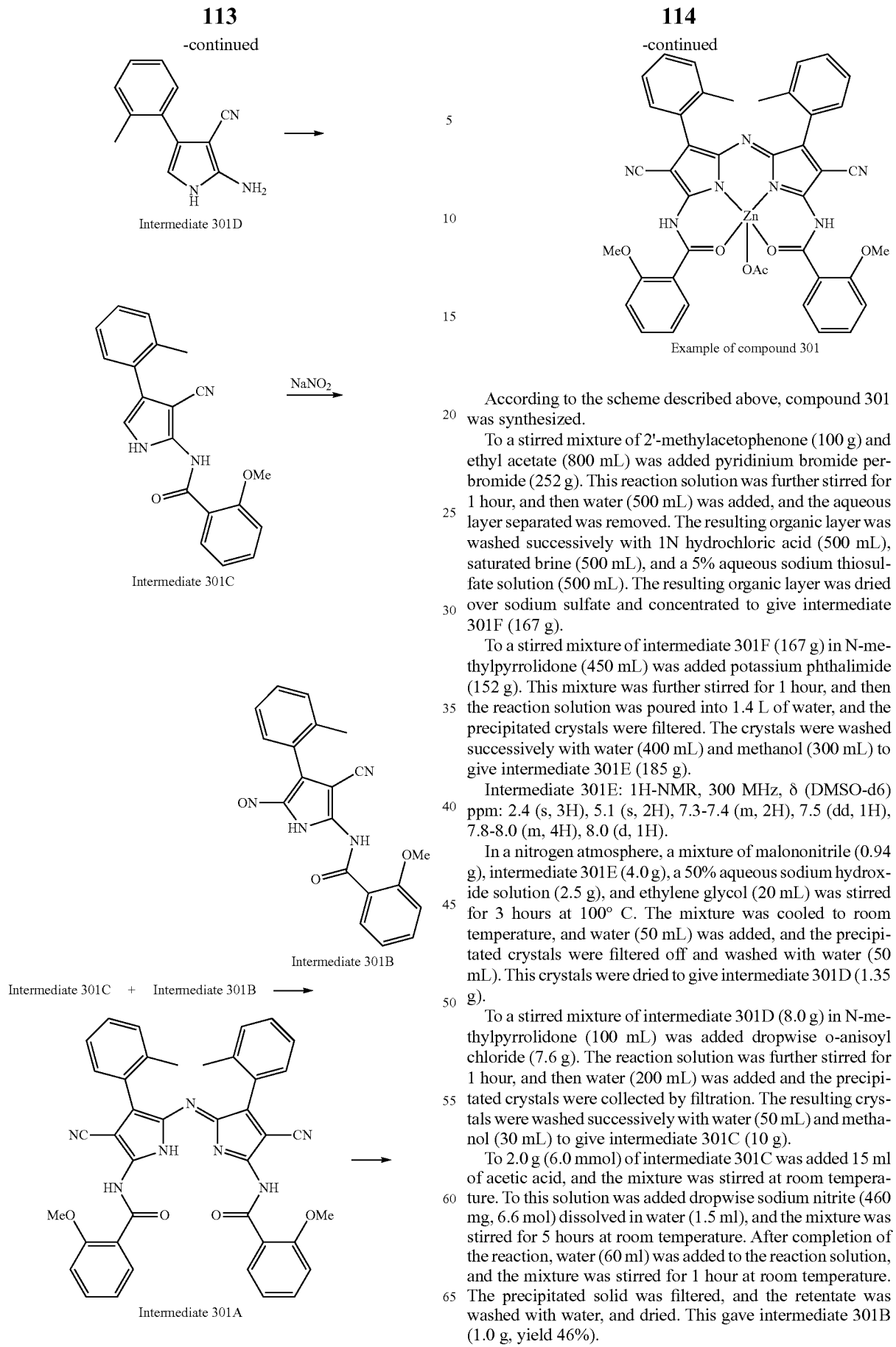

Example of compound 301

According to the scheme described above, compound 301 was synthesized.

To a stirred mixture of 2'-methylacetophenone (100 g) and ethyl acetate (800 mL) was added pyridinium bromide perbromide (252 g). This reaction solution was further stirred for 1 hour, and then water (500 mL) was added, and the aqueous layer separated was removed. The resulting organic layer was washed successively with 1N hydrochloric acid (500 mL), saturated brine (500 mL), and a 5% aqueous sodium thiosulfate solution (500 mL). The resulting organic layer was dried over sodium sulfate and concentrated to give intermediate 301F (167 g).

To a stirred mixture of intermediate 301F (167 g) in N-methylpyrrolidone (450 mL) was added potassium phthalimide (152 g). This mixture was further stirred for 1 hour, and then the reaction solution was poured into 1.4 L of water, and the precipitated crystals were filtered. The crystals were washed successively with water (400 mL) and methanol (300 mL) to give intermediate 301E (185 g).

Intermediate 301E: 1H-NMR, 300 MHz, δ (DMSO-d6) ppm: 2.4 (s, 3H), 5.1 (s, 2H), 7.3-7.4 (m, 2H), 7.5 (dd, 1H), 7.8-8.0 (m, 4H), 8.0 (d, 1H).

In a nitrogen atmosphere, a mixture of malononitrile (0.94 g), intermediate 301E (4.0 g), a 50% aqueous sodium hydroxide solution (2.5 g), and ethylene glycol (20 mL) was stirred for 3 hours at 100° C. The mixture was cooled to room temperature, and water (50 mL) was added, and the precipitated crystals were filtered off and washed with water (50 mL). This crystals were dried to give intermediate 301D (1.35 g).

To a stirred mixture of intermediate 301D (8.0 g) in N-methylpyrrolidone (100 mL) was added dropwise o-anisoyl chloride (7.6 g). The reaction solution was further stirred for 1 hour, and then water (200 mL) was added and the precipitated crystals were collected by filtration. The resulting crystals were washed successively with water (50 mL) and methanol (30 mL) to give intermediate 301C (10 g).

To 2.0 g (6.0 mmol) of intermediate 301C was added 15 ml of acetic acid, and the mixture was stirred at room temperature. To this solution was added dropwise sodium nitrite (460 mg, 6.6 mol) dissolved in water (1.5 ml), and the mixture was stirred for 5 hours at room temperature. After completion of the reaction, water (60 ml) was added to the reaction solution, and the mixture was stirred for 1 hour at room temperature. The precipitated solid was filtered, and the retentate was washed with water, and dried. This gave intermediate 301B (1.0 g, yield 46%).

Into acetic acid (6 ml) were added intermediate 301C (1.0 g, 3.0 mmol) and intermediate 301B (1.1 g, 3.0 mmol), and the mixture was stirred at room temperature. To this solution was added trifluoroacetic acid (3.5 ml), and mixture was stirred for 16 hours at room temperature. After completion of the reaction, water (60 ml) was added to the reaction solution, and the mixture was stirred for 1 hour at room temperature. The precipitated solid was filtered, and the retentate was washed with water, acetonitrile, and ethyl acetate, and the resulting solid was dried. This gave intermediate 301A (0.30 g, yield 15%).

$^1$H-NMR (DMSO) δ: 12.13 (s, 2H), 10.72 (s, 1H), 7.95-7.11 (m, 16H), 4.00 (s, 6H), 2.53 (s, 6H).

To 12 ml of chloroform was added 0.10 g (0.15 mmol) of intermediate 3, and the mixture was stirred at room temperature, and then 35 mg (0.16 mmol) of zinc acetate dihydrate was added, and the mixture was stirred for 2 hours at room temperature. Then, the precipitated solid was filtered, and washed with water, and the resulting solid was dried to give 0.10 g (84%) of compound 301.

The wavelength of maximum absorption λmax was determined to show that the wavelength of maximum absorption λmax of compound 301 was 639 nm.

Synthesis of Compound 302

Compound 201A + Cu(OAc)$_2$ ⟶

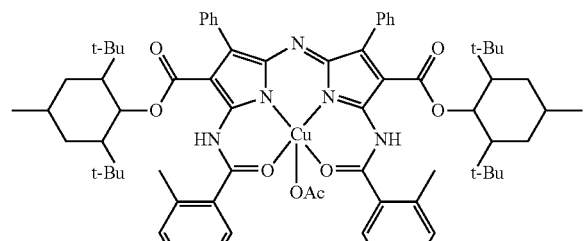

Example of compound 302

Compound 201A (0.50 g, 0.53 mmol) was added to tetrahydrofuran (5 ml) and methanol (5 ml), and the mixture was stirred at room temperature, and then copper acetate (0.11 g, 0.58 mmol) was added, and the mixture was stirred for 2 hours at room temperature. Subsequently, the precipitated solid was filtered, and washed with water, and the resulting solid was dried to give compound 302 (0.50 g, yield 790).

The wavelength of maximum absorption λmax was determined to show that the wavelength of maximum absorption λmax of compound 302 was 635 nm (in tetrahydrofuran).

Compound 303

Compound 201A + Co(OAc)$_2$ ⟶

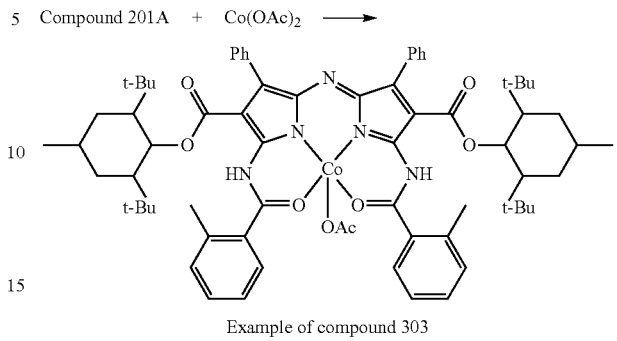

Example of compound 303

Compound 201A (0.50 g, 0.53 mmol) was added to tetrahydrofuran (5 ml) and methanol (5 ml), and the mixture was stirred at room temperature, and then cobalt acetate tetrahydrate (0.14 g, 0.58 mmol) was added, and the mixture was stirred for 2 hours at room temperature. Subsequently, the precipitated solid was filtered, and washed with water, and the resulting solid was dried to give compound 303 (0.45 g, yield 72%).

The wavelength of maximum absorption λmax was determined to show that the wavelength of maximum absorption λmax of compound 303 was 630 nm (in tetrahydrofuran).

Synthesis Example of Compound 304

Compound 201A + FeCl$_3$ ⟶

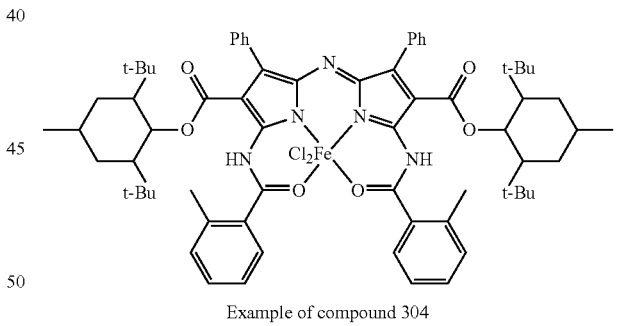

Example of compound 304

Compound 201A (0.50 g, 0.53 mmol) was added to tetrahydrofuran (5 ml) and methanol (5 ml), and the mixture was stirred at room temperature, and then iron (III) chloride (94 mg, 0.58 mmol) was added, and the mixture was stirred for 2 hours at room temperature. Subsequently, the precipitated solid was filtered, and washed with water, and the resulting solid was dried to give compound 304 (0.52 g, yield 82%).

The wavelength of maximum absorption λmax was determined to show that the wavelength of maximum absorption λmax of compound 304 was 610 nm (in tetrahydrofuran).

Synthesis Example of Compound 305

Compound 201A + GaCl₃ ⟶

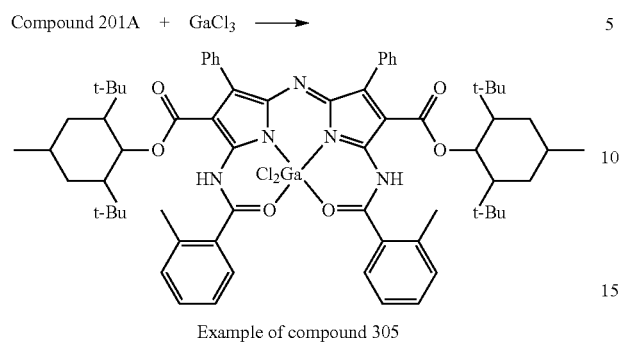

Example of compound 305

Compound 201A (0.50 g, 0.53 mmol) was added to tetrahydrofuran (5 ml) and methanol (5 ml), and the mixture was stirred at room temperature, and then gallium (III) chloride (0.10 g, 0.58 mmol) was added, and the mixture was stirred for 2 hours at room temperature. Subsequently, the precipitated solid was filtered, and washed with water, and the resulting solid was dried to give compound 305 (0.48 g, yield 75%).

The wavelength of maximum absorption λmax was determined to show that the wavelength of maximum absorption λmax of compound 305 was 630 nm (in tetrahydrofuran).

Synthesis Example of Compound 306

Compound 201A + VCl₃ ⟶

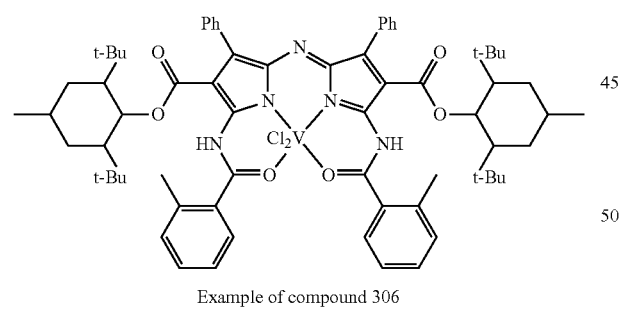

Example of compound 306

Compound 201A (0.50 g, 0.53 mmol) was added to tetrahydrofuran (5 ml) and methanol (5 ml), and the mixture was stirred at room temperature, and then vanadium (III) chloride (91 mg, 0.58 mmol) was added, and the mixture was stirred for 2 hours at room temperature. Subsequently, the precipitated solid was filtered, and washed with water, and the resulting solid was dried to give compound 306 (0.46 g, yield 73%).

The wavelength of maximum absorption λmax was determined to show that the wavelength of maximum absorption λmax of compound 306 was 625 nm (in tetrahydrofuran).

Synthesis Example of Compound 307

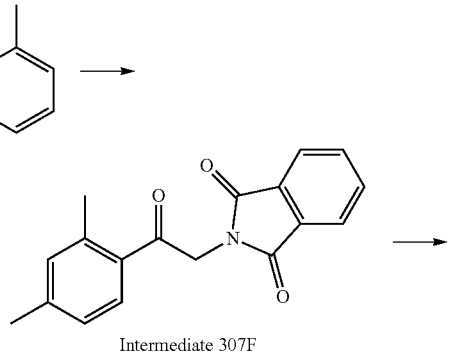

Intermediate 307F

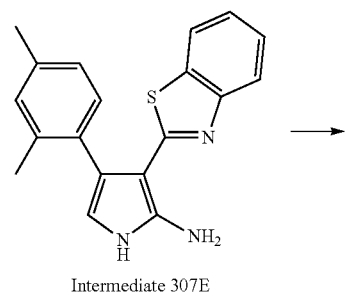

Intermediate 307E

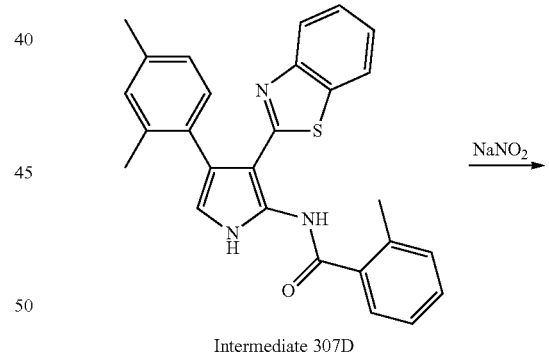

Intermediate 307D

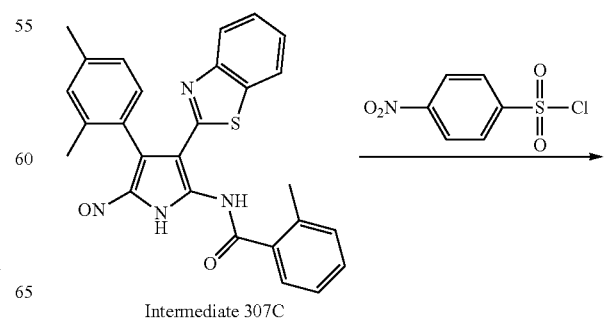

Intermediate 307C

-continued

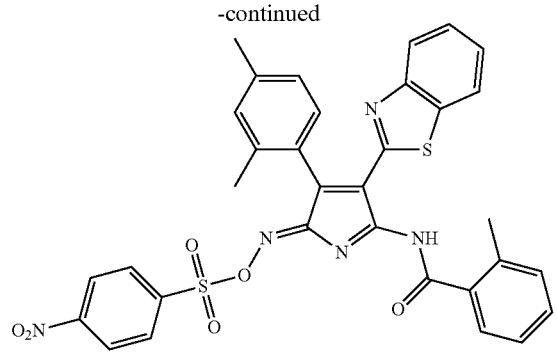
Intermediate 307B

Intermediate 307D + Intermediate 307B ⟶

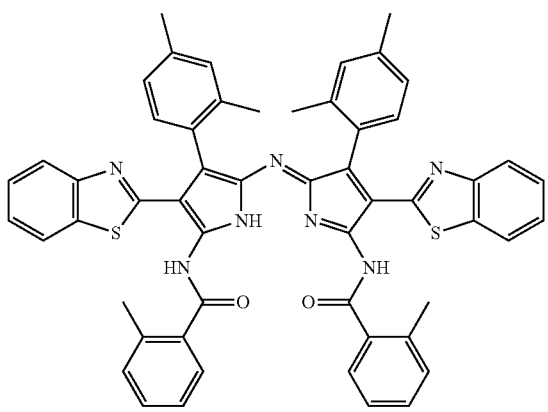
Intermediate 307A

Intermediate 307A +

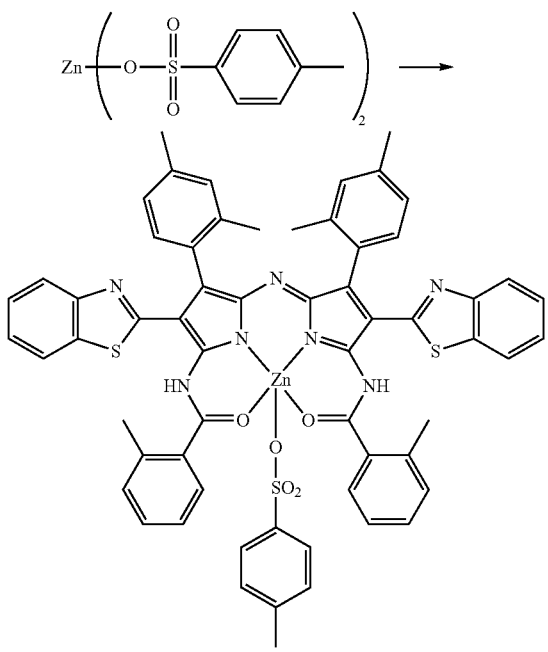
Example of compound 307

To an ice-cooled mixture of m-xylene (159 g), chloroacetyl chloride (185 g), and chloroform (800 mL) was added aluminum chloride (220 g) by portions. The resulting reaction solution was further stirred for 30 minutes, and then 1 L of water was added. The aqueous layer was removed, and then the organic layer was washed with 500 mL of 1N hydrochloric acid three times. The organic layer was dried over sodium sulfate, and then concentrated under reduced pressure. To the resulting residue was added N-methylpyrrolidone (600 mL), and potassium phthalimide (306 g) was added by portions to keep the internal temperature at or below 50° C. The reaction solution was stirred for 30 minutes, and then water (1 L) was added. The precipitated crystals were filtered off, and washed with methanol (1 L) to give intermediate 307F (375 g).

Intermediate 307F: 1H-NMR, 300 MHz, δ (DMSO-d6) ppm: 2.3 (s, 3H), 2.4 (s, 3H), 5.1 (s, 2H), 7.2-7.3 (m, 2H), 7.9-8.0 (m, 3H).

In a nitrogen atmosphere, a mixture of intermediate 307F (29.3 g), 2-(cyanomethyl)benzothiazole (17.4 g), a 20% aqueous sodium hydroxide solution (40 g), and 1-butanol (60 mL) was stirred for 3 hours at 95° C. After cooling to 0° C., 60 mL of water was added dropwise, and the mixture was stirred for further 30 minutes. The precipitated crystals were filtered off, washed with cold water and then dried under vacuum to give intermediate 307E (18.5 g).

Intermediate 307E: 1H-NMR, 300 MHz, δ (CDCl$_3$) ppm: 2.2 (s, 3H), 2.4 (s, 3H), 5.6-5.9 (bs, 2H), 6.2 (s, 1H), 7.0-7.4 (m, 5H), 7.7 (d, 1H), 7.6-7.8 (bs, 1H), 7.8 (d, 1H).

To a mixture of intermediate 307E (3.2 g) in N-methylpyrrolidone (15 mL) was added dropwise o-toluoyl chloride (1.6 g). This mixture was further stirred for 30 minutes, and then water (50 mL) was added, and the precipitated crystals were filtered off, and washed with methanol (30 mL) to give intermediate 307D (3.9 g).

To intermediate 307D (2.0 g, 4.5 mmol) was added acetic acid (20 ml), and the mixture was stirred at room temperature. To this solution was added dropwise a 43% solution of nitrosylsulfuric acid in sulfuric acid (1.5 g, 5.0 mol), and the mixture was stirred for 1 hour at room temperature. After completion of the reaction, water (80 ml) was added to the reaction solution, and the mixture was stirred for 1 hour at room temperature. The precipitated solid was filtered, and the retentate was washed with water, and dried. This gave intermediate 307C (2.0 g, yield 94%).

To intermediate 307C (2.0 g, 4.3 mmol) was added acetonitrile (15 ml), and the mixture was stirred with ice-cooling. To this solution was added pyridine (0.51 g, 6.5 mmol), and then 4-nitrobenzenesulfonyl chloride (1.0 g, 4.7 mmol) was added dropwise, and the mixture was stirred for 1 hour with ice-cooling. After completion of the reaction, water (80 ml) was added to the reaction solution, and the mixture was stirred for 1 hour at room temperature. The precipitated solid was filtered, and the retentate was washed with methanol and dried. This gave intermediate 307B (2.4 g, yield 87%).

Into acetic acid (6 ml) were added intermediate 307D (1.0 g, 2.3 mmol), intermediate 307B (1.5 g, 2.3 mmol), and potassium acetate (0.23 g, 2.3 mmol), and the mixture was stirred for 1 hour at 60° C. To this solution was added trifluoroacetic acid (3.5 ml), and the mixture was stirred for 12 hours at room temperature. After completion of the reaction, 200 ml of water was added to the reaction solution, and the mixture was stirred for 1 hour at room temperature. The precipitated solid was filtered, and the retentate was washed with water and ethyl acetate, and dried. This gave intermediate 307A (0.42 g, 20%).

Intermediate 307A (0.50 g, 0.56 mmol) was added to tetrahydrofuran (5 ml) and methanol (5 ml), and the mixture was stirred at room temperature, and then zinc bis(4-methylbenzenesulfonate) (0.25 g, 0.62 mmol) was added, and the mixture was stirred for 1 hour at room temperature. Subsequently, the precipitated solid was filtered, and washed with methanol, and the resulting solid was dried to give compound 307 (0.53 g, yield 84%).

The wavelength of maximum absorption λmax was determined to show that the wavelength of maximum absorption λmax of compound 307 was 672 nm (in ethyl acetate).

Synthesis Example of Compound 308

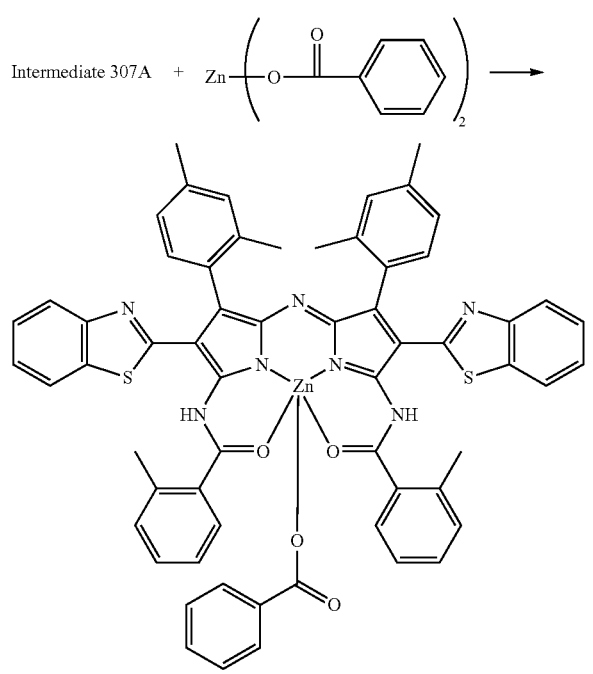

Example of compound 308

Intermediate 307A (0.50 g, 0.56 mmol) was added to tetrahydrofuran (5 ml) and methanol (5 ml), and the mixture was stirred at room temperature, and then zinc bisbenzoate (0.19 g, 0.62 mmol) was added, and the mixture was stirred for 1 hour at room temperature. Subsequently, the precipitated solid was filtered, and washed with methanol, and the resulting solid was dried to give compound 308 (0.47 g, yield 78%).

The wavelength of maximum absorption λmax was determined to show that the wavelength of maximum absorption λmax of compound 308 was 672 nm (in ethyl acetate).

Synthesis Example of Compound 309

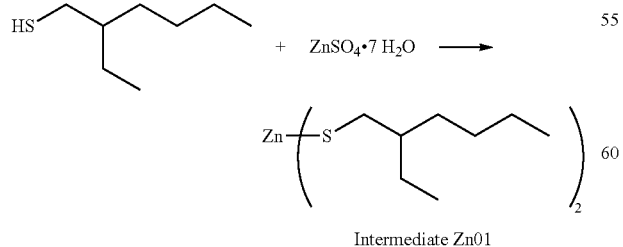

Intermediate 307A + Intermediate Zn01 ⟶

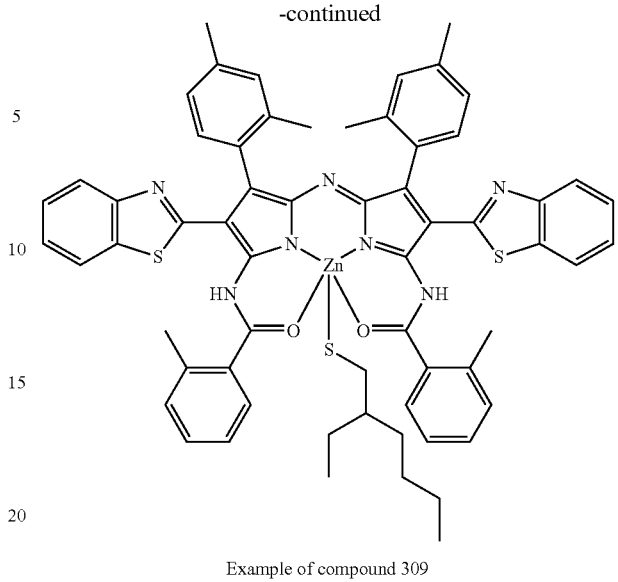

Example of compound 309

To a mixed solvent of water (10 ml) and methanol (12 ml) were added 2-ethylhexylthiol (2.0 g, 14 mmol) and a 28% solution of sodium methoxide in methanol (2.6 g, 14 mmol), and the mixture was stirred at room temperature. To this solution was added a solution of zinc sulfate heptahydrate (1.8 g, 6.2 mmol) dissolved in 2 ml of water, and the mixture was stirred for 1 hour at room temperature. After stirring was completed, the resulting precipitate was filtered, and the retentate was washed with water and methanol, and the resulting solid was dried. This gave intermediate Zn01 (2.0 g, yield 90%).

Intermediate 307A (0.50 g, 0.56 mmol) was added to toluene (10 ml), and the mixture was stirred at room temperature, and then intermediate Zn03 (0.22 g, 0.62 mmol) was added, and the mixture was stirred for 8 hours at room temperature. Subsequently, the precipitated solid was filtered, and washed with isopropyl alcohol, and the resulting solid was dried to give compound 309 (0.11 g, yield 59%).

The wavelength of maximum absorption λmax was determined to show that the wavelength of maximum absorption λmax of compound 309 was 672 nm (in ethyl acetate).

Synthesis Example of Compound 310

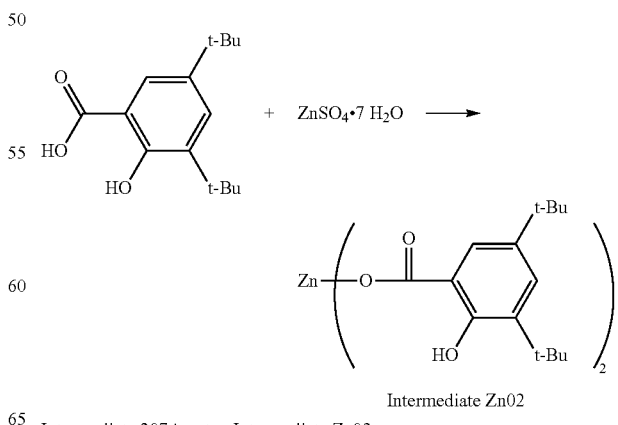

Intermediate 307A + Intermediate Zn02 ⟶

-continued

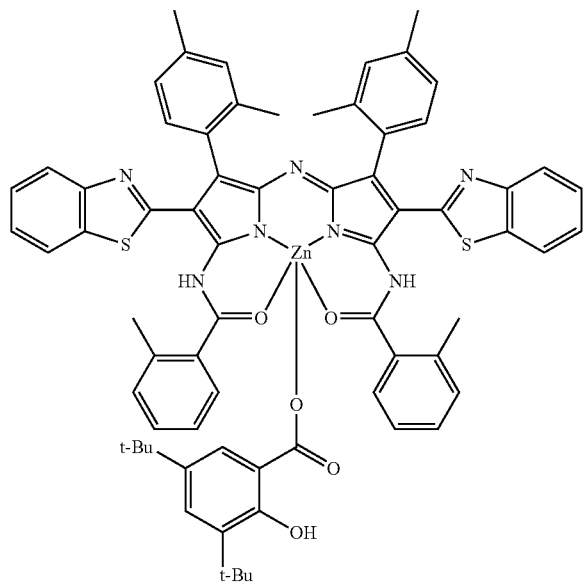

Example of compound 310

To a mixed solvent of water (10 ml) and methanol (15 ml) were added 5.8 g (23 mmol) of 3,5-di-t-butyl salicylic acid and a 28% solution of sodium methoxide in methanol (4.4 g, 23 mmol), and the mixture was stirred at room temperature. To this solution was added a solution of zinc sulfate heptahydrate (3.0 g, 10 mmol) dissolved in water (4 ml), and the mixture was stirred for 1 hour at room temperature. After stirring was completed, the resulting precipitate was filtered, and the retentate was washed with water and methanol, and the resulting solid was dried. This gave intermediate Zn02 (4.8 g, 85%).

Intermediate 307A (0.50 g, 0.56 mmol) was added to tetrahydrofuran (5 ml) and methanol (5 ml), and the mixture was stirred at room temperature, and then intermediate Zn02 (0.35 g, 0.62 mmol) was added, and the mixture was stirred for 2 hours at room temperature. Subsequently, the precipitated solid was filtered, and washed with methanol, and the resulting solid was dried to give compound 310 (0.57 g, yield 91%).

The wavelength of maximum absorption λmax was determined to show that the wavelength of maximum absorption λmax of compound 310 was 671 nm (in ethyl acetate).

Synthesis Example of Compound 311

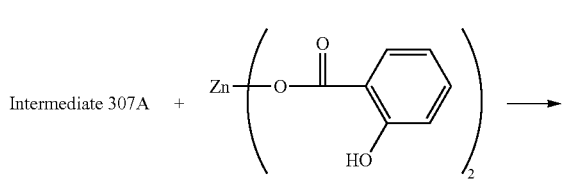

-continued

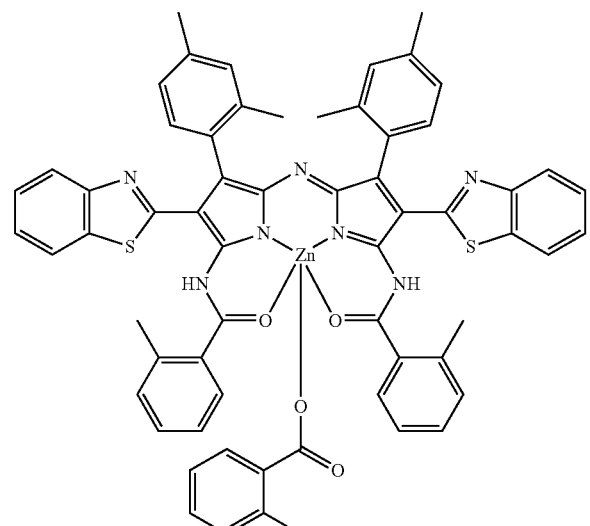

Example of compound 311

Intermediate 307A (0.50 g, 0.56 mmol) was added to tetrahydrofuran (5 ml) and methanol (5 ml), and the mixture was stirred at room temperature, and then zinc bis(2-hydroxybenzoate) (0.21 g, 0.62 mmol) was added, and the mixture was stirred for 4 hours at room temperature. Subsequently, the precipitated solid was filtered, and washed with methanol, and the resulting solid was dried to give compound 311 (0.46 g, yield 76%).

The wavelength of maximum absorption λmax was determined to show that the wavelength of maximum absorption λmax of compound 311 was 671 nm (in ethyl acetate).

Synthesis Example of Compound 312

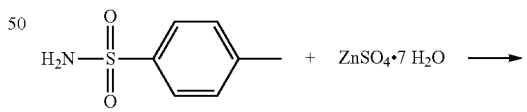

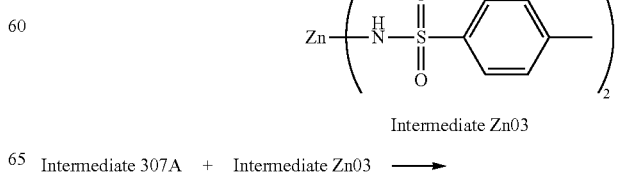

Intermediate Zn03

Intermediate 307A + Intermediate Zn03 ⟶

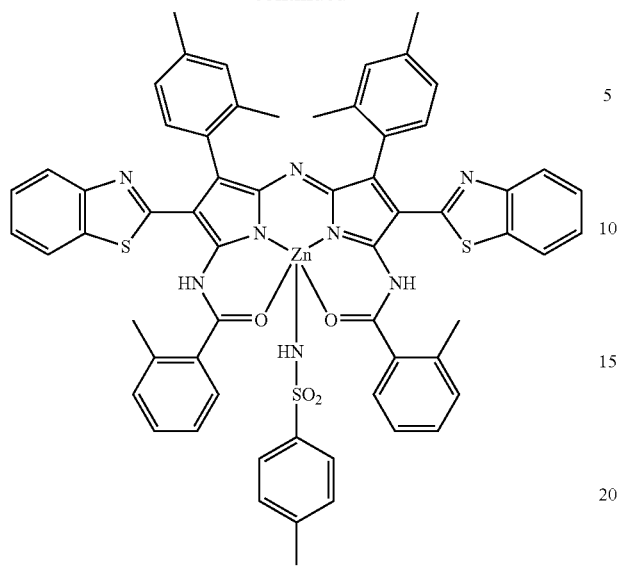

Example of compound 312

To a mixed solvent of water (10 ml) and methanol (12 ml) were added p-toluenesulfonamide (2.0 g, 12 mmol) and a 28% solution of sodium methoxide in methanol (2.3 g, 12 mmol), and the mixture was stirred at room temperature. To this solution was added a solution of zinc sulfate heptahydrate (1.6 g, 5.5 mmol) dissolved in water (2 ml), and the mixture was stirred for 1 hour at room temperature. After stirring was completed, the resulting precipitate was filtered, and the retentate was washed with water and methanol, and the resulting solid was dried. This gave intermediate Zn03 (1.8 g, yield 80%).

Intermediate 307A (0.50 g, 0.56 mmol) was added to tetrahydrofuran (5 ml) and methanol (5 ml), and the mixture was stirred at room temperature, and then intermediate Zn03 (0.25 g, 0.62 mmol) was added, and the mixture was stirred for 8 hours at room temperature. Subsequently, the precipitated solid was filtered, and washed with methanol, and the resulting solid was dried to give compound 312 (0.30 g, yield 48%).

The wavelength of maximum absorption λmax was determined to show that the wavelength of maximum absorption λmax of compound 312 was 672 nm (in ethyl acetate).

Synthesis Example of Compound 313

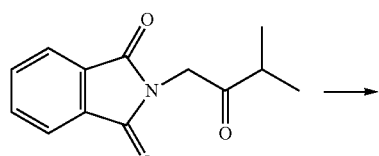

Intermediate 313E

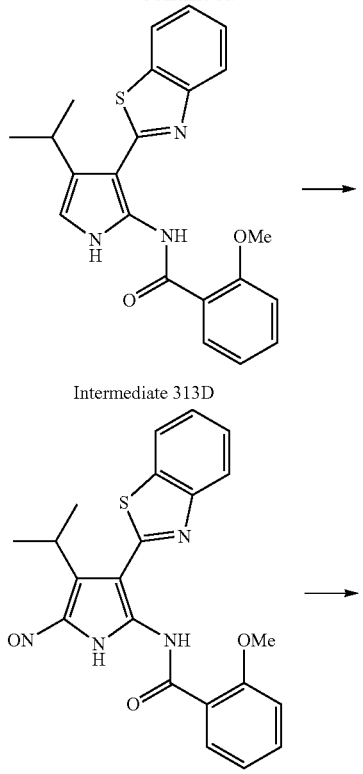

Intermediate 313D

Intermediate 313C

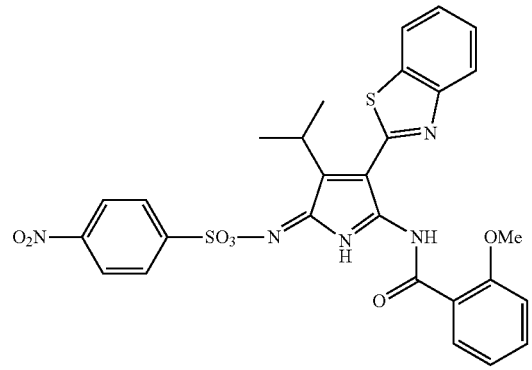

Intermediate 313B

To a mixture of intermediate 313E (7.7 g), 2-(cyanomethyl)benzothiazole (5.2 g), and 1-methoxy-2-propanol (60 mL) was added a 50% aqueous sodium hydroxide solution (5.3 mL) under a stream of nitrogen gas, and the mixture was stirred for 30 minutes at room temperature, then for 3 hours at 90° C. This reaction mixture was combined with water (135 mL) and extracted with ethyl acetate (45 mL) three times.

The resulting ethyl acetate phase was cooled to 5° C. or less, and a 8% aqueous sodium hydroxide solution (150 mL) was added. To this was added dropwise 2-methoxybenzoyl chloride (10 g) while maintaining the temperature at 5° C. or less, and the mixture was stirred for 1 hour at 10° C. or less. The aqueous phase was removed by phase separation from this reaction mixture, and the remaining ethyl acetate phase was washed with aqueous sodium bicarbonate and brine, and dried over magnesium sulfate, and then the solvent was distilled off. The resulting oil was dissolved in heated methanol and then cooled to give crystals, which were collected by filtration to give intermediate 313D (4.5 g).

To intermediate 313D (2.0 g) dissolved in acetic acid (25 mL) was added dropwise a solution of sodium nitrite (380 mg) dissolved in water (1 mL) while maintaining the temperature at 5 to 10° C. This mixture was stirred for 1 hour at room temperature, and then water (50 mL) was added. The resulting solid was collected by filtration to give intermediate 313C (2.1 g).

1H-NMR, 300 MHz, δ (CDCl$_3$) ppm: 1.8 (d, 6H), 4.0 (s, 3H), 4.1 (m, 1H), 7.1 (d, 1H), 7.2 (t, 1H), 7.4 (t, 1H), 7.5-7.7 (m, 2H), 8.0 (d, 2H), 8.2 (d, 1H), 12.9 (s, 1H).

To a suspension of intermediate 313C (1.1 g) in THF (5 mL) was added triethylamine (0.6 mL). This mixture was cooled to 5° C. or less, and a solution of p-nitrobenzenesulfonyl chloride (0.66 g) dissolved in THF (2 mL) was added dropwise. The mixture was stirred for 20 minutes at room temperature, and then water (25 mL) was added, and the resulting solid was collected by filtration. This solid was added to methanol (30 mL), and the mixture was stirred for 1 hour at room temperature, and undissolved solids were collected by filtration to give intermediate 313B (1.4 g).

1H-NMR, 300 MHz, δ (CDCl$_3$) ppm: 1.4 (d, 6H), 4.0 (s, 3H), 4.6 (m, 1H), 7.0-7.2 (m, 2H), 7.4-7.6 (m, 3H), 8.0 (d, 1H), 8.2 (d, 1H), 8.3 (d, 2H), 8.4 (d, 2H), 8.5 (d, 1H), 10.6 (s, 1H).

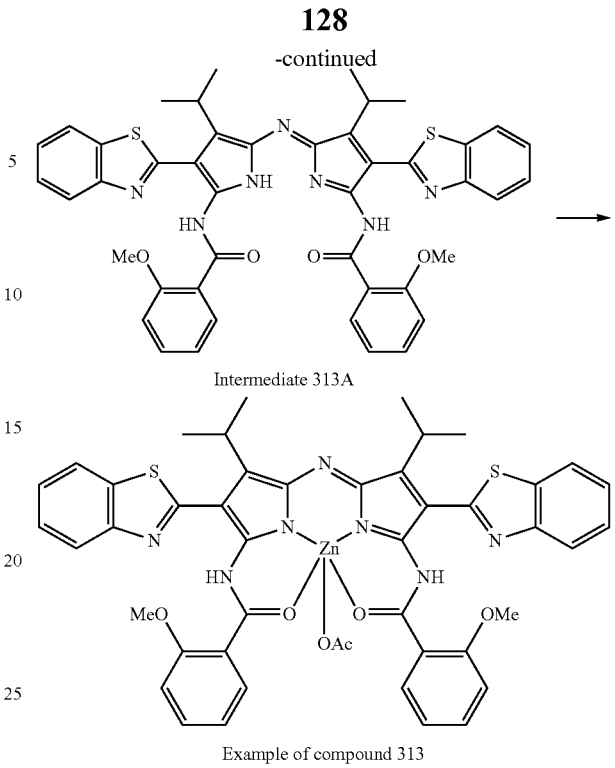

Intermediate 313D (0.7 g) and intermediate 313B (1.1 g) were dissolved in toluene (8 mL), and acetic acid (0.1 mL) was added. This mixture was stirred for 2 hours at 70° C., and then toluene was distilled off under reduced pressure. Colored components were separated from this residue by silica gel column chromatography, and washed successively with ethyl acetate and acetonitrile to give intermediate 313A (70 mg).

1H-NMR, 300 MHz, δ (CDCl$_3$) ppm: 1.7 (d, 12H), 3.8-4.0 (m, 8H), 7.1 (d, 2H), 7.2 (t, 2H), 7.4 (t, 2H), 7.4-7.6 (m, 4H), 7.9 (d, 4H), 8.3 (d, 2H), 12.6 (s, 2H).

UV-visible absorption spectrum λmax=599 nm (ethyl acetate). To a solution of intermediate 313A (36 mg) dissolved in THF (1.8 mL) was added dropwise a solution of zinc acetate (12 mg) in methanol (0.3 mL). This mixture was stirred for 20 minutes at room temperature, and then methanol (2 mL) was added. The precipitated solid was collected by filtration to give compound 313 (37 mg).

1H-NMR, 300 MHz, δ (CDCl$_3$) ppm: 1.6 (d, 12H), 1.9 (s, 3H), 3.7-4.0 (m, 8H), 7.1 (d, 2H), 7.2 (t, 2H), 7.4 (t, 2H), 7.5 (t, 2H), 7.6 (t, 2H), 7.9 (m, 4H), 8.3 (d, 2H), 13.1 (s, 2H). UV-visible absorption spectrum λmax=661 nm (ethyl acetate).

Synthesis Example of Compound 314

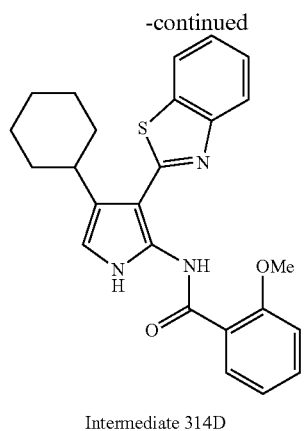

Intermediate 314D

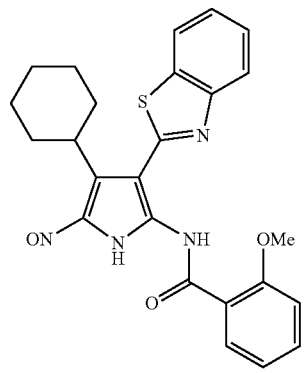

Intermediate 314C

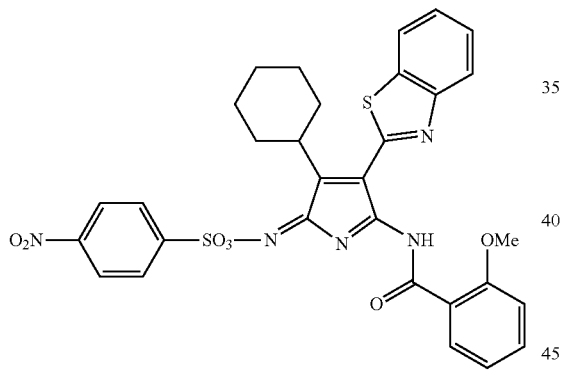

Intermediate 314B

1H-NMR, 300 MHz, δ (DMSO-d6) ppm: 1.2-2.1 (m, 10H), 3.0 (m, 1H), 4.1 (s, 3H), 6.4 (s, 1H), 7.2 (t, 1H), 7.4 (m, 2H), 7.5 (d, 1H), 7.6 (t, 1H), 7.9 (d, 1H), 8.0 (d, 1H), 8.1 (d, 1H), 11.7 (s, 1H), 12.4 (s, 1H).

To a suspension of intermediate 314D (1.7 g) in 20 mL of acetic acid was added dropwise a solution of sodium nitrite (304 mg) dissolved in 1 mL of water while maintaining the suspension at 5 to 10° C. This mixture was stirred for 30 minutes at room temperature, and then water (30 mL) was added. The resulting solid was collected by filtration to give intermediate 314C (1.8 g).

1H-NMR, 300 MHz, δ (CDCl$_3$) ppm: 1.4-1.7 (m, 3H), 1.8 (br, 1H), 2.0 (br, 2H), 2.2 (br, 2H), 2.4 (br, 2H), 3.6 (t, 1H), 4.0 (s, 3H), 7.1-7.2 (m, 2H), 7.5 (t, 1H), 7.5-7.7 (m, 2H), 7.9-8.0 (m, 2H), 8.1 (d, 1H).

To a suspension of intermediate 314C (0.92 g) in acetonitrile (60 mL) was added pyridine (0.32 g). This mixture was cooled to 5° C. or less, and p-nitrobenzenesulfonyl chloride (0.53 g) was added. This mixture was stirred for 1 hour at 5° C. and then methanol (10 mL) was added, and the resulting solid was collected by filtration to give intermediate 314B (1.16 g).

1H-NMR, 300 MHz, δ (CDCl$_3$) ppm: 1.2-2.0 (m, 10H), 4.0 (s, 3H), 4.3 (m, 1H), 7.0-7.2 (m, 2H), 7.4-7.6 (m, 3H), 8.0 (d, 1H), 8.1 (d, 1H), 8.3 (d, 2H), 8.4 (d, 2H), 8.5 (d, 1H), 10.6 (s, 1H).

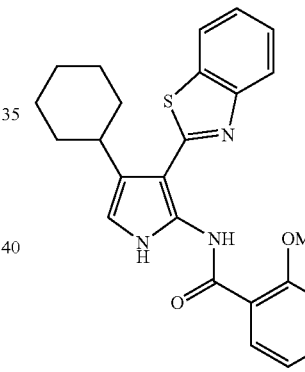

Intermediate 314D

According to the procedure described at page 302 of WO2011/40628, intermediate 314E was obtained from cyclohexyl methyl ketone.

1H-NMR, 300 MHz, δ (CDCl$_3$) ppm: 1.2-1.6 (m, 5H), 1.7 (br, 1H), 1.8 (br, 2H), 2.0 (br, 2H), 2.5 (tt, 1H), 4.6 (s, 2H), 7.7 (d, 2H), 7.9 (d, 2H).

To a mixture of intermediate 314E (6.6 g), 2-(cyanomethyl)benzothiazole (3.8 g), and 1-methoxy-2-propanol (50 mL) was added a 50% aqueous sodium hydroxide solution (4.0 mL) under a stream of nitrogen gas, and the mixture was stirred for 30 minutes at room temperature, and then for 5 hours at 90° C. To this reaction mixture was added water (50 mL), and the precipitated solid was collected by filtration.

The resulting solid was dissolved in 25 mL of N,N-dimethylacetamide, and 2-methoxybenzoyl chloride (7.5 g) was added dropwise while maintaining the temperature at 5° C. or less. This was stirred for 1 hour at room temperature to precipitate crystals, which were collected by filtration to give intermediate 314D (3.5 g).

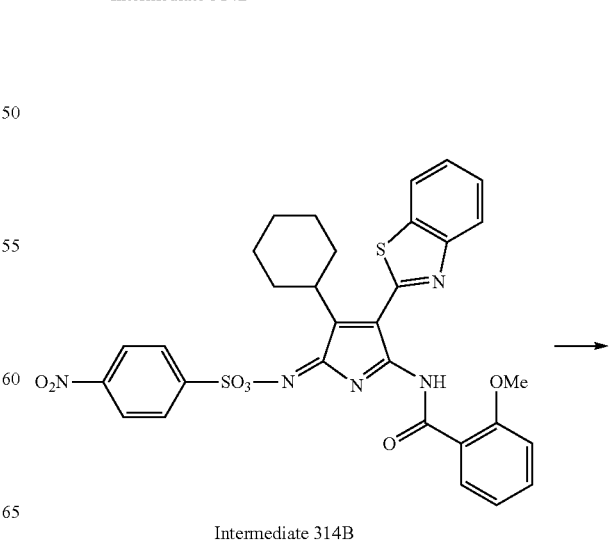

Intermediate 314B

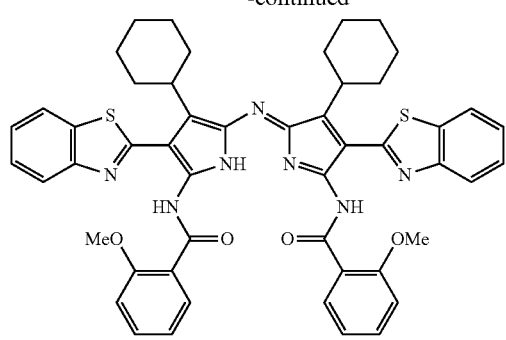

Intermediate 314A

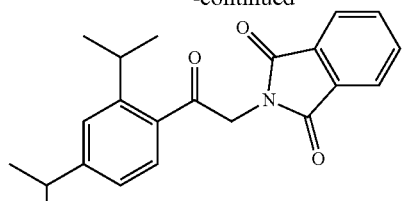

Intermediate 315F

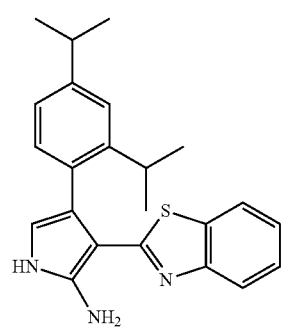

Intermediate 315E

Example of compound 314

To a suspension of intermediate 314D (367 mg) in toluene (4 mL) was added acetic acid (0.1 mL). To a solution obtained by heating this mixture to 95° C. was added intermediate 314B (549 mg) by portions. The mixture was stirred for 10 minutes at 95° C., and then toluene was distilled off under reduced pressure. Colored components were separated from this residue by silica gel column chromatography, and washed with ethyl acetate to give intermediate 314A (18 mg).

UV-visible absorption spectrum $\lambda$max=599 nm (ethyl acetate) Intermediate 314A (17 mg) was dissolved in THF (1.0 mL), and a solution of zinc acetate (5 mg) dissolved in methanol (0.2 mL) was added dropwise. This mixture was stirred for 10 minutes at room temperature, and then methanol (2 mL) was added. The precipitated solid was collected by filtration to give compound 314 (9 mg).

UV-visible absorption spectrum $\lambda$max=660 nm (ethyl acetate).

Synthesis Example of Compound 315

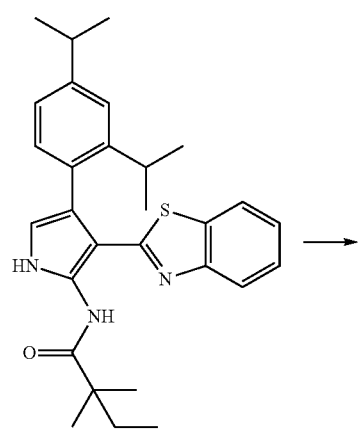

Intermediate 315D

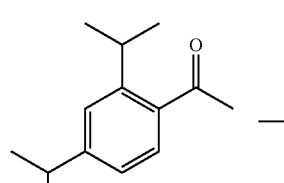

Intermediate 315G

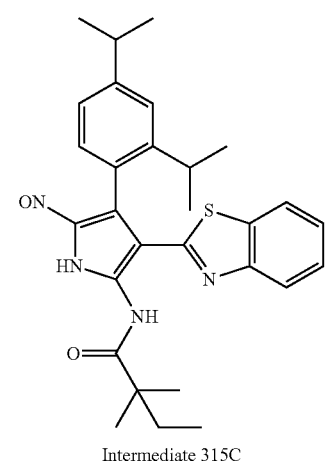

Intermediate 315C

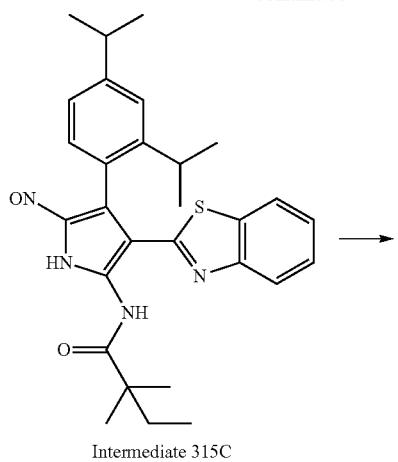

Intermediate 315C

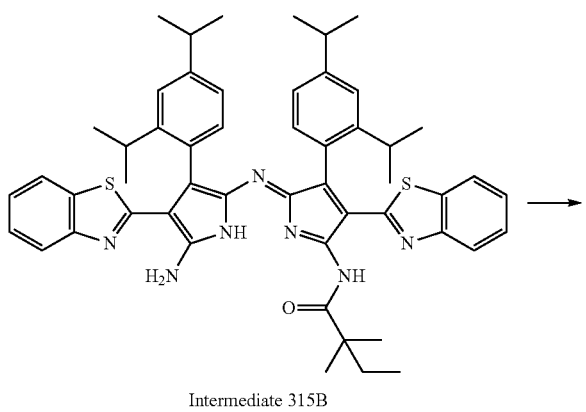

Intermediate 315B

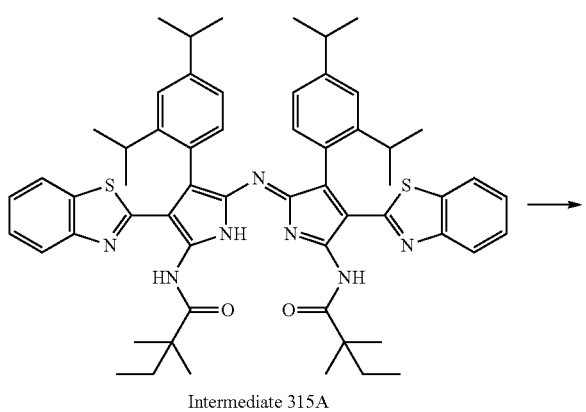

Intermediate 315A

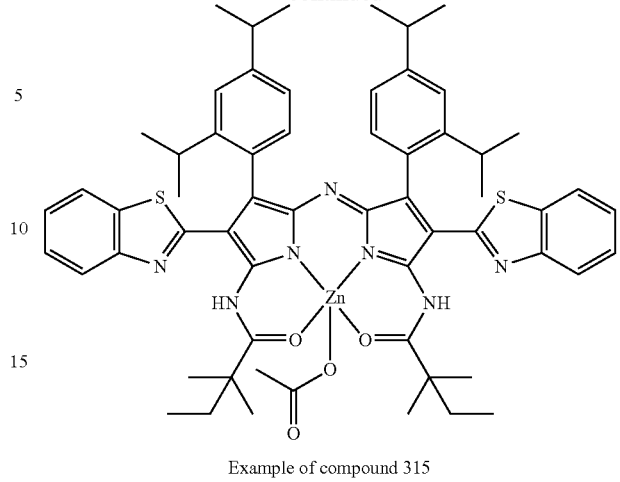

Example of compound 315

A flask was charged with 1,3-diisopropylbenzene (162 g) and chloroform (500 mL), and stirring was started in an ice-water bath. To this was slowly added dropwise acetyl chloride (94 g), and then aluminum chloride (160 g) was added by portions to keep the internal temperature at or below 20° C. After one hour, the contents of the flask were poured on iced water (1 L), and extracted with ethyl acetate (1 L). The organic layer was dried over sodium sulfate and concentrated to give intermediate 315G (184 g). A flask was charged with intermediate 315G (183 g) and ethyl acetate (1 L), and stirring was started. To this was added slowly pyridinium bromide perbromide (303 g), and the mixture was further stirred for 1 hour. To this was added water (1 L), and the aqueous layer was removed, and the resulting organic layer was concentrated. To the residue was added N-methylpyrrolidone (600 mL), and stirring was started. To this was added potassium phthalimide (183 g), and the mixture was further stirred for 2 hours. When the resulting reaction solution was poured into 1.8 L of water, the mixture was separated into a gum-like liquid and an aqueous layer. The aqueous layer was removed, and isopropyl alcohol (400 mL) was added and the precipitated crystals were collected by filtration to give intermediate 315F (93 g).

1H-NMR, 300 MHz, δ (DMSO-d6) ppm: 1.1 (d, 6H), 1.1 (d, 6H), 3.0 (sep, 1H), 3.4 (sep, 1H), 5.1 (s, 2H), 7.3 (d, 1H), 7.4 (s, 1H), 7.9-8.1 (m, 5H).

A flask was charged with intermediate 315F (11.6 g), 2-(cyanomethyl)benzothiazole (5.8 g), 1-butanol (20 mL), a 50% aqueous sodium hydroxide solution (5.3 g), and water (5.3 g), and the mixture was heated under reflux at 130° C. for 2 hours under a stream of nitrogen gas. After cooling to room temperature, toluene (50 mL) and water (50 mL) were added, and the aqueous layer was removed to give a toluene solution of intermediate 315E. To this toluene solution were added a 50% aqueous sodium hydroxide solution (13.2 g) and water (50 mL), and stirring was started in an ice water bath. To this was added dropwise 2,2-dimethyl butyryl chloride (10 g), and the mixture was further stirred for one hour. The aqueous layer was removed from the reaction solution, and the mixture was further washed with a saturated aqueous sodium bicarbonate solution (50 mL) three times. The resulting organic layer was dried over sodium sulfate and then concentrated, and the resulting residue was washed with methanol (50 mL) with heating. The precipitated crystals were filtered off to give intermediate D (4.59 g).

1H-NMR, 300 MHz, δ (DMSO-d6) ppm: 0.9 (t, 3H), 1.1 (d, 6H), 1.3 (d, 6H), 1.4 (s, 6H), 1.7 (q, 2H), 2.8-3.1 (m, 2H), 6.4 (s, 1H), 7.1 (m, 2H), 7.2-7.3 (2H), 7.4 (dd, 1H), 7.8 (d, 1H), 7.9 (d, 1H), 11.7 (s, 1H), 11.9 (s, 1H).

A flask was charged with intermediate D (4.59 g) and acetic acid (46 mL), and stirring was started in a water bath. To this was slowly added dropwise nitrosylsulfuric acid (40% in sulfuric acid) (4.48 g), and the mixture was further stirred for 30 minutes. The flask was placed in an ice water bath, and 150 mL of water was added dropwise. After the dropwise addition, the mixture was stirred for 1 hour, and then the precipitated solid was collected by filtration, and the resulting crystals were washed with water and air-dried at room temperature to give intermediate 315C.

A flask was charged with intermediate 315F (11.6 g), 2-(cyanomethyl)benzothiazole (5.8 g), 1-butanol (20 mL), a 50% aqueous sodium hydroxide solution (5.3 g), and water (8 g), and the mixture was heated under reflux at 130° C. for 2 hours under a stream of nitrogen gas. This was cooled with an ice bath, and water (20 mL) was added dropwise. The precipitated solid was removed, and the resulting filtrate was combined with concentrated hydrochloric acid (20 mL) to precipitate a gum. The aqueous layer was removed, and the gum was combined with ethyl acetate (50 mL) to precipitate crystals. The crystals were collected by filtration to give a mixture of a hydrochloride of intermediate 315E and phthalimide (3.6 g). A flask was charged with 3.6 g of this mixture, intermediate C (3.6 g), potassium acetate (3.8 g), and acetic acid (30 mL), and the mixture was stirred for 1.5 hours at room temperature. To this was added methanol (60 mL), and the precipitated crystals were collected by filtration, and the collected crystals were washed successively with methanol (30 mL) and water (200 mL) to give intermediate 315B (3.51 g).

1H-NMR, 300 MHz, δ (DMSO-d6) ppm: 0.4 (t, 3H), 0.6-0.8 (m, 2H), 0.8-1.0 (m, 10H), 1.3 (m, 12H), 1.4 (s, 6H), 1.8 (q, 2H), 2.7-3.0 (m, 4H), 6.9-4.8 (m, 10H), 7.8 (d, 1H), 7.9 (d, 1H), 8.0 (d, 1H), 8.1 (d, 1H), 8.5-8.9 (m, 2H), 12.2-12.3 (m, 1H), 12.8-13.0 (m, 1H).

A flask was charged with intermediate 315B (3.45 g), toluene (20 mL), a 50% aqueous sodium hydroxide solution (3.2 g), tetrabutylammonium bromide (3.9 g), and water (20 mL), and stirring was started in an ice water bath. To this was added dropwise 2,2-dimethyl butyryl chloride (4 g), and the mixture was stirred for 3 hours. To the reaction solution was added ethyl acetate (50 mL), and the aqueous layer was removed, and the resulting organic layer was further washed with a saturated aqueous sodium bicarbonate solution (100 mL) three times and with saturated brine (100 mL) twice. This organic layer was dried over sodium sulfate and then concentrated, and the resulting residue was washed with methanol (50 mL) with heating. The precipitated crystals were collected by filtration to give intermediate 315A (2.2 g).

1H-NMR, 300 MHz, δ (CDCl₃) ppm: 0.5 (d, 6H), 0.9 (d, 6H), 1.1 (t, 6H), 1.3 (dd, 12H), 1.5 (s, 1H), 1.9 (q, 4H), 6.9-7.1 (m, 6H), 7.2-7.3 (m, 2H), 7.4 (dd, 2H), 7.7 (d, 2h), 7.9 (d, 2H), 12.3 (s, 2H).

A flask was charged with intermediate 315A (2.0 g), zinc acetate dihydrate (1.0 g), tetrahydrofuran (20 mL), and acetic acid (0.2 mL), and the mixture was stirred for 30 minutes. To this was added 30 mL of water, and the precipitated solid was filtered off to give compound 315 (2.0 g).

1H-NMR, 300 MHz, δ (CDCl₃) ppm: 0.5 (d, 6H), 0.9 (d, 6H), 1.1 (t, 6H), 1.3 (m, 12H), 1.5 (s, 12H), 1.9 (q, 4H), 2.0 (s, 3H), 2.8 (sep, 2H), 3.0 (sep, 2H), 6.9-7.1 (m, 6H), 7.3 (dd, 2H), 7.4 (dd, 2H), 7.7 (d, 2H), 7.8 (d, 2H), 12.7 (s, 2H).

Synthesis Example of Compound 316

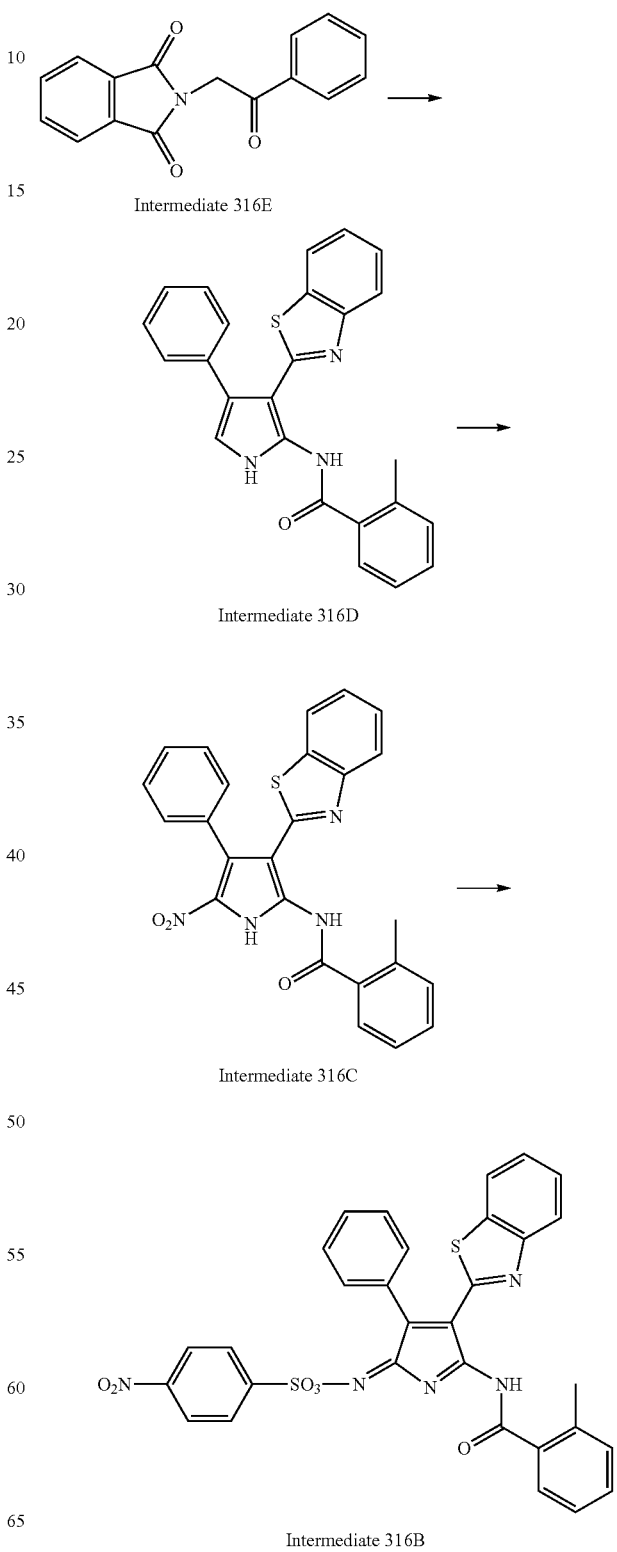

Intermediate 316E

Intermediate 316D

Intermediate 316C

Intermediate 316B

137

-continued

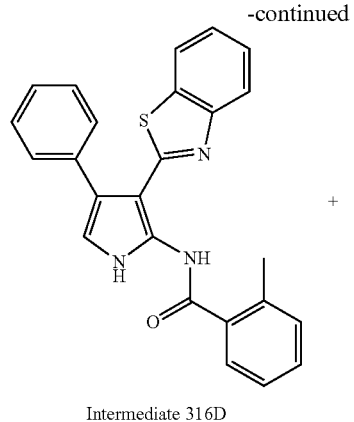

Intermediate 316D

+

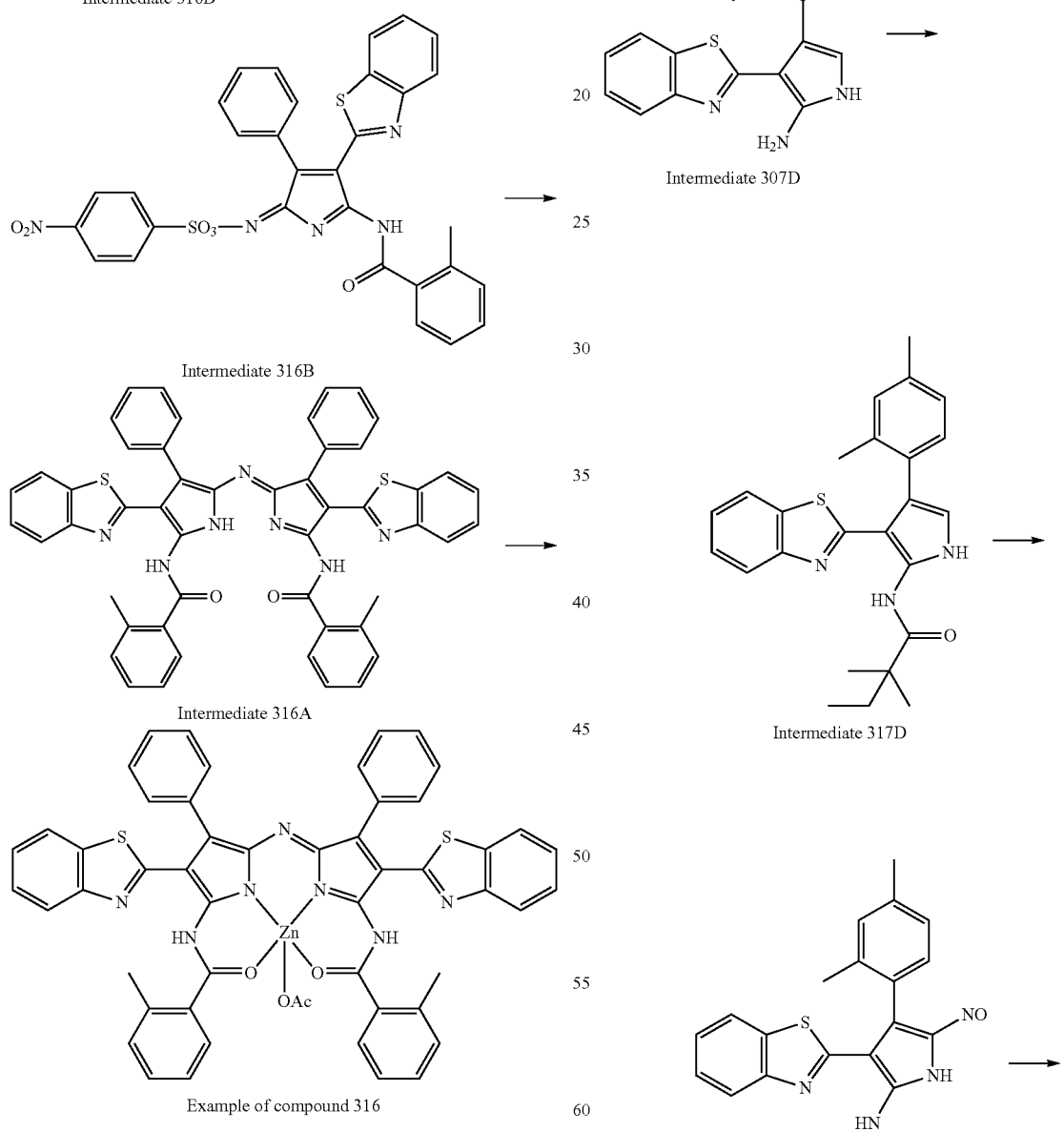

The title compound was synthesized according to the procedure described for compound 314 except that intermediate 314E was replaced by, intermediate 316E and 2-methoxybenzoyl chloride was replaced by o-toluoyl chloride during the step of synthesizing intermediate 316D.

138

Intermediate 316A: 1H-NMR, 300 MHz, δ (CDCl$_3$) ppm: 2.8 (s, 6H), 7.2-7.6 (m, 20H), 7.7 (d, 2H), 7.8 (d, 2H), 8.0 (d, 2H), 12.8 (s, 2H).

Compound 316: 1H-NMR, 300 MHz, δ (CDCl$_3$) ppm: 2.0 (s, 3H), 3.8 (s, 6H), 7.2-7.6 (m, 20H), 7.7 (d, 2H), 7.8 (d, 2H), 8.0 (d, 2H), 13.3 (s, 2H).

Synthesis Example of Compound 317

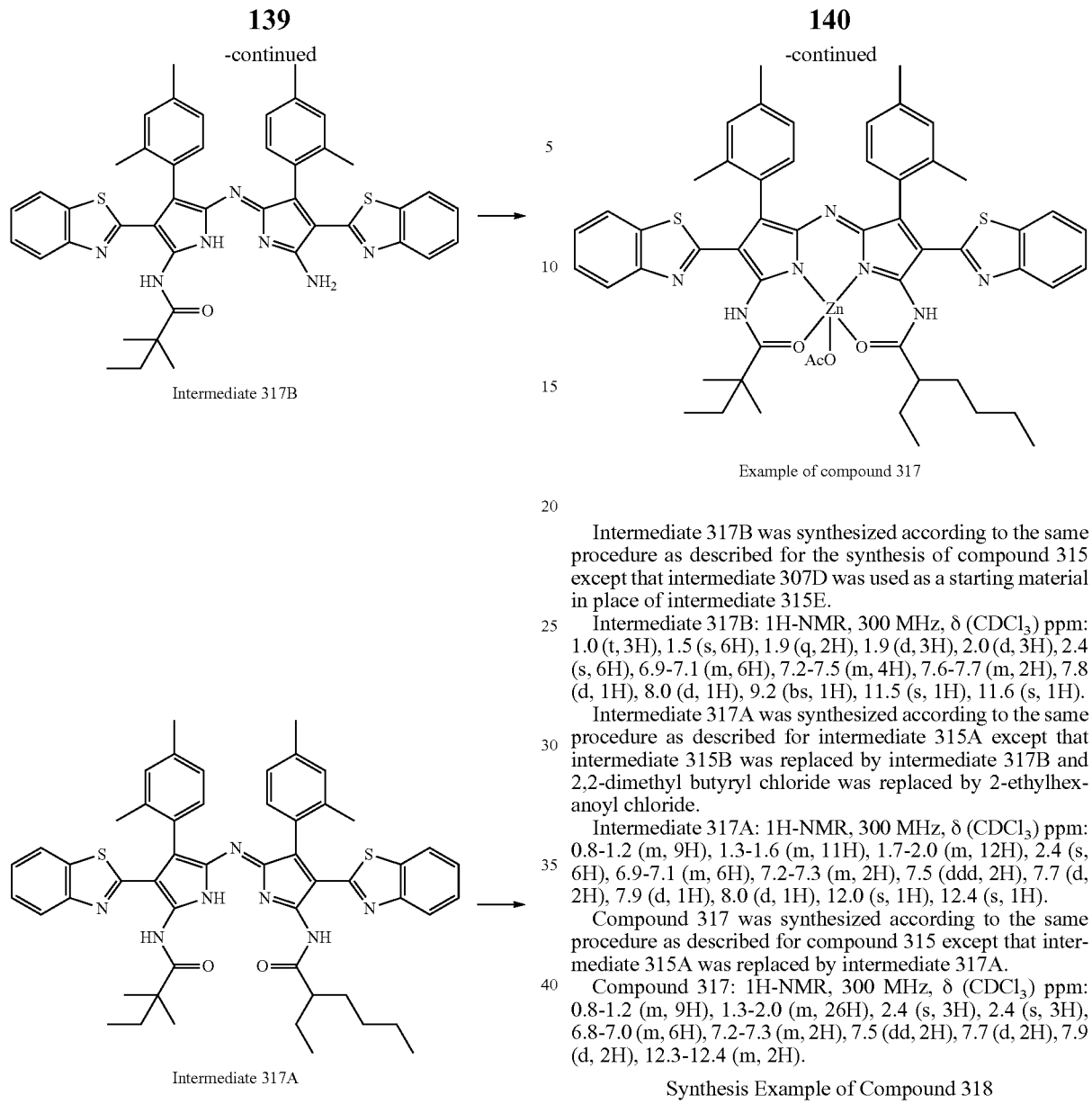

Example of compound 317

Intermediate 317B was synthesized according to the same procedure as described for the synthesis of compound 315 except that intermediate 307D was used as a starting material in place of intermediate 315E.

Intermediate 317B: 1H-NMR, 300 MHz, δ (CDCl$_3$) ppm: 1.0 (t, 3H), 1.5 (s, 6H), 1.9 (q, 2H), 1.9 (d, 3H), 2.0 (d, 3H), 2.4 (s, 6H), 6.9-7.1 (m, 6H), 7.2-7.5 (m, 4H), 7.6-7.7 (m, 2H), 7.8 (d, 1H), 8.0 (d, 1H), 9.2 (bs, 1H), 11.5 (s, 1H), 11.6 (s, 1H).

Intermediate 317A was synthesized according to the same procedure as described for intermediate 315A except that intermediate 315B was replaced by intermediate 317B and 2,2-dimethyl butyryl chloride was replaced by 2-ethylhexanoyl chloride.

Intermediate 317A: 1H-NMR, 300 MHz, δ (CDCl$_3$) ppm: 0.8-1.2 (m, 9H), 1.3-1.6 (m, 11H), 1.7-2.0 (m, 12H), 2.4 (s, 6H), 6.9-7.1 (m, 6H), 7.2-7.3 (m, 2H), 7.5 (ddd, 2H), 7.7 (d, 2H), 7.9 (d, 1H), 8.0 (d, 1H), 12.0 (s, 1H), 12.4 (s, 1H).

Compound 317 was synthesized according to the same procedure as described for compound 315 except that intermediate 315A was replaced by intermediate 317A.

Compound 317: 1H-NMR, 300 MHz, δ (CDCl$_3$) ppm: 0.8-1.2 (m, 9H), 1.3-2.0 (m, 26H), 2.4 (s, 3H), 2.4 (s, 3H), 6.8-7.0 (m, 6H), 7.2-7.3 (m, 2H), 7.5 (dd, 2H), 7.7 (d, 2H), 7.9 (d, 2H), 12.3-12.4 (m, 2H).

Synthesis Example of Compound 318

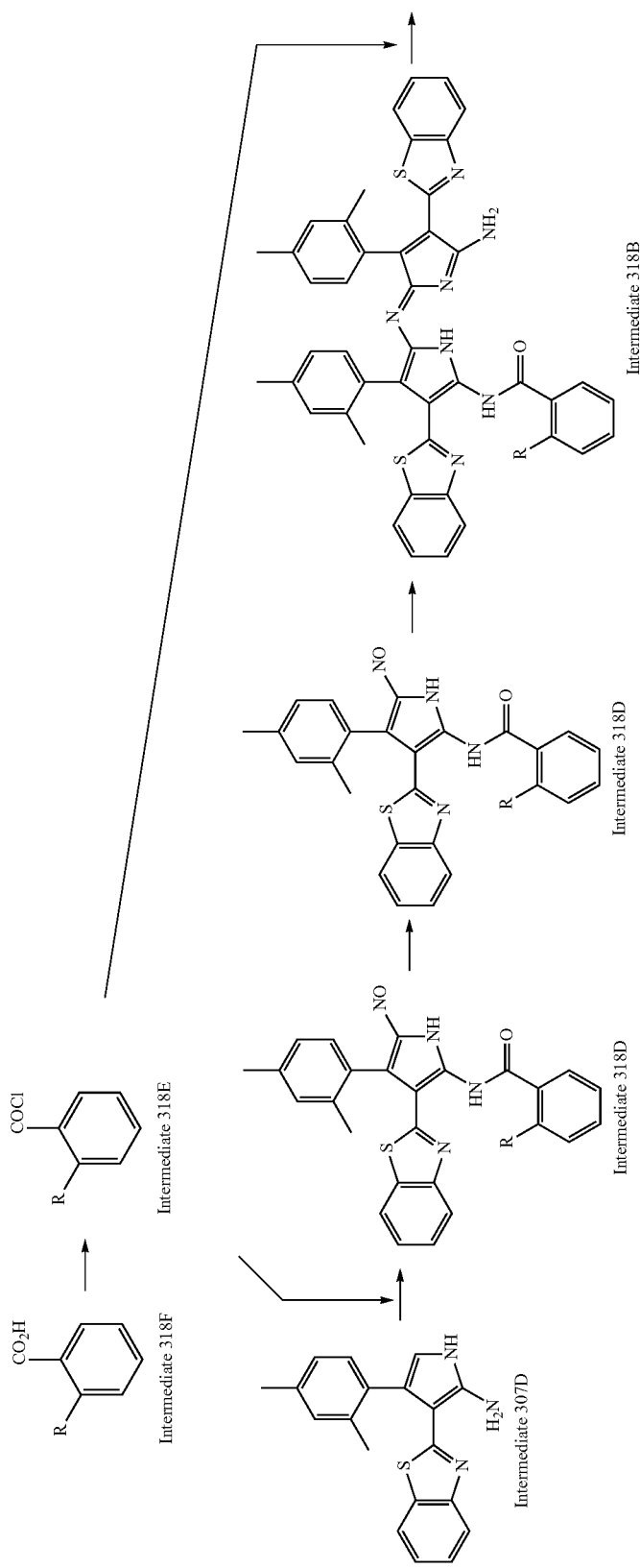

-continued
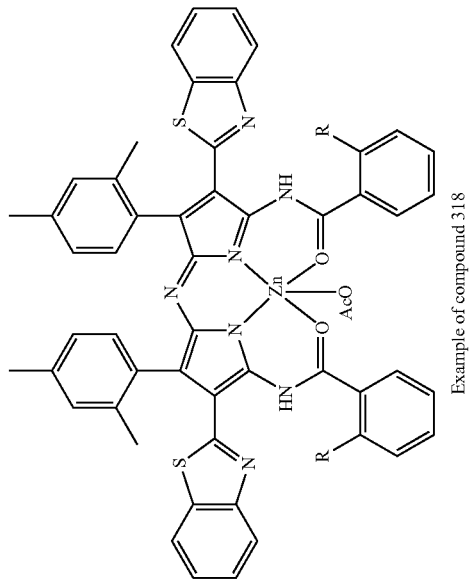
Example of compound 318
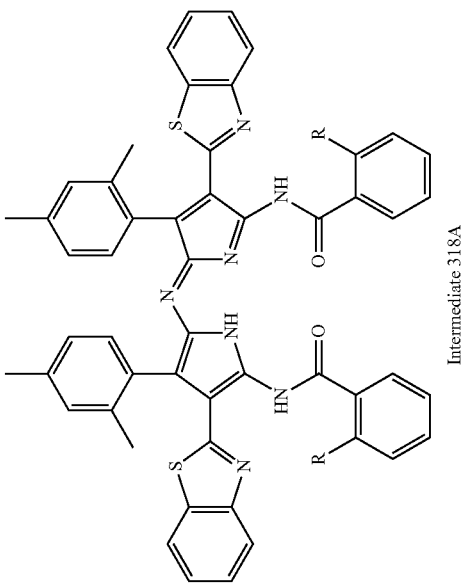
Intermediate 318A
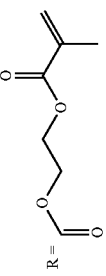

Intermediate 318F (9.18 g) and oxalyl chloride (4.61 g) were mixed for 2 hours at room temperature, and the mixture was concentrated under reduced pressure at room temperature to give intermediate 318E.

To a stirred mixture of intermediate 307D (9.58 g), toluene (30 mL), a 50% aqueous sodium hydroxide solution (7.2 g), water (30 mL), and tetraammonium chloride (3.2 g) was added dropwise intermediate 318D (8 g). This reaction solution was stirred for 1 hour, and then extracted with ethyl acetate, and the organic layer was washed with brine. The organic layer was dried over sodium sulfate, and then purified by silica gel column chromatography (eluent: ethyl acetate/hexane=1/2) to give intermediate 318D. Intermediate 318D to compound 318 were synthesized according to the same procedure as described for exemplary compound 317.

Intermediate 318B: 1H-NMR, 300 MHz, δ (CDCl$_3$) ppm: 1.9 (s, 3H), 2.1 (S, 6H), 2.1-2.2 (m, 2H), 2.4 (s, 6H), 4.4 (d, 2H), 4.6 (d, 2H), 5.4 (s, 1H), 6.1 (s, 1H), 6.9-8.1 (m, 18H), 12.5 (s, 1H).

Intermediate 318A: 1H-NMR, 300 MHz, δ (CDCl$_3$) ppm: 1.2-1.4 (m, 1H), 1.8-1.9 (m, 6H), 2.0 (d, 6H), 2.4 (d, 6H), 4.3-4.6 (m, 4H), 5.4-5.6 (m, 2H), 6.0-6.2 (m, 2H), 6.9-8.1 (m, 22H), 12.5-12.6 (m, 2H).

Compound 318: 1H-NMR, 300 MHz, δ (CDCl$_3$) ppm: 2.1 (s, 3H), 2.4 (s, 6H), 2.5 (s, 6H), 4.4 (t, 4H), 4.5 (t, 4H), 5.5 (s, 2H), 6.1 (s, 2H), 6.9-8.1 (m, 22H), 13.3-13.5 (m, 2H).

Synthesis Example of Compound 319

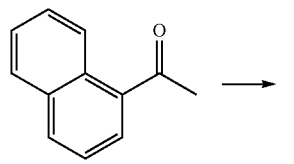

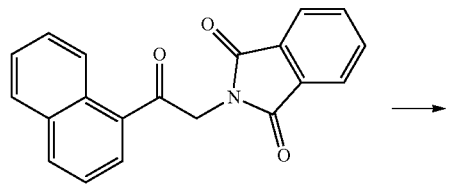

Intermediate 319F

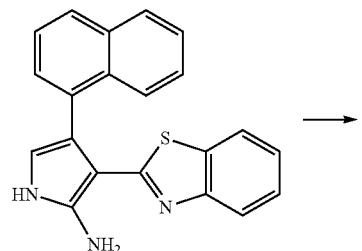

Intermediate 319E

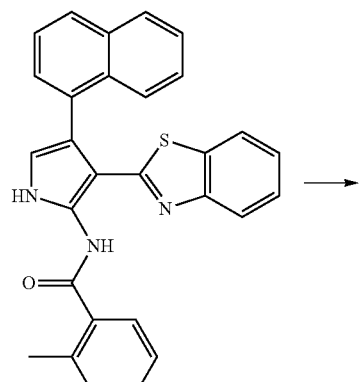

Intermediate 319D

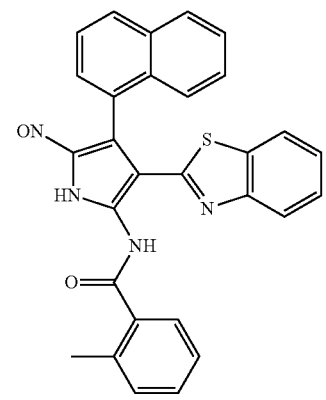

Intermediate 319C

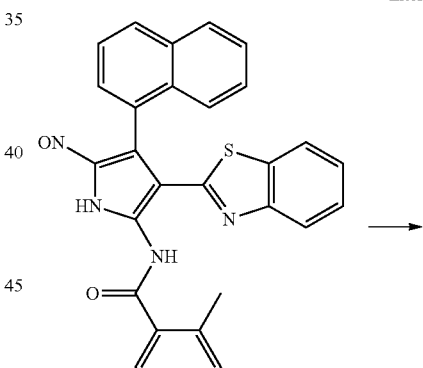

Intermediate 319C

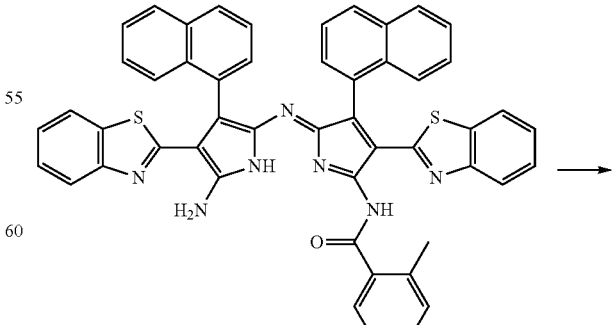

Intermediate 319B

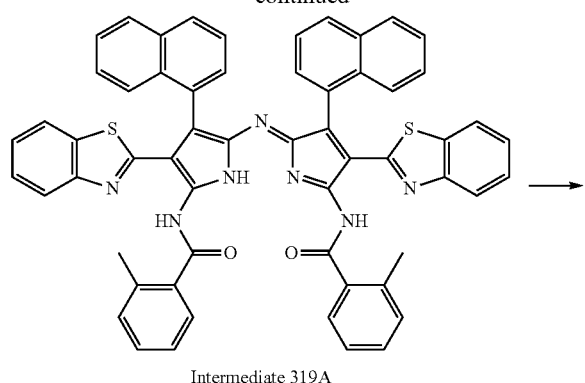
Intermediate 319A
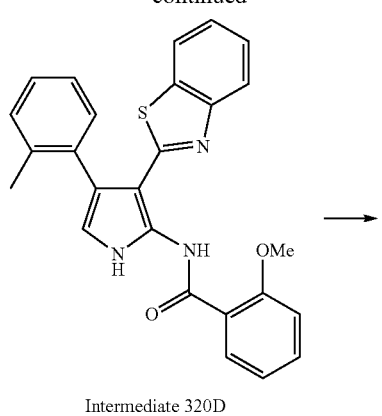
Intermediate 320D
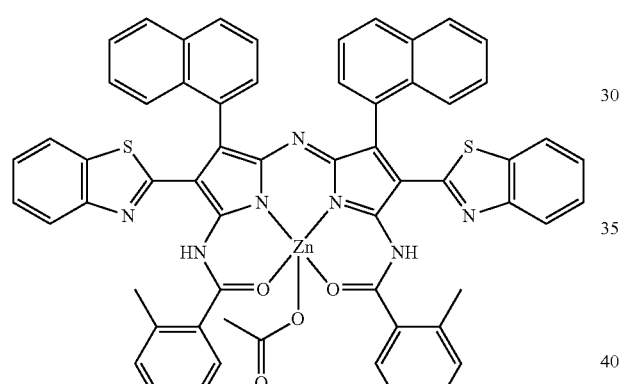
Example of compound 319
The title compound was synthesized using the procedure for synthesizing compound 315.
The wavelength of maximum absorption λmax of compound 312 was 683 nm (in chloroform).
Compound 318: 1H-NMR, 300 MHz, δ (CDCl$_3$) ppm: 2.0 (s, 3H), 2.9 (s, 6H), 7.2-7.9 (m, 28H), 8.0 (d, 2H), 13.2 (s, 2H).
Synthesis Example of Compound 320
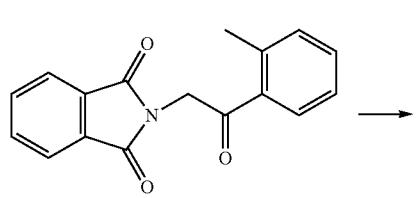
Intermediate 301E
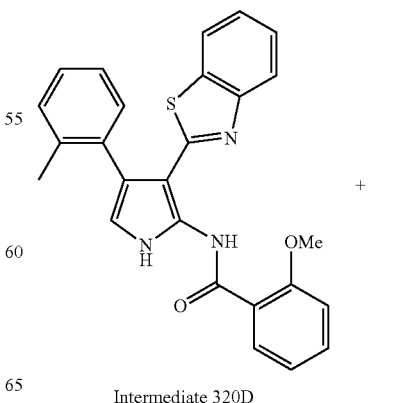
Intermediate 320C
Intermediate 320B
Intermediate 320D -continued

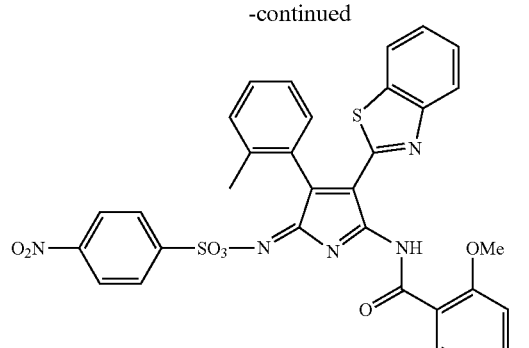
Intermediate 320B

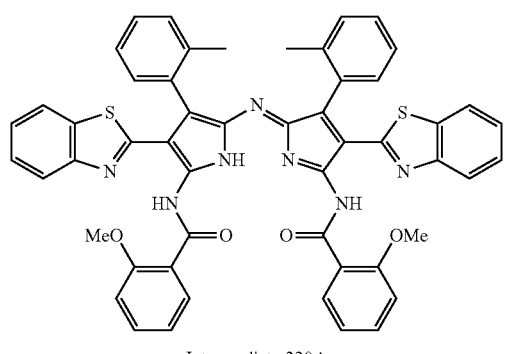
Intermediate 320A

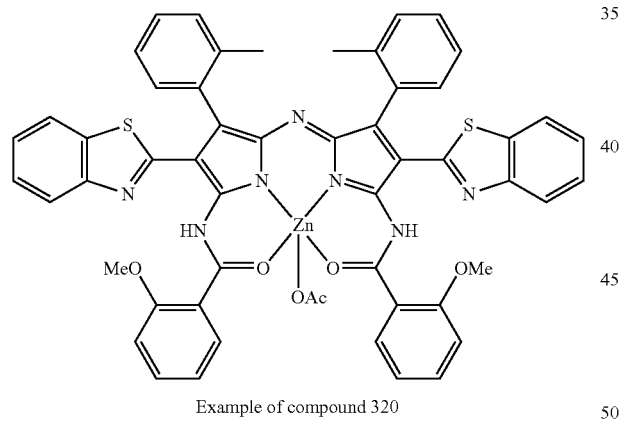
Example of compound 320

The title compound was synthesized using the procedure for synthesizing compound 314 except that intermediate 314E was replaced by intermediate 301E.

Intermediate 320D: 1H-NMR, 300 MHz, δ (DMSO-d6) ppm: 2.1 (s, 3H), 4.1 (s, 3H), 6.5 (s, 1H), 7.1-7.5 (m, 8H), 7.6 (dd, 1H), 7.8-7.9 (m, 2H), 8.1 (d, 1H), 12.0 (s, 1H), 12.4 (s, 1H).

Intermediate 320C: 1H-NMR, 300 MHz, δ (CDCl₃) ppm: 2.0 (s, 3H), 3.9 (s, 3H), 8.0 (d, 1H), 7.0-7.9 (m, 10H), 8.2 (d, 1H), 8.5 (bs, 1H).

Intermediate 320B: 1H-NMR, 300 MHz, δ (CDCl₃) ppm: 2.0 (s, 3H), 3.9 (s, 3H), 7.0-8.3 (m, 16H), 12.8 (s, 1H)

Intermediate 320A: 1H-NMR, 300 MHz, δ (CDCl₃) ppm: 2.1 (s, 6H), 4.0 (s, 6H), 7.1-7.3 (m, 14H), 7.4 (dd, 2H), 7.6 (dd, 2H), 7.7 (d, 2H), 7.9 (d, 2H), 8.4 (d, 2H), 12.8 (s, 2H)

Compound 320: 1H-NMR, 300 MHz, δ (CDCl₃) ppm: 1.9 (s, 3H), 2.0-2.2 (bs, 6H), 4.1 (s, 6H), 7.1-7.3 (m, 14H), 7.4 (dd, 2H), 7.6-7.7 (m, 4H), 7.9 (d, 2H), 8.4 (d, 2H), 13.2 (s, 2H).

Synthesis Example of Compound 321

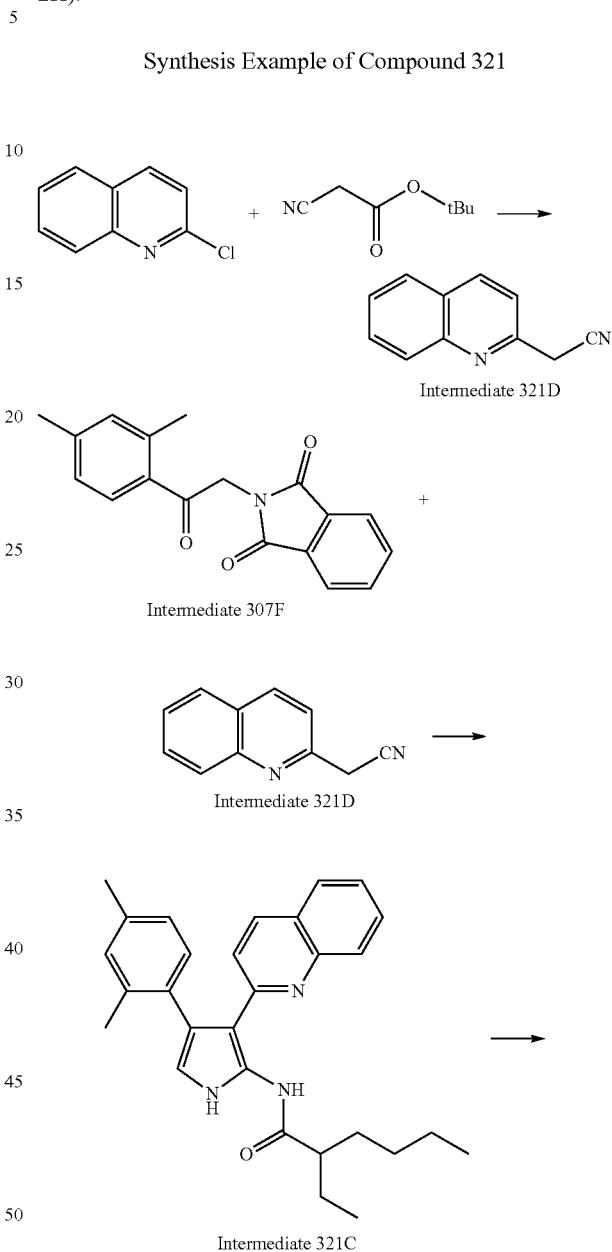

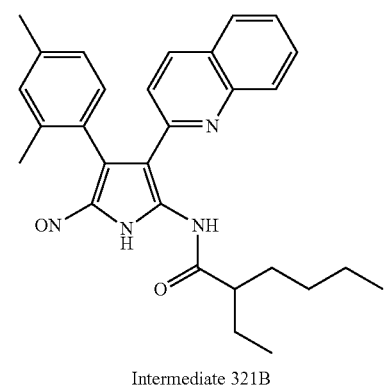
Intermediate 321B

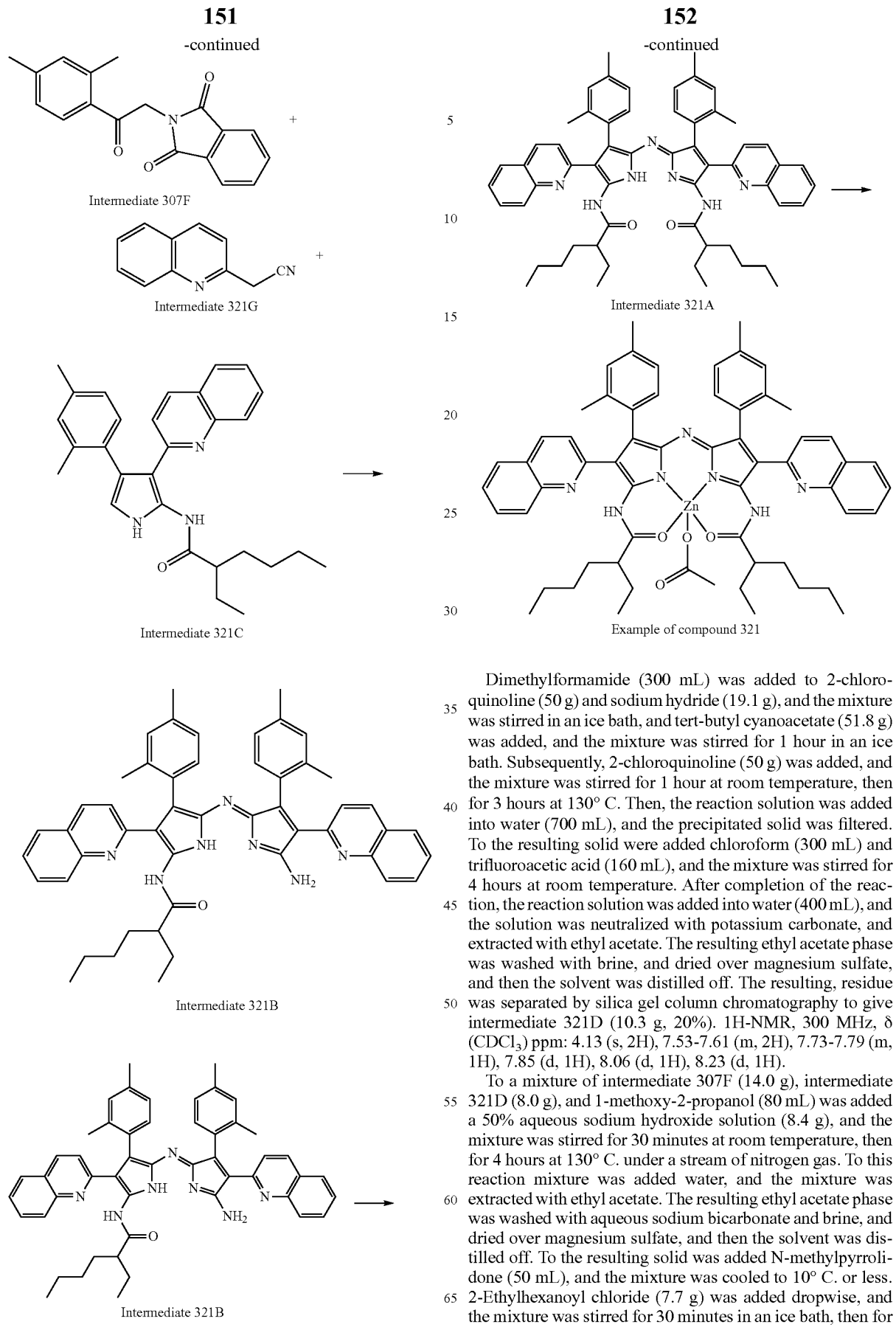

Dimethylformamide (300 mL) was added to 2-chloroquinoline (50 g) and sodium hydride (19.1 g), and the mixture was stirred in an ice bath, and tert-butyl cyanoacetate (51.8 g) was added, and the mixture was stirred for 1 hour in an ice bath. Subsequently, 2-chloroquinoline (50 g) was added, and the mixture was stirred for 1 hour at room temperature, then for 3 hours at 130° C. Then, the reaction solution was added into water (700 mL), and the precipitated solid was filtered. To the resulting solid were added chloroform (300 mL) and trifluoroacetic acid (160 mL), and the mixture was stirred for 4 hours at room temperature. After completion of the reaction, the reaction solution was added into water (400 mL), and the solution was neutralized with potassium carbonate, and extracted with ethyl acetate. The resulting ethyl acetate phase was washed with brine, and dried over magnesium sulfate, and then the solvent was distilled off. The resulting, residue was separated by silica gel column chromatography to give intermediate 321D (10.3 g, 20%). 1H-NMR, 300 MHz, δ (CDCl$_3$) ppm: 4.13 (s, 2H), 7.53-7.61 (m, 2H), 7.73-7.79 (m, 1H), 7.85 (d, 1H), 8.06 (d, 1H), 8.23 (d, 1H).

To a mixture of intermediate 307F (14.0 g), intermediate 321D (8.0 g), and 1-methoxy-2-propanol (80 mL) was added a 50% aqueous sodium hydroxide solution (8.4 g), and the mixture was stirred for 30 minutes at room temperature, then for 4 hours at 130° C. under a stream of nitrogen gas. To this reaction mixture was added water, and the mixture was extracted with ethyl acetate. The resulting ethyl acetate phase was washed with aqueous sodium bicarbonate and brine, and dried over magnesium sulfate, and then the solvent was distilled off. To the resulting solid was added N-methylpyrrolidone (50 mL), and the mixture was cooled to 10° C. or less. 2-Ethylhexanoyl chloride (7.7 g) was added dropwise, and the mixture was stirred for 30 minutes in an ice bath, then for 1 hour at room temperature. After completion of the reaction, water was added to the reaction solution, and the mixture was extracted with ethyl acetate. The resulting ethyl acetate phase was washed with dilute hydrochloric acid and brine, and dried over magnesium sulfate, and then the solvent was distilled off. The resulting solid was washed with acetonitrile and methanol to give intermediate 321C (3.7 g, 18%).

1H-NMR, 300 MHz, δ (CDCl$_3$) ppm: 0.88 (t, 3H), 1.05 (t, 3H), 1.36 to 1.91 (m, 8H), 2.12 (s, 3H), 2.34 to 2.41 (m, 4H), 6.40 (d, 1H), 6.92 (d, 1H), 7.05-7.10 (m, 2H), 7.22 (d, 1H), 7.35-7.41 (m, 1H), 7.62-7.67 (m, 2H), 7.76 (d, 1H), 7.86 (d, 1H).

To intermediate 321C (2.0 g) in acetic acid (20 mL) was added dropwise nitrosylsulfuric acid (43% in sulfuric acid) (1.5 g), and the mixture was stirred for 1 hour at room temperature. After completion of the reaction, water (20 mL) was added, and the resulting solid was filtered, and the retained solid was dried. This gave intermediate 312B (1.5 g, yield 71%).

1H-NMR, 300 MHz, δ (CDCl$_3$) ppm: 0.88 (t, 3H), 1.05 (t, 3H), 1.34 to 1.91 (m, 8H), 2.20 (s, 3H), 2.44 to 2.56 (m, 4H), 7.02-7.28 (m, 3H), 7.39 (d, 1H), 7.54-7.59 (m, 1H), 7.75-7.80 (m, 2H), 7.96 (d, 2H).

To a mixture of intermediate 307F (7.7 g), intermediate 321D (4.4 g), and 1-methoxy-2-propanol (40 mL) was added a 50% aqueous sodium hydroxide solution (8.4 g), and the mixture was stirred for 30 minutes at room temperature, then for 4 hours at 130° C. under a stream of nitrogen gas. To this reaction mixture was added water, and the mixture was extracted with ethyl acetate. The resulting ethyl acetate phase was washed with aqueous sodium bicarbonate and brine, and dried over magnesium sulfate, and then the solvent was distilled off. To the resulting residue were added acetic acid (60 mL) and intermediate 321B (7.2 g), and the mixture was stirred for 3 hours at room temperature, and then 200 mL of water was added. The resulting crystals were washed with methanol with heating to give intermediate 321A (0.5 g, yield 3%).

1H-NMR, 300 MHz, δ (CDCl$_3$) ppm: 0.89 (t, 3H), 1.09 (t, 3H), 1.25 to 2.02 (m, 14H), 2.36 to 2.47 (m, 7H), 6.86-7.28 (m, 10H), 7.36-7.41 (m, 1H), 7.46-7.51 (m, 1H), 7.63-7.89 (m, 6H), 8.05 (m, 1H), 13.20 (s, 1H).

To intermediate 321A (270 mg) in tetrabutylammonium bromide (1140 mg) were added toluene (9 mL), water (9 mL), and a 50% aqueous sodium hydroxide solution (1130 mg), and the mixture was stirred at room temperature. Then, 2-ethylhexanoyl chloride (290 mg) was added dropwise, and the mixture was stirred for 2 hours at room temperature. After completion of the reaction, the mixture was extracted with toluene, and the resulting toluene phase was washed with aqueous sodium bicarbonate, dilute hydrochloric acid and brine, and dried over magnesium sulfate, and then the solvent was distilled off. To the resulting solid were added zinc acetate dihydrate (95 mg), tetrahydrofuran (5 mL), and acetic acid (2.5 mL), and the mixture was stirred for 1 hour at room temperature. After completion of the reaction, water was added, and the precipitated solid was filtered, and dried. This gave compound 321 (320 mg, yield 89%). 1H-NMR, 300 MHz, δ (CDCl$_3$) ppm: 0.90 (m, 6H), 1.17 (m, 6H), 1.32 to 2.02 (m, 25H), 2.37 (s, 3H), 2.61 (m, 2H), 6.88 (m, 4H), 7.05 (m, 2H), 7.19-7.27 (m, 2H), 7.44-7.49 (m, 2H), 7.68-7.73 (m, 4H), 7.81-7.92 (m, 4H), 13.62 (m, 2H);

UV-visible absorption spectrum λmax=656 nm (CHCl$_3$).

Synthesis Example of Compound 322

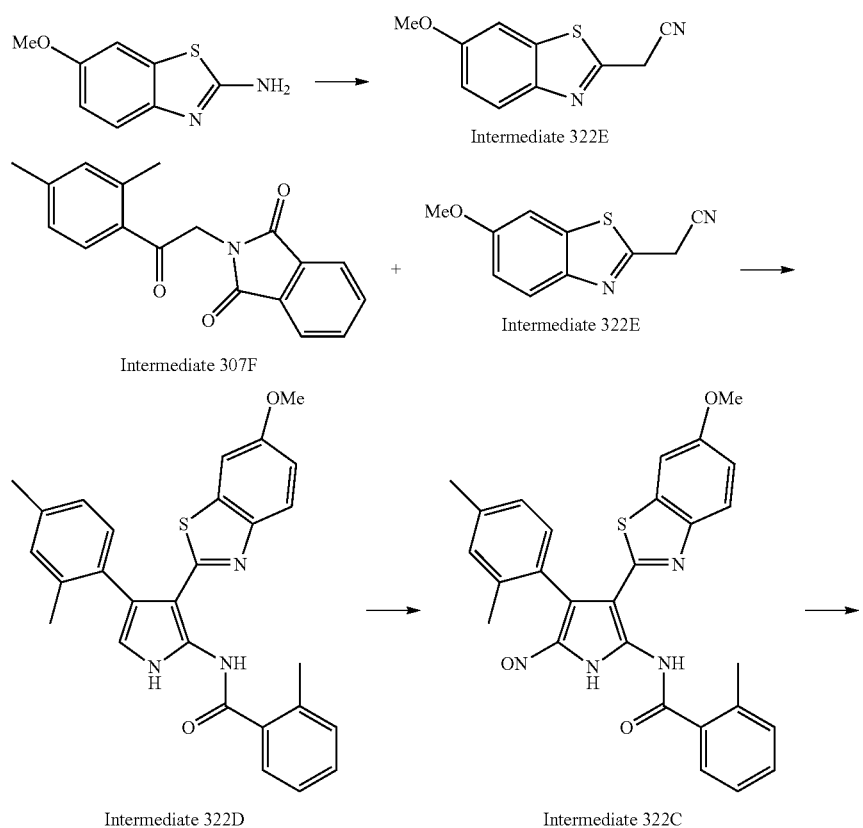

-continued

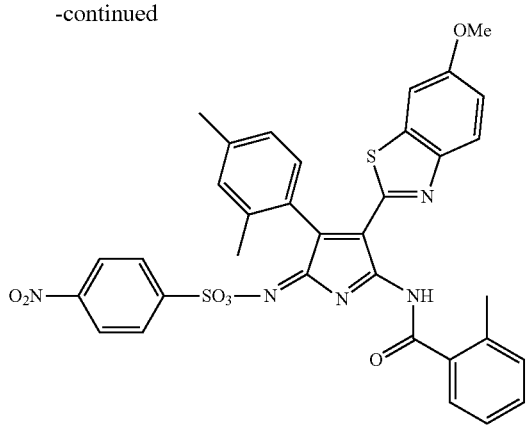
Intermediate 322B

Intermediate 322D + Intermediate 322B ⟶

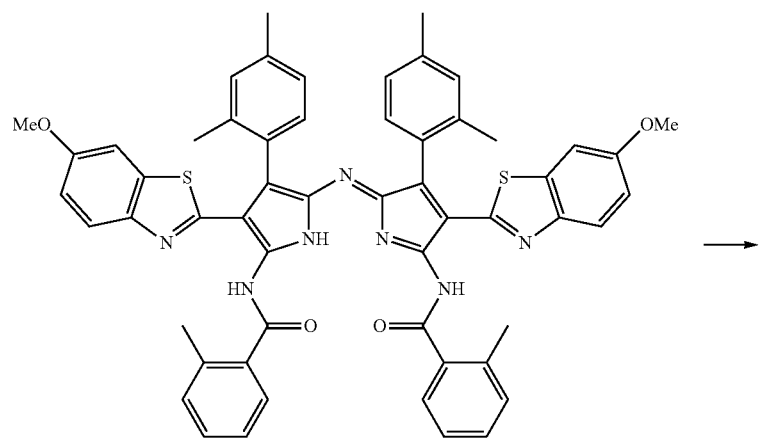
Intermediate 322A

⟶

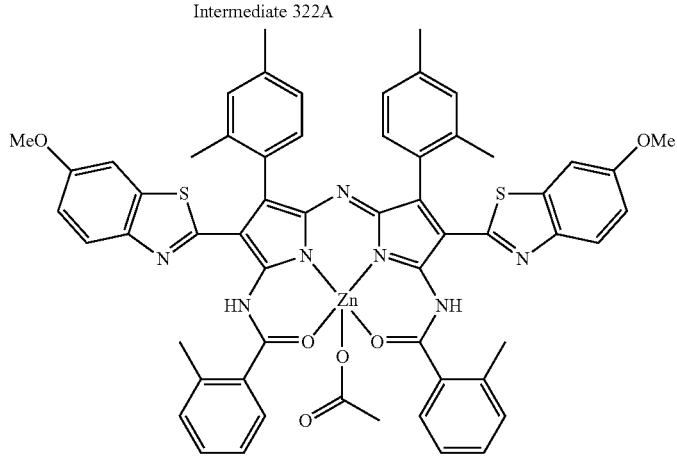
Example of compound 322

A 30% by weight aqueous potassium hydroxide solution (560 mL) was added to 2-amino-6-methoxybenzothiazole (50 g), and the mixture was stirred for 16 hours at 100° C. After stirring was completed, the reaction solution was neutralized with a 50% aqueous acetic acid solution, and the precipitated solid was filtered. To the resulting solid were added acetic acid (200 mL) and malononitrile (22.2 g), and the mixture was stirred for 1 hour at 80° C. After completion of the reaction, the reaction solution was cooled, and the precipitated solid was filtered, and the retentate was washed with methanol and dried. This gave intermediate 322E (24.6 g, yield 44%).

1H-NMR, 300 MHz, δ (DMSO-d6) ppm: 3.84 (s, 3H), 4.69 (s, 2H), 7.12-7.16 (dd, 1H), 7.71 (d, 1H), 7.92 (d, 1H).

To a mixture of intermediate 307F (14.4 g), intermediate 322E (10.0 g), and 1-methoxy-2-propanol (80 mL) was added a 50% aqueous sodium hydroxide solution (8.6 g), and the mixture was stirred for 30 minutes at room temperature, then for 4 hours at 130° C., under a stream of nitrogen gas. To this reaction mixture was added water, and the mixture was extracted with ethyl acetate. The resulting ethyl acetate phase was washed with aqueous sodium bicarbonate and brine, and dried over magnesium sulfate, and then the solvent was distilled off. To the resulting solid was added N-methylpyrrolidone (20 mL), and the mixture was cooled to 10° C. or less. To this was added dropwise o-toluoyl chloride (11.4 g), and the mixture was stirred for 30 minutes in an ice bath, then for 1 hour at room temperature. After completion of the reaction, water was added to the reaction solution, and the mixture was extracted with ethyl acetate. The resulting ethyl acetate phase was washed with dilute hydrochloric acid and brine, and dried over magnesium sulfate, and then the solvent was distilled off. The resulting solid was washed with acetonitrile and methanol to give intermediate 322D (4.3 g, yield 19%).

1H-NMR, 300 MHz, δ (CDCl$_3$) ppm: 2.17 (s, 3H), 2.45 (s, 3H), 2.69 (s, 3H), 3.79 (s, 3H), 6.45 (d, 1H), 6.94 (m, 1H), 7.10-7.48 (m, 7H), 7.58 (d, 1H), 7.80 (m, 1H), 10.89 (s, 1H), 12.05 (s, 1H).

To intermediate 322D (1.0 g) in acetic acid (10 mL) was added dropwise nitrosylsulfuric acid (43% in sulfuric acid) (0.7 g), and the mixture was stirred for 1 hour at room temperature. After completion of the reaction, water (20 mL) was added, and the resulting solid was filtered, and the retained solid was dried. This gave intermediate 322C (0.9 g, yield 90%).

1H-NMR, 300 MHz, δ (CDCl$_3$) ppm: 2.24 (s, 3H), 2.47 (s, 3H), 2.69 (s, 3H), 3.83 (s, 3H), 7.06 (m, 1H), 7.19-7.56 (m, 7H), 7.69 (d, 1H), 7.89 (m, 1H).

To intermediate 322C (1.7 g) was added acetonitrile (15 mL), and the mixture was stirred in an ice bath. Under a stream of nitrogen gas, pyridine (0.4 g) and p-nitrobenzenesulfonyl chloride (0.8 g) were successively added, and the mixture was stirred for 10 minutes. After completion of the reaction, the precipitated solid was filtered, and washed with acetonitrile to give intermediate 322B (1.7 g, yield 74%).

1H-NMR, 300 MHz, δ (CDCl$_3$) ppm: 2.00 (s, 3H), 2.51 (s, 3H), 2.69 (s, 3H), 3.85 (s, 3H), 6.97 to 8.34 (m, 14H), 12.79 (s, 1H).

To intermediate 322D (1.1 g) and potassium acetate (1.2 g) was added acetic acid (15 mL), and the mixture was stirred at 85° C. under a stream of nitrogen gas. To the reaction mixture was added intermediate 322D (1.7 g) by portions, and the mixture was stirred for 30 minutes. After completion of the reaction, acetonitrile was added, and the precipitated solid was filtered, and the retentate was washed with acetonitrile, methanol and ethyl acetate. This gave intermediate 322A (0.5 g, yield 22%).

1H-NMR, 300 MHz, δ (CDCl$_3$) ppm: 2.05 (s, 6H), 2.40 (s, 6H), 2.82 (s, 6H), 3.80 (s, 6H), 6.99-7.47 (m, 16H), 7.65 (d, 2H), 7.95 (d, 2H), 12.59 (s, 2H).

To intermediate 322A (50 mg) and zinc acetate dihydrate (14 mg) was added chloroform (1.5 mL), and the mixture was stirred for 3 hours at room temperature. After completion of the reaction, hexane was added, and the precipitated solid was filtered, and dried.

This gave compound 322 (20 mg, yield 35%).

1H-NMR, 300 MHz, δ (CDCl$_3$) ppm: 2.08 (s, 6H), 2.39 (s, 6H), 2.81 (s, 6H), 3.81 (s, 6H), 6.99-7.51 (m, 16H), 7.64 (d, 2H), 7.97 (d, 2H), 13.02 (s, 2H).

UV-visible absorption spectrum λmax=688 nm (CHCl$_3$).

Synthesis Example of Compound 323

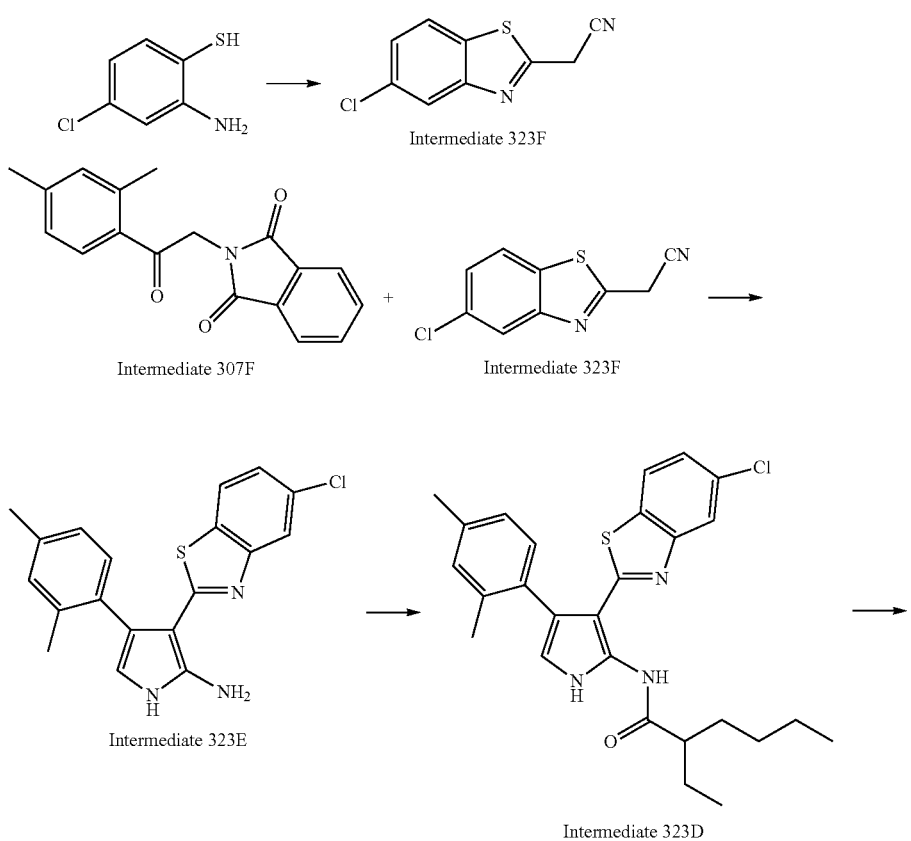

-continued
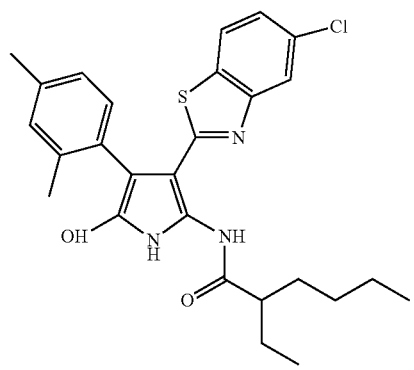
Intermediate 323C
Intermediate 323E + Intermediate 323C ⟶ 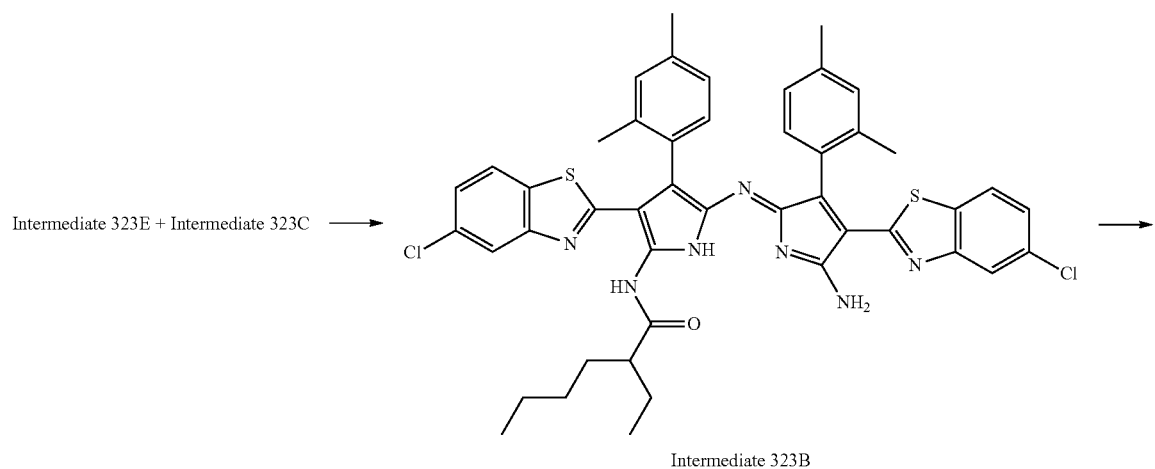 ⟶
Intermediate 323B
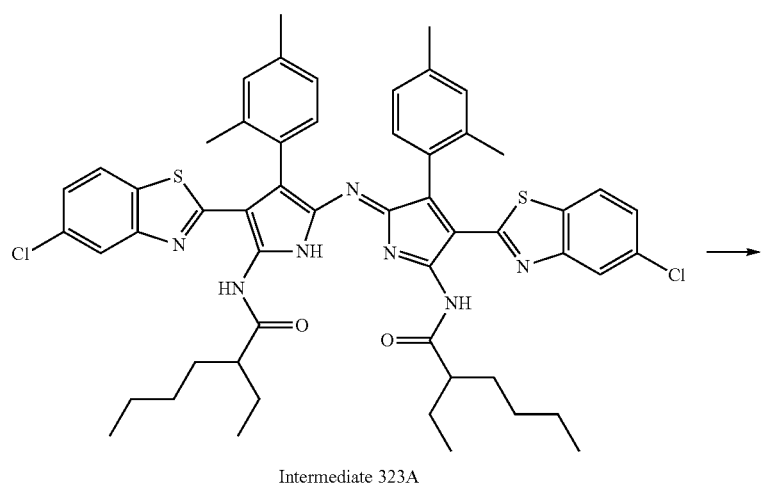 ⟶
Intermediate 323A

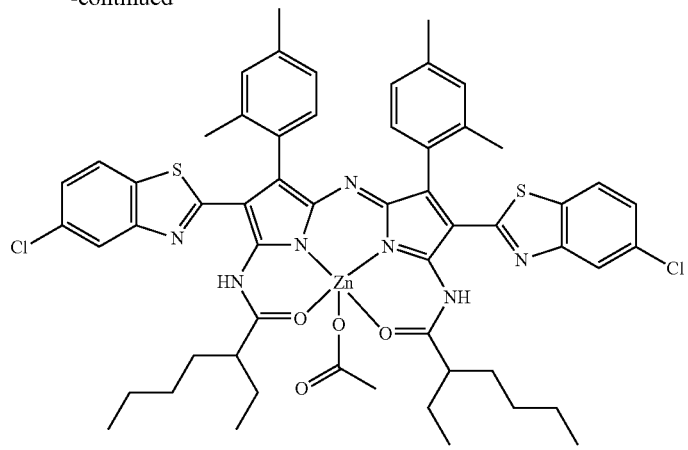

Example of compound 323

Acetic acid (120 mL) and malononitrile (33.8 g) were added to 2-amino-4-chlorobenzenethiol (68 g), and the mixture was stirred for 2 hours at 90° C. After completion of the reaction, methanol was added to the reaction solution, and the precipitated solid was filtered, and dried. This gave intermediate 323F (56.2 g, yield 63%).

1H-NMR, 300 MHz, δ (DMSO-d6) ppm: 4.78 (s, 2H), 7.54 (d, 1H), 8.15 to 8.19 (m, 2H).

To a mixture of intermediate 307F (7.0 g), intermediate 323F (5.0 g), and 1-methoxy-2-propanol (12 mL) was added a 20% aqueous sodium hydroxide solution (9.6 g), and the mixture was stirred for 30 minutes at room temperature, then for 2 hours at 130° C. under a stream of nitrogen gas. To this reaction mixture was added water, and the mixture was extracted with toluene. The resulting toluene phase was washed with aqueous sodium bicarbonate and brine, and dried over magnesium sulfate, and then the solvent was distilled off. This gave intermediate 323E (5.7 g, yield 67%).

1H-NMR, 300 MHz, δ (CDCl₃) ppm: 2.15 (s, 3H), 2.43 (s, 3H), 5.74 (br, 2H), 6.40 (m, 1H), 7.09-7.26 (m, 4H), 7.46 (d, 1H), 7.64 (m, 1H), 7.75 (m, 1H).

To intermediate 323E (10 g) was added N-methylpyrrolidone (25 mL), and the mixture was cooled to 10° C. or less. 2-Ethylhexanoyl chloride (4.6 g) was added dropwise, and the mixture was stirred for 30 minutes in an ice bath, then for 1 hour at room temperature. After completion of the reaction, water was added to the reaction solution, and the mixture was extracted with toluene. The resulting toluene phase was washed with dilute hydrochloric acid and brine, and dried over magnesium sulfate, and then the solvent was distilled off. The resulting solid was washed with acetonitrile to give intermediate 323D (8.4 g, yield 62%).

1H-NMR, 300 MHz, δ (CDCl₃) ppm: 0.92 (m, 3H), 1.05 (t, 3H), 1.41 (m, 4H), 1.67 to 1.84 (m, 4H), 2.15 (s, 3H), 2.35 to 2.44 (m, 4H), 6.40 (m, 1H), 7.09-7.28 (m, 4H), 7.52 (d, 1H), 7.77 (m, 1H).

To intermediate 323D (4.0 g) in acetic acid (40 mL) was added dropwise nitrosylsulfuric acid (43% in sulfuric acid) (2.9 g), and the mixture was stirred for 1 hour at room temperature. After completion of the reaction, 40 mL of water was added, and the resulting solid was filtered, and the retained solid was dried. This gave 4.0 g (94%) of intermediate 323C. 1H-NMR, 300 MHz, δ (CDCl₃) ppm: 0.92 (t, 3H), 1.05 (t, 3H), 1.41 (m, 4H), 1.67 to 1.88 (m, 4H), 2.24 (s, 3H), 2.42 to 2.50 (m, 4H), 7.21-7.40 (m, 4H), 7.65 (d, 1H), 7.89 (d, 1H).

To intermediate 323E (2.1 g) and intermediate 323C (3.0 g) was added acetic acid (40 mL), and the mixture was stirred for 2 hours at room temperature under a stream of nitrogen gas. After completion of the reaction, water was added, and the precipitated solid was filtered, and the retentate was washed with methanol. This gave intermediate 323B (2.4 g, yield 48%).

1H-NMR, 300 MHz, δ (CDCl₃) ppm: 0.92 (t, 3H), 1.10 (t, 3H), 1.44 (m, 4H), 1.67 to 1.95 (m, 10H), 2.40 to 2.50 (m, 7H), 6.88-7.34 (m, 8H), 7.53-7.61 (m, 2H), 7.81 (m, 1H), 8.00 (m, 1H), 12.20 (d, 1H).

To intermediate 323B (0.6 g) and tetrabutylammonium bromide (2.3 g) were added toluene (20 mL) and a 50% aqueous sodium hydroxide solution (2.3 g), and the mixture was stirred at room temperature. Then, 2-ethylhexanoyl chloride (0.6 g) was added dropwise, and the mixture was stirred for 2 hours at room temperature. After completion of the reaction, the mixture was extracted with toluene, and the resulting toluene phase was washed with dilute hydrochloric acid and brine, and dried over magnesium sulfate, and then the solvent was distilled off. The resulting solid was washed with methanol to give intermediate 323A (0.6 g, yield 81%).

1H-NMR, 300 MHz, δ (CDCl₃) ppm: 0.94 (t, 6H), 1.14 (t, 6H), 1.39 to 2.01 (m, 22H), 2.39 (m, 6H), 6.96-7.00 (m, 6H), 7.22 (m, 2H), 7.56 (m, 2H), 7.90 (s, 2H), 11.83 (s, 2H).

To intermediate 323A (240 mg) and zinc acetate dihydrate (80 mg) was added tetrahydrofuran (2.5 mL), and the mixture was stirred for 1 hour at room temperature. After completion of the reaction, water was added, and the precipitated solid was filtered, and dried. This gave compound 323 (197 mg, yield 73%).

1H-NMR, 300 MHz, δ (CDCl₃) ppm: 0.94 (t, 6H), 1.14 (t, 6H), 1.39 to 2.01 (m, 22H), 2.38 (s, 6H), 2.54 to 2.62 (m, 2H), 6.94-7.05 (m, 6H), 7.23 (m, 2H), 7.56 (d, 2H), 7.81 (d, 2H), 12.25 (d, 2H).

UV-visible absorption spectrum λmax=665 nm (CHCl$_3$).

Comparative Compound 101

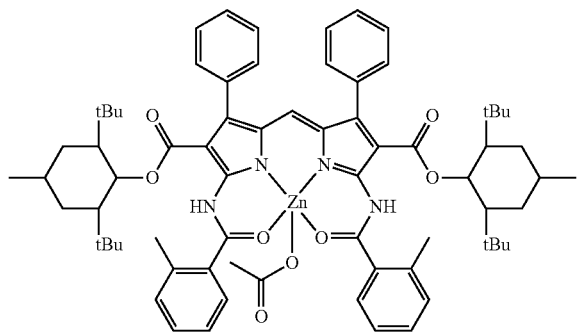

Materials Used

Various components used for preparing curable colored compositions are shown below.

(YD-1) A pigment dispersion obtained by mixing C.I. Pigment Yellow 150 (PY150, 12.8 parts) and an acrylic pigment dispersant (7.2 parts) with propylene glycol monomethyl ether acetate (80.0 parts) and thoroughly dispersing the pigment using a bead mill.

(YD-2) A solution of C.I. Solvent Yellow 162 (SY162, 10.0 parts) dissolved in propylene glycol monomethyl ether acetate (90.0 parts).

(GD-1) A pigment dispersion obtained by mixing C.I. Pigment Green 58 (PG58, 10.0 parts) and an acrylic pigment dispersant (5.0 parts) with propylene glycol monomethyl ether acetate (80.0 parts) and thoroughly dispersing the pigment using a bead mill.

(GD-2) A pigment dispersion obtained by mixing C.I. Pigment Green 7 (PG7, 10.0 parts) and an acrylic pigment dispersant (10.0 parts) with propylene glycol monomethyl ether acetate (80.0 parts) and thoroughly dispersing the pigment using a bead mill.

(Cyan dye solution 201) A mixture of compound 201 described above (10.0 parts) and propylene glycol monomethyl ether acetate (90.0 parts).

(T-1) Photopolymerizable compound: KAYARAD DPHA (a mixture of dipentaerythritol pentaacrylate and dipentaerythritol hexaacrylate available from Nippon Kayaku Co., Ltd.).

(U-1) Binder resin: a solution of benzyl methacrylate/methacrylic acid (75/25 [mass ratio] copolymer (weight average molecular weight: 12,000)) in propylene glycol monomethyl ether acetate (solids content 40.0% by mass).

(V-1) Photoinitiator:
2-(benzoyloxyimino)-1-[4-(phenylthio)phenyl]-1-octanone (V-2) Photoinitiator:
2-(acetoxyimino)-4-(4-chlorophenylthio)-1-[9-ethyl-6-(2-methylbenzoyl)-9H-carbazole-3-yl]-1-butanone (W-1) Co-Photoinitiator:
4,4'-bis(diethylamino)benzophenone (X-1) Solvent: propylene glycol monomethyl ether acetate (X-2) Solvent: ethyl 3-ethoxypropionate (Y-1) Surfactant: Megafac F781-F (from DIC Corporation).

Preparation and Evaluation of Cyan-Colored Films
1. Preparation of a Curable Colored Composition (Coating Solution)

The components in the composition shown below were mixed to prepare curable colored composition 1.

Composition

| | | |
|---|---|---|
| Cyan dye solution 201 defined above | 6.9 | parts by mass |
| (T-1) defined above | 103.4 | parts by mass |
| (U-1) defined above | 212.2 | parts by mass |
| | (84.9 | parts by mass of solids) |
| (V-1) defined above | 21.2 | parts by mass |
| (W-1) defined above | 3.5 | parts by mass |
| (X-1) defined above | 71.9 | parts by mass |
| (X-2) defined above | 3.6 | parts by mass |
| (Y-1) defined above | 0.06 | parts by mass. |

2. Preparation of Colored Films Using Curable Colored Compositions

The curable colored composition (color resist solution) described above was applied on a glass substrate of 100 mm×100 mm (1737 from Corning Incorporated) at a spin speed controlled to show a maximum absorbance of 1.5 at 600 to 700 nm, and dried in an oven at 100° C. for 180 seconds to prepare a colored film on the substrate (Example 1).

Substrates of Example 2 and Comparative example 1 were prepared and evaluated in the same manner as in Example 1 except that compound 201 was replaced by the compounds shown in the table below.

3. Evaluation of the Colored Films Using Curable Colored Compositions

The substrates obtained above were evaluated as follows.

Evaluation of Hue

The colored films prepared were analyzed for absorbances at 550 nm and 650 nm by a UV-Vis Spectrophotometer (UV2400-PC from Shimadzu Corporation), and the ratio between the absorbances at 550 nm and 650 nm ($Abs_{550nm}/Abs_{650nm}$) was calculated. The evaluation results are shown in the table below.

Evaluation of Heat Resistance

The substrates prepared in the Examples and Comparative example were evaluated for heat resistance. They were heated on a hot plate at 150° C. for 5 minutes. All of the substrates prepared in the Examples and Comparative example showed that 90% or more of the dye compounds remained, verifying that they have excellent heat resistance.

TABLE 1

| | Dye compound | $Abs_{550\,nm}/Abs_{650\,nm}$ |
|---|---|---|
| Comparative example1 | Compound101 | 10000 |
| Example1 | Compound201 | 0.05 |
| Example2 | Compound202 | 0.06 |

The table above shows that the compounds of the present invention have high transmittance in the magenta region so that they are superior as cyan dyes. Especially, Comparative example 1 and Example 1 differ in only one atom in their compounds, revealing that such a difference in structure has a great influence.

Preparation and Evaluation of Green-Colored Films

1. Preparation of a Curable Colored Composition (Coating Solution)

The components in the composition shown below were mixed to prepare a curable colored composition.

Composition

| | | |
|---|---|---|
| Cyan dye solution 201 defined above | 6 parts by mass | |
| Yellow dye compound (YD-1) added in an amount controlled to adjust the ratio of absorbances (absorbance at 450 nm/absorbance at 650 nm) in the range of 0.95 to 1.05. | | |
| (T-1) defined above | 103.4 | parts by mass |
| (U-1) defined above | 212.2 | parts by mass |
| | (84.9 | parts by mass of solids) |
| (V-1) defined above | 21.2 | parts by mass |
| (W-1) defined above | 3.5 | parts by mass |
| (X-1) defined above | 71.9 | parts by mass |
| (X-2) defined above | 3.6 | parts by mass |
| (Y-1) defined above | 0.06 | parts by mass. |

2. Preparation of Colored Films Using Curable Colored Composition

The curable colored composition (color resist solution) obtained above was applied on a glass substrate of 100 mm×100 mm (1737 from Corning Incorporated) to show a maximum absorbance of 1.9 to 2.1 at 600 to 700 nm, and dried in an oven at 100° C. for 180 seconds to prepare a colored film on the substrate (Example 101).

Comparative Example 101

A colored film was prepared in the same manner as in Example 101 except that compound 201 was replaced by compound 101.

Comparative Example 102

A colored film was prepared in the same manner as in Example 101 except that the cyan dye solution 201 of the present invention was replaced by GD-1 (containing dye compound PG58) (60 parts by mass).

Comparative Example 103

A colored film was prepared in the same manner as in Example 101 except that the cyan dye solution 201 of the present invention was replaced by GD-2 (containing dye compound PG7) (60 parts by mass) and YD-1 (containing dye compound PY150) was replaced by YD-2 (containing dye compound SY150).

Example 102

A colored film was prepared in the same manner as in Example 101 except that compound 201 was replaced by compound 202 and YD-1 (containing dye compound PY150) was replaced by YD-2 (containing dye compound SY150).

Example 103

A colored film was prepared in the same manner as in Example 101 except that the amount of the cyan dye solution of the present invention added was changed to 2 parts by weight and 40 parts by mass of GD-1 (containing dye compound PG58) was further added.

Example 104

A colored film was prepared in the same manner as in Example 101 except that the amount of the cyan dye solution of the present invention added was changed to 2 parts by weight and 40 parts by mass of GD-2 (containing dye compound PG7) was further added and YD-1 (containing dye compound PY150) was replaced by YD-2 (containing dye compound SY162).

Example 105

A colored film was prepared in the same manner as in Example 103 except that the cyan dye of the present invention was replaced by compound 202.

Example 106

A colored film was prepared in the same manner as in Example 101 except that compound 201 in the cyan dye solution of the present invention was replaced by compound 202 in an amount of 2 parts by weight and 40 parts by mass of GD-1 (containing dye compound PG58) was further added.

3. Evaluation of the Colored Films Using Curable Colored Compositions

The substrates obtained above were evaluated as follows.

Evaluation of Hue

The colored films prepared were analyzed for absorbances by a UV-Vis Spectrophotometer (UV2400-PC from Shimadzu Corporation), and the ratio between the absorbances at 550 nm and 650 nm ($Abs_{550nm}/Abs_{650nm}$) was calculated. The evaluation results are shown in Table 2 below.

Evaluation of Heat Resistance

The substrates prepared in the Examples and Comparative examples were evaluated for heat resistance. They were heated on a hot plate at 150° C. for 5 minutes. All of the substrates prepared in the Examples and Comparative examples showed that 90% or more of the absorption in the cyan region remained, verifying that they have excellent heat resistance.

TABLE 2

| | Dye compound | | | $Abs_{550\,nm}/Abs_{650\,nm}$ |
|---|---|---|---|---|
| Comparative example101 | Compound101 | — | PY150 | 12000 |
| Comparative example102 | PG58 | — | PY150 | 0.04 |
| Comparative example103 | PG7 | — | PY150 | 0.07 |
| Example101 | Compound201 | — | PY150 | 0.05 |
| Example102 | Compound201 | — | SY162 | 0.06 |
| Example103 | Compound201 | PG58 | PY150 | 0.03 |
| Example104 | Compound201 | PG7 | SY162 | 0.05 |
| Example105 | Compound202 | — | PY150 | 0.06 |
| Example106 | Compound202 | PG58 | PY150 | 0.03 |

A comparison of Example 101 vs. Comparative example 101 shows that a green-colored product having a high transmittance in the magenta region was obtained. Further, a comparison of Example 103 vs. Comparative example 102, Example 104 vs. Comparative example 103, and Example 106 vs. Comparative example 103 shows that green-colored products having a high transmittance in the magenta region are obtained by using a green pigment in combination with a dye of the present invention.

Especially, it is very important to increase the transmittance in the 550 nm region to improve luminance (energy conservation). It is shown that the range of concentrations in the Examples are very effective for improving luminance because an increase of 0.01 point in $Abs_{550nm}/Abs_{650nm}$ leads to an increase of about 2% in transmittance.

Examples 201 to 223

Colored films were prepared in the same manner as in Example 106 except that compound 202 in the cyan dye solution of the present invention was replaced by compounds 301 to 323, respectively. The resulting substrates were evaluated in the same manner as in Example 1.

3. Evaluation of the Colored Films Using Curable Colored Compositions

The substrates obtained above were evaluated as follows.

Evaluation of Hue

The colored films prepared were analyzed for absorbances by a UV-Vis Spectrophotometer (UV2400-PC from Shimadzu Corporation), and the ratio between the absorbances at 550 nm and 650 nm ($Abs_{550nm}/Abs_{650nm}$) was calculated. The evaluation results are shown in the table below.

Evaluation of Heat Resistance

The substrates prepared in the Examples were evaluated for heat resistance. They were heated on a hot plate at 150° C. for 5 minutes. All of the substrates prepared in the Examples showed that 90% or more of the absorption in the cyan region remained, verifying that they have excellent heat resistance.

TABLE 3

| | Dye compound | | | $Abs_{550\,nm}/Abs_{650\,nm}$ |
|---|---|---|---|---|
| Example201 | Compound301 | PG58 | PY150 | 0.035 |
| Example202 | Compound302 | PG58 | PY150 | 0.03 |
| Example203 | Compound303 | PG58 | PY150 | 0.03 |
| Example204 | Compound304 | PG58 | PY150 | 0.035 |
| Example205 | Compound305 | PG58 | PY150 | 0.04 |
| Example206 | Compound306 | PG58 | PY150 | 0.035 |
| Example207 | Compound307 | PG58 | PY150 | 0.025 |
| Example208 | Compound308 | PG58 | PY150 | 0.02 |
| Example209 | Compound309 | PG58 | PY150 | 0.03 |
| Example210 | Compound310 | PG58 | PY150 | 0.025 |
| Example211 | Compound311 | PG58 | PY150 | 0.03 |
| Example212 | Compound312 | PG58 | PY150 | 0.02 |
| Example213 | Compound313 | PG58 | PY150 | 0.03 |
| Example214 | Compound314 | PG58 | PY150 | 0.025 |
| Example215 | Compound315 | PG58 | PY150 | 0.03 |
| Example216 | Compound316 | PG58 | PY150 | 0.035 |
| Example217 | Compound317 | PG58 | PY150 | 0.02 |
| Example218 | Compound318 | PG58 | PY150 | 0.03 |
| Example219 | Compound319 | PG58 | PY150 | 0.035 |
| Example220 | Compound320 | PG58 | PY150 | 0.02 |
| Example221 | Compound321 | PG58 | PY150 | 0.03 |
| Example222 | Compound322 | PG58 | PY150 | 0.02 |
| Example223 | Compound323 | PG58 | PY150 | 0.025 |

The table above shows that these compounds also provide green-colored products having an excellent transmittance in the magenta region.

The invention claimed is:

1. A curable colored composition comprising a metal complex in which a compound represented by formula (1) below is coordinated to a metal atom or a metal compound:

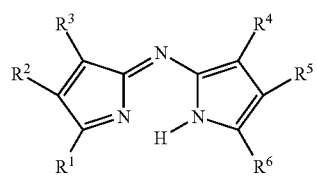

Formula (1)

wherein in formula (1), $R^1$, $R^3$, $R^4$, and $R^6$ each represents a hydrogen atom or a substituent; and
$R^2$ and $R^5$ are each represented by formula (18-1) below:

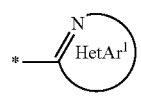

Formula (18-1)

wherein in formula (18-1), $HetAr^1$ represents an optionally substituted heteroaryl ring, the substituents may be joined together to form a single ring or a fused ring system, and $R^2$ and $R^5$ are each attached to the central moiety at *.

2. The curable colored composition according to claim 1, wherein the metal complex is represented by formula (2) below:

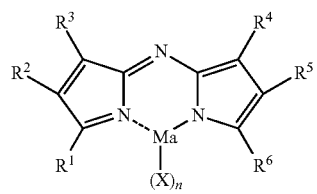

Formula (2)

wherein in formula (2), $R^1$, $R^3$, $R^4$, and $R^6$ each represents a hydrogen atom or a substituent; $R^2$ and $R^5$ have the same meaning as in claim 1; Ma represents a metal atom or a metal compound; each X represents a substituent; Ma and X form a covalent bond, coordinate bond or ionic bond; and n is an integer of 2 to 4.

3. The curable colored composition according to claim 1, wherein the metal complex is represented by formula (2-2) below:

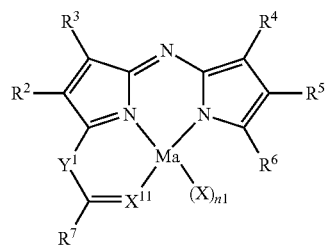

Formula (2-2)

wherein in formula (2-2), $R^3$, $R^4$, and $R^6$ each represents a hydrogen atom or a substituent; $R^2$ and $R^5$ have the same meaning as in claim 1; $R^7$ represents alkyl, alkenyl, aryl, heterocyclyl, alkoxy, aryloxy, alkylamino, arylamino, or heterocyclylamino; Ma represents a metal atom or a metal compound; each X represents a substituent; $X^{11}$ represents a nitrogen atom, an oxygen atom, a sulfur atom, or NR, wherein R represents a hydrogen atom, alkyl, alkenyl, aryl, heterocyclyl, acyl, alkylsulfonyl, or aryl sulfonyl; $Y^1$ represents a nitrogen atom, a carbon atom, or NRc, wherein Rc represents a hydrogen atom, alkyl, alkenyl, aryl, heterocyclyl, acyl, alkylsulfonyl, or arylsulfonyl; Ma and X form a covalent bond, coordinate bond or ionic bond; and n1 is an integer of 2 to 4.

4. The curable colored composition according to claim 1, wherein the metal complex is represented by formula (3) below:

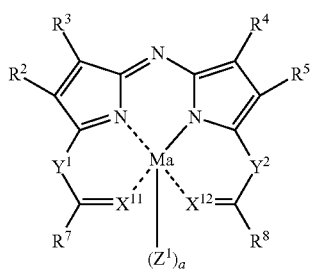

Formula (3)

wherein in formula (3), $R^3$ and $R^4$ each represents a hydrogen atom or a substituent; $R^2$ and $R^5$ have the same meaning as in claim 1; $R^7$ and $R^8$ each represents alkyl, alkenyl, aryl, heterocyclyl, alkoxy, aryloxy, alkylamino, arylamino or heterocyclylamino; Ma represents a metal atom or a metal compound; $X^{11}$ and $X^{12}$ each represents a nitrogen atom, an oxygen atom, a sulfur atom, or NR, wherein R represents a hydrogen atom, alkyl, alkenyl, aryl, heterocyclyl, acyl, alkylsulfonyl, or arylsulfonyl; $Y^1$ and $Y^2$ each represents a nitrogen atom, a carbon atom, or NRc, wherein Rc represents a hydrogen atom, alkyl, alkenyl, aryl, heterocyclyl, acyl, alkylsulfonyl, or arylsulfonyl; $Z^1$ represents a group capable of forming a bond with Ma; and a represents 0, 1 or 2.

5. The curable colored composition according to claim 1, wherein the metal complex is represented by formula (4) below:

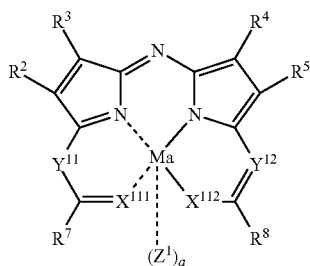

Formula (4)

wherein in formula (4), $R^3$ and $R^4$ each represents a hydrogen atom or a substituent; $R^2$ and $R^5$ have the same meaning as in claim 1; $R^7$ and $R^8$ each represents alkyl, alkenyl, aryl, heterocyclyl, alkoxy, aryloxy, alkylamino, arylamino or heterocyclylamino; Ma represents a metal atom or a metal compound; $X^{111}$ represents a nitrogen atom, an oxygen atom, a sulfur atom, or NR, wherein R represents a hydrogen atom, alkyl, alkenyl, aryl, heterocyclyl, acyl, alkylsulfonyl, or arylsulfonyl; $X^{112}$ represents an oxygen atom, a sulfur atom, or NRa, wherein Ra represents a hydrogen atom, alkyl, alkenyl, aryl, heterocyclyl, acyl, alkylsulfonyl, or arylsulfonyl; $Y^{11}$ represents a nitrogen atom, a carbon atom, or NRc, wherein Rc represents a hydrogen atom, alkyl, alkenyl, aryl, heterocyclyl, acyl, alkylsulfonyl, or arylsulfonyl; $Y^{12}$ represents a nitrogen atom or a carbon atom; $Z^2$ represents a group capable of forming a bond with Ma; and a represents 0, 1 or 2.

6. The curable colored composition according to claim 1, wherein $R^2$ and $R^5$ are each represented by any one of formulae (19-1) to (19-5):

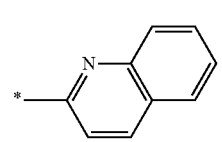

Formula (19-1)

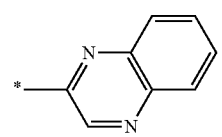

Formula (19-2)

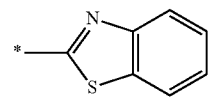

Formula (19-3)

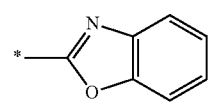

Formula (19-4)

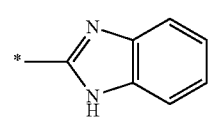

Formula (19-5)

wherein in formulae (19-1) to (19-5) above, $R^2$ and $R^5$ are each attached to the central moiety at *; and these groups may be substituted.

7. The curable colored composition according to claim 1, further comprising a yellow dye.

8. The curable colored composition according to claim 1, further comprising a green dye.

9. The curable colored composition according to claim 1, further comprising a monomer and a polymerization initiator.

10. A color filter comprising a colored layer using the curable colored composition according to claim.

11. A liquid crystal display device comprising the color filter according to claim 10.

12. A solid-state image sensor comprising the color filter according to claim claim 10.

13. A process for preparing a color filter, comprising: applying the curable colored composition according to claim 1 to form a colored layer; and exposing the resulting colored layer in a pattern.

14. A compound represented by formula (5-3) below:
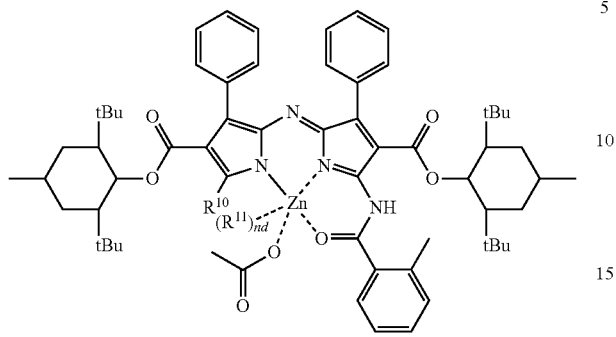
Formula (5-3)
wherein in formula (5-3), $R^{10}$ represents a substituent containing a nitrogen atom; $R^{11}$ represents a substituent, or $R^{10}$ and $R^{11}$ may be joined together to form a ring; and nd represents 0 or 1.
* * * * *